US011267807B2

(12) United States Patent
Feinberg et al.

(10) Patent No.: US 11,267,807 B2
(45) Date of Patent: Mar. 8, 2022

(54) USE OF SMALL MOLECULE INHIBITORS TO KLF10 FOR MODULATION OF T REGULATORY CELLS AND CANCER IMMUNOTHERAPY

(71) Applicants: THE BRIGHAM AND WOMEN'S HOSPITAL, INC., Boston, MA (US); BETH ISRAEL DEACONESS MEDICAL CENTER, INC., Boston, MA (US)

(72) Inventors: Mark Feinberg, Newton, MA (US); Santosh A. Khedkar, Lexington, MA (US)

(73) Assignees: The Brigham and Women's Hospital, Inc., Boston, MA (US); Beth Isreal Deaconess Medical Center, Inc., Boston, MA (US)

(*) Notice: Subject to any disclaimer, the term of this patent is extended or adjusted under 35 U.S.C. 154(b) by 147 days.

(21) Appl. No.: 15/337,633

(22) Filed: Oct. 28, 2016

(65) Prior Publication Data
US 2017/0121318 A1    May 4, 2017

Related U.S. Application Data

(60) Provisional application No. 62/247,431, filed on Oct. 28, 2015.

(51) Int. Cl.

| | | |
|---|---|---|
| C07D 409/12 | (2006.01) |
| C07C 49/35 | (2006.01) |
| C07D 207/44 | (2006.01) |
| C07C 39/04 | (2006.01) |
| C07D 311/62 | (2006.01) |
| C07D 239/52 | (2006.01) |
| C07D 239/38 | (2006.01) |
| C07C 233/34 | (2006.01) |
| C07C 251/86 | (2006.01) |
| C07C 49/84 | (2006.01) |
| C07C 39/15 | (2006.01) |
| C07C 205/45 | (2006.01) |
| C07C 217/48 | (2006.01) |

(52) U.S. Cl.
CPC ............ C07D 409/12 (2013.01); C07C 39/15 (2013.01); C07C 49/84 (2013.01); C07C 205/45 (2013.01); C07C 217/48 (2013.01); C07C 251/86 (2013.01); C07D 207/44 (2013.01); C07D 239/38 (2013.01); C07D 239/52 (2013.01); C07D 311/62 (2013.01)

(58) Field of Classification Search
None
See application file for complete search history.

(56) References Cited

U.S. PATENT DOCUMENTS

| | | | | |
|---|---|---|---|---|
| 7,074,770 B1 * | 7/2006 | Charo | ............... | A61K 39/0008 514/44 R |
| 7,438,916 B2 * | 10/2008 | Rathore | ............... | C07K 14/445 424/191.1 |
| 8,691,572 B2 | 4/2014 | Feinberg | | |
| 9,500,658 B2 | 11/2016 | Feinberg et al. | | |

FOREIGN PATENT DOCUMENTS

WO    WO2014059404    *    4/2014

OTHER PUBLICATIONS

Khedkar et al., Discovery of Small Molecule Inhibitors to Kruppel-like Factor 10 (KLF10): Implications for Modulation of T Regulatory Cell Differentiation. Journal of Medicinal Chemistry, 2015, 58, 1466-1478.*
Garai et al., The basics and advances of immunomodulators and antigen presentation: a key to development of potent memory response against pathogens. Expert Opinion on Biological Therapy, 2014, 14, 1383-1397.*
Caplus printout of U.S. Pat. No. 7,438,916, published on Oct. 21, 2008.*
Chemical Abstract Registry No. 473877-91-7, indexed in the Registry File on STN CAS Online Nov. 19, 2002.*
Chemical Abstract Registyr No. 1298498-18-6, indexed in the Registry File on STN CAS Online May 22, 2011.*
Chemical Abstract Registyr No. 1210501-30-6, indexed in the Registry File on STN CAS Online Mar. 16, 2010.*
Chemical Abstract Registyr No. 1210000-39-7, indexed in the Registry File on STN CAS Online Mar. 15, 2010.*
Chemical Abstract Registyr No. 1090001-18-5, indexed in the Registry File on STN CAS Online Dec. 25, 2008.*
Updated CAPLUS printout of U.S. Pat. No. 7,438,916, published on Oct. 21, 2008.*
Chemical Abstract Registry No. 1197834-98-2, indexed in the Registry File on STN CAS Online Dec. 16, 2009.*
Chemical Abstract Registry No. 1061980-21-9, indexed in the Registry File on STN CAS Online Oct. 16, 2008.*
Berg T., "Inhibition of transcription factors with small organic molecules", Current Opinion in Chemical Biology 12:464-471 (2008).
Bluestone et al., "How do CD4+ CD25+ regulatory T cells control autoimmunity?", Current Opinion in Immunology 17:638-642 (2005).
Cao et al., "Kruppel-like Factor KLF10 Targets Transforming Growth Factor-β1 to Regulate CD4+ CD25- T Cells and T Regulatory Cells", The Journal of Biological Chemistry 284(37):24914-24924 (2009).
Cao et al., "Role of Krüppel-like factors in leukocyte development, function, and disease", Blood 116(22):4404-4414 (2010).

(Continued)

*Primary Examiner* — Po-Chih Chen
(74) *Attorney, Agent, or Firm* — Nixon Peabody LLP; David S. Resnick; Ravinderjit Braich

(57) ABSTRACT

The invention relates to compositions and methods for inhibiting Krüppel-like Factor 10 (KLF10) for modulation of T regulatory cells and cancer immunotherapy.

16 Claims, 42 Drawing Sheets
(23 of 42 Drawing Sheet(s) Filed in Color)
Specification includes a Sequence Listing.

(56) References Cited

OTHER PUBLICATIONS

Chrisman et al., "Identification and Characterization of a Consensus DNA Binding Element for the Zinc Finger Transcription Factor TIEG/EGRα", DNA and Cell Biology 22(3):187-199 (2003).

Fontenot et al., "Foxp3 programs the development and function of CD4+ CD25+ regulatory T cells", Nature Immunology 4(4):330-336 (2003).

Frankel et al., "Both CD4 and CD8 T Cells Mediate Equally Effective In Vivo Tumor Treatment When Engineered with a Highly Avid TCR Targeting Tyrosinase", The Journal of Immunology 184:5988-5998 (2010).

Koehler A., "A complex task? Direct modulation of transcription factors with small molecules", Current Opinion in Chemical Biology 14(3):331-340 (2010).

Lauth et al., "Inhibition of GLI-mediated transcription and tumor cell growth by small-molecule antagonists", Proceedings of the National Academy of Sciences 104(20):8455-8460 (2007).

Lin et al., "Small-Molecule Switches for Zinc Finger Transcription Factors", Journal of the American Chemical Society 125(3):612-613 (2003).

Majmudar et al., "Chemical approaches to transcriptional regulation", Current Opinion in Chemical Biology 9:467-474 (2005).

Piccirillo et al., "Naturally-occurring CD4+ CD25+ immunoregulatory T cells: central players in the arena of peripheral tolerance", Seminars in Immunology 16:81-88 (2004).

Robert et al., "Pembrolizumab versus Ipilimumab in Advanced Melanoma", The New England Journal of Medicine 372(26):2521-2532 (2015).

Sakaguchi S., "Naturally arising Foxp3-expressing CD25+ CD4+ regulatory T cells in immunological tolerance to self and non-self", Nature Immunology 6(4):345-352 (2005).

Venuprasad et al., "The E3 ubiquitin ligase Itch regulates expression of transcription factor Foxp3 and airway inflammation by enhancing the function of transcription factor TIEG1", Nature Immunology 9(3):245-253 (2008).

Virgin et al., "Redefining Chronic Viral Infection", Cell 138:30-50 (2009).

Yet et al., "Human EZF, a Krüppel-like Zinc Finger Protein, Is Expressed in Vascular Endothelial Cells and Contains Transcriptional Activation and Repression Domains", The Journal of Biological Chemistry 273(2):1026-1031 (1998).

* cited by examiner

- Charged (negative)
- Charged (positive)
- Polar
- Hydrophobic
- Glycine
- Metal
- Water
- Hydration site
- Displaced hydration site
- π-π stacking
- π-cation
- H-bond (backbone)
- H-bond (side chain)
- Metal coordination
- Salt Bridge
- Solvent exposure

FIG. 19

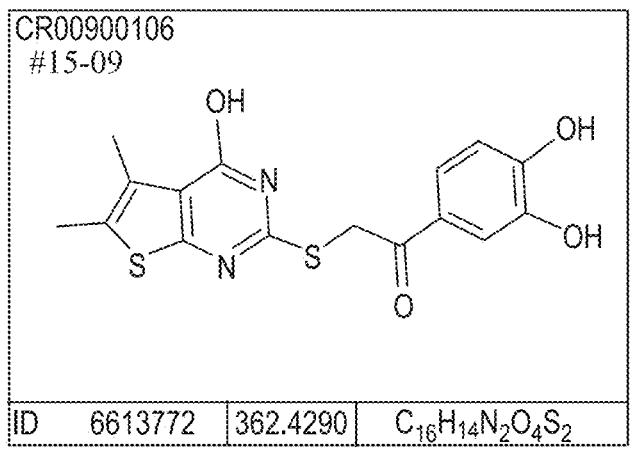

```
Data File R:\HPLC\AUTO\CR009001\1FA-3401.D
Sample Name: CR009001P1-F-01
Instrument 1 25/09/2012 16:04:52
Column: Onyx C18 50x4.6mm | 3.75ml/min | Columns Reg Valve
Gradient: "A"->@14.8min->"B"->@15.min->"A"->PostRun
PMP1, Solvent A           : 0.1%TFA in ACN/H2O (2.5:97.5)
PMP1, Solvent B           : 0.1% TFA in ACN
PMP1, Solvent C           : 0.1%FA in ACN/H2O (2.5:97.5)
PMP1, Solvent D           : 0.1%FA in ACN
Ionization mode           :     API-ES Positive Signal 1: ADC1 A, ELSD
Peak RetTime Type  Width     Area      Height     Area
  #   [min]        [min]    [mV*s]      [mV]       %
----|-------|----|-------|----------|----------|--------|
  1   4.705 VV   0.0584 1090.21191  286.33060 100.0000
Totals :                 1090.21191  286.33060

Signal 2: DAD1 A, Sig=300,200 Ref=off
Peak RetTime Type  Width     Area      Height     Area
  #   [min]        [min]    [mAU*s]     [mAU]      %
----|-------|----|-------|----------|----------|--------|
  1   4.636 MM   0.0934 9776.12793 1744.08984 100.0000
Totals :                 9776.12793 1744.08984

Signal 3: MSD1 TIC, MS File
Peak RetTime Type  Width     Area      Height     Area
  #   [min]        [min]                           %
----|-------|----|-------|----------|----------|--------|
  1   4.643 MM   0.1986 8.56525e6  7.18809e5 100.0000
Totals :                 8.56525e6  7.18809e5
```

FIG. 20

| | CD4+CD25+ (%) | (%)* |
|---|---|---|
| DMSO | 70.43 | 100.00 |
| | 75.99 | |
| | 75.55 | |
| #48 | 29.37 | 44.51 |
| | 36.84 | |
| | 32.59 | |
| #48-15 | 39.83 | 40.92 |
| | 16.02 | |
| | 34.98 | |
| #15-9 | 53.92 | 70.83 |
| | 52.70 | |
| | 50.61 | |

*, Values were compared with DMSO condition, which were set to 100 %.

FIG. 21

| Cells | Treatments | Average Ct Values FoxP3 | β-Actin | Fold change |
|---|---|---|---|---|
| CD4+CD25- | | 28.36 | 19.77 | 1 |
| Conversion of | DMSO | 29.95 | 23.18 | 3.52 |
| CD4+CD25- | #48 | 33.45 | 23.97 | 0.54 |
| to CD4+CD25+ | #48-15 | 32.19 | 23.02 | 0.66 |
| cells | #15-9 | 36.91 | 26.82 | 0.35 |

FIG. 22

| Code # | Vendor Code/Name | Glide-rank-150 | GlideXP-Score | Surflex-rank-150 | Surflex-Score | Flexx-rank-150 | Flexx-Total-Score |
|---|---|---|---|---|---|---|---|
| AR_001 | ZINC00151535 | 1 | -8.28 | 81 | 4.35 | 90 | -14.26 |
| AR_002 | ZINC00389130 | 2 | -7.57 | 97 | 4.27 | 101 | -13.99 |
| AR_003 | ZINC00040342 | 3 | -7.30 | 108 | 4.15 | 46 | -16.33 |
| AR_004 | ZINC00056609 | 4 | -7.25 | 13 | 6.10 | 2 | -24.65 |
| AR_005 | 1-(5-Hydroxy-pyridine-3-carbonyl)-pyrrolidine-2-carboxylic acid | 107 | -7.23 | 80 | 5.43 | 140 | -12.42 |
| AR_006 | ZINC00429664 | 126 | -7.15 | 107 | 4.17 | 43 | -16.77 |
| AR_007 | 796263_1 | 101 | -6.87 | 33 | 5.38 | 39 | -16.83 |
| AR_008 | ZINC02007905 | 104 | -6.85 | 126 | 3.98 | 20 | -18.21 |
| AR_009 | ZINC02579359 | 117 | -6.71 | 25 | 5.64 | 8 | -21.12 |
| AR_010 | 4-(3-Hydroxy-propylamino)-3-nitro-benzoic acid | 72 | -6.66 | 144 | 3.85 | 31 | -17.35 |
| AR_011 | ZINC00266187 | 57 | -6.50 | 50 | 5.05 | 112 | -13.57 |
| AR_012 | ZINC00895472 | 83 | -6.50 | 42 | 5.17 | 129 | -12.99 |
| AR_013 | ZINC00539105 | 5 | -6.45 | 92 | 4.35 | 25 | -17.80 |
| AR_014 | ZINC02505891 | 50 | -6.44 | 68 | 4.80 | 133 | -13.24 |
| AR_015 | 7116840_1 | 34 | -6.44 | 79 | 4.52 | 73 | -14.95 |
| AR_016 | ZINC00895459 | 57 | -6.36 | 66 | 4.93 | 6 | -21.86 |
| AR_017 | ZINC00062059 | 98 | -6.31 | 131 | 3.97 | 23 | -17.97 |
| AR_018 | 836609_1 | 40 | -6.29 | 73 | 4.65 | 92 | -14.26 |
| AR_019 | 3-(4-Hydroxy-1,1-dioxo-tetrahydro-1lambda*6*-thiophen-3-ylamino)-propionic acid | 54 | -6.09 | 58 | 4.87 | 103 | -13.97 |
| AR_020 | ZINC00391975 | 71 | -5.96 | 48 | 5.11 | 29 | -17.57 |
| AR_021 | ZINC02527749 | 21 | -5.95 | 11 | 6.18 | 131 | -12.91 |
| AR_022 | ZINC00226748 | 39 | -5.90 | 74 | 4.62 | 5 | -22.42 |
| AR_023 | 7615720_1 | 121 | -5.87 | 23 | 5.72 | 42 | -16.74 |
| AR_024 | ZINC02040854 | 12 | -5.85 | 2 | 6.78 | 150 | -9.61 |
| AR_025 | 122621 | 89 | -5.84 | 39 | 5.25 | 50 | -16.17 |
| AR_026 | ZINC00518738 | 74 | -5.80 | 143 | 3.86 | 85 | -14.45 |
| AR_027 | 6910218_1 | 114 | -5.78 | 123 | 4.02 | 15 | -19.00 |
| AR_028 | ZINC01827766 | 58 | -5.77 | 55 | 4.99 | 143 | -11.42 |
| AR_029 | ZINC00058791 | 64 | -5.71 | 148 | 3.82 | 34 | -17.17 |
| AR_030 | ZINC00902215 | 79 | -5.70 | 44 | 5.16 | 99 | -14.09 |
| AR_031 | ZINC01827765 | 29 | -5.69 | 84 | 4.46 | 142 | -12.15 |
| AR_032 | 134478 | 17 | -5.69 | 7 | 6.59 | 126 | -13.10 |
| AR_033 | ZINC02566273 | 125 | -5.69 | 21 | 5.74 | 82 | -14.62 |
| AR_034 | 5790116_1 | 70 | -5.63 | 146 | 3.85 | 81 | -14.66 |
| AR_035 | ZINC00402807 | 91 | -5.61 | 98 | 5.27 | 60 | -15.87 |
| AR_036 | ZINC02522644 | 51 | -5.60 | 62 | 4.81 | 115 | -13.52 |
| AR_037 | 5131602_1 | 63 | -5.59 | 52 | 5.04 | 40 | -16.81 |
| AR_038 | ZINC02450093 | 25 | -5.59 | 83 | 4.39 | 109 | -13.68 |
| AR_039 | ZINC00895334 | 99 | -5.59 | 34 | 5.37 | 7 | -21.71 |
| AR_040 | ZINC00152602 | 38 | -5.57 | 75 | 4.61 | 53 | -16.06 |
| AR_041 | ZINC00401167 | 47 | -5.55 | 66 | 4.79 | 119 | -13.35 |
| AR_042 | ZINC02040855 | 143 | -5.52 | 15 | 5.94 | 97 | -14.10 |
| AR_043 | ZINC00317204 | 68 | -5.46 | 146 | 3.83 | 136 | -12.72 |

FIG. 22 (cont.)

| ID | ZINC/Ref | Col3 | Col4 | Col5 | Col6 | Col7 |
|---|---|---|---|---|---|---|
| AR_044 | ZINC02575475 | 137 | -5.45 | 17 | 5.90 | -17.68 |
| AR_045 | ZINC00392006 | 19 | -5.40 | 9 | 6.34 | -14.30 |
| AR_046 | 1500137 | 53 | -5.39 | 60 | 4.85 | -18.13 |
| AR_047 | 41355 | 26 | -5.38 | 87 | 4.41 | -15.53 |
| AR_048 | 5141477 | 59 | -5.37 | 54 | 5.00 | -13.30 |
| AR_049 | ZINC00143501 | 110 | -5.30 | 125 | 4.00 | -14.68 |
| AR_050 | ZINC02545129 | 85 | -5.29 | 41 | 5.19 | -16.39 |
| AR_051 | ZINC00524386 | 144 | -5.26 | 88 | 4.28 | -18.38 |
| AR_052 | ZINC02458678 | 136 | -5.19 | 114 | 4.09 | -12.44 |
| AR_053 | ZINC02105896 | 11 | -5.15 | 1 | 7.96 | -15.77 |
| AR_054 | 5483658 | 139 | -5.09 | 113 | 4.10 | -13.02 |
| AR_055 | ZINC00968043 | 113 | -5.09 | 27 | 5.54 | -15.88 |
| AR_056 | ZINC00140411 | 94 | -5.06 | 130 | 3.96 | -19.23 |
| AR_057 | ZINC00366295 | 6 | -5.05 | 94 | 4.31 | -13.17 |
| AR_058 | ZINC00093281 | 75 | -5.03 | 48 | 5.12 | -20.75 |
| AR_059 | ZINC00075602 | 149 | -5.02 | 100 | 4.24 | -16.98 |
| AR_060 | 350191 | 97 | -5.02 | 85 | 5.35 | -14.70 |
| AR_061 | ZINC00402806 | 37 | -5.01 | 78 | 4.60 | -17.09 |
| AR_062 | 6366304 | 32 | -4.99 | 81 | 4.51 | -23.57 |
| AR_063 | ZINC00119457 | 14 | -4.95 | 4 | 6.72 | -20.38 |
| AR_064 | 6091005 | 61 | -4.90 | 53 | 5.04 | -17.14 |
| AR_065 | 5266104 | 82 | -4.88 | 138 | 3.89 | -13.85 |
| AR_066 | ZINC00354972 | 138 | -4.88 | 100 | 4.19 | -16.68 |
| AR_067 | (4-Hydroxy-1,1-dioxo-tetrahydro-1lambda*6*-thiophen-3-ylamino)-acetic acid | 52 | -4.88 | 61 | 4.83 | -11.20 |
| AR_068 | ZINC00970164 | 86 | -4.74 | 107 | 3.91 | -14.94 |
| AR_069 | ZINC02166236 | 49 | -4.73 | 84 | 4.80 | -12.50 |
| AR_070 | 163326 | 87 | -4.73 | 49 | 5.21 | -16.46 |
| AR_071 | 6318933 | 84 | -4.71 | 138 | 3.91 | -13.46 |
| AR_072 | ZINC00161424 | 92 | -4.70 | 134 | 3.94 | -19.94 |
| AR_073 | ZINC02015035 | 119 | -4.70 | 24 | 5.68 | -15.88 |
| AR_074 | 5258649 | 27 | -4.69 | 88 | 4.42 | -14.46 |
| AR_075 | ZINC00188127 | 95 | -4.69 | 36 | 5.35 | -17.77 |
| AR_076 | 5-Guanidino-2-[(5-oxo-pyrrolidine-2-carbonyl)-amino]-pentanoic acid | 13 | -4.67 | 3 | 6.73 | -24.43 |
| AR_077 | 5738812 | 135 | -4.67 | 108 | 4.19 | -17.28 |
| AR_078 | ZINC00161426 | 127 | -4.65 | 117 | 4.07 | -16.22 |
| AR_079 | ZINC00170344 | 122 | -4.65 | 119 | 4.05 | -14.15 |
| AR_080 | 16335 | 131 | -4.64 | 19 | 5.81 | -15.07 |
| AR_081 | ZINC02140959 | 93 | -4.64 | 37 | 5.31 | -14.81 |
| AR_082 | 5260802 | 78 | -4.62 | 141 | 3.88 | -17.39 |
| AR_083 | ZINC00582079 | 118 | -4.62 | 121 | 4.03 | -14.72 |
| AR_084 | ZINC00226226 | 145 | -4.60 | 101 | 4.23 | -14.57 |
| AR_085 | 5233960 | 81 | -4.57 | 43 | 5.17 | -14.84 |
| AR_086 | 5780308 | 103 | -4.53 | 115 | 4.09 | -17.16 |
| AR_087 | ZINC02111574 | 140 | -4.53 | 18 | 5.91 | -14.92 |
| AR_088 | ZINC02385763 | 16 | -4.53 | 6 | 6.68 | -18.92 |

FIG. 22 (cont.)

| | | | | | | |
|---|---|---|---|---|---|---|
| AR_089 | ZINC02050000 | 148 | -4.52 | 95 | 4.29 | 14 | -19.11 |
| AR_090 | ZINC02262056 | 33 | -4.51 | 80 | 4.52 | 141 | -12.27 |
| AR_091 | ZINC00034160 | 56 | -4.49 | 57 | 4.91 | 91 | -14.26 |
| AR_092 | 1503938 | 115 | -4.49 | 28 | 5.60 | 127 | -13.02 |
| AR_093 | ZINC00157995 | 120 | -4.49 | 129 | 4.05 | 24 | -17.91 |
| AR_094 | 1502155 | 22 | -4.48 | 12 | 6.18 | 1 | -28.37 |
| AR_095 | ZINC00156508 | 99 | -4.46 | 135 | 3.92 | 22 | -18.10 |
| AR_096 | 5626437 | 8 | -4.41 | 109 | 4.15 | 65 | -15.66 |
| AR_097 | ZINC00039035 | 20 | -4.39 | 10 | 6.22 | 64 | -15.66 |
| AR_098 | ZINC00901817 | 132 | -4.38 | 105 | 4.19 | 105 | -13.89 |
| AR_099 | 14161 | 128 | -4.37 | 20 | 5.78 | 61 | -15.82 |
| AR_100 | ZINC00193719 | 124 | -4.37 | 116 | 4.07 | 48 | -16.24 |
| AR_101 | ZINC00967235 | 65 | -4.35 | 136 | 3.92 | 144 | -11.36 |
| AR_102 | ZINC02216764 | 73 | -4.35 | 47 | 5.12 | 19 | -18.26 |
| AR_103 | ZINC00035764 | 116 | -4.33 | 122 | 4.03 | 87 | -14.38 |
| AR_104 | ZINC00612242 | 95 | -4.31 | 132 | 3.97 | 57 | -15.89 |
| AR_105 | ZINC00967233 | 108 | -4.30 | 128 | 4.00 | 52 | -16.13 |
| AR_106 | ZINC00154988 | 62 | -4.26 | 149 | 3.81 | 110 | -13.67 |
| AR_107 | 3-(1,1-Dioxo-tetrahydro-1lambda*6*-thiophen-3-ylamino)-propane-1,2-diol | 46 | -4.24 | 67 | 4.77 | 148 | -10.51 |
| AR_108 | 186915 | 134 | -4.21 | 18 | 5.84 | 51 | -16.14 |
| AR_109 | ZINC00065259 | 10 | -4.17 | 98 | 4.27 | 139 | -12.43 |
| AR_110 | ZINC00473749 | 77 | -4.17 | 45 | 5.15 | 114 | -13.55 |
| AR_111 | ZINC00000558 | 31 | -4.16 | 62 | 4.51 | 102 | -13.97 |
| AR_112 | ZINC00401915 | 30 | -4.16 | 83 | 4.47 | 56 | -15.92 |
| AR_113 | ZINC00392004 | 147 | -4.14 | 14 | 6.08 | 85 | -14.42 |
| AR_114 | ZINC00040580 | 66 | -4.13 | 147 | 3.83 | 117 | -13.37 |
| AR_115 | ZINC00967837 | 44 | -4.13 | 89 | 4.74 | 120 | -13.33 |
| AR_116 | ZINC00043862 | 45 | -4.12 | 88 | 4.77 | 135 | -12.72 |
| AR_117 | ZINC00900185 | 80 | -4.12 | 140 | 3.89 | 100 | -14.02 |
| AR_118 | ZINC00050134 | 9 | -4.10 | 93 | 4.34 | 93 | -14.22 |
| AR_119 | ZINC00001762 | 103 | -4.08 | 82 | 5.39 | 130 | -12.98 |
| AR_120 | ZINC00035767 | 130 | -4.06 | 116 | 4.09 | 147 | -10.56 |
| AR_121 | 5155819 | 150 | -4.05 | 119 | 4.12 | 96 | -14.15 |
| AR_122 | ZINC00895060 | 111 | -4.04 | 28 | 5.50 | 111 | -13.67 |
| AR_123 | ZINC00268033 | 42 | -4.03 | 71 | 4.71 | 69 | -15.29 |
| AR_124 | ZINC00092200 | 41 | -4.02 | 72 | 4.67 | 118 | -13.35 |
| AR_125 | ZINC00376788 | 102 | -4.00 | 129 | 3.98 | 55 | -15.93 |
| AR_126 | ZINC00164358 | 112 | -3.99 | 124 | 4.01 | 28 | -17.63 |
| AR_127 | ZINC01584114 | 15 | -3.98 | 5 | 6.71 | 62 | -15.82 |
| AR_128 | ZINC00899004 | 76 | -3.97 | 142 | 3.87 | 134 | -12.75 |
| AR_129 | 136035 | 18 | -3.97 | 8 | 6.36 | 72 | -15.07 |
| AR_130 | ZINC00156821 | 100 | -3.96 | 130 | 3.98 | 67 | -15.49 |
| AR_131 | ZINC00192456 | 55 | -3.94 | 68 | 4.88 | 113 | -13.57 |
| AR_132 | ZINC00226260 | 49 | -3.94 | 70 | 4.74 | 11 | -20.13 |
| AR_133 | ZINC01669687 | 7 | -3.94 | 89 | 4.25 | 122 | -13.27 |

FIG. 22 (cont.)

| | | | | | | |
|---|---|---|---|---|---|---|
| AR_134 | ZINC02584441 | | 105 | -3.94 | 31 | 5.41 | 70 | -15.10 |
| AR_135 | ZINC00388969 | | 23 | -3.94 | 80 | 4.36 | 149 | -10.01 |
| AR_136 | ZINC00169710 | | 106 | -3.93 | 127 | 3.99 | 47 | -16.28 |
| AR_137 | 4-(3-Methoxy-propylamino)-1,1-dioxo-tetrahydro-1lambda*6*-thiophen-3-ol | 109 | -3.92 | 29 | 5.46 | 132 | -12.79 |
| AR_138 | ZINC00051582 | | 24 | -3.91 | 89 | 4.39 | 145 | -11.33 |
| AR_139 | ZINC00392420 | | 69 | -3.91 | 49 | 5.08 | 54 | -16.06 |
| AR_140 | ZINC00488339 | | 146 | -3.91 | 111 | 4.12 | 133 | -12.75 |
| AR_141 | 664900 | | 35 | -3.90 | 78 | 4.55 | 108 | -13.80 |
| AR_142 | ZINC00407921 | | 123 | -3.89 | 22 | 5.74 | 98 | -14.10 |
| AR_143 | ZINC00156841 | | 65 | -3.88 | 51 | 5.05 | 107 | -13.84 |
| AR_144 | ZINC00358668 | | 141 | -3.81 | 102 | 4.23 | 32 | -17.30 |
| AR_145 | ZINC02257536 | | 28 | -3.81 | 85 | 4.46 | 94 | -14.18 |
| AR_146 | ZINC00154204 | | 129 | -3.81 | 106 | 4.18 | 68 | -15.40 |
| AR_147 | ZINC00006220 | | 60 | -3.80 | 150 | 3.35 | 104 | -13.93 |
| AR_148 | ZINC00156565 | | 142 | -3.80 | 112 | 4.11 | 16 | -18.96 |
| AR_149 | ZINC00057542 | | 48 | -3.76 | 65 | 4.80 | 125 | -13.13 |
| AR_150 | ZINC00322432 | | 36 | -3.67 | 77 | 4.59 | 88 | -14.36 |

SEQUENCE LISTING

<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcagtgaaaa gggggtgtgt caggatgc                                    28

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcatcctgac acacccctt ttcactgc                                     28

USE OF SMALL MOLECULE INHIBITORS TO KLF10 FOR MODULATION OF T REGULATORY CELLS AND CANCER IMMUNOTHERAPY

CROSS-REFERENCE TO RELATED APPLICATION

This application claims the benefit under 35 U.S.C. § 119(e) of U.S. Provisional Patent Application No. 62/247,431 filed on Oct. 28, 2015, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 19, 2016, is named 043214-088281_SL.TXT and is 832 bytes in size.

TECHNICAL FIELD

The invention relates to compositions and methods for inhibiting Krüppel-like Factor 10 (KLF10) for modulation of T regulatory cells and cancer immunotherapy.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Zinc fingers (ZFs) are the most ubiquitous family of transcription factors (TFs) with more than 1000 members, comprising ~1% of the human genome.[1] The Krüppel-like family of transcription factors (KLFs), so named for their homology to the *Drosophila melanogaster* Krüppel protein, is a $C_2H_2$-type zinc finger (containing 2 cysteine and 2 histidine residues) with a simple structure consisting of 25-30 amino acid residues that includes two β-pleated sheets in the amino terminal half and an α-helix in the carboxyl terminal half, held together at the base by a zinc ($Zn^{+2}$) ion.[2-4] The ZFTFs are responsible for interacting with either a CACCC-element or GC-rich sites in the promoter region of target genes, thereby regulating transcriptional activity and gene expression.[5] These DNA binding proteins are requisite components of the transcriptional machinery involved in mediating cellular phenotypic responses to extracellular signals. The KLF family currently includes 18 members, namely KLF 1-18 with distinct cell-type expression patterns.[6] Furthermore, KLFs participate in various functional aspects of cell growth and differentiation, activation, or development. As such, therapeutic targeting of select KLF family members may be desirable for achieving distinct biological effects.

CD4+CD25+ T regulatory cells (T regs) actively participate in the maintenance of self-tolerance and immune suppression and constitute a significant obstacle for effective tumor immunosurveillance, vaccine-induced anti-tumor immune responses, and clearance of bacterial pathogens.[7-11] KLF10 deficiency (inhibiting KLF10) has been shown to result in impaired T reg (CD4+ CD25%) cell differentiation and susceptibility to colitis. Inhibiting KLF10 transcriptional activity is useful to reduce T reg cell numbers and function in disease such as enhanced antitumor immunity. T cells can also be inhibited by T regulatory cells (Schwartz, R. Nature Immunology, 6:327-330 (2005)). T regs have been shown to suppress tumor-specific T cell immunity, and may contribute to the progression of human tumors (Liyanage, U. K., et al., J. Immunol. 169:2756-2761 (2002)). In mice, depletion of T reg cells leads to more efficient tumor rejection (Viehl, C. T., et al., Ann. Surg. Oncol. 13:1252-1258 (2006)).

We and others have previously demonstrated that KLF10, a transforming growth factor β1 (TGF-β1)-responsive transcription factor, is a critical regulator of T reg cell differentiation and function in vitro and in vivo.[12, 13] KLF10−/− mice exhibit reduced peripheral T reg cells with reduced expression of Foxp3, a hallmark of T reg cell differentiation. Indeed, KLF10 mediates this effect, in part, by binding to the proximal CACCC sites of the Foxp3 and TGF-β1 promoters. These observations raise the possibility that KLF10 may be an excellent therapeutic target for a range of disease states in which reduced T reg cell numbers or function would be advantageous such as enhanced anti-tumor immunity.[7-11]

Currently, there is no clinically available treatment that specifically targets T reg cells using a small drug-like molecule. Herein, we report computational discovery of small molecule inhibitors of the KLF10-DNA interaction interface, an effect that reduced KLF10-DNA binding and transcriptional activity. Furthermore, we also report an investigation into the effects of our inhibitor compounds on the conversion of CD4+CD25− T cells to CD4+CD25+ T regs and FoxP3 expression. Overall, our findings support the feasibility of using computer-aided drug design (CADD) with functional assays to identify small molecules that target members of the KLF subfamily of transcription factors to regulate biological functions.

As such, there still exists a great need for compositions, methods, and kits that provide a clinical treatment the specifically targets T reg cells using small drug-like molecules.

SUMMARY

The following embodiments and aspects thereof are described and illustrated in conjunction with systems, compositions and methods which are meant to be exemplary and illustrative, not limiting in scope.

Herein, we report computational discovery of small molecule inhibitors of the KLF10-DNA interaction interface, an effect that reduced KLF10-DNA binding and transcriptional activity. Furthermore, we also report an investigation into the effects of our inhibitor compounds on the conversion of CD4+CD25− T cells to CD4+CD25+ T regs and FoxP3 expression. Overall, our findings support the feasibility of using computer-aided drug design (CADD) with functional assays to identify small molecules that target members of the KLF subfamily of transcription factors to regulate biological functions. In addition, it is an object of the invention to provide an immunomodulatory composition of a KLF10 inhibitor and enhance immune responses.

Various embodiments of the present invention provide a compound selected from:

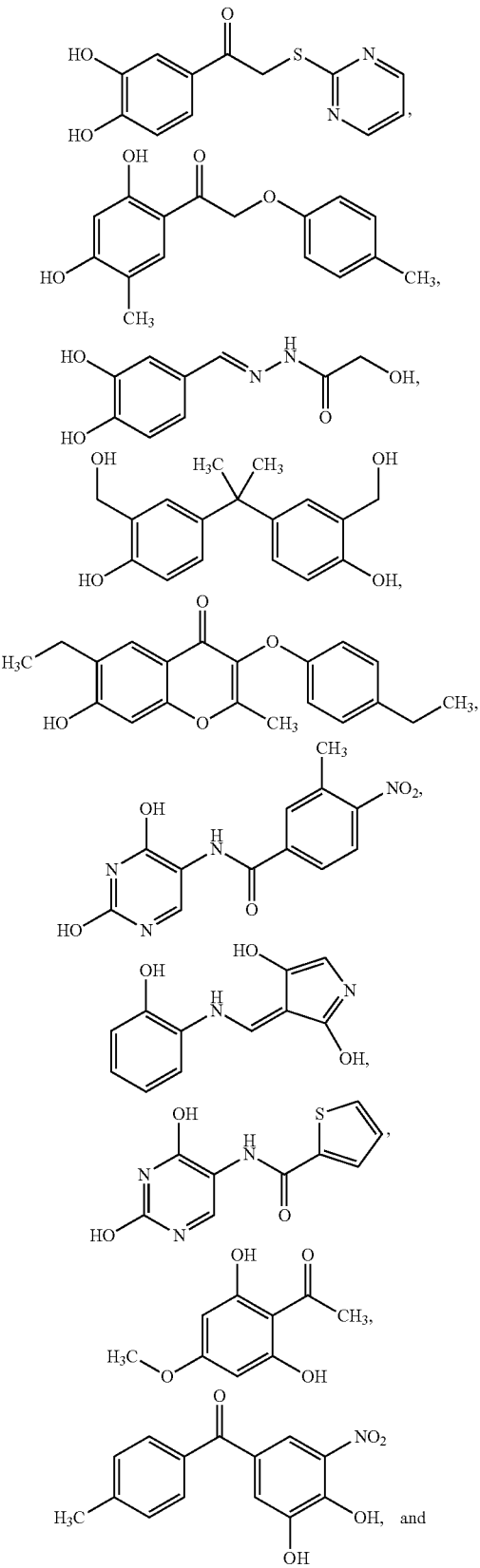

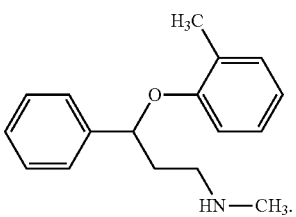

Various embodiments of the present invention provide a compound of formula:

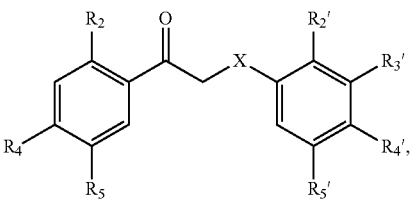

wherein,
R$_2$ is selected from H, OH, CH$_3$, and OCH$_3$;
R$_4$ is selected from H, OH, and OCH$_3$;
R$_5$ is selected from H, CH$_3$, and C$_2$H$_5$;
X is selected from H, O, and OC(=O);
R$_2$' is selected from H and OH;
R$_3$' is selected from H, OCH$_3$, and CH=CH—CH=CH;
R$_4$' is selected from H, CH$_3$, C$_2$H$_5$, CH(CH$_3$)$_2$, OCH$_3$, Ph, F, I, and CH=CH—CH=CH; and
R$_5$' is selected from H, CH$_3$, and OCH$_3$, wherein two or more of R$_2$, R$_4$, R$_5$ may be optionally connected, and two or more of R$_2$', R$_3$', R$_4$' R$_5$' may be optionally connected.

Various embodiments of the present invention provide a compound of formula:

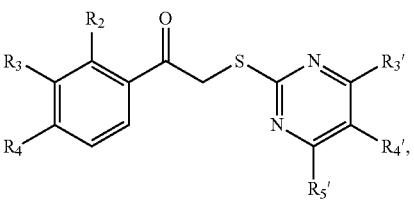

wherein,
R$_2$ is selected from H, OH, and OCH$_3$;
R$_3$ is selected from H, OH, OCH$_3$, and COOCH$_3$;
R$_4$ is selected from H, OH, and CH$_3$;
R$_3$' is selected from H, CH$_3$, CH=CH—CH=CH, and S—C(—CH$_3$)=C(—CH$_3$);
R$_4$' is selected from H and OH; and
R$_5$' is selected from H, OH, and CH$_3$, wherein two or more of R$_2$, R$_3$, R$_4$ may be optionally connected, and two or more of R$_3$', R$_4$' R$_5$' may be optionally connected.

Various embodiments of the present invention provide a compound selected from:

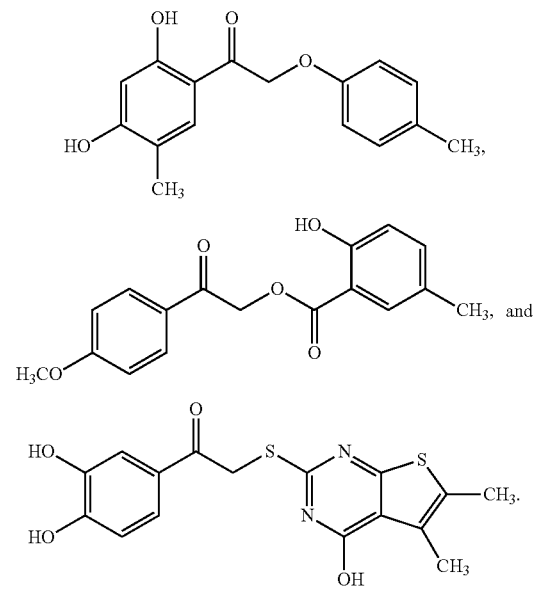

Various embodiments of the present invention provide a method of modulating an immune response, comprising: administering to a subject an effective amount of an inhibitor of KLF10, wherein the inhibitor of KLF10 is a compound selected from:

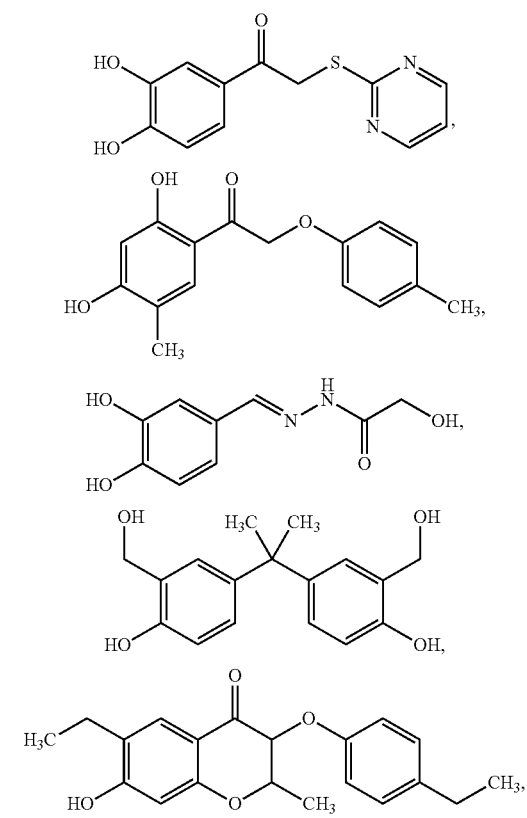

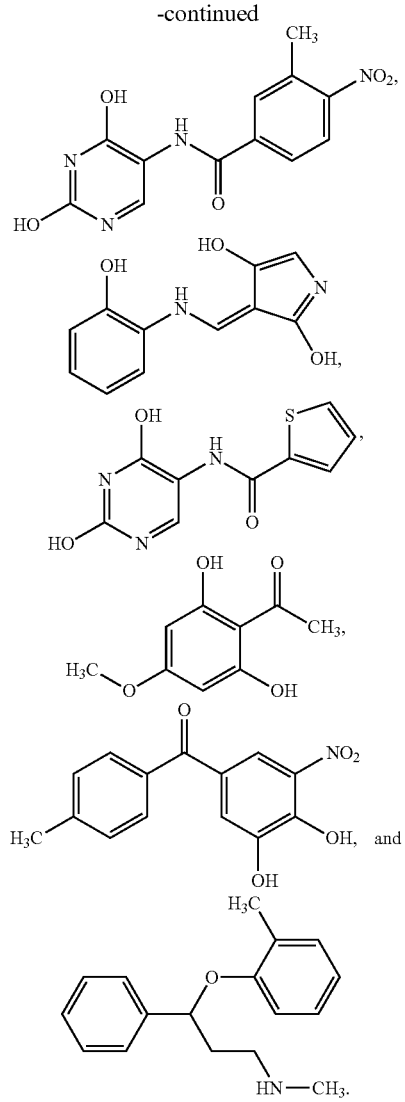

In some embodiments, inhibiting KLF10 decreases T regulatory (T reg) cells at a tumor site or a pathogen infected area of the subject. In some embodiments, the T reg cells are CD4+/CD25+ T reg cells or CD4+/CD25+/Fox3p+ T reg cells. In some embodiments, the infection is a chronic viral infection, a bacterial infection, a fungal infection, a mycoplasm infection, a parasitic infection, elicits disease mediated by a toxin during the acute phase of infection or where the infection is characterized by reduced T cell response. In some embodiments, the viral infection is an infection with a hepatitis virus, a human immunodeficiency virus, a human T-lymphotrophic virus, a herpes virus, an Epstein-Barr virus, filovirus, a human papilloma virus, an Epstein Barr virus, an influenza virus, a respiratory synticial virus, an encephalitis virus, a dengue fever virus, and a papilloma virus. In some embodiments, the parasitic infection is malaria or *Leishmania*. In some embodiments, the bacterial infection is caused by a bacterium selected from the group consisting of *Mycobacterium tuberculosis, Bacillus anthracis, Staphylococcus, Listeria*, and *Clamydia trachomatis*. In some embodiments, the method further comprises administering with the inhibitor of KLF10 an additional active agent selected from the group consisting of immunomodulators, agents that deplete or inhibit the function of T regs, and costimulatory molecules. In some embodiments, the method further comprises administering a disease antigen in combination with the immunomodulatory agent to enhance an immune response against the disease. In some embodiments, the tumor is selected from the group consisting of sarcoma, melanoma, lymphoma, neuroblastoma, and carcinoma.

Various embodiments of the present invention provide a method of modulating an immune response, comprising: administering to a subject an effective amount of an inhibitor of KLF10, wherein the inhibitor of KLF10 is a compound of formula:

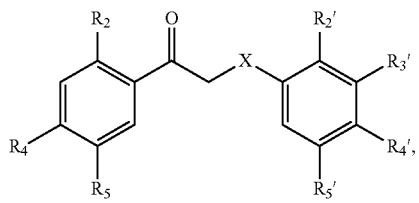

wherein,
$R_2$ is selected from H, OH, $CH_3$, and $OCH_3$;
$R_4$ is selected from H, OH, and $OCH_3$;
$R_5$ is selected from H, $CH_3$, and $C_2H_5$;
X is selected from H, O, and OC(=O);
$R_2'$ is selected from H and OH;
$R_3'$ is selected from H, $OCH_3$, and CH=CH—CH=CH;
$R_4'$ is selected from H, $CH_3$, $C_2H_5$, $CH(CH_3)_2$, $OCH_3$, Ph, F, I, and CH=CH—CH=CH; and
$R_5'$ is selected from H, $CH_3$, and $OCH_3$, wherein two or more of $R_2$, $R_4$, $R_5$ may be optionally connected, and two or more of $R_2'$, $R_3'$, $R_4'$ $R_5'$ may be optionally connected. In some embodiments, inhibiting KLF10 decreases T regulatory (T reg) cells at a tumor site or a pathogen infected area of the subject. In some embodiments, the T reg cells are CD4+/CD25+ T reg cells or CD4+/CD25+/Fox3p+ T reg cells. In some embodiments, the infection is a chronic viral infection, a bacterial infection, a fungal infection, a mycoplasm infection, a parasitic infection, elicits disease mediated by a toxin during the acute phase of infection or where the infection is characterized by reduced T cell response. In some embodiments, the viral infection is an infection with a hepatitis virus, a human immunodeficiency virus, a human T-lymphotrophic virus, a herpes virus, an Epstein-Barr virus, filovirus, a human papilloma virus, an Epstein Barr virus, an influenza virus, a respiratory syntical virus, an encephalitis virus, a dengue fever virus, and a papilloma virus. In some embodiments, the parasitic infection is malaria or *Leishmania*. In some embodiments, the bacterial infection is caused by a bacterium selected from the group consisting of *Mycobacterium tuberculosis, Bacillus anthracis, Staphylococcus, Listeria*, and *Clamydia trachomatis*. In some embodiments, the method further comprises administering with the inhibitor of KLF10 an additional active agent selected from the group consisting of immunomodulators, agents that deplete or inhibit the function of T regs, and costimulatory molecules. In some embodiments, the method further comprises administering a disease antigen in combination with the immunomodulatory agent to enhance an immune response against the disease. In some embodiments, the tumor is selected from the group consisting of sarcoma, melanoma, lymphoma, neuroblastoma, and carcinoma.

Various embodiments of the present invention provide a method of modulating an immune response, comprising: administering to a subject an effective amount of an inhibitor of KLF10, wherein the inhibitor of KLF10 is a compound of formula:

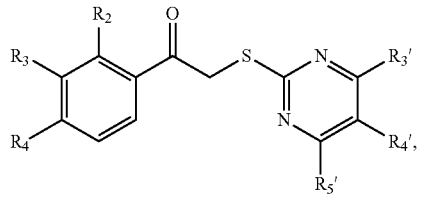

wherein,
$R_2$ is selected from H, OH, and $OCH_3$;
$R_3$ is selected from H, OH, $OCH_3$, and $COOCH_3$;
$R_4$ is selected from H, OH, and $CH_3$;
$R_3'$ is selected from H, $CH_3$, CH=CH—CH=CH, and S—C(—$CH_3$)=C(—$CH_3$);
$R_4'$ is selected from H and OH; and
$R_5'$ is selected from H, OH, and $CH_3$, wherein two or more of $R_2$, $R_3$, $R_4$ may be optionally connected, and two or more of $R_3'$, $R_4'$ $R_5'$ may be optionally connected. In some embodiments, inhibiting KLF10 decreases T regulatory (T reg) cells at a tumor site or a pathogen infected area of the subject. In some embodiments, the T reg cells are CD4+/CD25+ T reg cells or CD4+/CD25+/Fox3p+ T reg cells. In some embodiments, the infection is a chronic viral infection, a bacterial infection, a fungal infection, a mycoplasm infection, a parasitic infection, elicits disease mediated by a toxin during the acute phase of infection or where the infection is characterized by reduced T cell response. In some embodiments, the viral infection is an infection with a hepatitis virus, a human immunodeficiency virus, a human T-lymphotrophic virus, a herpes virus, an Epstein-Barr virus, filovirus, a human papilloma virus, an Epstein Barr virus, an influenza virus, a respiratory syntical virus, an encephalitis virus, a dengue fever virus, and a papilloma virus. In some embodiments, the parasitic infection is malaria or *Leishmania*. In some embodiments, the bacterial infection is caused by a bacterium selected from the group consisting of *Mycobacterium tuberculosis, Bacillus anthracis, Staphylococcus, Listeria*, and *Clamydia trachomatis*. In some embodiments, the method further comprises administering with the inhibitor of KLF10 an additional active agent selected from the group consisting of immunomodulators, agents that deplete or inhibit the function of T regs, and costimulatory molecules. In some embodiments, the method further comprises administering a disease antigen in combination with the immunomodulatory agent to enhance an immune response against the disease. In some embodiments, the tumor is selected from the group consisting of sarcoma, melanoma, lymphoma, neuroblastoma, and carcinoma.

Various embodiments of the present invention provide a method of modulating an immune response, comprising: administering to a subject an effective amount of an inhibitor of KLF10, wherein the inhibitor of KLF10 is a compound selected from:

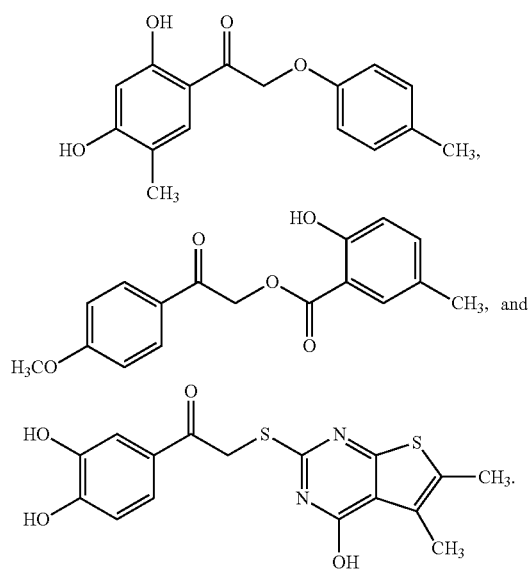

In some embodiments, inhibiting KLF10 decreases T regulatory (T reg) cells at a tumor site or a pathogen infected area of the subject. In some embodiments, the T reg cells are CD4+/CD25+ T reg cells or CD4+/CD25+/Fox3p+ T reg cells. In some embodiments, the infection is a chronic viral infection, a bacterial infection, a fungal infection, a mycoplasm infection, a parasitic infection, elicits disease mediated by a toxin during the acute phase of infection or where the infection is characterized by reduced T cell response. In some embodiments, the viral infection is an infection with a hepatitis virus, a human immunodeficiency virus, a human T-lymphotrophic virus, a herpes virus, an Epstein-Barr virus, filovirus, a human papilloma virus, an Epstein Barr virus, an influenza virus, a respiratory synticial virus, an encephalitis virus, a dengue fever virus, and a papilloma virus. In some embodiments, the parasitic infection is malaria or *Leishmania*. In some embodiments, the bacterial infection is caused by a bacterium selected from the group consisting of *Mycobacterium tuberculosis, Bacillus anthracis, Staphylococcus, Listeria*, and *Clamydia trachomatis*. In some embodiments, the method further comprises administering with the inhibitor of KLF10 an additional active agent selected from the group consisting of immunomodulators, agents that deplete or inhibit the function of T regs, and costimulatory molecules. In some embodiments, the method further comprises administering a disease antigen in combination with the immunomodulatory agent to enhance an immune response against the disease. In some embodiments, the tumor is selected from the group consisting of sarcoma, melanoma, lymphoma, neuroblastoma, and carcinoma.

Various embodiments of the present invention provide a composition, comprising: an effective amount of an inhibitor of KLF10 to decrease T regulatory (T reg) cells at a tumor site or a pathogen infected area of a subject, wherein the inhibitor of KLF10 is a compound selected from:

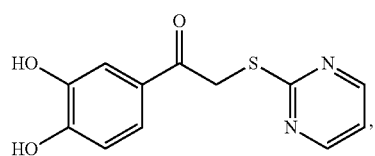

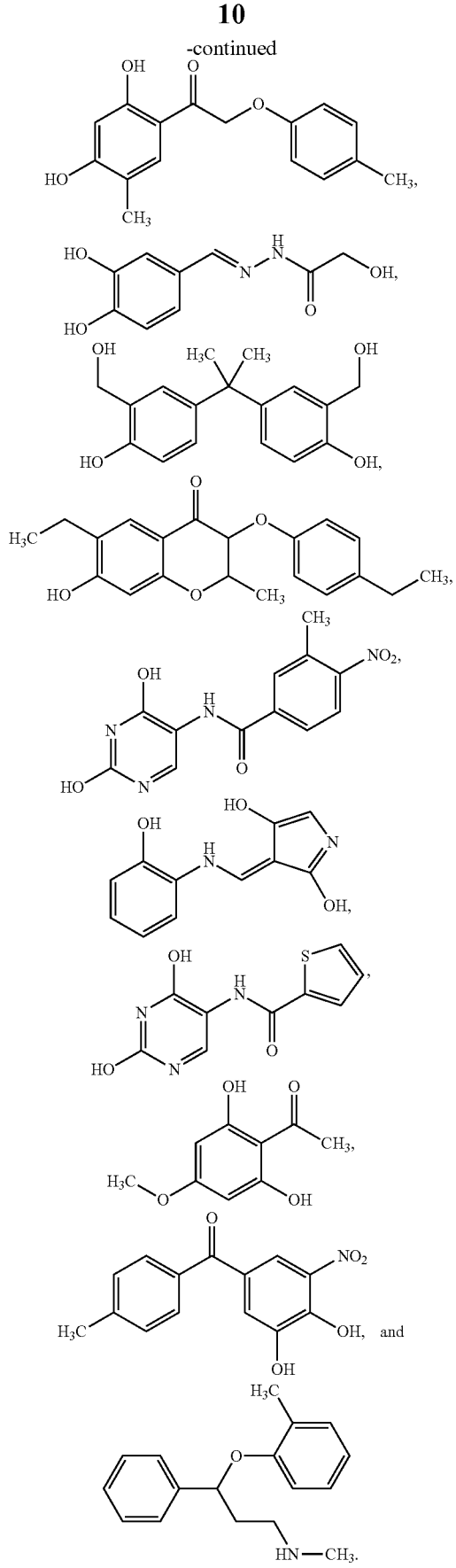

Various embodiments of the present invention provide a composition, comprising: an effective amount of an inhibitor of KLF10 to decrease T regulatory (T reg) cells at a tumor site or a pathogen infected area of a subject, wherein the inhibitor of KLF10 is a compound of formula:

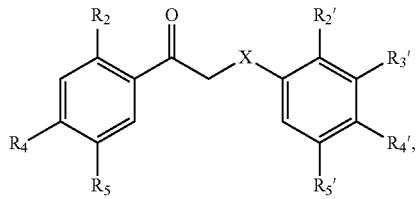

wherein, $R_2$ is selected from H, OH, CH$_3$, and OCH$_3$;

$R_4$ is selected from H, OH, and OCH$_3$;

$R_5$ is selected from H, CH$_3$, and C$_2$H$_5$;

X is selected from H, O, and OC(=O);

$R_2'$ is selected from H and OH;

$R_3'$ is selected from H, OCH$_3$, and CH=CH—CH=CH;

$R_4'$ is selected from H, CH$_3$, C$_2$H$_5$, CH(CH$_3$)$_2$, OCH$_3$, Ph, F, I, and CH=CH—CH=CH; and $R_5'$ is selected from H, CH$_3$, and OCH$_3$, wherein two or more of $R_2$, $R_4$, $R_5$ may be optionally connected, and two or more of $R_2'$, $R_3'$, $R_4'$ $R_5'$ may be optionally connected.

Various embodiments of the present invention provide a composition, comprising: an effective amount of an inhibitor of KLF10 to decrease T regulatory (T reg) cells at a tumor site or a pathogen infected area of a subject, wherein the inhibitor of KLF10 is a compound of formula:

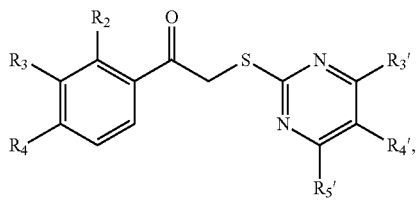

wherein, $R_2$ is selected from H, OH, and OCH$_3$;

$R_3$ is selected from H, OH, OCH$_3$, and COOCH$_3$;

$R_4$ is selected from H, OH, and CH$_3$;

$R_3'$ is selected from H, CH$_3$, CH=CH—CH=CH, and S—C(—CH$_3$)=C(—CH$_3$);

$R_4'$ is selected from H and OH; and $R_5'$ is selected from H, OH, and CH$_3$, wherein two or more of $R_2$, $R_3$, $R_4$ may be optionally connected, and two or more of $R_3'$, $R_4'$ $R_5'$ may be optionally connected.

Various embodiments of the present invention provide a composition, comprising: an effective amount of an inhibitor of KLF10 to decrease T regulatory (T reg) cells at a tumor site or a pathogen infected area of a subject, wherein the inhibitor of KLF10 is a compound selected from:

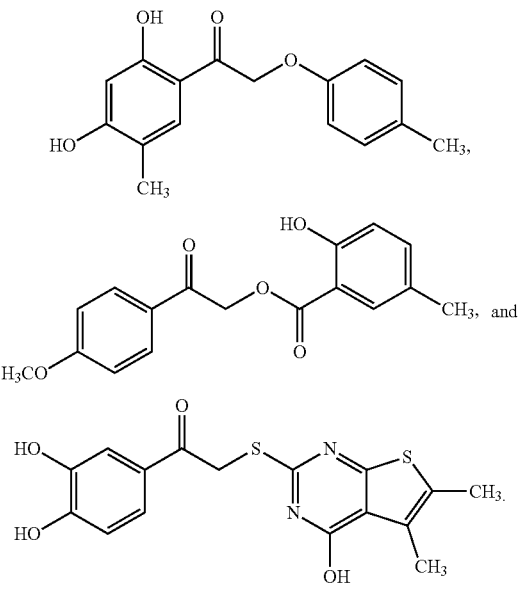

Various embodiments of the present invention provide a composition, comprising: an effective amount of an inhibitor of KLF10 to decrease T regulatory (T reg) cells at a tumor site or a pathogen infected area of a subject in combination with one or more disease antigens, wherein the inhibitor of KLF10 is a compound selected from:

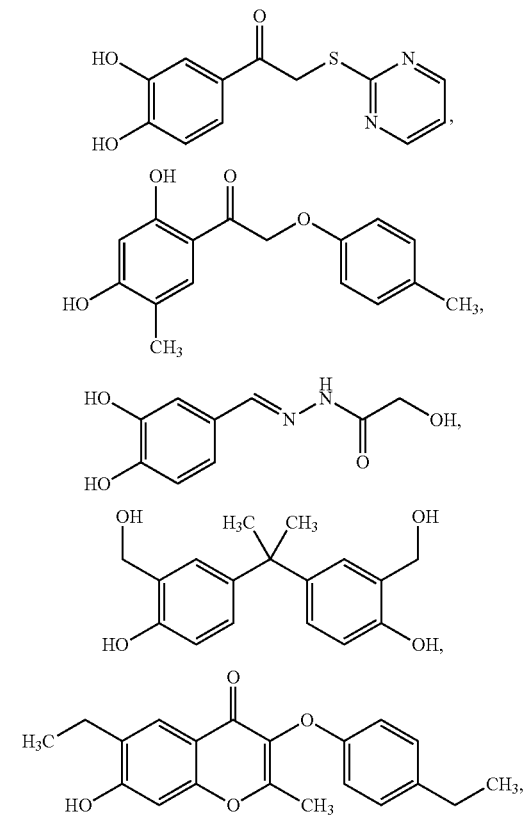

-continued

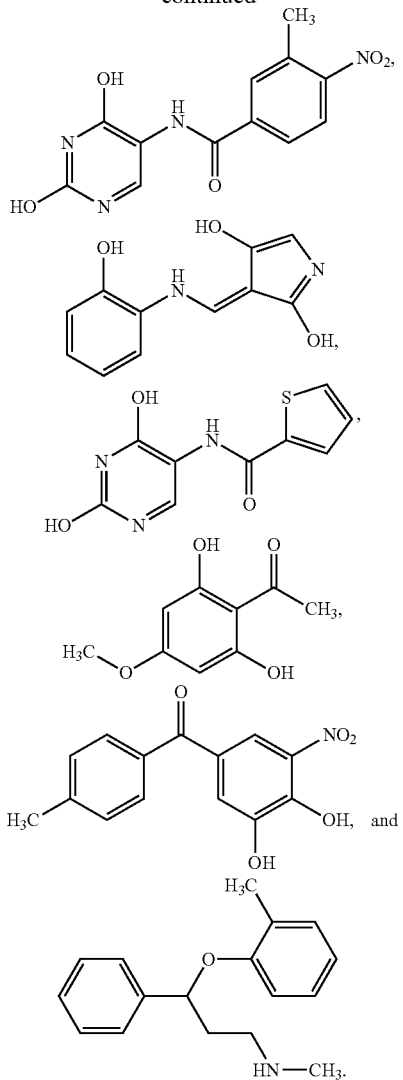

Various embodiments of the present invention provide a composition, comprising: an effective amount of an inhibitor of KLF10 to decrease T regulatory (T reg) cells at a tumor site or a pathogen infected area of a subject in combination with one or more disease antigens, wherein the inhibitor of KLF10 is a compound of formula:

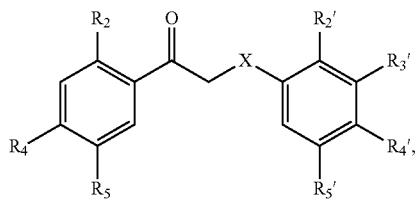

wherein,
$R_2$ is selected from H, OH, $CH_3$, and $OCH_3$;
$R_4$ is selected from H, OH, and $OCH_3$;
$R_5$ is selected from H, $CH_3$, and $C_2H_5$;
X is selected from H, O, and OC(=O);
$R_2'$ is selected from H and OH;
$R_3'$ is selected from H, $OCH_3$, and CH=CH—CH=CH;
$R_4'$ is selected from H, $CH_3$, $C_2H_5$, $CH(CH_3)_2$, $OCH_3$, Ph, F, I, and CH=CH—CH=CH; and
$R_5'$ is selected from H, $CH_3$, and $OCH_3$, wherein two or more of $R_2$, $R_4$, $R_5$ may be optionally connected, and two or more of $R_2'$, $R_3'$, $R_4'$ $R_5'$ may be optionally connected.

Various embodiments of the present invention provide a composition, comprising: an effective amount of an inhibitor of KLF10 to decrease T regulatory (T reg) cells at a tumor site or a pathogen infected area of a subject in combination with one or more disease antigens, wherein the inhibitor of KLF10 is a compound of formula:

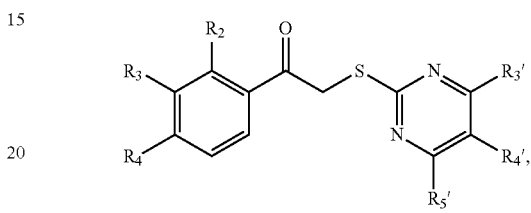

wherein,
$R_2$ is selected from H, OH, and $OCH_3$;
$R_3$ is selected from H, OH, $OCH_3$, and $COOCH_3$;
$R_4$ is selected from H, OH, and $CH_3$;
$R_3'$ is selected from H, $CH_3$, CH=CH—CH=CH, and S—C(—$CH_3$)=C(—$CH_3$);
$R_4'$ is selected from H and OH; and
$R_5'$ is selected from H, OH, and $CH_3$, wherein two or more of $R_2$, $R_3$, $R_4$ may be optionally connected, and two or more of $R_3'$, $R_4'$ $R_5'$ may be optionally connected.

Various embodiments of the present invention provide a composition, comprising: an effective amount of an inhibitor of KLF10 to decrease T regulatory (T reg) cells at a tumor site or a pathogen infected area of a subject in combination with one or more disease antigens, wherein the inhibitor of KLF10 is a compound selected from:

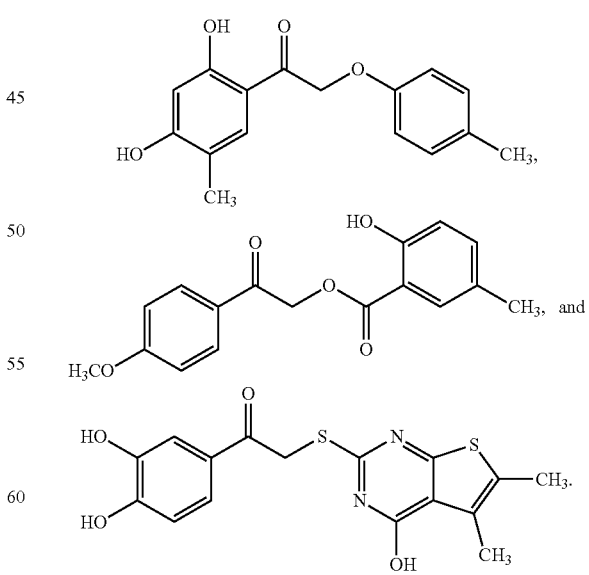

Various embodiments of the present invention provide composition, comprising: an effective amount of an inhibitor of KLF10 to decrease T regulatory (T reg) cells at a tumor site or a pathogen infected area of a subject in combination with a vaccine, wherein the inhibitor of KLF10 is a compound is selected from:

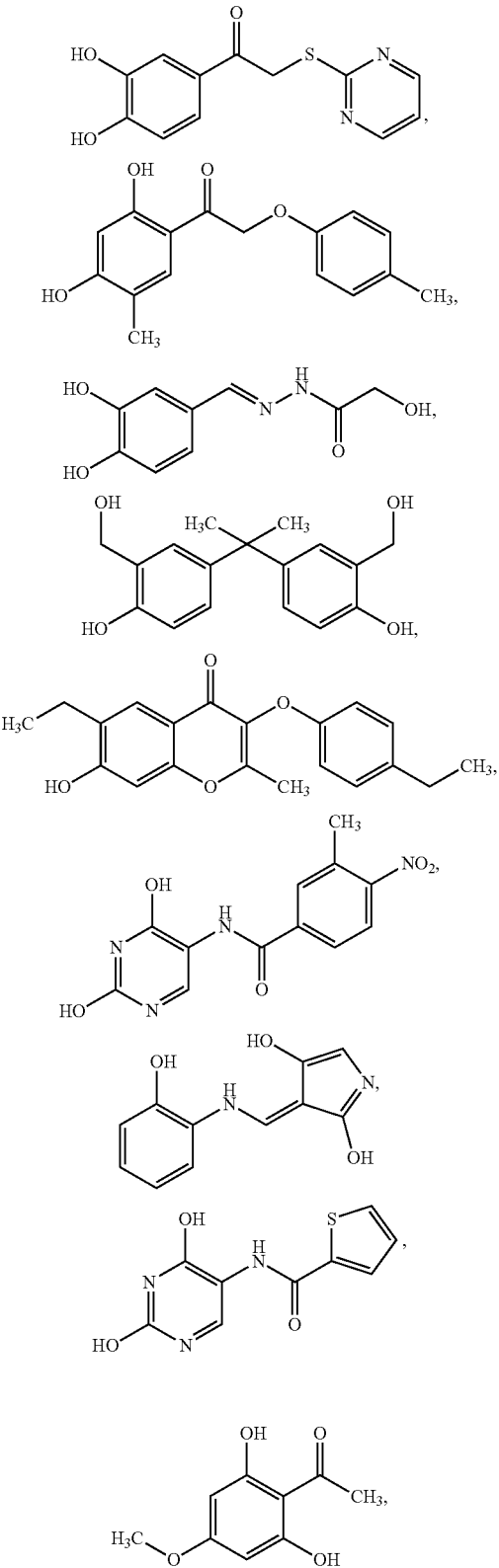

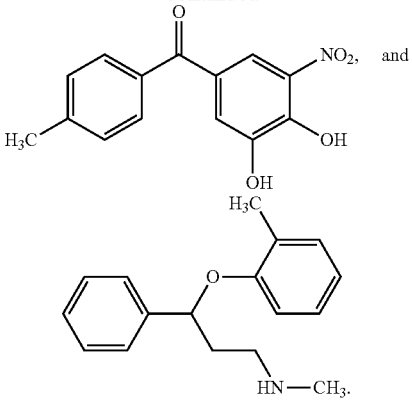

Various embodiments of the present invention provide composition, comprising: an effective amount of an inhibitor of KLF10 to decrease T regulatory (T reg) cells at a tumor site or a pathogen infected area of a subject in combination with a vaccine, wherein the inhibitor of KLF10 is a compound of formula:

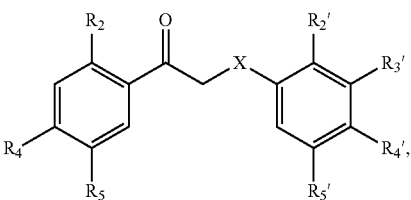

wherein,
R$_2$ is selected from H, OH, CH$_3$, and OCH$_3$;
R$_4$ is selected from H, OH, and OCH$_3$;
R$_5$ is selected from H, CH$_3$, and C$_2$H$_5$;
X is selected from H, O, and OC(=O);
R$_2$' is selected from H and OH;
R$_3$' is selected from H, OCH$_3$, and CH=CH—CH=CH;
R$_4$' is selected from H, CH$_3$, C$_2$H$_5$, CH(CH$_3$)$_2$, OCH$_3$, Ph, F, I, and CH=CH—CH=CH; and
R$_5$' is selected from H, CH$_3$, and OCH$_3$, wherein two or more of R$_2$, R$_4$, R$_5$ may be optionally connected, and two or more of R$_2$', R$_3$', R$_4$' R$_5$' may be optionally connected.

Various embodiments of the present invention provide composition, comprising: an effective amount of an inhibitor of KLF10 to decrease T regulatory (T reg) cells at a tumor site or a pathogen infected area of a subject in combination with a vaccine, wherein the inhibitor of KLF10 is a compound of formula:

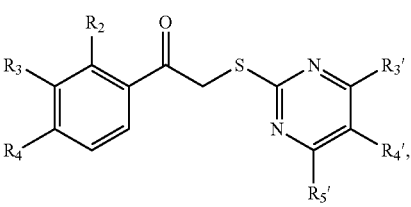

wherein,
R$_2$ is selected from H, OH, and OCH$_3$;
R$_3$ is selected from H, OH, OCH$_3$, and COOCH$_3$;

$R_4$ is selected from H, OH, and $CH_3$;

$R_3'$ is selected from H, $CH_3$, CH=CH—CH=CH, and S—C(—$CH_3$)=C(—$CH_3$);

$R_4'$ is selected from H and OH; and $R_5'$ is selected from H, OH, and $CH_3$, wherein two or more of $R_2$, $R_3$, $R_4$ may be optionally connected, and two or more of $R_3'$, $R_4'$ $R_5'$ may be optionally connected.

Various embodiments of the present invention provide composition, comprising: an effective amount of an inhibitor of KLF10 to decrease T regulatory (T reg) cells at a tumor site or a pathogen infected area of a subject in combination with a vaccine, wherein the inhibitor of KLF10 is a compound is selected from:

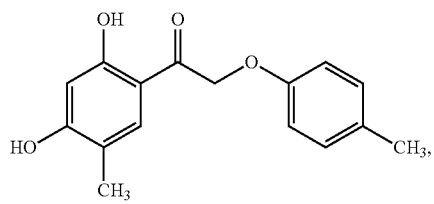

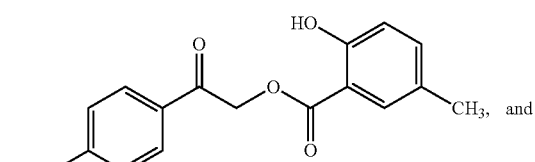

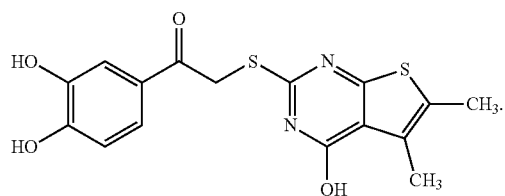

Various embodiments of the present invention provide a method for treating cancer in a subject, comprising: administering the subject a composition comprising an inhibitor of KLF10, wherein the inhibitor of KLF10 is a compound selected from:

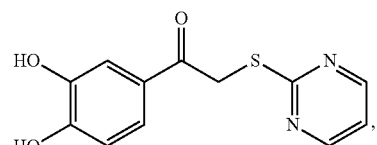

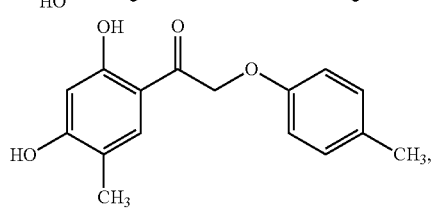

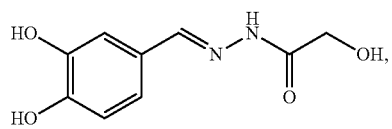

-continued

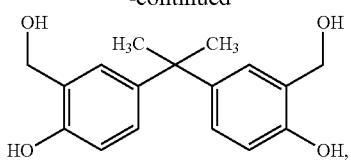

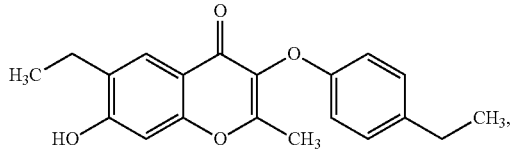

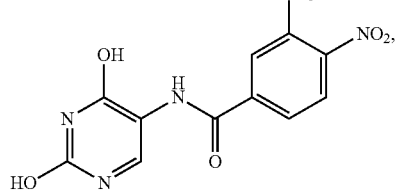

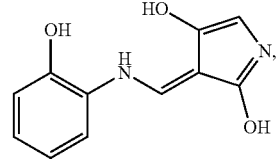

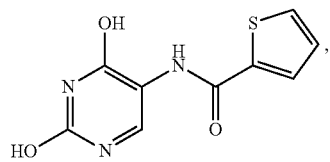

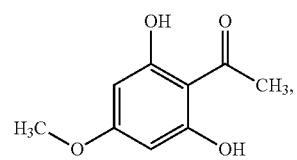

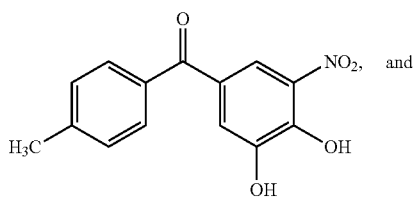

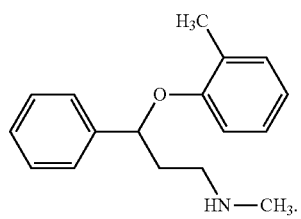

Various embodiments of the present invention provide a method for treating cancer in a subject, comprising: administering the subject a composition comprising an inhibitor of KLF10, wherein the inhibitor of KLF10 is a compound of formula:

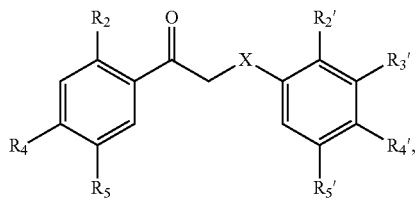

wherein,
- $R_2$ is selected from H, OH, $CH_3$, and $OCH_3$;
- $R_4$ is selected from H, OH, and $OCH_3$;
- $R_5$ is selected from H, $CH_3$, and $C_2H_5$;
- X is selected from H, O, and OC(=O);
- $R_2'$ is selected from H and OH;
- $R_3'$ is selected from H, $OCH_3$, and CH=CH—CH=CH;
- $R_4'$ is selected from H, $CH_3$, $C_2H_5$, $CH(CH_3)_2$, $OCH_3$, Ph, F, I, and CH=CH—CH=CH; and
- $R_5'$ is selected from H, $CH_3$, and $OCH_3$, wherein two or more of $R_2$, $R_4$, $R_5$ may be optionally connected, and two or more of $R_2'$, $R_3'$, $R_4'$ $R_5'$ may be optionally connected.

Various embodiments of the present invention provide a method for treating cancer in a subject, comprising: administering the subject a composition comprising an inhibitor of KLF10, wherein the inhibitor of KLF10 is a compound of formula:

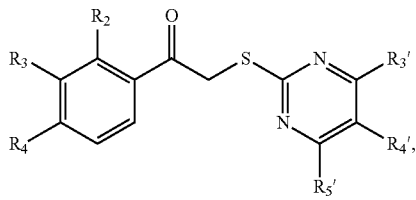

wherein,
- $R_2$ is selected from H, OH, and $OCH_3$;
- $R_3$ is selected from H, OH, $OCH_3$, and $COOCH_3$;
- $R_4$ is selected from H, OH, and $CH_3$;
- $R_3'$ is selected from H, $CH_3$, CH=CH—CH=CH, and S—C(—$CH_3$)=C(—$CH_3$);
- $R_4'$ is selected from H and OH; and
- $R_5'$ is selected from H, OH, and $CH_3$, wherein two or more of $R_2$, $R_3$, $R_4$ may be optionally connected, and two or more of $R_3'$, $R_4'$ $R_5'$ may be optionally connected.

Various embodiments of the present invention provide a method for treating cancer in a subject, comprising: administering the subject a composition comprising an inhibitor of KLF10, wherein the inhibitor of KLF10 is a compound selected from:

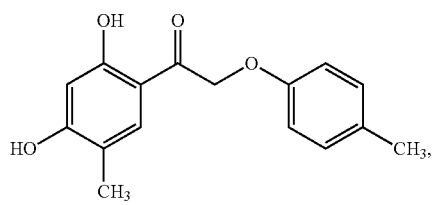

-continued

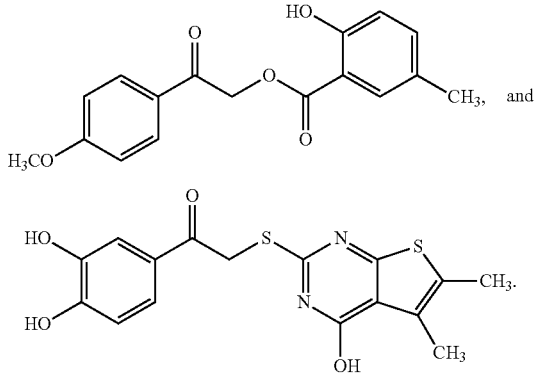

Various embodiments of the present invention provide a pharmaceutical composition, comprising: at least one compound selected from:

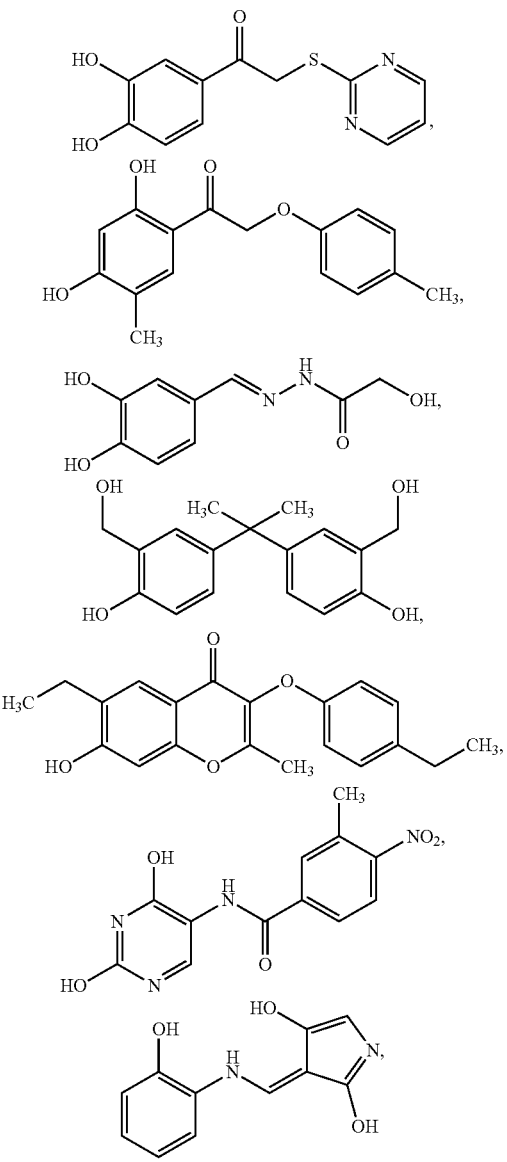

-continued

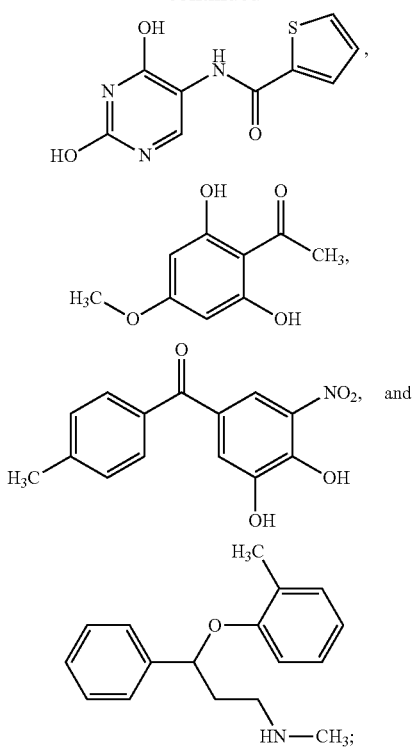

and a pharmaceutically acceptable carrier.

Various embodiments of the present invention provide a pharmaceutical composition, comprising: at least one compound of formula:

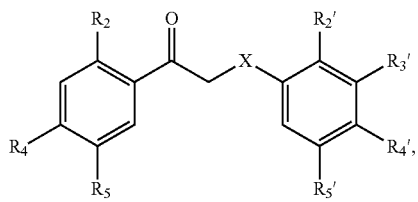

wherein,
R$_2$ is selected from H, OH, CH$_3$, and OCH$_3$;
R$_4$ is selected from H, OH, and OCH$_3$;
R$_5$ is selected from H, CH$_3$, and C$_2$H$_5$;
X is selected from H, O, and OC(=O);
R$_2$' is selected from H and OH;
R$_3$' is selected from H, OCH$_3$, and CH=CH—CH=CH;
R$_4$' is selected from H, CH$_3$, C$_2$H$_5$, CH(CH$_3$)$_2$, OCH$_3$, Ph, F, I, and CH=CH—CH=CH; and
R$_5$' is selected from H, CH$_3$, and OCH$_3$, wherein two or more of R$_2$, R$_4$, R$_5$ may be optionally connected, and two or more of R$_2$', R$_3$', R$_4$' R$_5$' may be optionally connected; and a pharmaceutically acceptable carrier.

Various embodiments of the present invention provide a pharmaceutical composition, comprising: at least one compound of formula:

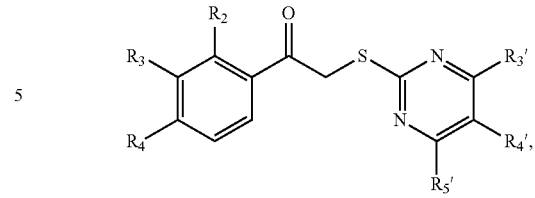

wherein,
R$_2$ is selected from H, OH, and OCH$_3$;
R$_3$ is selected from H, OH, OCH$_3$, and COOCH$_3$;
R$_4$ is selected from H, OH, and CH$_3$;
R$_3$' is selected from H, CH$_3$, CH=CH—CH=CH, and S—C(—CH$_3$)=C(—CH$_3$);
R$_4$' is selected from H and OH; and
R$_5$' is selected from H, OH, and CH$_3$, wherein two or more of R$_2$, R$_3$, R$_4$ may be optionally connected, and two or more of R$_3$', R$_4$' R$_5$' may be optionally connected; and a pharmaceutically acceptable carrier.

Various embodiments of the present invention provide a pharmaceutical composition, comprising: at least one compound selected from:

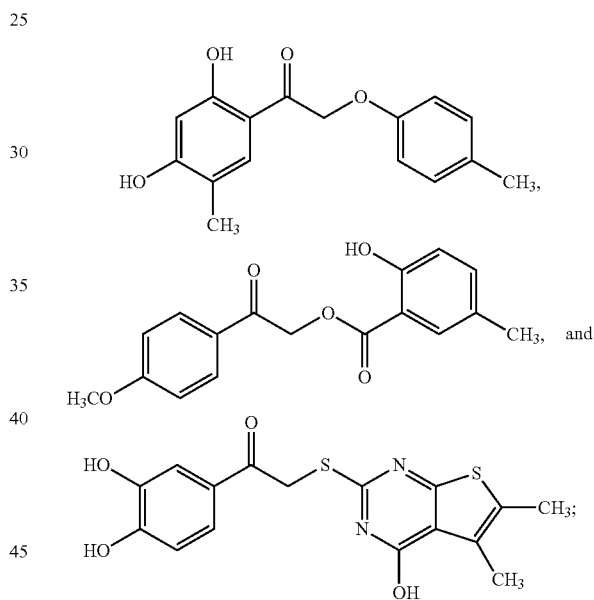

and a pharmaceutically acceptable carrier.

Various embodiments of the present invention provide a kit, comprising: at least one compound selected from:

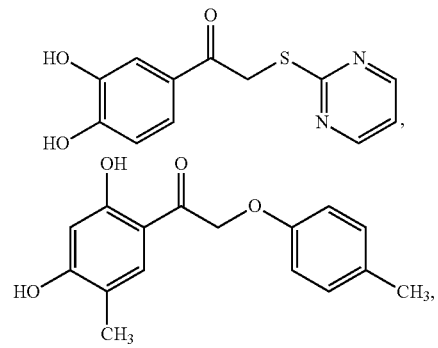

-continued

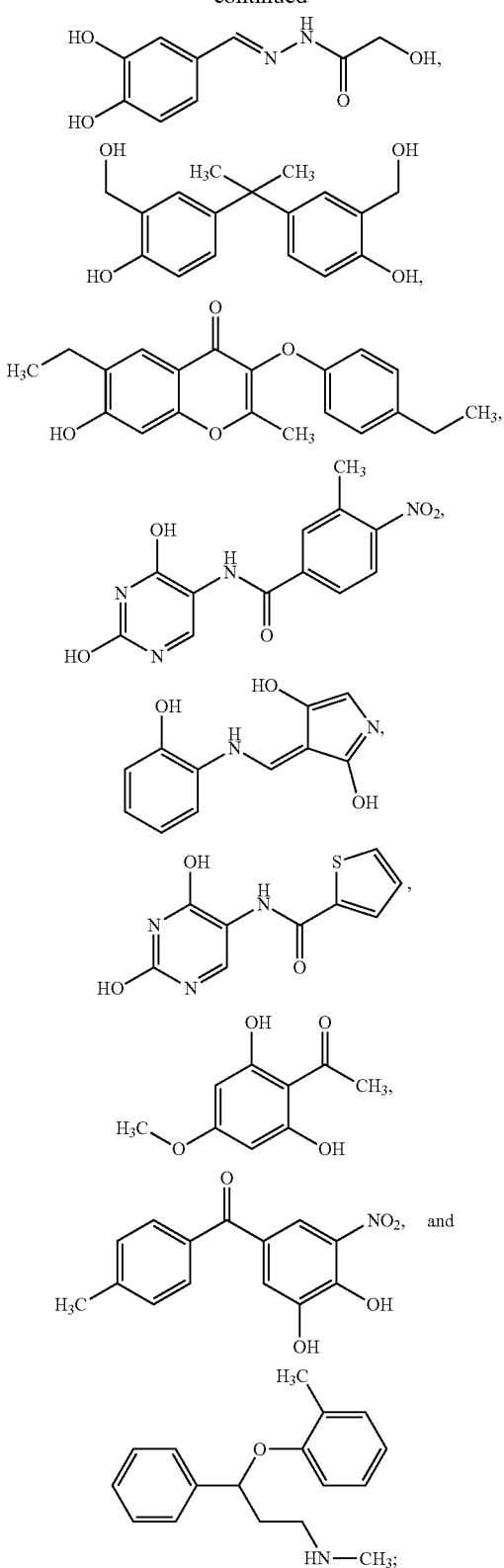

and instructions for administration to a subject.

Various embodiments of the present invention provide a kit, comprising: at least one compound of formula:

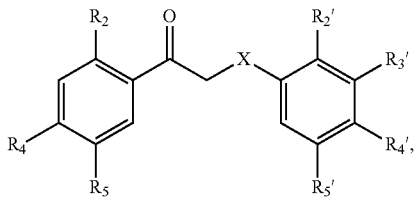

wherein,
R$_2$ is selected from H, OH, CH$_3$, and OCH$_3$;
R$_4$ is selected from H, OH, and OCH$_3$;
R$_5$ is selected from H, CH$_3$, and C$_2$H$_5$;
X is selected from H, O, and OC(=O);
R$_2$' is selected from H and OH;
R$_3$' is selected from H, OCH$_3$, and CH=CH—CH=CH;
R$_4$' is selected from H, CH$_3$, C$_2$H$_5$, CH(CH$_3$)$_2$, OCH$_3$, Ph, F, I, and CH=CH—CH=CH; and
R$_5$' is selected from H, CH$_3$, and OCH$_3$, wherein two or more of R$_2$, R$_4$, R$_5$ may be optionally connected, and two or more of R$_2$', R$_3$', R$_4$' R$_5$' may be optionally connected; and instructions for administration to a subject.

Various embodiments of the present invention provide a kit, comprising: at least one compound of formula:

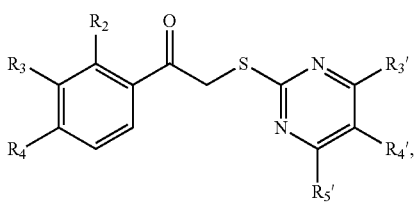

wherein,
R$_2$ is selected from H, OH, and OCH$_3$;
R$_3$ is selected from H, OH, OCH$_3$, and COOCH$_3$;
R$_4$ is selected from H, OH, and CH$_3$;
R$_3$' is selected from H, CH$_3$, CH=CH—CH=CH, and S—C(—CH$_3$)=C(—CH$_3$);
R$_4$' is selected from H and OH; and
R$_5$' is selected from H, OH, and CH$_3$, wherein two or more of R$_2$, R$_3$, R$_4$ may be optionally connected, and two or more of R$_3$', R$_4$' R$_5$' may be optionally connected; and instructions for administration to a subject.

Various embodiments of the present invention provide a kit, comprising: at least one compound selected from:

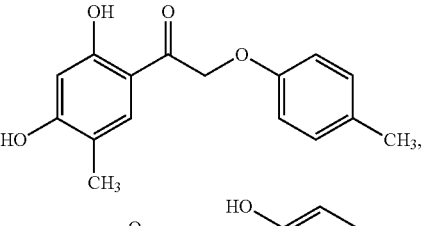

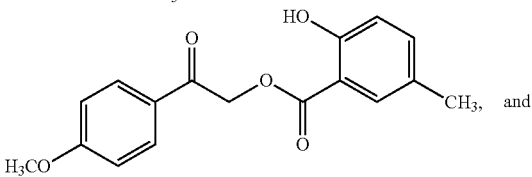

and

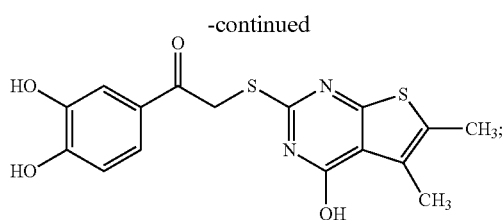

and instructions for administration to a subject.

BRIEF DESCRIPTION OF THE DRAWINGS

This application file contains at least one drawing executed in color. Copies of this patent application publication with color drawings will be provided by the Office upon request and payment of the necessary fee. Exemplary embodiments are illustrated in referenced figures. It is intended that the embodiments and figures disclosed herein are to be considered illustrative rather than restrictive.

(FIG. 3A) GST-KLF10 specifically bound to a KLF10 consensus DNA-binding sequence. Small molecule compounds #48 (FIG. 3B), #48-15 (FIG. 3C), and #15-09 (FIG. 3D) inhibited KLF10 DNAbinding activity. (FIG. 3E-FIG. 3F) In contrast, there was no inhibition of DNA-protein binding of the related KLF, KLF1, by small molecules.

FIG. 20 depicts in accordance with various embodiments of the invention, raw data for FIG. 4. Inhibition of conversion of CD4+CD25− T cells to CD4+CD25+ T regulatory cells by small molecule compounds #48, #48-15, and #15-09.

FIG. 21 depicts in accordance with various embodiments of the invention, raw data for FIG. 5. qPCR Ct values of FoxP3 and β-Actin, and fold changes of FoxP3.

FIG. 22 depicts in accordance with various embodiments of the invention, molecules from the SBVS-150 set.

DETAILED DESCRIPTION

Figure 1A:
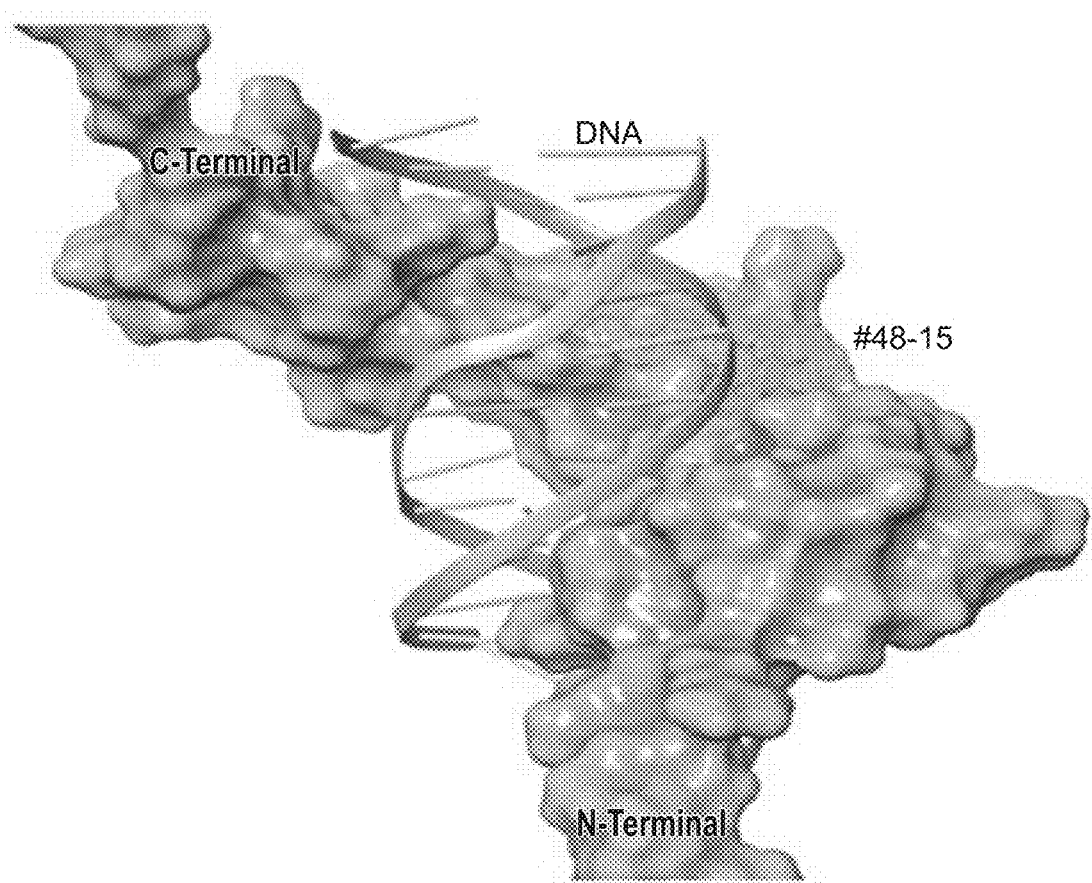
FIG. 1A-FIG. 1F depicts in accordance with various embodiments of the invention, homology model of KLF10 protein revealing the proposed pocket of small molecule binding and its relative location in the DNA-bound complex (FIG. 1A-FIG. 1B): Molecular surface of DNA-binding domain of KLF10 protein (blue) along with DNA strands (plum) shown to represent the relative orientation/location of proposed binding pockets along with compound #48-15 (FIG. 1A; green, mesh representation). Proposed binding pocket within second zinc finger of KLF10 (electrostatic surface; blue color for positive potential and red color for negative potential), with α and β subpockets separated by Glu415 side chain (FIG. 1B). Inhibition of KLF10 transcriptional activity by small molecule compounds #48, #48-15, and #15-09 (FIG. 1C-FIG. 1E): HeLa cells were transiently transfected with human KLF10 and a CACCC-luciferase reporter. After transfection, cells were allowed to grow for 24 hrs and subsequently treated with compounds #48 (FIG. 1C), #48-15 (FIG. 1D), and #15-09 (FIG. 1E) for another 24 hrs at which time they were harvested for luciferase activity assays. In (FIG. 1F), HeLa cells were transfected in a similar manner as above, except they were treated with small molecule compounds #3, #23, #37, #40, #65, #79, #83, #96, #104, #106, #114, #118, #121, #126, and #146. Data show mean±SD, n=3. *, P<0.01. Con, empty-vector control.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual 4th ed.*, Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 Jul. 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. It should be understood that this invention is not limited to the particular methodology, protocols, and reagents, etc., described herein and as such can vary. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

Various non-limiting examples of abbreviations used herein include CD4, cluster of differentiation 4; CD25, cluster of differentiation 25; eMBrAcE, Multi-Ligand Bimolecular Association with Energetics; Foxp3, forkhead box P3; HTD, high throughput docking; KLF10, Krüppel-Like Factor 10; PAINS, Pan Assay Interference compounds; TFs, transcription factors; T regs, T regulatory cells; TGF-β1, transforming growth factor beta-1; SP, standard precision; SD, standard deviation; XP, extra precision; ZFs, Zinc fingers.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective"

if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of a tumor, delay or slowing of a tumor, and amelioration or palliation of symptoms associated with a tumor.

"Disorders", "diseases", "conditions" and "disease conditions," as used herein may include, but are in no way limited to any form of malignant neoplastic cell proliferative disorders or diseases. Examples of such disorders include but are not limited to cancer and tumor.

A "cancer" or "tumor" as used herein refers to an uncontrolled growth of cells which interferes with the normal functioning of the bodily organs and systems, and/or all neoplastic cell growth and proliferation, whether malignant or benign, and all pre-cancerous and cancerous cells and tissues. A subject that has a cancer or a tumor is a subject having objectively measurable cancer cells present in the subject's body. Included in this definition are benign and malignant cancers, as well as dormant tumors or micrometastasis. Cancers which migrate from their original location and seed vital organs can eventually lead to the death of the subject through the functional deterioration of the affected organs. As used herein, the term "invasive" refers to the ability to infiltrate and destroy surrounding tissue.

As used herein, the term "administering," refers to the placement an agent as disclosed herein into a subject by a method or route which results in at least partial localization of the agents at a desired site. "Route of administration" may refer to any administration pathway known in the art, including but not limited to aerosol, nasal, via inhalation, oral, transmucosal, transdermal, parenteral, enteral, topical or local. "Parenteral" refers to a route of administration that is generally associated with injection, including intracranial, intraventricular, intrathecal, epidural, intradural, intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. In accordance with the present invention, "administering" can be self-administering. For example, it is considered as "administering" that a subject consumes a composition as disclosed herein.

The term "sample" or "biological sample" as used herein denotes a sample taken or isolated from a biological organism, e.g., a tumor sample from a subject. Exemplary biological samples include, but are not limited to, cheek swab; mucus; whole blood, blood, serum; plasma; urine; saliva; semen; lymph; fecal extract; sputum; other body fluid or biofluid; cell sample; tissue sample; tumor sample; and/or tumor biopsy etc. The term also includes a mixture of the above-mentioned samples. The term "sample" also includes untreated or pretreated (or pre-processed) biological samples. In some embodiments, a sample can comprise one or more cells from the subject. In some embodiments, a sample can be a tumor cell sample, e.g. the sample can comprise cancerous cells, cells from a tumor, and/or a tumor biopsy.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets. In one embodiment, the subject is human.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., cancer) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

Herein, we report computational discovery of small molecule inhibitors of the KLF10-DNA interaction interface, an effect that reduced KLF10-DNA binding and transcriptional activity. Furthermore, we also report an investigation into the effects of our inhibitor compounds on the conversion of CD4+CD25− T cells to CD4+CD25+ T regs and FoxP3 expression. Overall, our findings support the feasibility of using computer-aided drug design (CADD) with functional assays to identify small molecules that target members of the KLF subfamily of transcription factors to regulate biological functions. In addition, it is an object of the invention to provide an immunomodulatory composition of a KLF10 inhibitor and enhance immune responses.

Homology Model of KLF10 Reveals a Large Binding Pocket within the DNA-Binding Region.

Figure 1B:
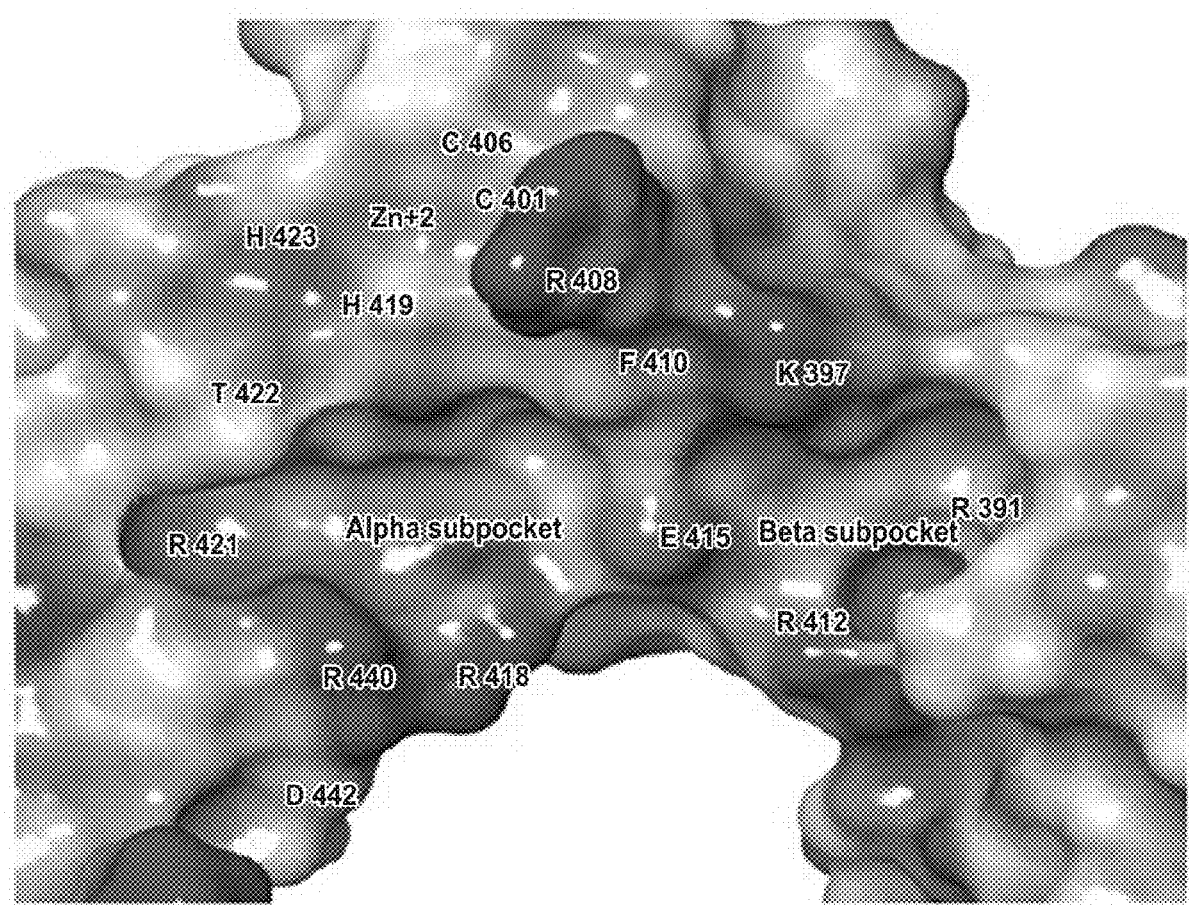

A homology model of KLF10 protein was generated using template coordinates of a DNA-binding protein having three consensus-sequence-based zinc finger domains. The overall topology of the KLF10 structure matches with the expected fold of classical $C_2H_2$ zinc finger domains in which two short strands of antiparallel 3 strands linked by a rubredoxin-like turn are followed by an α-helix that contains two $Zn^{+2}$-coordinating histidine residues. In our current efforts to identify modulators of TF-dependent transcription, we hypothesized that small organic molecules capable of binding to the KLF10 zinc finger region that interfaces the DNA, would be able to inhibit the binding of KLF10 with DNA and, subsequently, reduce transcriptional activity. An analysis of the zinc finger-DNA binding region using multiple binding pocket identification programs such as SiteMap[14,15] (Schrodinger), MolCad[16] (Tripos) and SiteFinder[17] (Chemical Computing Group), uniquely identified a relatively large pocket in the middle zinc finger which has maximum surface contacts with the DNA (FIG. 1A-FIG. 1B). We subclassified this binding pocket into α- and β-pockets depending on the proximity with α-helix or β-sheet residues encompassing it.

In Silico Screens Identified Small Molecule Inhibitors of KLF10.

High-throughput docking of chemical libraries using Glide docking[18,19] with extra precision (XP)[20] scoring into grids encompassing the α- and β-pockets resulted in ~1400 unique hits. This subset was further evaluated with another two independently developed dockers: Surflex[21] and FlexX.[22] The highest scored 700 molecules were then subjected to consensus scoring and ADME/Tox profiling analysis to select 40 molecules, which were subsequently tested in KLF10 reporter assays as detailed below.

Identified Compounds Inhibit KLF10 Transcriptional Activity.

Figure 1C:
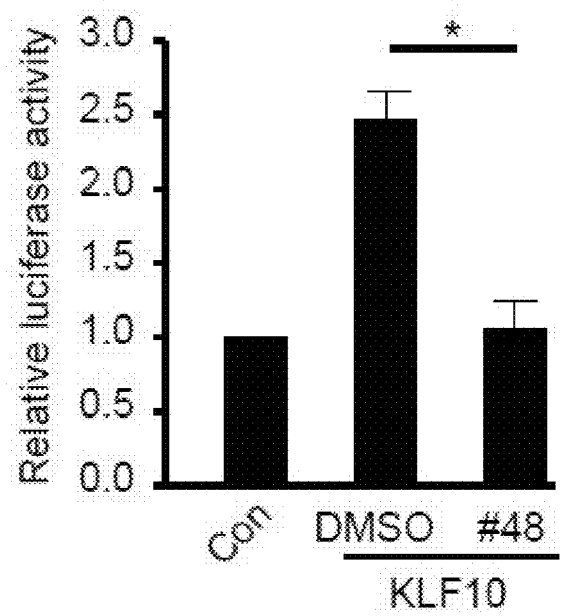
Figure 1D:
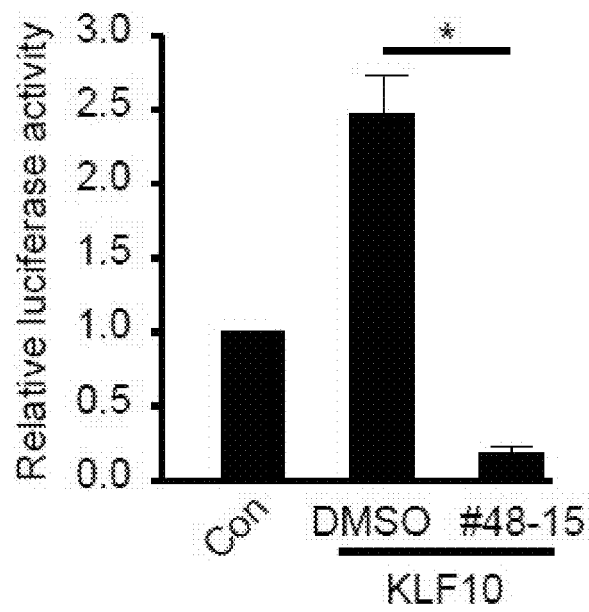
Figure 1E:
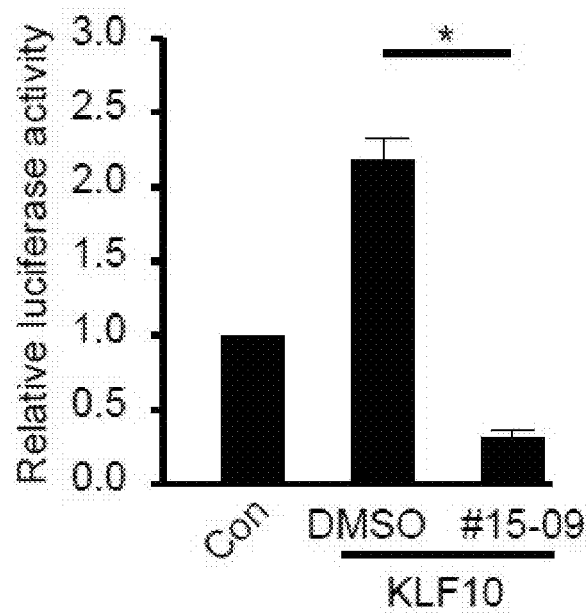
Figure 1F:
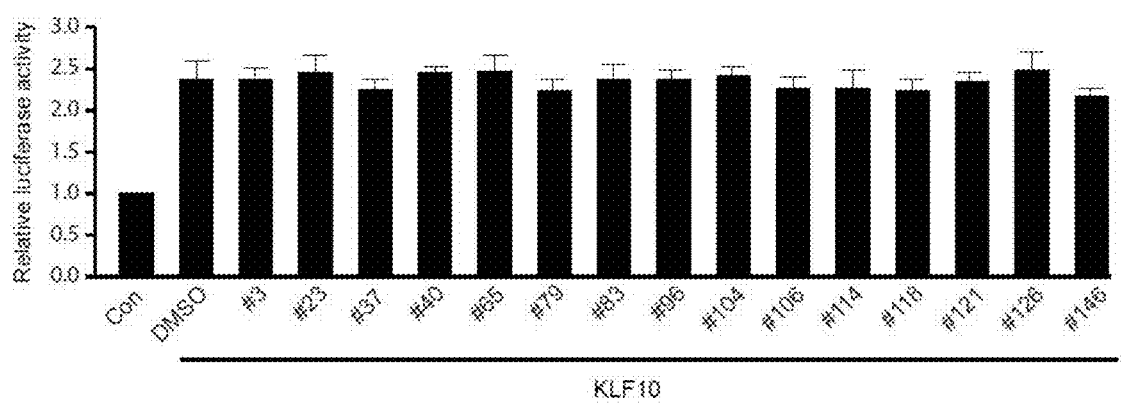

We developed a cell-based reporter assay to test the transcriptional activity of in silico identified compounds. A KLF10 expression plasmid and luciferase reporter driven by a CACCC-responsive promoter were transfected into HeLa cells. Exogenous KLF10-induced luciferase activity was approximately 2.5-fold compared with transfection of empty vector (FIG. 1C-FIG. 1E). In vitro screening using this luciferase reporter assay resulted in the discovery of 11 inhibitors of KLF10 reporter activity (Table 1). Several structural analogs of two scaffolds, #48 and #15 (Table 2 and Table 3) were computationally investigated to explore the chemical space governing the activity; many of these analogs showed equal or better potency than the parent compound in luciferase reporter assays. For example, the induction of luciferase activity by exogenous KLF10 expression was almost completely blocked by 100 μM of compound #48 (96.6%, FIG. 1C). In the presence of 100 μM of compound #48-15, reporter activity was reduced to even lower than basal conditions (−20% vs. control, FIG. 1D). Similarly, compound #15-09 also potently inhibited KLF10 induced luciferase activity to −31% of basal conditions (FIG. 1E). In contrast, small molecule compounds #3, #23, #37, #40, #65, #79, #83, #96, #104, #106, #114, #118, #121, #126, and #146 had no effect on KLF10-induced luciferase activity (FIG. 1F).

TABLE 1

The First-Generation Inhibitors of KLF10 Reporter Activity.[a]

| Compound ID | % Inhibition at 100 μM (± sd)[§] | IC50 (μM)[¶] | Glide Rank[π] | Surflex Rank[π] | FlexX Rank[π] | Chemical Structure |
| --- | --- | --- | --- | --- | --- | --- |
| #15 | 45.5 ± 4.1 | n.d. | 34 | 79 | 76 | 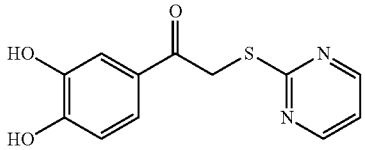 [SMILES: O=C(CSc1ncccn1)c1ccc(O)c(O)c1] |
| #48 | 54.5 ± 8.0 | 112 | 59 | 54 | 122 | 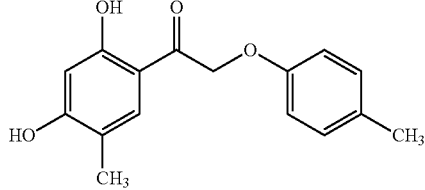 [SMILES: Cc1ccc(OCC(=O)c2cc(C)c(O)cc2O)cc1] |
| #57 | 33.1 ± 5.6 | n.d. | 6 | 94 | 128 | 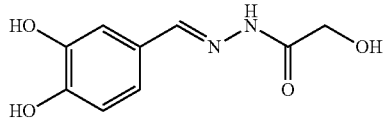 [SMILES: O=C(CO)N/N=C/c1ccc(O)c(O)c1] |

TABLE 1-continued

The First-Generation Inhibitors of KLF10 Reporter Activity.[a]

| Compound ID | % Inhibition at 100 μM (± sd)[§] | IC50 (μM)[¶] | Glide Rank[ϖ] | Surflex Rank[ϖ] | FlexX Rank[ϖ] | Chemical Structure |
|---|---|---|---|---|---|---|
| #71 | 41.4 ± 4.2 | 100 | 84 | 138 | 140 | 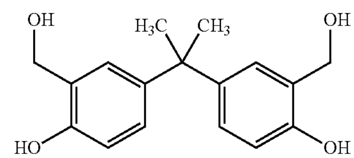 [SMILES: CC(C)(c1ccc(O)c(CO)c1)c1ccc(O)c(CO)c1] |
| #71-S | 46.7 ± 3.0 | n.d. | N.A. | N.A. | N.A. | 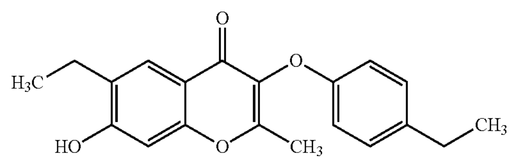 [SMILES: CCc1ccc(Oc2c(C)oc3cc(O)c(CC)cc3c2=O)cc1] |
| #77 | 61.7 ± 2.6 | 10 | 135 | 104 | 16 | 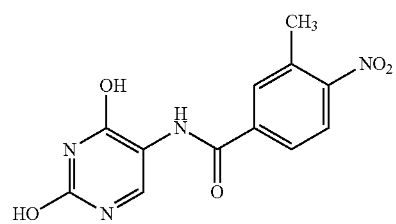 [SMILES: Cc1cc(C(=O)Nc2cnc(O)nc2O)ccc1[N+](=O)[O-]] |
| #82 | 31.9 ± 0.4 | n.d. | 78 | 141 | 66 | 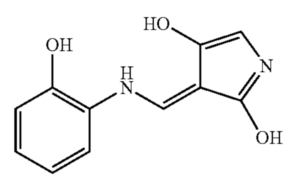 [SMILES: OC1=CN=C(O)/C1=C/Nc1ccccc1O] |
| #86 | 57.6 ± 2.3 | n.d. | 133 | 115 | 30 | 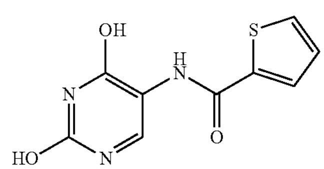 [SMILES: O=C(Nc1cnc(O)nc1O)c1cccs1] |
| #117 | 37.6 ± 7.1 | 200 | 80 | 140 | 105 | 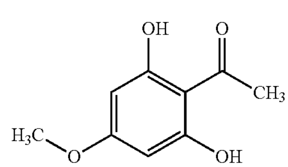 |
| Tolcapone[ϵ] | 71.8 ± 0.9 | 50 | N.A. | N.A. | N.A. | |

TABLE 1-continued

The First-Generation Inhibitors of KLF10 Reporter Activity.[a]

| Compound ID | % Inhibition at 100 μM (± sd)[§] | IC50 (μM)[¶] | Glide Rank[π] | Surflex Rank[π] | FlexX Rank[π] | Chemical Structure |
|---|---|---|---|---|---|---|
| Atomoxetine[ε] | 47.1 ± 4.6 | 100 | N.A. | N.A. | N.A. | 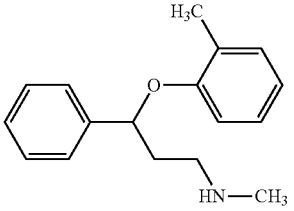 [SMILES: CNCCC(Oc1ccccc1C)c1ccccc1] |

[a]Footnotes: [§]Percent inhibition at 100 μM (sd, standard deviation);
[¶]Compound concentration in μM that inhibited 50% of KLF10 reporter activity;
n.d., not determined.
Tolcapone (Tasmar ™; Catechol-O-methyl transferase inhibitor) and Atomoxetine (Strattera ™; Norepinephrine reuptake inhibitor) are approved drugs.
[π]Represents respective rank order within SBVS-150 set by Glide XP, Surflex, and FlexX dockers scores.
N.A. indicate hits which are not part of the original consensus docking protocol, but were included later to test similar molecule (#71-S) or repurposing of approved drugs[ε].

TABLE 2

Chemical Expansion (Structure-Activity Relationship) of Hit Compound #48 Scaffold.

| Compound ID | % Inhibition 100 μM (± sd)[a] | IC$_{50}$ (μM)[b] | R$_2$ | R$_4$ | R$_5$ | X | R$_2$' | R$_3$' | R$_4$' | R$_5$' |
|---|---|---|---|---|---|---|---|---|---|---|
| #48 | 54.5 ± 8.0 | 112 | OH | OH | CH$_3$ | O | H | H | CH$_3$ | H |
| #48-02 | 62.1 ± 0.5 | n.d. | OH | OH | C$_2$H$_5$ | O | H | H | C$_2$H$_5$ | H |
| #48-03 | 41.1 ± 2.6 | n.d. | OH | OH | C$_2$H$_5$ | O | H | H | H | H |
| #48-04 | 75.65 ± 1.9 | n.d. | OH | OH | C$_2$H$_5$ | O | H | CH=CH—CH=CH | H |
| #48-05 | 91.4 ± 0.6 | n.d. | OH | OH | C$_2$H$_5$ | O | H | H | CH(CH$_3$)$_2$ | H |
| #48-06 | 91.6 ± 4.6 | n.d. | OH | OH | C$_2$H$_5$ | O | H | H | Ph | H |
| #48-07 | 49.3 ± 1.0 | n.d. | OH | OH | C$_2$H$_5$ | O | H | H | F | H |
| #48-08 | 39.0 ± 3.5 | n.d. | OCH$_3$ | H | H | OCO | OH | H | H | CH$_3$ |
| #48-09 | 43.5 ± 0.7 | n.d. | OCH$_3$ | OCH$_3$ | H | OCO | OH | H | H | CH$_3$ |
| #48-10 | 39.6 ± 2.6 | n.d. | OCH$_3$ | OCH$_3$ | H | OCO | OH | H | H | OCH$_3$ |
| #48-11 | 81.5 ± 3.3 | n.d. | OH | OH | C$_2$H$_5$ | H | H | H | OCH$_3$ | H |
| #48-12 | 83.5 ± 0.4 | n.d. | OH | OH | H | O | H | H | C$_2$H$_5$ | H |
| #48-13 | 41.4 ± 5.0 | n.d. | OH | OH | CH$_3$ | O | H | H | F | H |
| #48-14 | 79.1 ± 1.4 | n.d. | OH | OH | C$_2$H$_5$ | O | H | H | I | H |
| #48-15 | 78.0 ± 1.3 | n.d. | H | OCH$_3$ | H | OCO | OH | H | H | CH$_3$ |
| #48-20 | 35.49 ± 3.4 | n.d. | OH | OH | H | O | H | CH$_3$ | H | H |
| #48-19 | 22.3 ± 2.4 | n.d. | CH$_3$ | H | CH$_3$ | OCO | OH | H | CH=CH—CH=CH | |

[a]Percent inhibition at 100 μM (sd, standard deviation);
[b]Compound concentration in μM that inhibited 50% of KLF10 reporter activity;
n.d., not determined.

TABLE 3

Chemical Expansion (Structure-Activity Relationship) of Hit Compound #15 Scaffold.

[Structure diagram of compound scaffold with substituents $R_2$, $R_3$, $R_4$ on phenyl ring attached to C=O-CH2-S-pyrimidine with substituents $R_3'$, $R_4'$, $R_5'$]

| Compound ID | % Inhibition 100 μM (± sd)[a] | $IC_{50}$ (μM)[b] | $R_2$ | $R_3$ | $R_4$ | $R_3'$ | $R_4'$ | $R_5'$ |
|---|---|---|---|---|---|---|---|---|
| #15 | 45.5 ± 4.1 | n.d. | H | OH | OH | H | H | H |
| #15-07 | 39.1 ± 0.6 | n.d. | H | OH | OH | $CH_3$ | H | $CH_3$ |
| #15-09 | 85.9 ± 1.3 | 43 | H | OH | OH | S—C(—$CH_3$)=C(—$CH_3$) | | OH |
| #15-11 | 39.3 ± 1.6 | n.d. | OH | H | OH | $CH_3$ | H | $CH_3$ |
| #15-13 | 32.6 ± 4.1 | n.d. | $OCH_3$ | $OCH_3$ | H | CH=CH—CH=CH | OH | H |
| #15-17 | 32.3 ± 5.8 | n.d. | H | $COOCH_3$ | OH | $CH_3$ | H | $CH_3$ |
| #15-21 | 37.4 ± 2.8 | n.d. | H | $CH_3$ | $CH_3$ | $CH_3$ | H | $CH_3$ |

[a] Percent inhibition at 100 μM (sd, standard deviation);
[b] Compound concentration in μM that inhibited 50% of KLF10 reporter activity;
n.d., not determined.

Figure 2A:
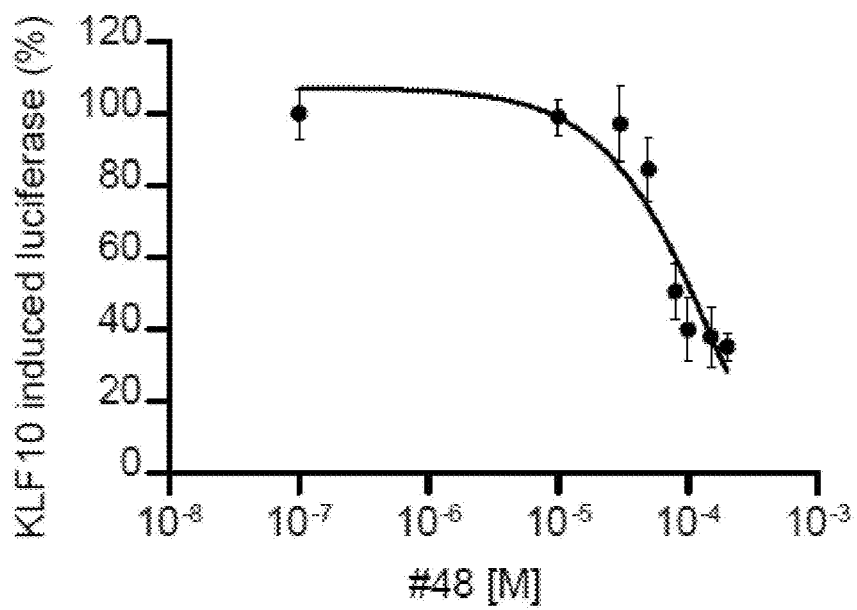
FIG. 2A-FIG. 2C depicts in accordance with various embodiments of the invention, dose-response curves of KLF10 transcriptional activity of HeLa cells treated with small molecule compounds #48, #48-15, and #15-09. HeLa cells were transiently transfected with human KLF10 and a CACCC-luciferase reporter. After transfection, cells were allowed to grow for 24 hrs and subsequently treated with different amounts of #48 (FIG. 2A), #48-15 (FIG. 2B), and #15-09 (FIG. 2C) for another 24 hrs at which time they were harvested for luciferase activity assays.
Figure 2B:
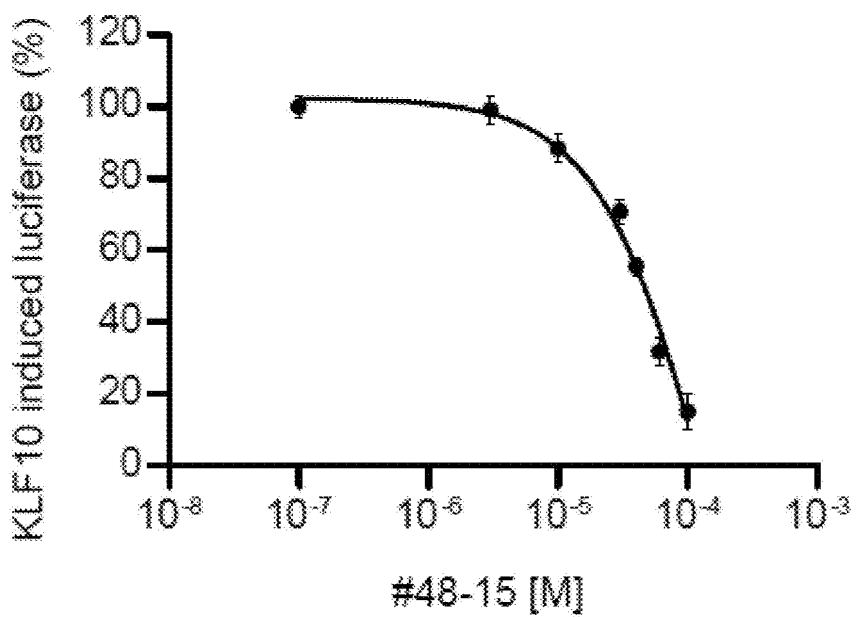
Figure 2C:
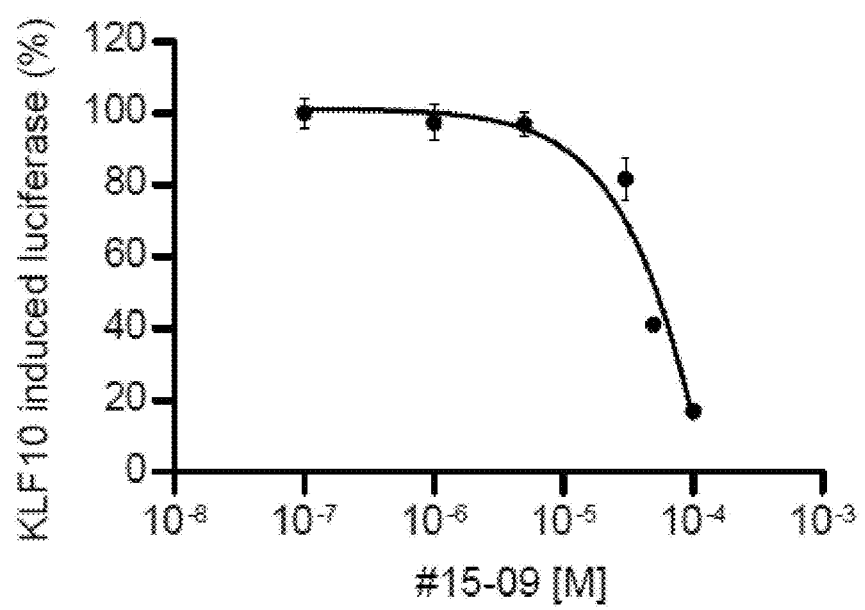

We also examined dose-dependent responses of compounds #48, #48-15, and #15-09 on KLF10 transcriptional activity. $IC_{50}$ values, calculated based on non-linear regression analysis, for compounds #48, #48-15, #15-09 were 112 μM, 40 μM, and 43 μM, respectively (FIG. 2A, FIG. 2B, FIG. 2C). Collectively, these findings highlight the identification of three small molecule compounds, #48, #48-15, and #15-09, which could effectively inhibit KLF10 transcriptional activity.

Lead Compounds Inhibit Binding of KLF10 to DNA.

Figure 3A:
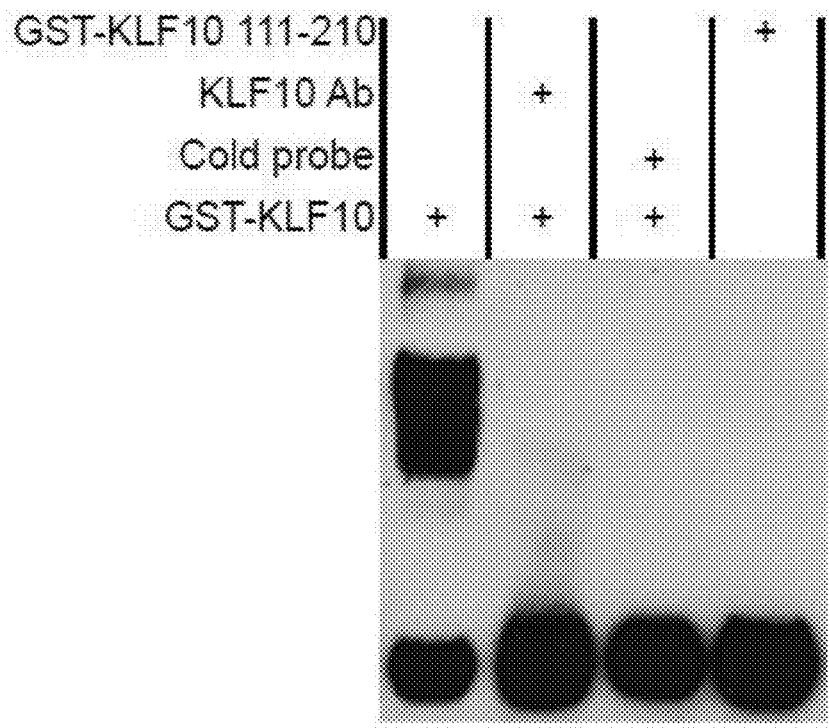
FIG. 3A-FIG. 3F depicts in accordance with various embodiments of the invention, effect of identified small molecule compounds on KLF10 DNA-binding activity by electromobility gel shift assays.
Figure 3B:
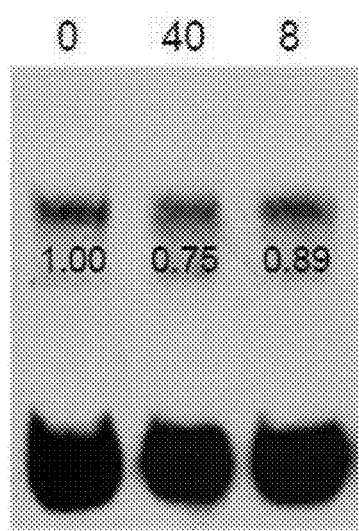
Figure 3C:
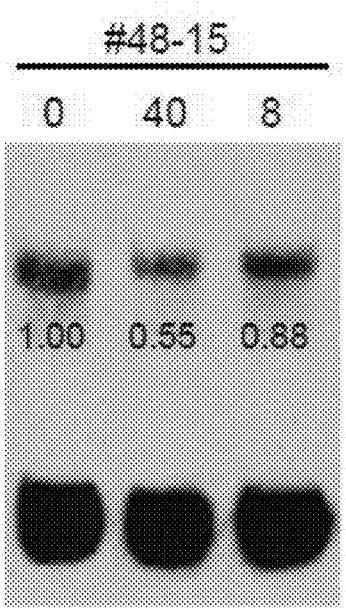
Figure 3D:
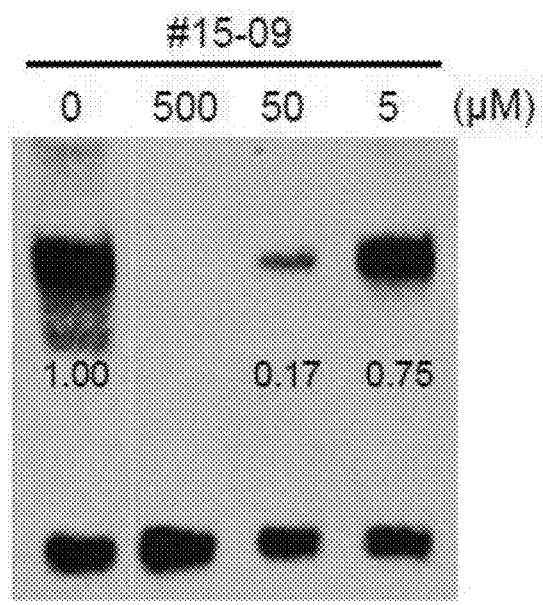
Figure 3E:
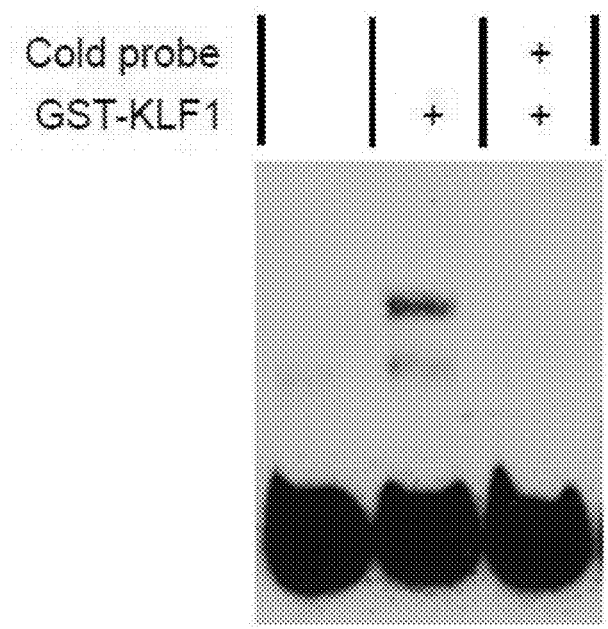
Figure 3F:
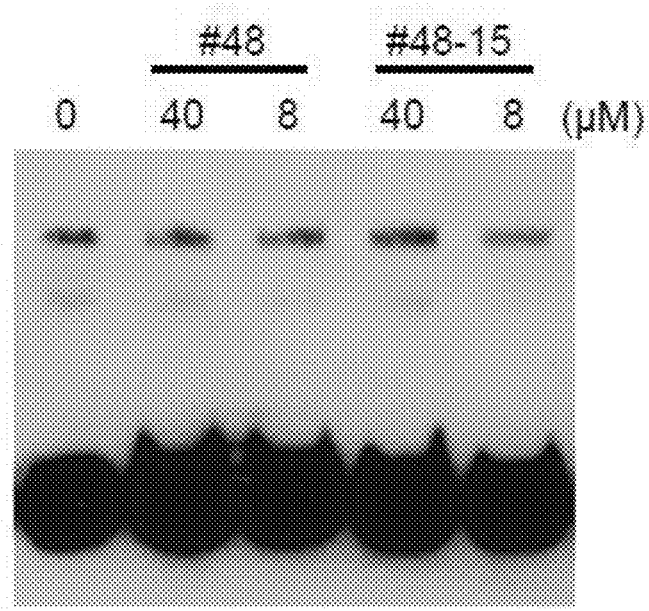

To determine whether identified compounds inhibit the binding of KLF10 to DNA, KLF10 was incubated with double-stranded DNA containing a KLF10 consensus binding site in the presence of identified compounds #48, #48-15, or #15-09, or DMSO control. We first validated that purified KLF10 protein bound to the KLF10 consensus DNA-binding site in a specific manner as the binding was completely blocked by unlabeled oligonucleotide DNA probe, and there was no binding using KLF10 protein lacking the DNA-binding domain (GST-KLF 10 amino acid 111-210); in addition, the KLF10 DNA-protein complex was super-shifted by a KLF10 antibody (FIG. 3A). The identified small molecule compounds were next examined for effects on KLF10 DNA-protein binding. As shown in FIG. 3B, compound #48 inhibited KLF10 DNA-binding activity by 25% and 11% at 40 μM and 8 μM, respectively. Compound #48-15 inhibited KLF10 DNA-binding activity by 45% and 12% at 40 μM and 8 μM, respectively (FIG. 3C). In addition, compound #15-09 inhibited KLF10 DNA-binding activity by 83% and 25% at 50 μM and 8 μM concentrations, respectively (FIG. 3D). In contrast, no dose-dependent inhibition on DNA-binding was observed for another member of the KLF family, KLF1 (FIG. 3E-FIG. 3F), showing specificity. Taken together, these data indicate that small molecule compounds #48, #48-15, and #15-09 could each inhibit binding of KLF10 protein to DNA.

Figure 4A:
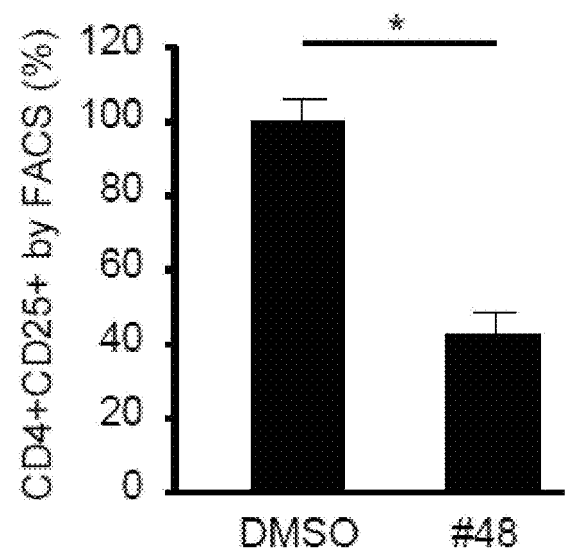
FIG. 4A-FIG. 4C depicts in accordance with various embodiments of the invention, inhibition of conversion of CD4+CD25− T cells to CD4+CD25+ T regs by small molecule compounds #48, #48-15, and #15-09. CD4+CD25− T cells were isolated and cultured for the conversion to CD4+CD25+ T regs in the presence or absence of small molecule compounds #48 (FIG. 4A), #48-15 (FIG. 4B), and #15-09 (FIG. 4C) for 3 days and harvested for analysis by flow cytometry. Data show mean±SD, n=3: *, P<0.05.
Figure 4B:
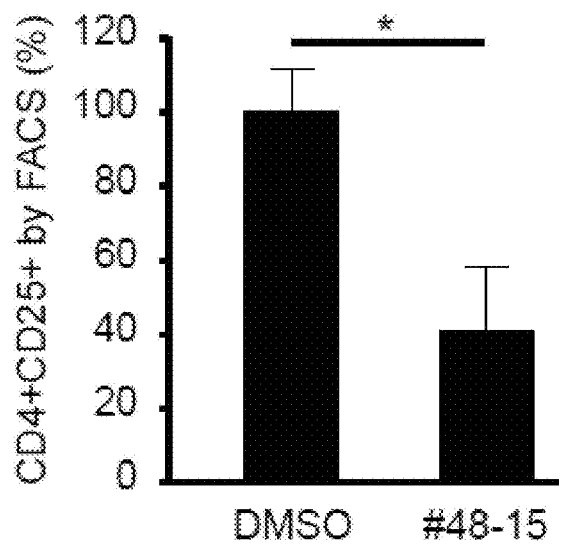
Figure 4C:
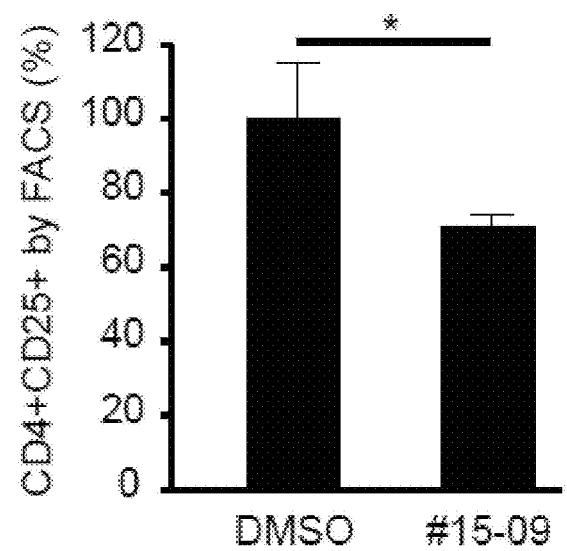
Figure 15:
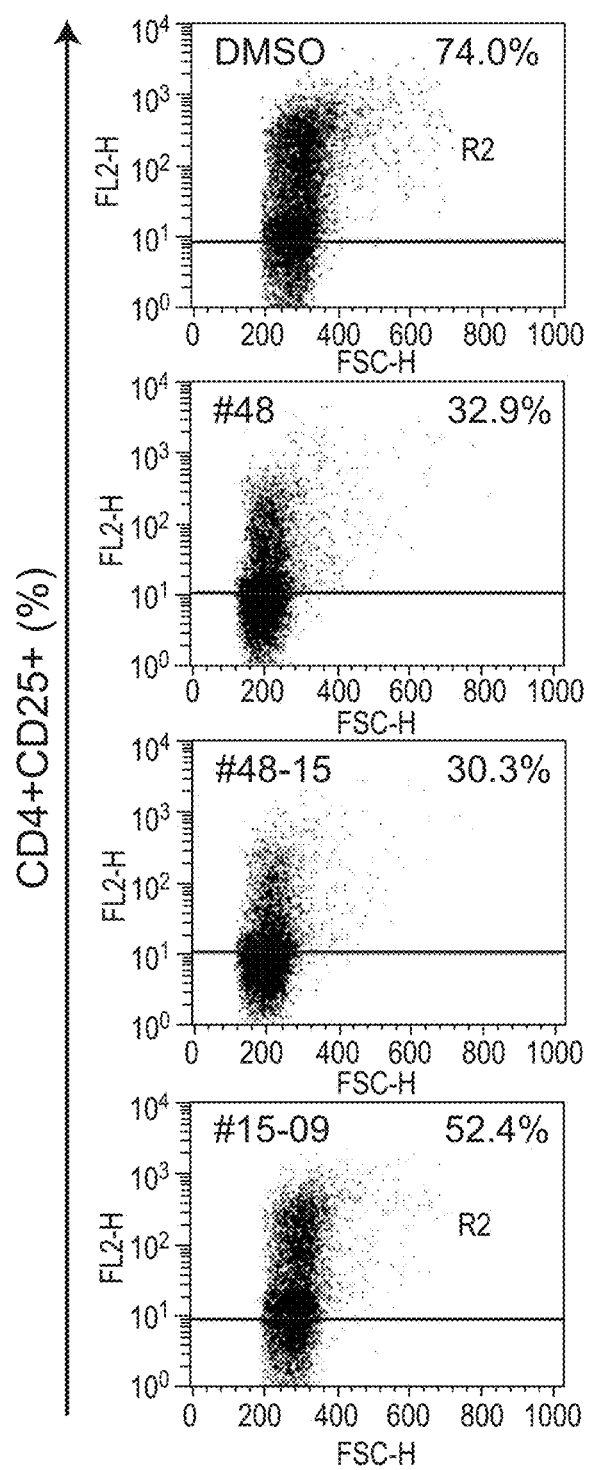
FIG. 15 depicts in accordance with various embodiments of the invention, representative flow cytometry is shown for each condition for FIG. 4. Inhibition of conversion of CD4+CD25− T cells to CD4+CD25+ T regs by small molecule compounds #48, #48-15, and #15-09.

Lead Compounds Inhibit Conversion of CD4+CD25− T Cells to CD4+CD25+ T Regulatory Cells Our previous work and that of others have identified a critical role for KLF10 in its ability to convert CD4+CD25− T cells into CD4+CD25+ T regs.[12, 13] To test if these lead compounds had any effect on T reg cell differentiation, CD4+CD25− T cells were cultured for the conversion of CD4+CD25− T cells to CD4+CD25+ T regulatory cells in the presence of the indicated small molecule compounds #48, #48-15, and #15-09. As shown in FIG. 4A-FIG. 4C; FIG. 15; FIG. 20, compound #48, #48-15, and #15-09 inhibited the percentage of CD4+CD25+ T regs by 57.4%, 59.1%, and 29.2%, respectively. Collectively, these findings suggest that small molecule compounds #48, #48-15, and #15-09 have the ability to alter T reg cell differentiation.

Identified Small Molecule Compounds Inhibited FoxP3 Expression During the Conversion of CD4+CD25− T Cells to CD4+CD25+ T Regulatory Cells.

Foxp3, a forkhead transcription factor, is a critical protein involved in the differentiation of T regs.[23-27] Indeed, our previous report demonstrated that KLF10 can potently induce Foxp3 expression by binding to an evolutionarily conserved CACCC DNA-binding site in the proximal Foxp3 promoter.[12] To examine the effects of the identified tool compounds #48, #48-15, and #15-09 on Foxp3 expression, CD4+CD25− T cells were cultured for the conversion to CD4+CD25+ T regs in the presence of each of the identified compounds. Compound #48, #48-15, and #15-09 inhibited Foxp3 expression by 84.7%, 82.5%, and 90.8%, respectively, at 50 μM (FIG. 5; FIG. 21). Taken together, these observations indicate that these compounds effectively suppress the KLF10 target gene Foxp3, a critical regulator of T reg cell differentiation.[28]

In recent years, in silico CADD and lead optimization strategies including structure-based and ligand-based virtual screens have become popular and, successfully complement or, in certain cases, replace HTS approaches for early stage identification of potential lead compounds with improved chemical diversity and enhanced pharmacodynamic and pharmacokinetic properties. KLFs constitute an important class of transcriptional regulators in diverse aspects of cell growth and differentiation. Furthermore, specific KLFs have been implicated in disease states ranging from tumorigenesis, inflammation, and cardiovascular disease, among others. However, given the lack of enzymatic activity, transcription factors in general have largely been considered 'non-druggable' to small molecule inhibition.[29-31] This provides an exciting and challenging opportunity for those in the field of drug discovery. To date, examples of small molecules targeting transcription factors have largely focused on protein-protein interactions of 'dimeric' transcription factors, so-called due to their need to form heterodimers or homodimers for efficient transcriptional activation and DNA binding including c-Myc/Max, HiF1-α/HIF-1β, and STAT3 dimers.[29-31]

Figure 16:
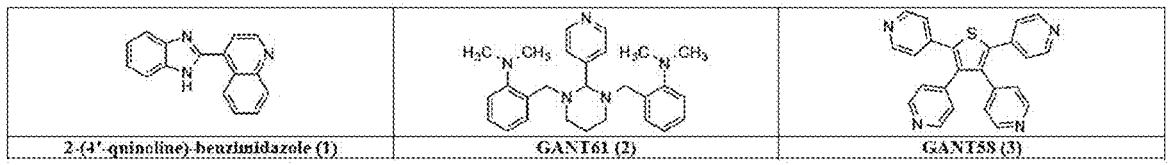
FIG. 16 depicts structures of earlier reported inhibitors of another transcription factor GLI.

There are few reported attempts of targeting other ZFTFs by small drug-like molecules. Lin et al.[32] screened a 250-membered heterocycle library containing diverse scaffolds for activation of the reporter gene after transfection with the zinc finger C7 protein, a structural variant of the murine zinc finger zif268. As a result, a potent 2-(4'-quinoline)benzimidazole compound was identified which induced luciferase activity by about 18-fold at 100 M concentration ($EC_{50}=35$ μM); however, at concentrations above 100 μM it exhibited significant cytotoxicity. Lauth et al.[33] used a cell-based screen to identify small-molecule antagonists of GLI-mediated transcription, thereby, inhibiting Hedgehog signaling implicated in several malignancies. They discovered two small molecules, GANT61 and GANT58 (NSC 136476 and NSC 75503, respectively; where GANT stands for Gli-antagonist), which inhibited the GLI-induced transcription in transfected HEK293 cells at 30 μM concentration (FIG. 16).

We report the first-in class discovery of inhibitors of the KLF10-DNA interaction interface using small 'drug-like' molecules. For structure-based screening, we generated a working homology model of KLF10 in association with DNA with attention to modeling of side chains of amino acids at the DNA interface (FIG. 1A). In the absence of prior knowledge of binding pocket or point-mutation data critical in DNA binding, we carefully studied the protein-DNA interface of KLF10 using independently developed pocket identification algorithms to identify, with consensus, a potentially druggable pocket for high throughput docking (HTD) of small molecule databases. A large, shallow pocket was observed within the middle zinc finger region and we sub-classified this binding pocket as α- and β-pocket depending on the proximity with α-helix or β-sheet residues surrounding it (FIG. 1B). We hypothesized that tighter binding of small molecules in this pocket would provide an opportunity to interfere with KLF10-DNA binding and subsequent inhibition of transcriptional activity.

A fast in silico HTD screen of publically available databases using the α- and β-pockets separately was performed with constrained Glide docking in SP settings. To offer both pockets an equal opportunity for binding, we selected ~1800 molecules that exhibited binding in both pockets. In the next level of filtering we provided every molecule in this set to dock without constraints and used a more accurate scoring function available through Glide XP docking. The outcome of this analysis showed that a good portion of these molecules (~400 molecules) were thrown away from this interface and ~1400 molecules (GlideXP-1400) were able to virtually bind in one of the proposed pockets.

Figure 5:
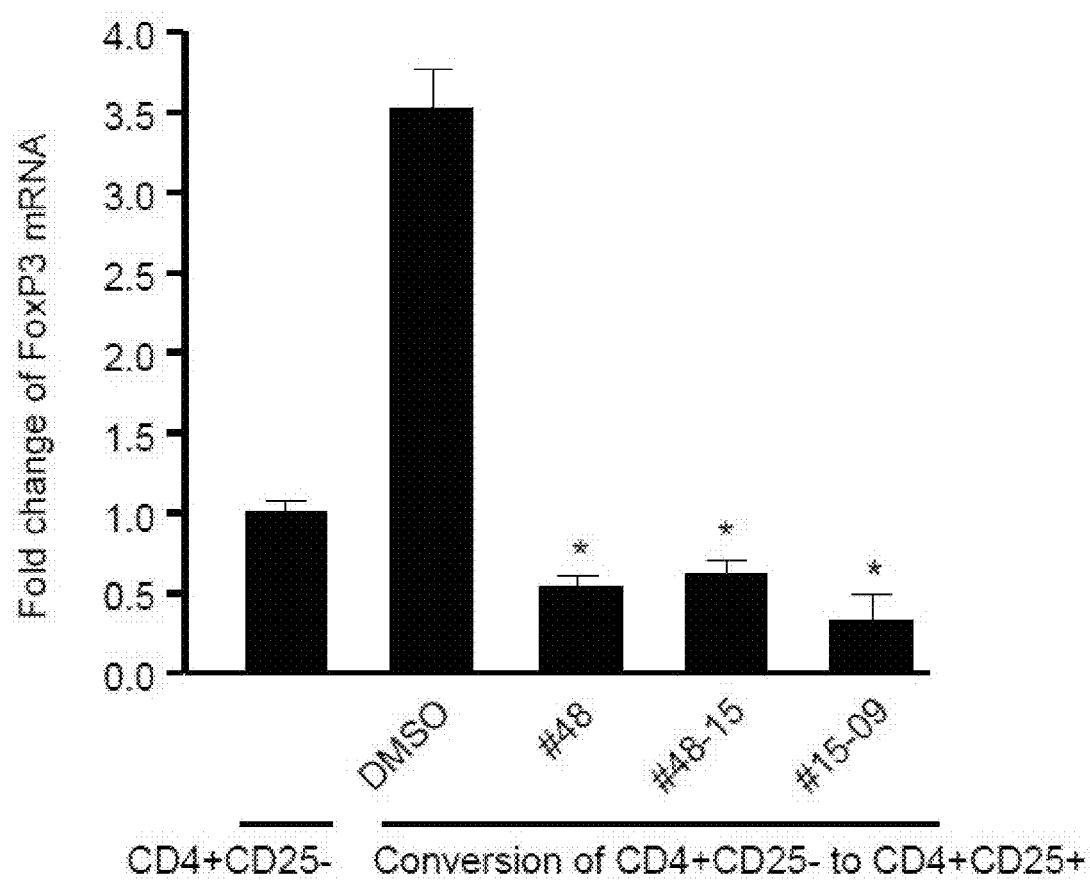
FIG. 5 depicts in accordance with various embodiments of the invention, inhibition of FoxP3 expression by small molecule compounds #48, #48-15, and #15-09. CD4+ CD25− T cells were isolated and cultured for the conversion to CD4+CD25+ T regs in the presence or absence of small molecule compounds #48 (50 µM), #48-15 (50 µM), and #15-09 (100 µM) and harvested for analysis by qPCR for Foxp3 expression. Data show mean±SD, n=3: *, P<0.01.

While the current state of the art in docking simulations and scoring technologies are very good at generating the correct binding pose of a given ligand, they are less facile in identifying the bioactive conformation as a top scoring pose (scoring issue) or rank-ordering the bioactive poses of different ligands (rank-ordering issue), effects that determine the success of a docker in high throughput virtual screening. Because none of the presently available dockers are capable of performing well in overcoming the scoring and rank-ordering issues, researchers apply consensus docking and scoring strategies to improve the enrichment of in silico screens[34] In the present study, we performed docking of the GlideXP-1400 molecule set using two additional well-known dockers commercially available to the scientific community: Surflex and FlexX. We selected 50% of the molecules top-ranked by all three dockers (Glide XP, Surflex and FlexX) and chose a common set of 150 molecules (SBVS-150) after performing ADME/Tox filtering analysis (FIG. 22). The KLF10 luciferase reporter screen of 40 molecules from the SBVS-150 set validated the activity of 11 structurally different inhibitor scaffolds (Table 1). We selected compounds #48 and #15 for further chemical space expansion leading to more than 30 additional inhibitors. Each of the three compounds #48, #48-15 and #15-09 inhibited KLF10 transcriptional activity (FIG. 1-FIG. 2), KLF10-DNA binding (gel mobility shift assay) (FIG. 3), conversion of CD4+CD25− T cells to CD4+CD25+ T regs (FIG. 4), and Foxp3 gene expression (FIG. 5).

Binding Mode and Molecular Interactions Analysis of Compounds #48, #48-15 and #15-09.

Owing to the shallow pocket, there was variation in top binding poses from different docking runs. In order to explore this variability problem in multiple scales of speed and accuracy, we performed two types of optimizations on the top 50 poses of #15 and #48 series of inhibitors obtained from the Glide XP docking run as below: (1) Glide "refinement", in which only the ligand was allowed to relax in the protein binding pocket followed by re-scoring of each pose with Glide XP function; and (2) eMBrAcE minimization, which allowed both ligand and its surrounding 5 Å residues to relax, followed by in-place scoring and ranking of eMBrAcE minimized complexes using Glide. An analysis of output of these two optimization procedures revealed that rank ordering or enrichment of eMBrAcE-optimized complexes correlated better to luciferase activity of these hits, justifying the need for protein and ligand relaxation to obtain a more stable binding pose (FIG. 6). However, none of these attempts categorically separated actives from false positives (decoys).

Figure 6A:
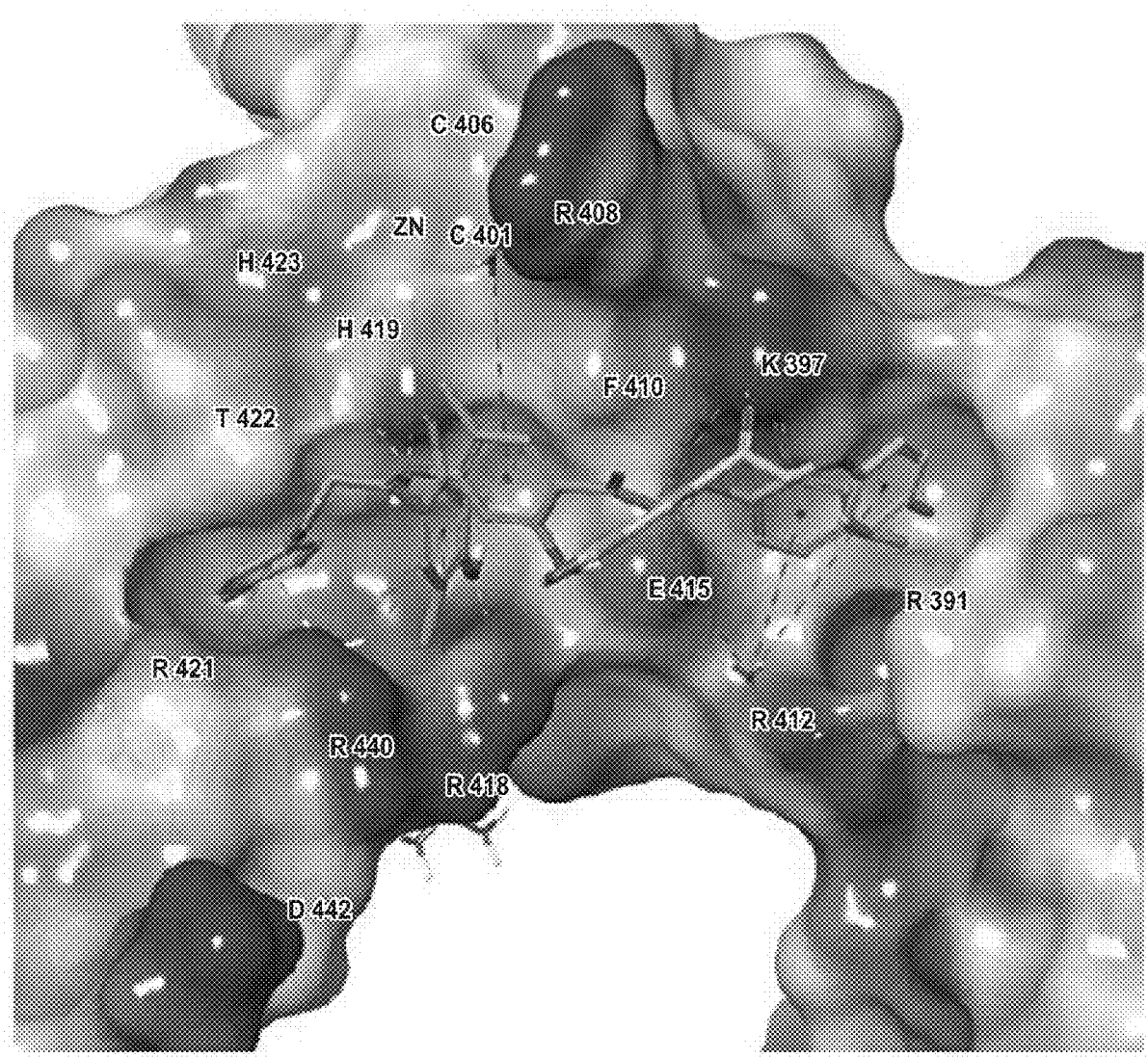
FIG. 6A-FIG. 6C depicts in accordance with various embodiments of the invention, binding modes of compounds #48 (FIG. 6A), #48-15 (FIG. 6B) and #15-09 (FIG. 6C) as predicted by Glide docking simulation. Protein side chains in green refer to the original position of receptor coordinates used in docking. The compound in gray stick refers to the rescored pose; the compound in torquise (sky blue) stick refers to the refined ligand pose; the compound in plum/pink stick refers to the eMBrAcE minimized (and xGlide rescored top) pose. Yellow dotted lines indicate H-bonds between ligand and receptor. The eMBrAcE minimization considers flexibility of both ligand and residues within 5 Å pocket surrounding the ligand and is shown superimposed (plum colored side chain) to outline the changes after minimization.
Figure 6A:
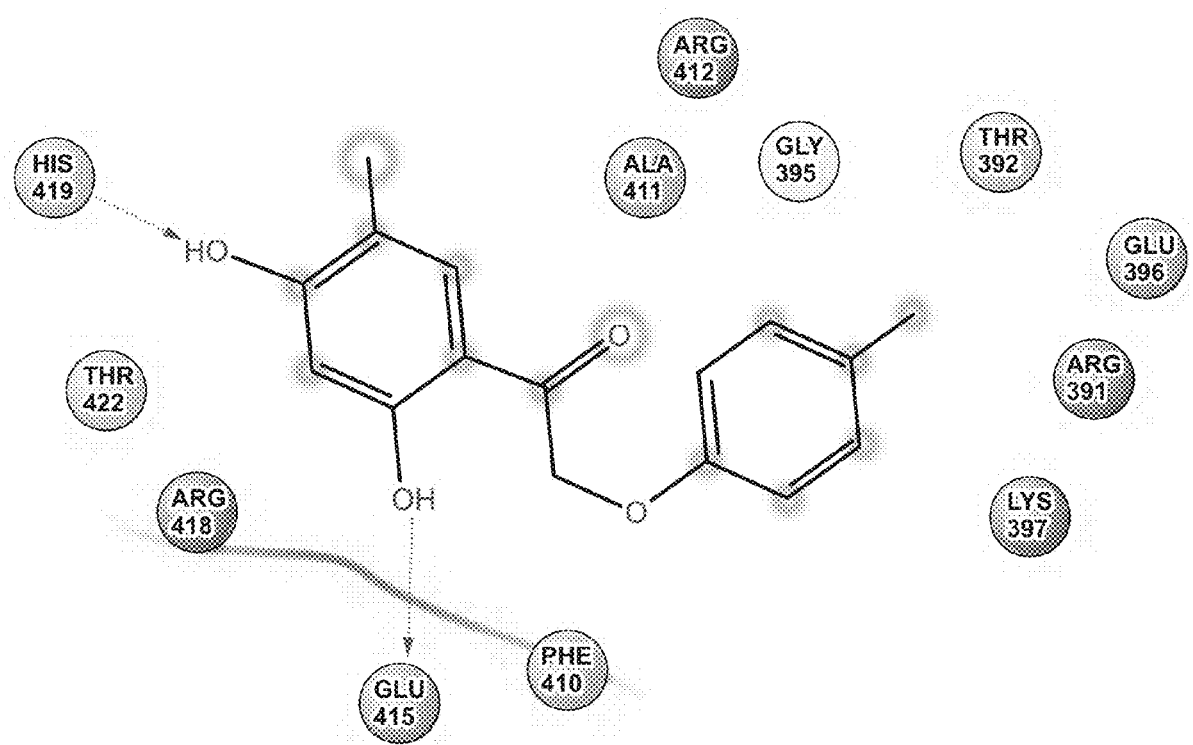
Figure 6B:
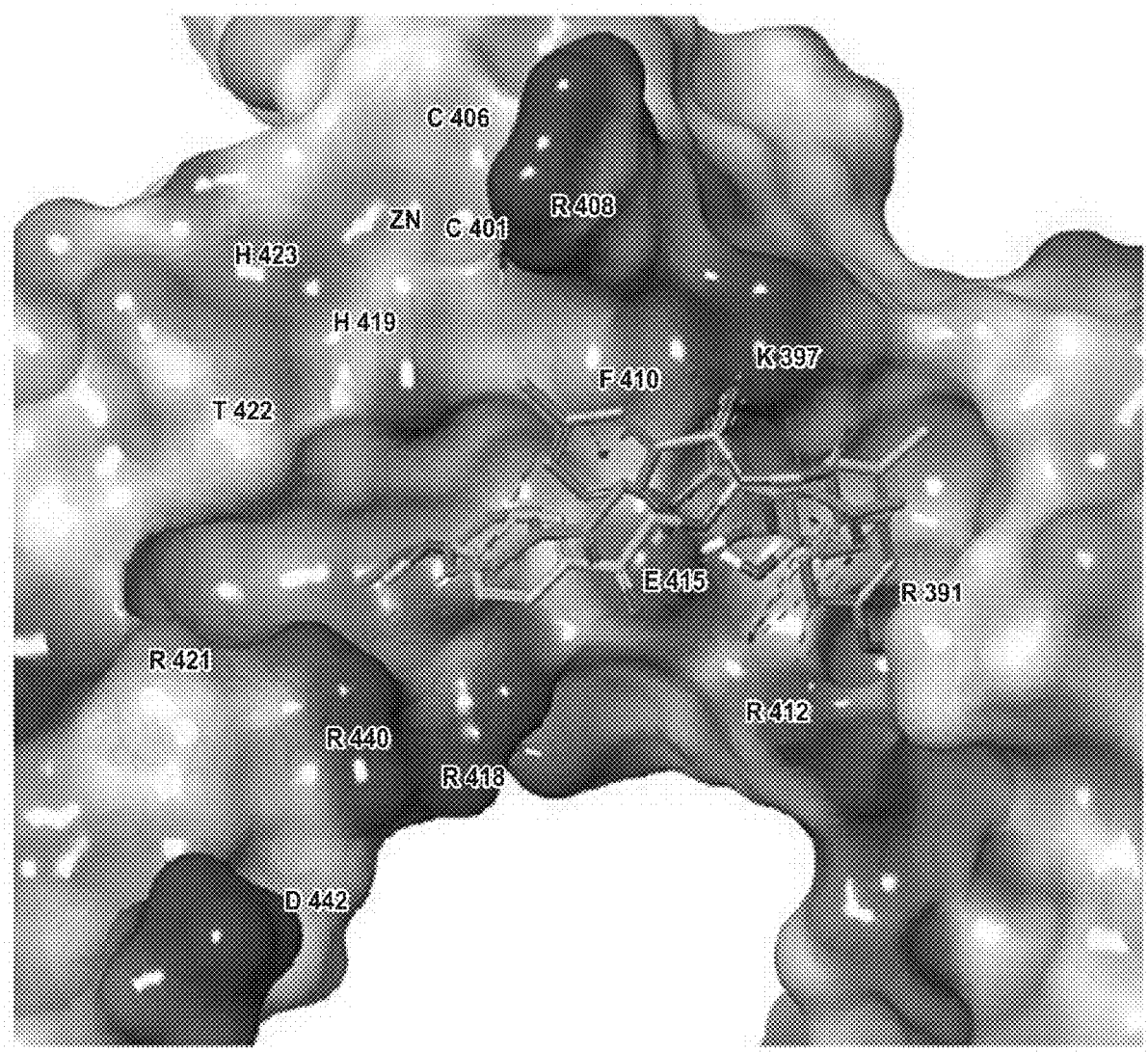
Figure 6B:
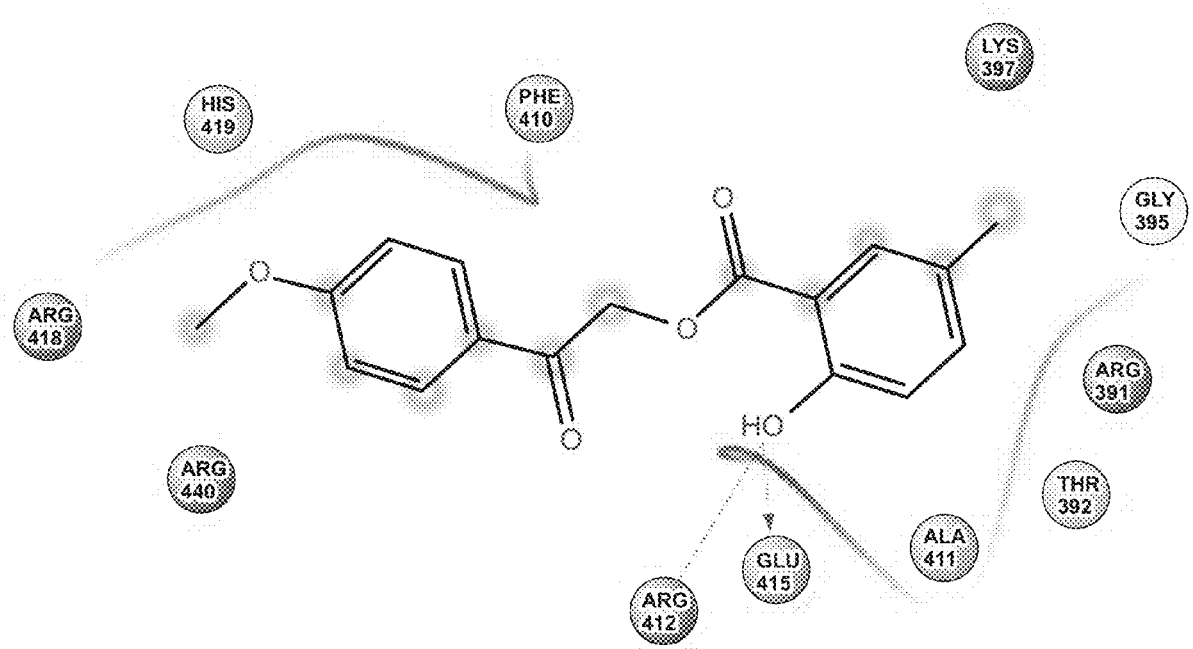
Figure 6C:
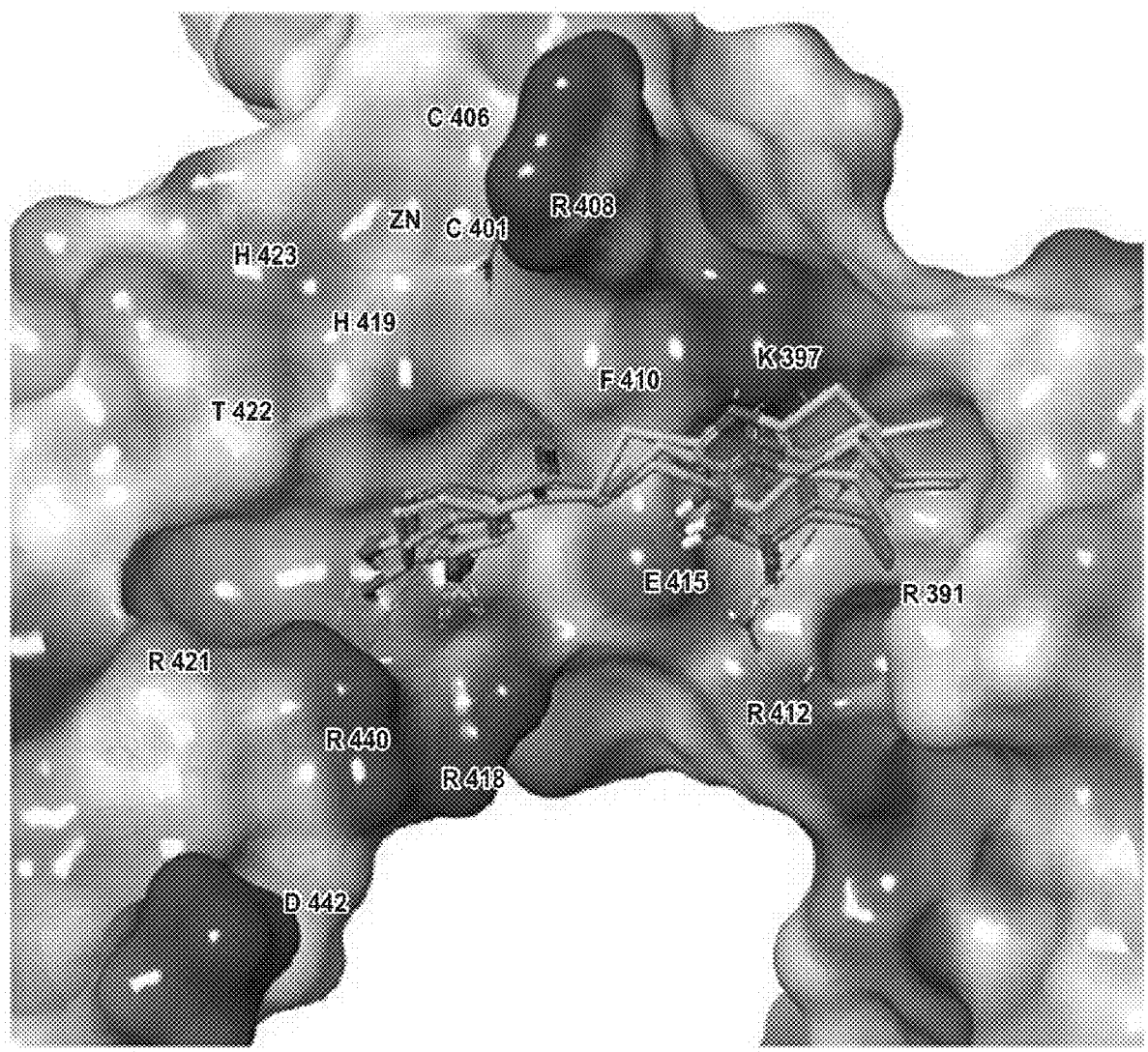
Figure 6C:
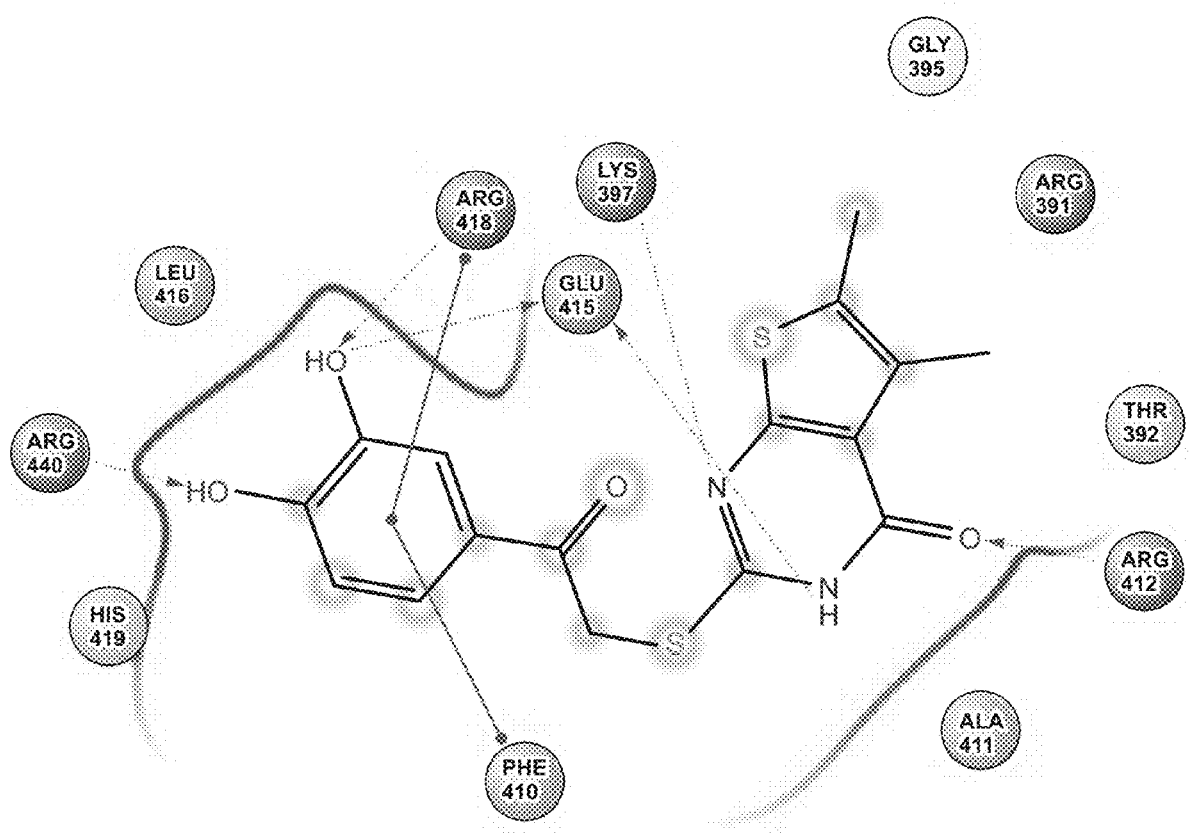
Figure 7:
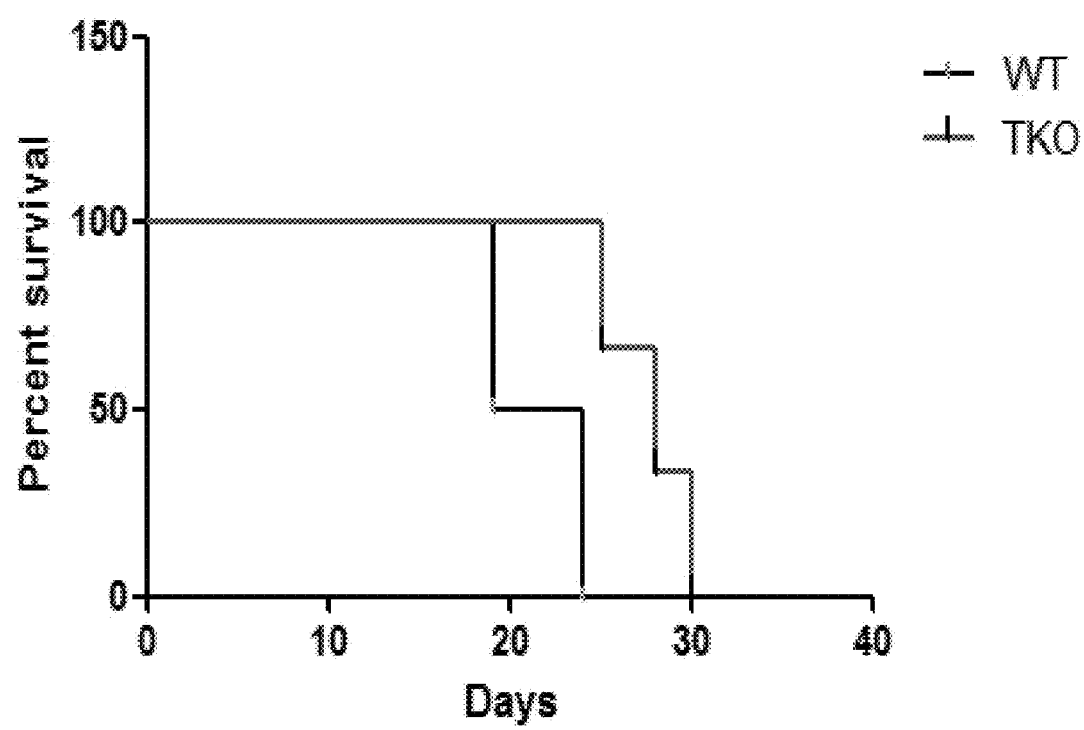
FIG. 7 depicts in accordance with various embodiments of the invention, CD4-KLF10-deficient (TKO) mice injected with B16 melanoma cells exhibit: 1) Improved survival; 2) Reduced tumor burden; 3) Reduced T reg cell accumulation in tumors.
Figure 7:
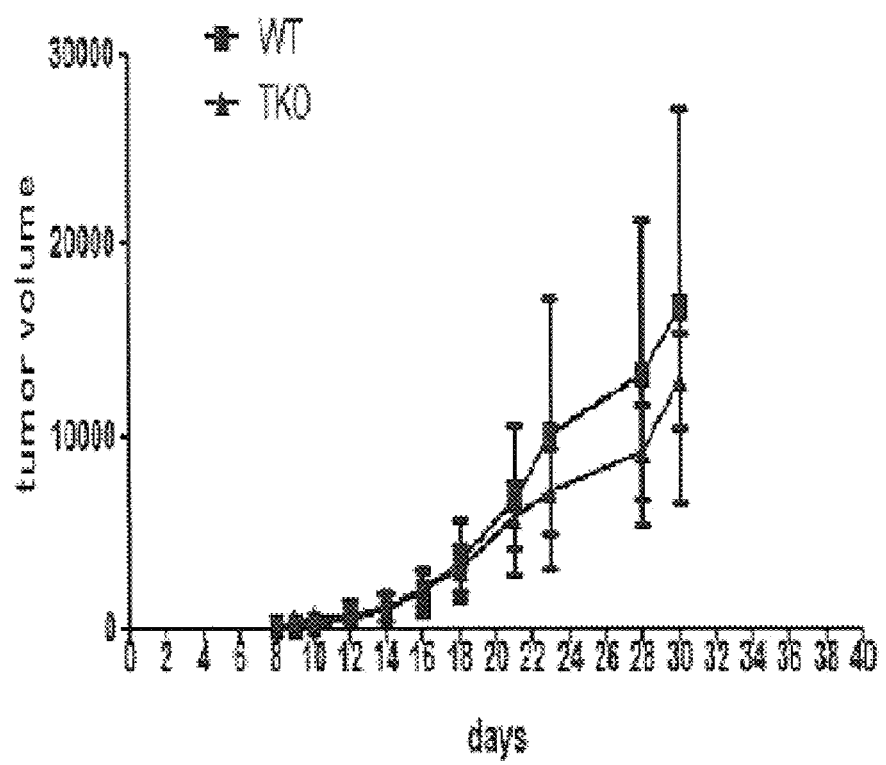
Figure 7:
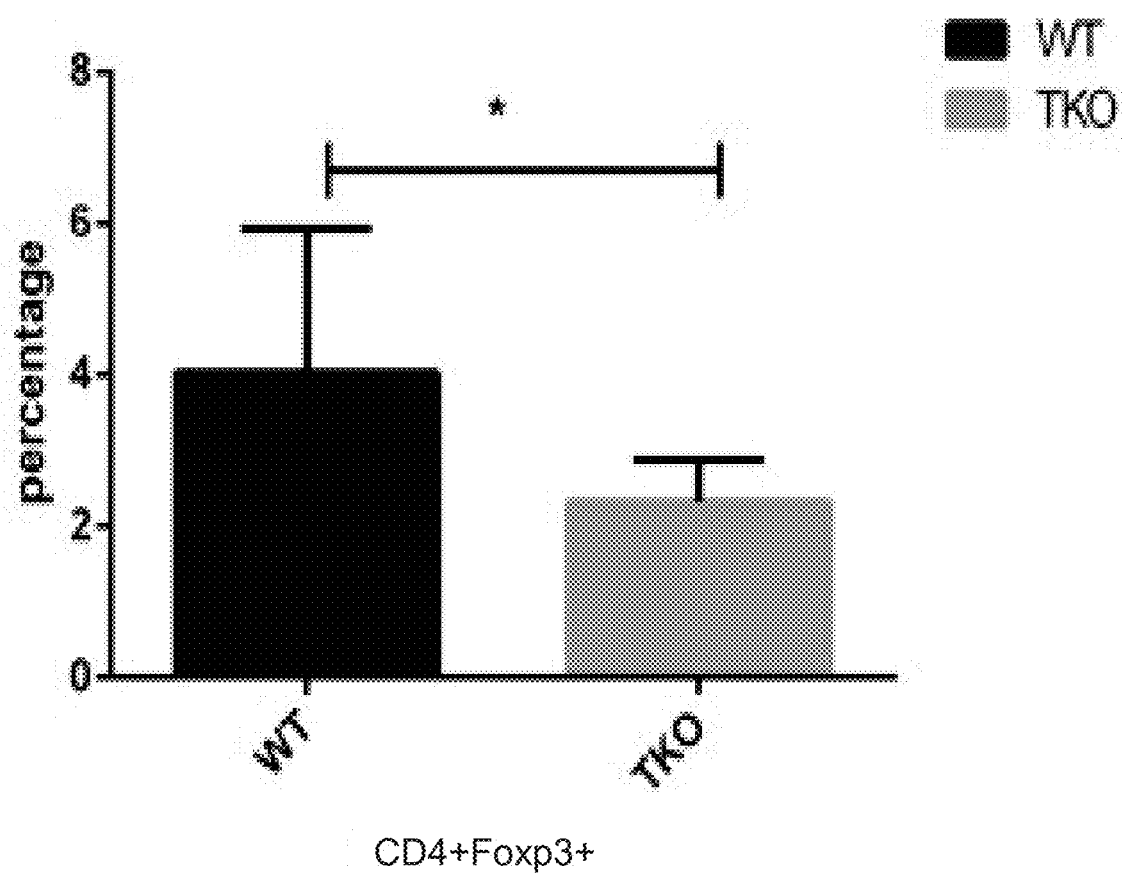
Figure 8:
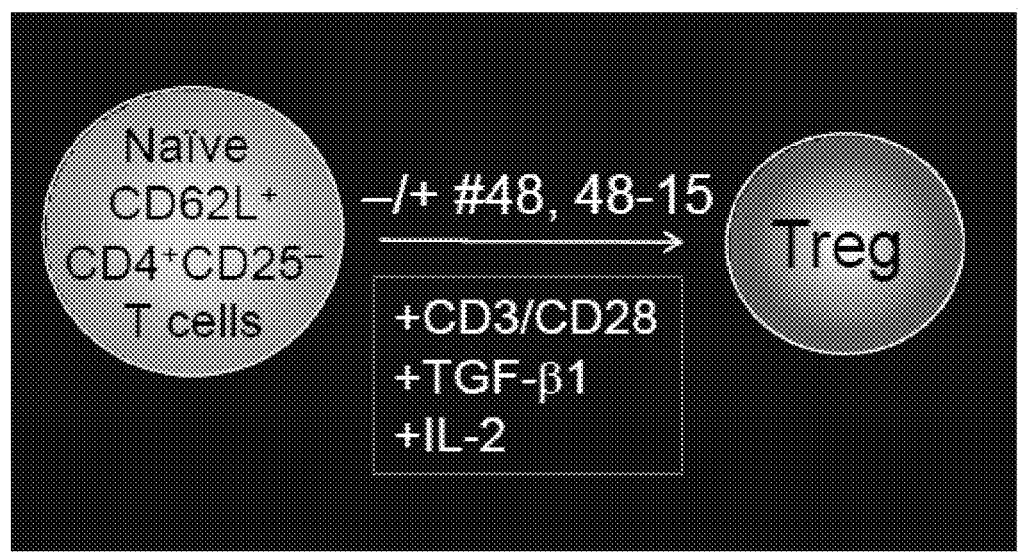
FIG. 8 depicts in accordance with various embodiments of the invention, small molecules inhibit PD1 and Foxp3 in iTregs (qRT-PCR analyses); n=5/group.
Figure 8:
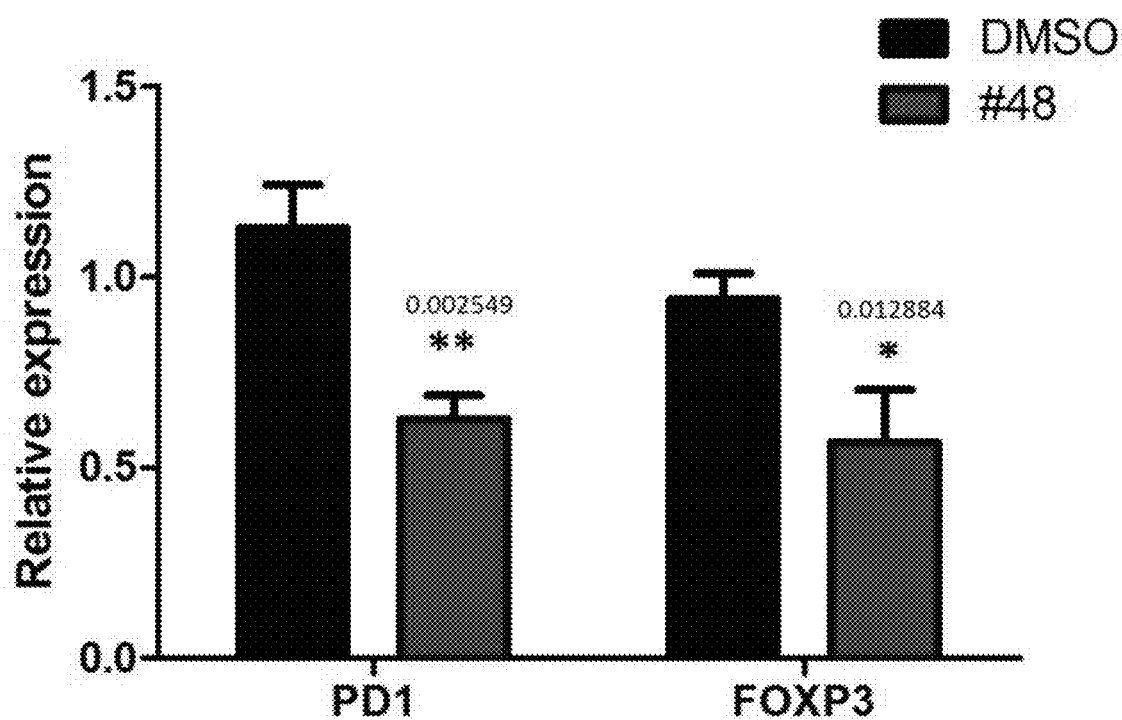
Figure 8:
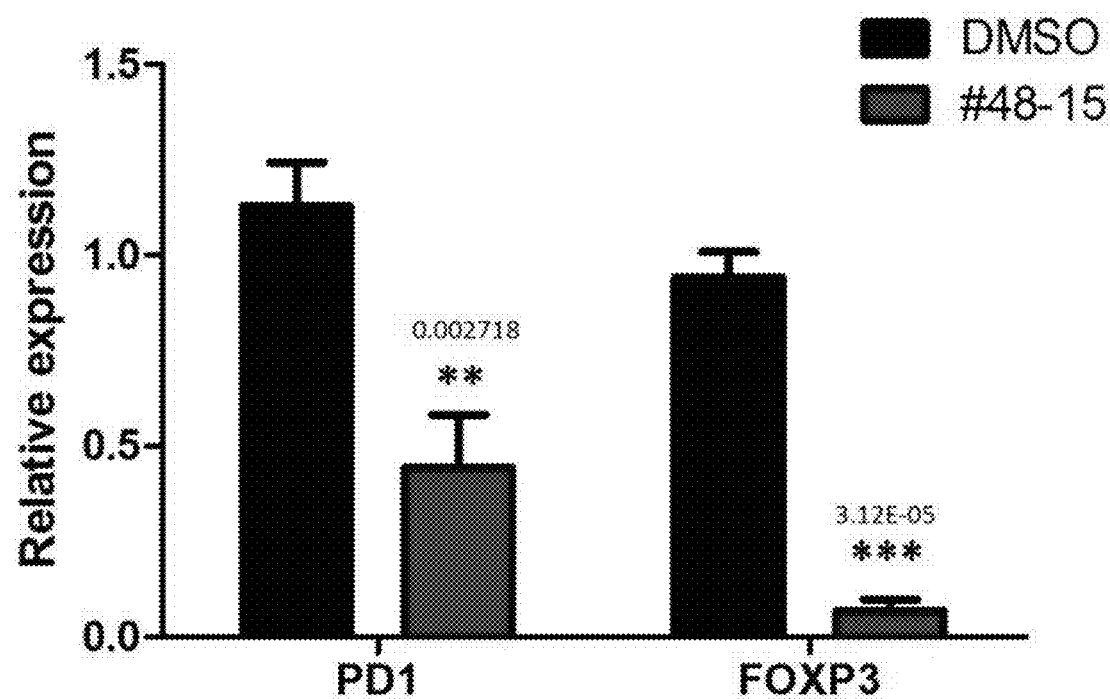
Figure 9:
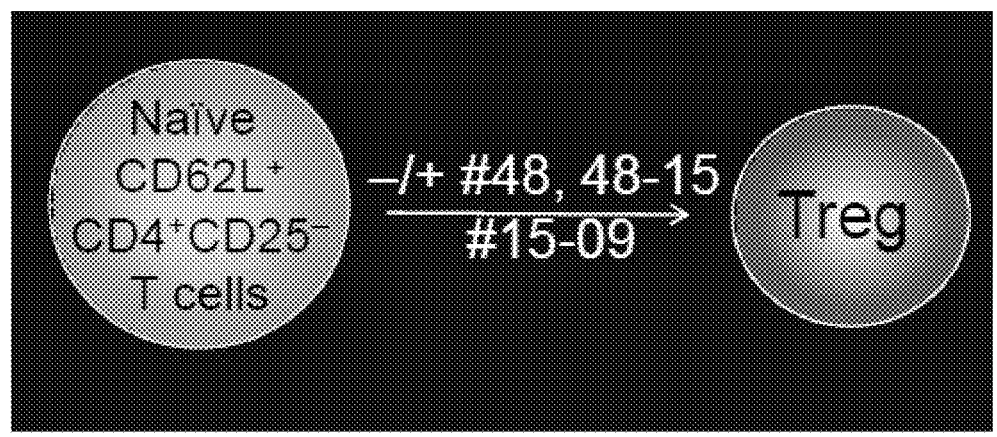
FIG. 9 depicts in accordance with various embodiments of the invention, small molecules dose-dependent inhibition of T regulatory cell differentiation; n=5/group.
Figure 9:
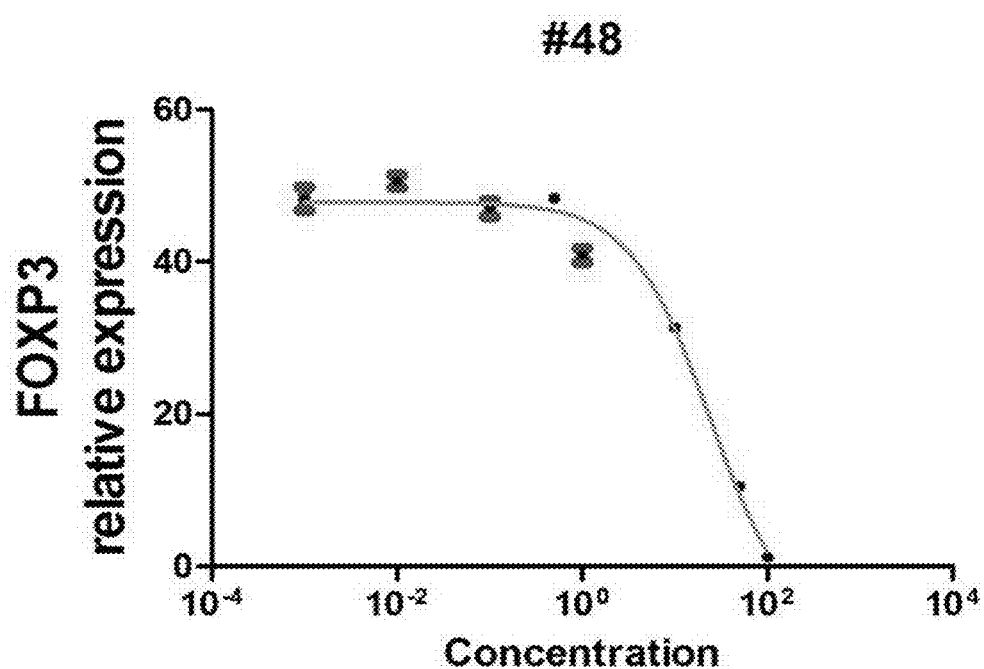
Figure 9:
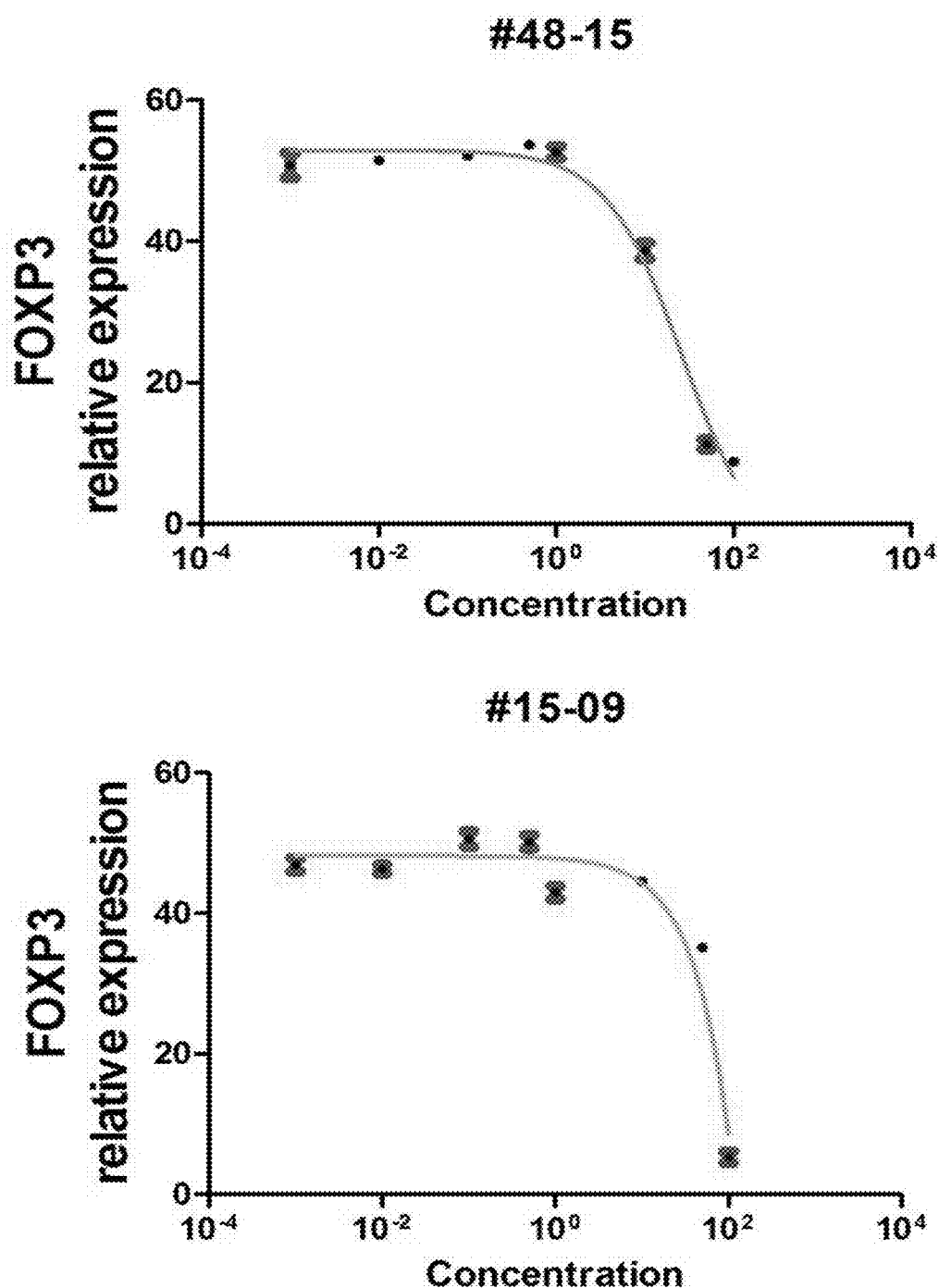
Figure 10:
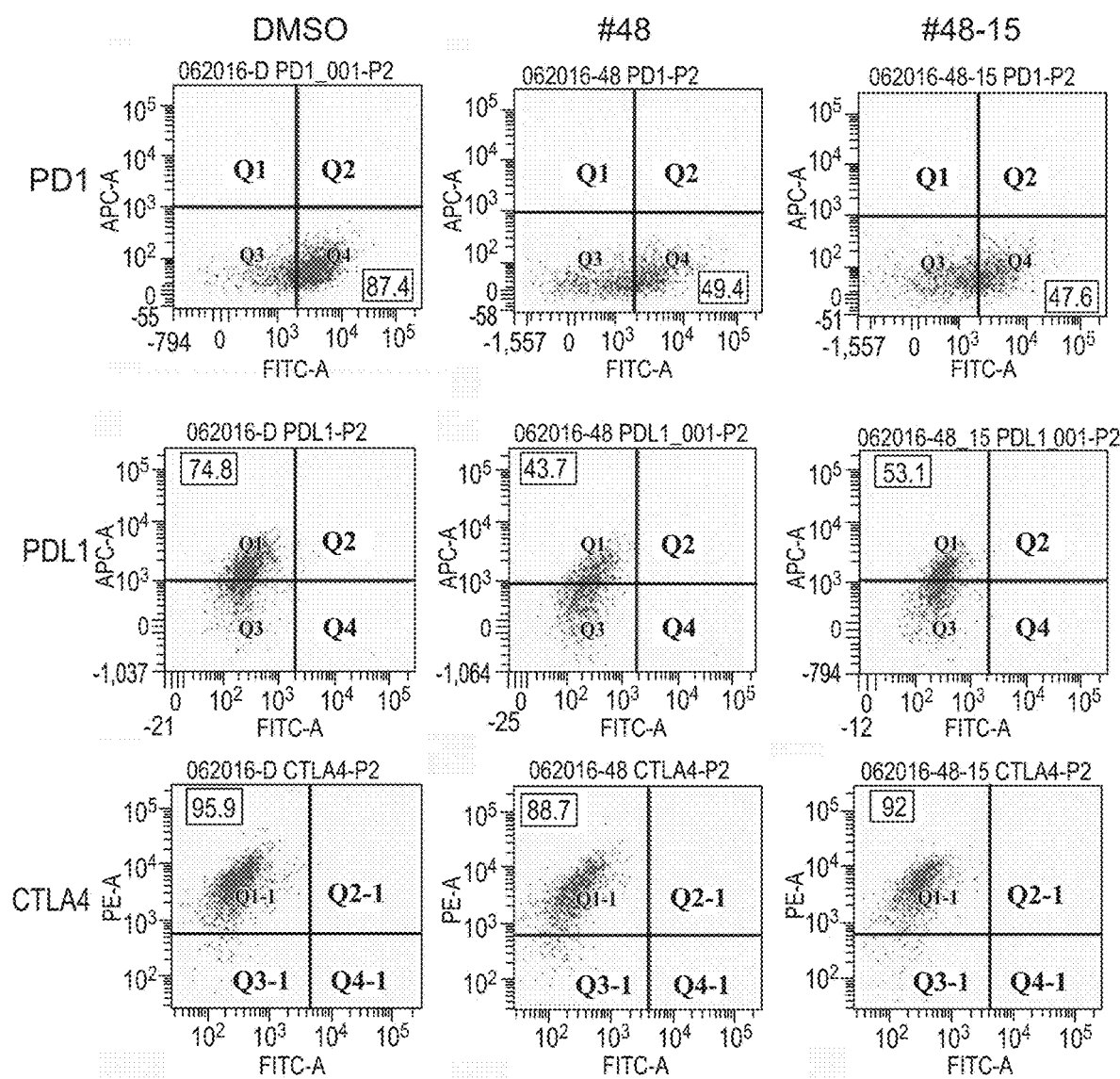
FIG. 10 depicts in accordance with various embodiments of the invention, small molecules inhibit checkpoint markers on iTregs (Flow Cytometry, PD1/PDL1/CTLA4); n=5/group.
Figure 10:
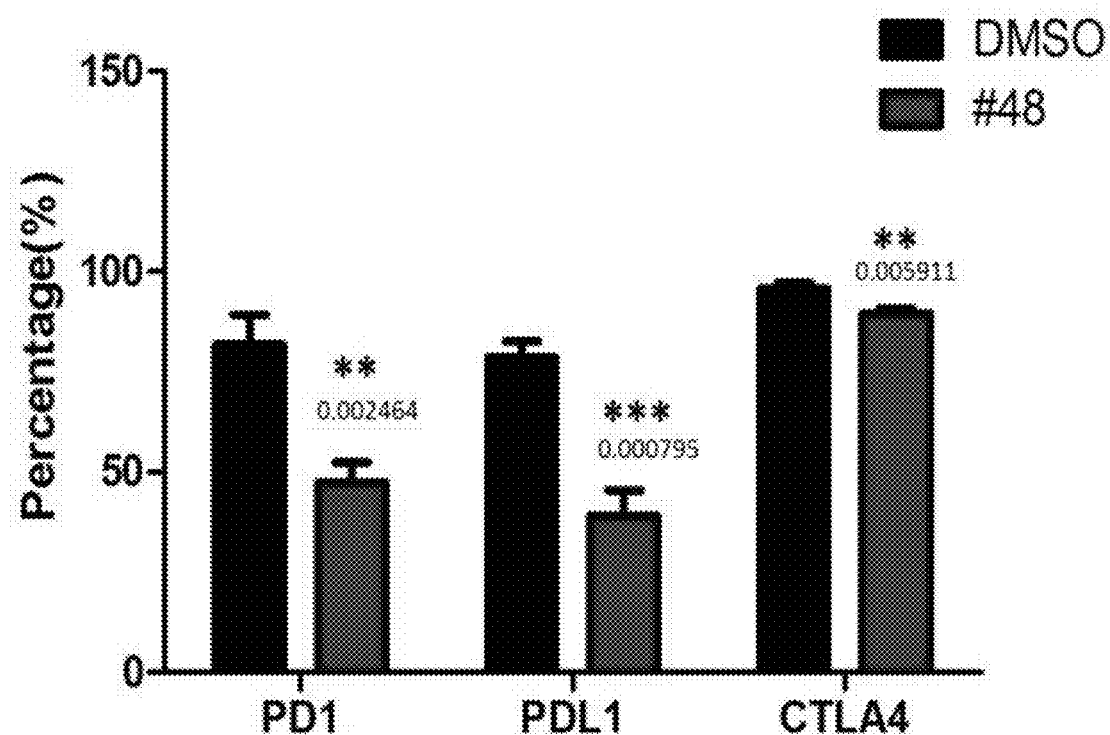
Figure 10:
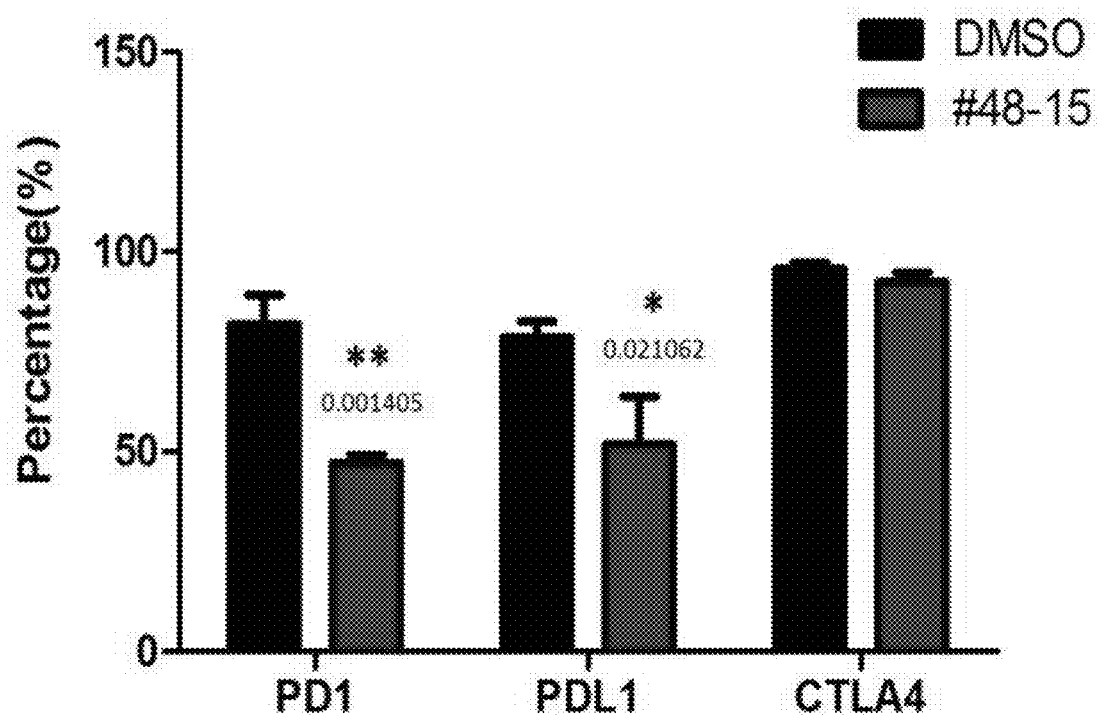
Figure 11:
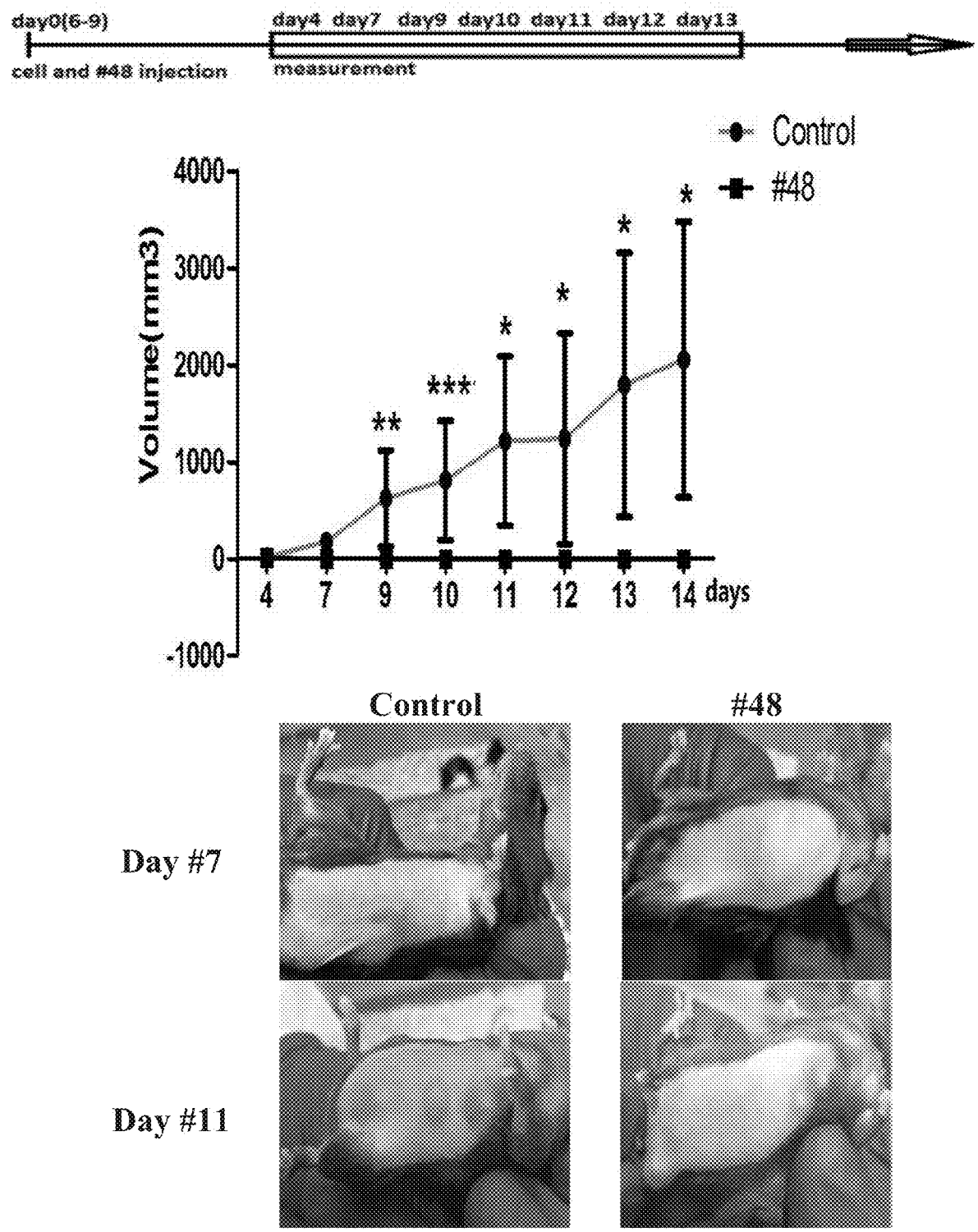
FIG. 11 depicts in accordance with various embodiments of the invention, small molecule #48 inhibits in vivo B16 melanoma tumor (local injection Day 0, 20 mg/kg); N=5/group, *P<0.01.
Figure 12:
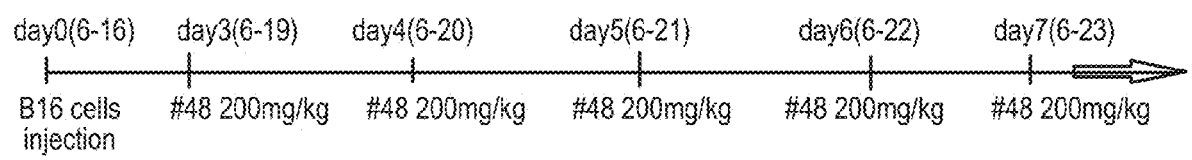
FIG. 12 depicts in accordance with various embodiments of the invention, small molecule #48 inhibits B16 melanoma tumor model (Systemic delivery i.p. Day 3, 200 mg/kg); N=5/group.
Figure 12:
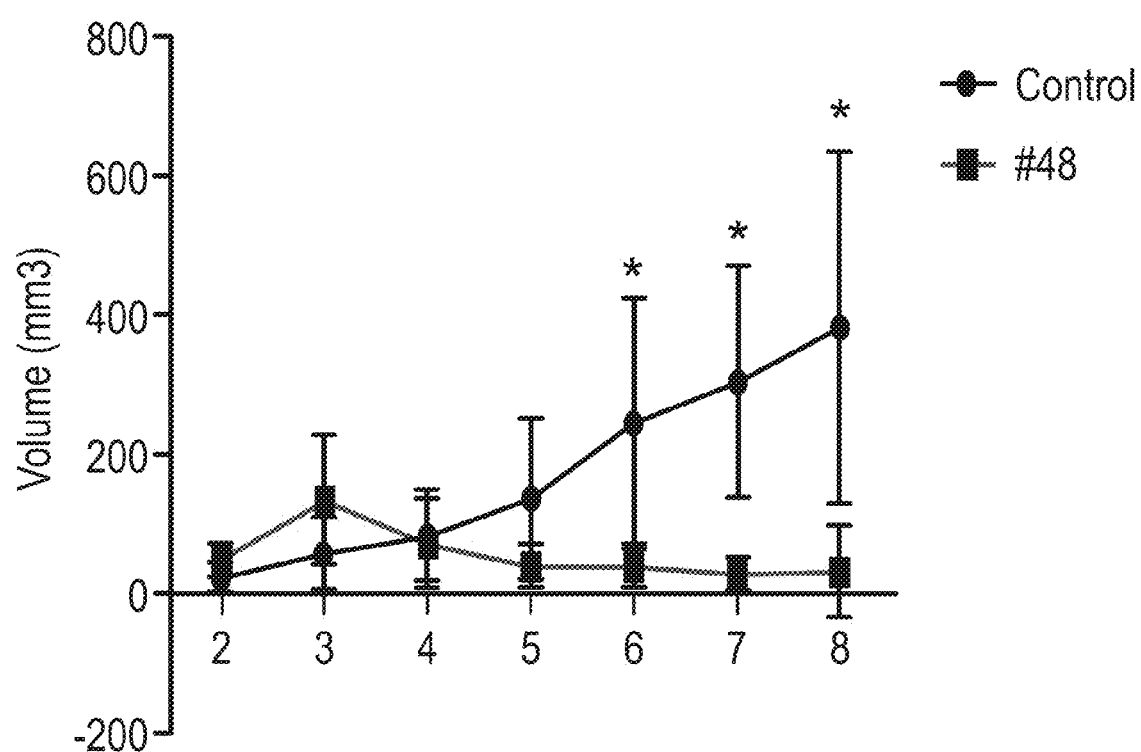
Figure 13:
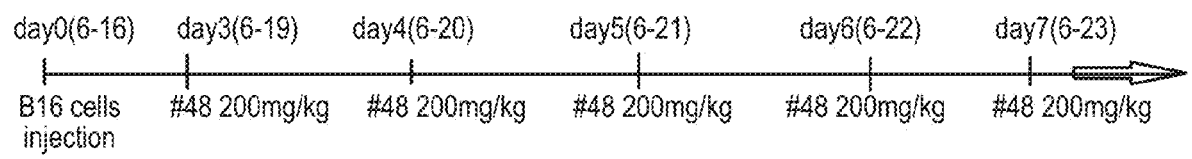
FIG. 13 depicts in accordance with various embodiments of the invention, small molecule #48 inhibits prostate TRAMP-C2 tumors (Systemic delivery i.p. Day 3, 200 mg/kg); N=5/group.
Figure 13:
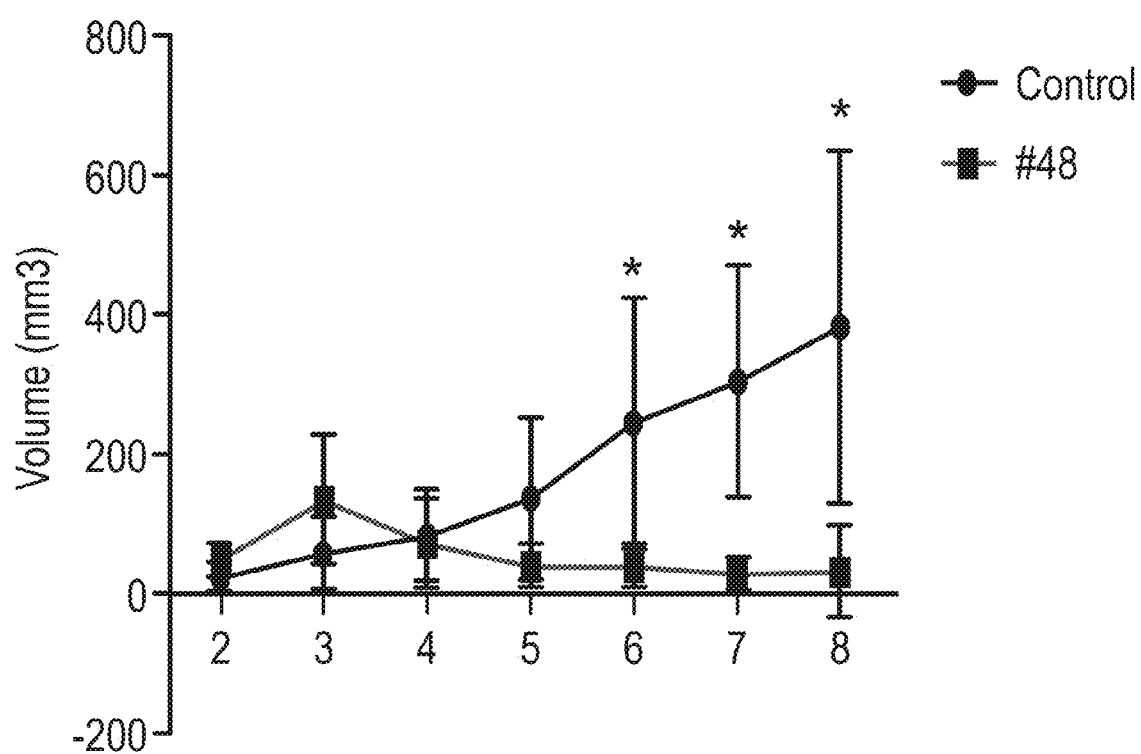
Figure 14:
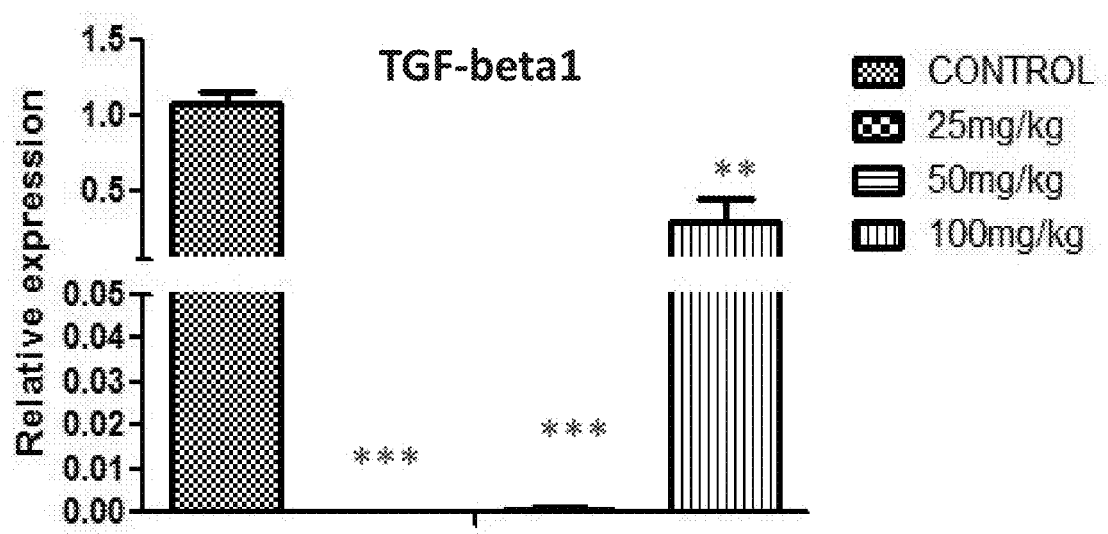
FIG. 14 depicts in accordance with various embodiments of the invention, CD4+ T cells isolated from B16 melanoma tumors from mice injected i.p. with small molecule #48 have reduced TGF-beta1 expression.

Docking with eMBrAcE minimization of compound #48 within the KLF10 pocket shows the possibility of various binding modes without substantial loss of binding energy (Docking Score, DS: −5.4 to −4.5), with its resorcinol ring occupying either the α- or β-pocket. The top pose of compound #48 stably docked in α-pocket (FIG. 6A), however other poses can also fit into β-pocket. In the α-pocket, the resorcinol ring of compound #48 participates in π-interactions with the phenyl ring of Phe410 and two hydroxyl groups form hydrogen bond interactions with side chains of His419 (through p-OH) and Glu415 (through o-OH). Among the Glide "refine" poses (FIG. 6A; green sticks), the top pose occupied only the α-pocket with two —OH forming hydrogen bonds with His419 (through o-OH) and Arg418 (through p-OH) and toluene ring resting in the extreme of the α-pocket, whereas the rest of the poses occupied both pockets with either of two possible sets of hydrogen bonds between hydroxyl groups of compound #48 and His419 and Glu415 or Glu415 and Lys397 (C=O). Compound #48-15 represents a binding mode with two rings occupying two subpockets and a hydroxyl group forming a hydrogen bond with either His419 or Glu415, an effect that may be due to its symmetrical linker (—CO—$CH_2$—CO—) connecting two rings (FIG. 6B). An analysis of Glide "refine" poses (FIG. 6B, green sticks) also revealed a unique binding mode occupying both pockets, with a hydroxyl group making hydrogen bonding interactions with the side chain carboxyl of Glu415 and the backbone amine of Ala411 (bifurcated H-bond), whereas the carbonyl oxygen of ester in compound #48-15 forms a hydrogen bond with Lys397. In the representative binding modes of the eMBrAcE minimized poses (FIG. 6B, plum sticks), the phenolic ring occupied β-pocket (in some cases it forms H-bond with carboxylic oxygen of Glu415), while oxygen of methyl ether in the α-pocket forms a hydrogen bond with side chain nitrogen of His419 and carbonyl oxygen of linker ester forms a hydrogen bond with Lys397.

The binding mode analysis of #15-09 revealed that it occupies both pockets (FIG. 6C; gray, green and plum sticks), with the pyrimidothiophene ring residing in the β-pocket and m-OH group of the other ring in the α-pocket, forming hydrogen bonds with the guanidinium side chain of Arg418, backbone oxygen of Glu415, and/or the side chain imidazole of His419. The Glide "refine" as well as eMBrAcE minimized poses also revealed the similar pattern of binding for compound #15-09 but more equivocally and with least variation in poses due to relaxation of ligand and/or receptor pocket after optimization.

Thus, the general binding patterns of compound #15 series scaffolds has an overall similarity with the binding pattern of #48 compound series scaffold such that two aromatic rings occupy the two pockets. This may be, in part, due to the similarity in the linker [—X—CH2-C(=O)—], separating the aromatic rings placed in two respective pockets and forming a bridge to connect them. This similarity, in part, may also underlie the mechanism of binding of these compounds, as has been reflected in their luciferase potencies ($IC_{50}$ values of #48-15 and #15-09 are ~40 M), ability to inhibit DNA binding, and T reg cell differentiation. The length and nature of the linker [X=O versus X=OC(=O)] in these series (Table 2 and Table 3) may play a serious role in proper placement of aromatic rings in respective pockets which may afford further stability through aromatic and hydrophobic interactions in addition to physical anchoring for tighter binding. As a result, modifying the linker could provide future scope for additional series of inhibitors, which may be even more potent than the ones reported here.

In summary, we demonstrate the discovery of small molecule inhibitors of the KLF10-DNA interaction interface using in silico screens of chemical libraries. Interrogation of a "druggable" pocket in the $2^{nd}$ zinc-finger of KLF10 revealed three molecules, #48, #48-15, and #15-09, with similar scaffolds and binding patterns. Indeed, each of these small molecules inhibited KLF10-DNA binding and transcriptional activity, conversion of CD4+CD25− T cells to CD4+CD25+ T regs, and KLF10 target gene expression. Taken together, these findings support the feasibility of using CADD with functional assays to identify small molecules that target members of the KLF subfamily of transcription factors to regulate biological functions in health and disease.

Non-Limiting Uses of Various Embodiments of the Present Invention

Various embodiments of the present invention provide compositions that induce robust effector responses and reduced T reg responses against tumors and chronic infections. Various embodiments of the present invention provide compositions that modulate Treg responses. Various embodiments of the present invention provide compositions and methods for decreasing T reg cells at a tumor site or pathogen infected area in a subject.

Therapeutic uses for the disclosed compositions include the treatment of one or more symptoms of cancer and/or induction of tumor immunity. Exemplary tumor cells that can be treated, include but not limited to, sarcoma, melanoma, lymphoma, leukemia, neuroblastoma, or carcinoma cells.

Representative infections that can be treated with the immunomodulatory agents include, but are not limited to, infections caused by a virus, bacterium, parasite, protozoan, or fungus. Exemplary viral infections that can be treated include, but are not limited to, infections caused by hepatitis virus, human immunodeficiency virus (HIV), human T-lymphotrophic virus (HTLV), herpes virus, influenza, Epstein-Barr virus, filovirus, or a human papilloma virus. Other infections that can be treated include those caused by *Plasmodium, Mycoplasma, M. tuberculosis, Bacillus anthracis, Staphylococcus*, and *C. trachomitis*. The compositions can be administered in combination or alternation with a vaccine containing one or more antigens such as viral antigens, bacterial antigens, protozoan antigens, and tumor specific antigens.

The compositions can be used as effective adjuvants with vaccines to increase primary immune responses and effector cell responses in subjects. Preferred subjects to be treated have a weakened or compromised immune system, are greater than 65 years old, or are less than 2 years of age.

In certain embodiments, the immunomodulatory agents decrease Treg cells at a tumor site or pathogen infected area. This decrease in Tregs can increase the number of Th17 cells and the level of IL-17 production. The immunomodulatory agents increase T cell cytotoxicity in a subject, induce a robust immune response in subjects and overcome T cell exhaustion and T cell anergy in the subject.

Methods of Use

Immunomodulatory agents describe herein can be used to inhibit KLF10, and suppress KLF10 mediated expression of KLF10 target gene Fox3p (a critical regulator of Treg cell differentiation) and decrease Treg cells at a tumor site or pathogen infected area. Blocking the interaction of KLF10-DNA interaction decreases KLF10 transcriptional activity and the differentation of T cells (CD4+CD25−) to Treg (CD4+CD25+) cells, and therefore the number of Tregs at a tumor site or site of infection. Thus, the suppressive function of Tregs is reduced at a tumor site or pathogen infected area. A reduction in the number of Tregs can lead to an increase in Th17 cell production and/or IL-17 production. Accordingly, a preferred immunomodulatory KLF10 inhibitors as disclosed herein results in decreased Tregs at a tumor site or a pathogen infected area.

Immunomodulatory polypeptide agents and variants thereof, as well as nucleic acids encoding these polypeptides and fusion proteins, or cells expressing immunomodulatory polypeptide can be used to enhance a primary immune response to an antigen as well as increase effector cell function such as increasing antigen-specific proliferation of T cells, enhance cytokine production by T cells, and stimulate differentiation. The immunostimulatory agents can be used to treat cancer.

The immunomodulatory polypeptide agents can be administered to a subject in need thereof in an effective amount to treat one or more symptoms associated with cancer, help overcome T cell exhaustion and/or T cell anergy. Overcoming T cell exhaustion or T cell anergy can be determined by measuring T cell function using known techniques.

In vitro application of the immunomodulatory agents can be useful, for example, in basic scientific studies of immune mechanisms or for production of activated T cells for use in studies of T cell function or, for example, passive immunotherapy.

Furthermore, immunomodulatory agents can be added to in vitro assays (e.g., T cell proliferation assays) designed to test for immunity to an antigen of interest in a subject from which the T cells were obtained. Addition of an immunomodulatory agents to such assays would be expected to result in a more potent, and therefore more readily detectable, in vitro response.

Administration of Immunomodulatory Agents for Immunoenhancement

Treatment of Cancer

The immunomodulatory agents provided herein are generally useful in vivo and ex vivo as immune response-stimulating therapeutics. In general, the disclosed immunomodulatory agent compositions are useful for treating a subject having or being predisposed to any disease or disorder to which the subject's immune system mounts an immune response. The ability of immunomodulatory agents to inhibit KLF10 or inhibit Treg cell differentiation enables a more robust immune response to be possible. The disclosed compositions are useful to stimulate or enhance immune responses involving T cells.

The disclosed immunomodulatory agents are useful for stimulating or enhancing an immune response in host for treating cancer by administering to a subject an amount of an immunomodulatory agent effective to stimulate T cells in the subject. The types of cancer that may be treated with the provided compositions and methods include, but are not limited to, the following: bladder, brain, breast, cervical, colorectal, esophageal, kidney, liver, lung, nasopharangeal, pancreatic, prostate, skin, stomach, uterine, ovarian, testicular and hematologic, and others.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

Treatment of Infections

The immunomodulatory agents are generally useful in vivo and ex vivo as immune response-stimulating therapeutics. In a preferred embodiment, the compositions are useful for treating infections in which T cell exhaustion or T cell anergy has occurred causing the infection to remain with the host over a prolonged period of time. Exemplary infections to be treated are chronic infections cause by a hepatitis virus, a human immunodeficiency virus (HIV), a human T-lymphotrophic virus (HTLV), a herpes virus, an Epstein-Barr virus, or a human papilloma virus. It will be appreciated that other infections can also be treated using the immunomodulatory agents. The disclosed compositions are also useful as part of a vaccine. In some embodiments, the type of disease to be treated or prevented is a chronic infectious disease caused by a bacterium, virus, protozoan, helminth, or other microbial pathogen that enters intracellularly and is attacked, i.e., by cytotoxic T lymphocytes.

Chronic infections in human and animal models are associated with a failure of the host immune response to generate and sustain functional $CD8^+$ and $CD4^+$ T-cell populations, which also results in poor antibody responses to neutralize infectivity. This loss of function is referred to as T cell exhaustion. T cell anergy is a tolerance mechanism in which the lymphocyte is intrinsically functionally inactivated following an antigen encounter, but remains alive for an extended period of time in a hyporesponsive state. One method for treating chronic infection is to revitalize exhausted T cells or to reverse T cell exhaustion in a subject as well as overcoming T cell anergy.

Because viral infections are cleared primarily by T-cells, an increase in T-cell activity is therapeutically useful in situations where more rapid or thorough clearance of an infective viral agent would be beneficial to an animal or human subject. Thus, the immunomodulatory agents can be administered for the treatment of local or systemic viral infections, including, but not limited to, immunodeficiency (e.g., HIV), papilloma (e.g., HPV), herpes (e.g., HSV), encephalitis, influenza (e.g., human influenza virus A), and common cold (e.g., human rhinovirus) viral infections. For example, pharmaceutical formulations including the immunomodulatory agent compositions can be administered topically to treat viral skin diseases such as herpes lesions or shingles, or genital warts. Pharmaceutical formulations of immunomodulatory compositions can also be administered to treat systemic viral diseases, including, but not limited to, AIDS, influenza, the common cold, or encephalitis.

Representative infections that can be treated, include but are not limited to infections cause by microoganisms including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus*, Hemophilus *influenza* type B (HIB), *Histoplasma, Hyphomicrobium, Legionella, Leishmania, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio, Yersinia, Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Plasmodium vivax, Trypanosoma brucei, Entamoeba histolytica, Toxoplasma gondii, Trichomonas vaginalis* and *Schistosoma mansoni*.

Use of Immunomodulatory Agents in Vaccines

The immunomodulatory agents may be administered alone or in combination with any other suitable treatment. In one embodiment the immunomodulatory agent can be administered in conjunction with, or as a component of a vaccine composition as described above. Suitable components of vaccine compositions are described above. The disclosed immunomodulatory agents can be administered prior to, concurrently with, or after the administration of a vaccine. In one embodiment the immunomodulatory agent composition is administered at the same time as administration of a vaccine.

Immunomodulatory agent compositions may be administered in conjunction with prophylactic vaccines, which confer resistance in a subject to subsequent exposure to infectious agents, or in conjunction with therapeutic vaccines, which can be used to initiate or enhance a subject's immune response to a pre-existing antigen, such as a viral antigen in a subject infected with a virus.

The desired outcome of a prophylactic, therapeutic or de-sensitized immune response may vary according to the disease, according to principles well known in the art. For example, an immune response against an infectious agent may completely prevent colonization and replication of an infectious agent, affecting "sterile immunity" and the absence of any disease symptoms. However, a vaccine against infectious agents may be considered effective if it reduces the number, severity or duration of symptoms; if it reduces the number of individuals in a population with symptoms; or reduces the transmission of an infectious agent. Similarly, immune responses against cancer, allergens or infectious agents may completely treat a disease, may alleviate symptoms, or may be one facet in an overall therapeutic intervention against a disease.

The immunomodulatory agents induce an improved effector cell response such as a CD4 T-cell immune response, against at least one of the component antigen(s) or antigenic compositions compared to the effector cell response obtained with the corresponding composition without the immunomodulatory polypeptide. The term "improved effector cell response" refers to a higher effector cell response such as a CD4 T cell response obtained in a human patient after administration of the vaccine composition than that obtained after administration of the same composition without an immunomodulatory polypeptide.

The improved effector cell response can be obtained in an immunologically unprimed patient, i.e. a patient who is seronegative to the antigen. This seronegativity may be the result of the patient having never faced the antigen (so-called "naive" patient) or, alternatively, having failed to respond to the antigen once encountered. Preferably the improved effector cell response is obtained in an immuno-compromised subject such as an elderly, typically 65 years of age or above, or an adult younger than 65 years of age with a high risk medical condition ("high risk" adult), or a child under the age of two.

The improved effector cell response can be assessed by measuring the number of cells producing any of the following cytokines: (1) cells producing at least two different cytokines (CD40L, IL-2, IFNy, TNF-a, IL-17); (2) cells producing at least CD40L and another cytokine (IL-2, TNF-a, IFNy, IL-17); (3) cells producing at least IL-2 and another cytokine (CD40L, TNF-alpha, IFNy, IL-17); (4) cells producing at least IFNy and another cytokine (IL-2, TNF-a, CD40L, IL-17); (5) cells producing at least TNF-a and another cytokine (IL-2, CD40L, IFNy, IL-17); and (6) cells producing at least IL-17 and another cytokine (TNF-alpha, IL-2, CD40L, IFNy, IL-17).

An improved effector cell response is present when cells producing any of the above cytokines will be in a higher amount following administration of the vaccine composition compared to the administration of the composition without an immunomodulatory agent as disclosed herein. Typically at least one, preferably two of the five conditions mentioned above will be fulfilled. In a preferred embodiment, cells producing all five cytokines (CD40L, IL-2, IFNy, TNF-α, IL-17) will be present at a higher number in the vaccinated group compared to the un-vaccinated group.

The immunogenic compositions may be administered by any suitable delivery route, such as intradermal, mucosal e.g. intranasal, oral, intramuscular or subcutaneous. Other delivery routes are well known in the art. The intramuscular delivery route is preferred for the immunogenic compositions. Intradermal delivery is another suitable route. Any suitable device may be used for intradermal delivery, for example short needle devices. Intradermal vaccines may also be administered by devices which limit the effective penetration length of a needle into the skin. Jet injection devices which deliver liquid vaccines to the dermis via a liquid jet injector or via a needle which pierces the stratum corneum and produces a jet which reaches the dermis can also be used. Jet injection devices are known in the art. Ballistic powder/particle delivery devices which use compressed gas to accelerate vaccine in powder form through the outer layers of the skin to the dermis can also be used. Additionally, conventional syringes can be used in the classical Mantoux method of intradermal administration.

Another suitable administration route is the subcutaneous route. Any suitable device may be used for subcutaneous delivery, for example classical needle. Preferably, a needle-free jet injector service is used. Needle-free injectors are known in the art. More preferably the device is pre-filled with the liquid vaccine formulation.

Alternatively the vaccine is administered intranasally. Typically, the vaccine is administered locally to the naso-pharyngeal area, preferably without being inhaled into the lungs. It is desirable to use an intranasal delivery device which delivers the vaccine formulation to the nasopharyngeal area, without or substantially without it entering the lungs. Preferred devices for intranasal administration of the vaccines are spray devices. Nasal spray devices are commercially available. Nebulizers produce a very fine spray which can be easily inhaled into the lungs and therefore does not efficiently reach the nasal mucosa. Nebulizers are therefore not preferred. Preferred spray devices for intranasal use are devices for which the performance of the device is not dependent upon the pressure applied by the user. These devices are known as pressure threshold devices. Liquid is released from the nozzle only when a threshold pressure is applied. These devices make it easier to achieve a spray with a regular droplet size. Pressure threshold devices suitable for use with the present invention are known in the art and are commercially available.

Preferred intranasal devices produce droplets (measured using water as the liquid) in the range 1 to 200 μm, preferably 10 to 120 μm. Below 10 μm there is a risk of inhalation, therefore it is desirable to have no more than about 5% of droplets below 10 μm. Droplets above 120 μm do not spread as well as smaller droplets, so it is desirable to have no more than about 5% of droplets exceeding 120 μm.

Bi-dose delivery is another feature of an intranasal delivery system for use with the vaccines. Bi-dose devices contain two sub-doses of a single vaccine dose, one sub-dose for administration to each nostril. Generally, the two sub-doses are present in a single chamber and the construction of the device allows the efficient delivery of a single sub-dose at a time. Alternatively, a monodose device may be used for administering the vaccines.

The immunogenic composition may be given in two or more doses, over a time period of a few days, weeks or months. In one embodiment, different routes of administration are utilized, for example, for the first administration may be given intramuscularly, and the boosting composition, optionally containing a immunomodulatory agent, may be administered through a different route, for example intradermal, subcutaneous or intranasal.

The improved effector cell response conferred by the immunogenic composition may be ideally obtained after one single administration. The single dose approach is extremely relevant in a rapidly evolving outbreak situation including bioterrorist attacks and epidemics. In certain circumstances, especially for the elderly population, or in the case of young children (below 9 years of age) who are vaccinated for the first time against a particular antigen, it may be beneficial to administer two doses of the same composition. The second dose of the same composition (still considered as "composition for first vaccination") can be administered during the on-going primary immune response and is adequately spaced in time from the first dose. Typically the second dose of the composition is given a few weeks, or about one month, e.g. 2 weeks, 3 weeks, 4 weeks, 5 weeks, or 6 weeks after the first dose, to help prime the immune system in unresponsive or poorly responsive individuals.

In a specific embodiment, the administration of the immunogenic composition alternatively or additionally induces an improved B-memory cell response in patients administered with the adjuvanted immunogenic composition compared to the B-memory cell response induced in individuals immunized with the un-adjuvanted composition. An improved B-memory cell response is intended to mean an increased frequency of peripheral blood B lymphocytes capable of differentiation into antibody-secreting plasma cells upon antigen encounter as measured by stimulation of in vitro differentiation (see Example sections, e.g. methods of Elispot B cells memory).

In a still another embodiment, the immunogenic composition increases the primary immune response as well as the CD8 T cell response. The administration of a single dose of the immunogenic composition for first vaccination provides better sero-protection and induces an improved CD4 T-cell, or CD8 T-cell immune response against a specific antigen compared to that obtained with the un-adjuvanted formulation. This may result in reducing the overall morbidity and mortality rate and preventing emergency admissions to hospital for pneumonia and other influenza-like illness. This method allows inducing a CD4 T cell response which is more persistent in time, e.g. still present one year after the first vaccination, compared to the response induced with the un-adjuvanted formulation.

Preferably the CD4 T-cell immune response, such as the improved CD4 T-cell immune response obtained in an unprimed subject, involves the induction of a cross-reactive CD4 T helper response. In particular, the amount of cross-reactive CD4 T cells is increased. The term "cross-reactive" CD4 response refers to CD4 T-cell targeting shared epitopes for example between influenza strains.

The dose of immunomodulatory agent enhances an immune response to an antigen in a human. In particular a suitable immunomodulatory agent amount is that which improves the immunological potential of the composition compared to the unadjuvanted composition, or compared to the composition adjuvanted with another immunomodulatory agent amount. Usually an immunogenic composition dose will range from about 0.5 ml to about 1 ml. Typical vaccine doses are 0.5 ml, 0.6 ml, 0.7 ml, 0.8 ml, 0.9 ml or 1 ml. In a preferred embodiment, a final concentration of 50 µg of immunomodulatory agent, preferably PD-L2-Ig, is contained per ml of vaccine composition, or 25 µg per 0.5 ml vaccine dose. In other preferred embodiments, final concentrations of 35.7 µg or 71.4 µg of immunomodulatory agent is contained per ml of vaccine composition. Specifically, a 0.5 ml vaccine dose volume contains 25 µg or 50 µg of immunomodulatory agent per dose. In still another embodiment, the dose is 100 µg or more. Immunogenic compositions usually contain 15 µg of antigen component as measured by single radial immunodiffusion (SRD) (J. M. Wood et al: J. Biol. Stand. 5 (1977) 237-247; J. M. Wood et al, J. Biol. Stand. 9 (1981) 317-330). Subjects can be revaccinated with the immunogenic compositions. Typically revaccination is made at least 6 months after the first vaccination(s), preferably 8 to 14 months after, more preferably at around 10 to 12 months after.

The immunogenic composition for revaccination (the boosting composition) may contain any type of antigen preparation, either inactivated or live attenuated. It may contain the same type of antigen preparation, for example split influenza virus or split influenza virus antigenic preparation thereof, a whole virion, a purified subunit vaccine or a virosome, as the immunogenic composition used for the first vaccination. Alternatively the boosting composition may contain another type of antigen, i.e. split influenza virus or split influenza virus antigenic preparation thereof, a whole virion, a purified subunit vaccine or a virosome, than that used for the first vaccination.

With regard to vaccines against a virus, a boosting composition, where used, is typically given at the next viral season, e.g. approximately one year after the first immunogenic composition. The boosting composition may also be given every subsequent year (third, fourth, fifth vaccination and so forth). The boosting composition may be the same as the composition used for the first vaccination.

Preferably revaccination induces any, preferably two or all, of the following: (i) an improved effector cell response against the antigenic preparation, or (ii) an improved B cell memory response or (iii) an improved humoral response, compared to the equivalent response induced after a first vaccination with the antigenic preparation without a Immunomodulatory agent. Preferably the immunological responses induced after revaccination with the immunogenic antigenic preparation containing the Immunomodulatory agent are higher than the corresponding response induced after the revaccination with the un-adjuvanted composition. The immunogenic compositions can be monovalent or multivalent, i.e, bivalent, trivalent, or quadrivalent. Preferably the immunogenic composition thereof is trivalent or quadrivalent. Multivalent refers to the number of sources of antigen, typically from different species or strains. With regard to viruses, at least one strain is associated with a pandemic outbreak or has the potential to be associated with a pandemic outbreak.

Combination Therapies

The immunomodulatory agent compositions can be administered to a subject in need thereof alone or in combination with one or more additional therapeutic agents. The additional therapeutic agents are selected based on the condition, disorder or disease to be treated. For example, an immunomodulatory agent can be co-administered with one or more additional agents that function to enhance or promote an immune response.

In a preferred embodiment, the additional therapeutic agent is cyclophosphamide. Cyclophosphamide (CPA, Cytoxan, or Neosar) is an oxazahosphorine drug and analogs include ifosfamide (IFO, Ifex), perfosfamide, trophosphamide (trofosfamide; Ixoten), and pharmaceutically acceptable salts, solvates, prodrugs and metabolites thereof (US patent application 20070202077 which is incorporated in its entirety). Ifosfamide (MITOXANAO) is a structural analog of cyclophosphamide and its mechanism of action is considered to be identical or substantially similar to that of cyclophosphamide.

Perfosfamide (4-hydroperoxycyclophosphamide) and trophosphamide are also alkylating agents, which are structurally related to cyclophosphamide. For example, perfosfamide alkylates DNA, thereby inhibiting DNA replication and R A and protein synthesis. New oxazaphosphorines derivatives have been designed and evaluated with an attempt to improve the selectivity and response with reduced host toxicity (Ref. Liang J, Huang M, Duan W, Yu XQ, Zhou S. Design of new oxazaphosphorine anticancer drugs. Curr Pharm Des. 2007; 13(9):963-78. Review). These include mafosfamide (NSC 345842), glufosfamide (D19575, beta-D-glucosylisophosphoramide mustard), S-(–)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled "Cyclophosphamide analogs useful as anti-tumor agents" which is incorporated herein by reference in its entirety. Additional therapeutic agents include is an agent that reduces activity and/or number of regulatory T lymphocytes (T-regs), preferably Sunitinib (SUTENT®), anti-TGFP or Imatinib (GLEE VAC®), . The recited treatment regimen may also include administering an adjuvant. Other additional therapeutic agents include mitosis inhibitors, such as paclitaxol, aromatase inhibitors (e.g. Letrozole), agniogenesis inhibitors (VEGF inhibitors e.g. Avastin, VEGF-Trap), anthracyclines, oxaliplatin, doxorubicin, TLR4 antagonists, and IL-18 antagonists.

In some embodiments, the KLF10 inhibitors as disclosed herein inhibit, block and/or reduce cell death of an anti-tumor CD8+ and/or CD4+ T cell; or stimulate, induce, and/or increase cell death of a pro-tumor T cell. T cell exhaustion is a state of T cell dysfunction characterized by progressive loss of proliferative and effector functions, culminating in clonal deletion (See, e.g., Virgin et al. (2009) Cell 138:30-50). Accordingly, as used herein the term "a pro-tumor T cell" refers to a state of T cell dysfunction that arises during many chronic infections and cancer. This dysfunction is defined by poor proliferative and/or effector functions, sustained expression of inhibitory receptors and a transcriptional state distinct from that of functional effector or memory T cells. Exhaustion prevents optimal control of infection and tumors. See Wherry, J. W. T cell exhaustion. *Nat Immunol* (2011) 12:492-499. In addition, as used herein, the term "an anti-tumor CD8+ and/or CD4+ T cell" refers to T cells that can mount an immune response to a tumor. Exemplary pro-tumor T cells include, but are not limited to, Tregs, CD4+ and/or CD8+ T cells expressing one or more checkpoint inhibitory receptors, Th2 cells and Th17 cells. The term "checkpoint inhibitory receptors", as used herein, refers to receptors (e.g. CTLA-4, B7-H3, B7-H4, PD-1, TIM-3) expressed on immune cells that prevent or inhibit uncontrolled immune responses. See Stagg, J. et al., Immunotherapeutic approach in triple-negative breast cancer. *Ther Adv Med Oncol.* (2013) 5(3):169-181. Thus, in some embodiments, inhibition of KLF10 with the compounds as disclosed herein can include reducing the level of and/or preventing the inhibition of T cell proliferation. In some embodiments, this can also be described as restoring and/or increasing T cell proliferation. In some embodiments, the inhibition of KLF10 activity can also be described as restoring and/or increasing myeloid cell proliferation, activation and/or differentiation; for example, activation of monocytes, macrophages, and/or dendritic cells.

In some embodiments, inhibition of KLF10 with the compounds as disclosed herein can inhibit or reduce immune modulation or immune tolerance to tumor cells. In some embodiments, inhibition of KLF10 with the compounds as disclosed herein can inhibit or reduces the activity or activation of one or more cells including, but not limited to: regulatory T-cells (Tregs); myeloid suppressor cells; tumor associated neutrophils (TANs) and tumor associated macrophages (TAMs).

In some embodiments, inhibition of KLF10 with the compounds as disclosed herein can enhance, restore, promote and/or stimulate immune modulation. In some embodiments, the antibodies enhance, restore, promote and/or stimulate the activity or activation of one or more immune cells against tumor cells including, but not limited to: T-cells, cytotoxic T lymphocytes, T helper cells, natural killer (NK) cells, natural killer T (NKT) cells, anti-tumor macrophages (e.g., M1 macrophages), macrophages, B-cells, and dendritic cells.

The therapeutic agents described herein prevent, inhibit and/or reduce uncommitted/promiscuous preFoxp3 cells (Foxp3+ regulatory (Treg) T cells that transiently express Foxp3, and/or Treg cells that can undergo reprogramming into a phenotype expressing proinflammatory cytokines) from becoming committed FoxP3+ Tregs (a lineage of committed Treg cells that show DNA demethylation of one of the conserved noncoding regions in the FoxP3 gene) called Treg cell-specific demethylation region or TDSR or T-cells.

Pharmaceutical Composition

In various embodiments, the present invention provides a pharmaceutical composition. The pharmaceutical compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal, parenteral or enteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Typically, the compositions are administered by injection. Methods for these administrations are known to one skilled in the art.

The pharmaceutical compositions according to the invention can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Before administration to patients, formulants may be added to the rAAV vector, the cell transfected with the rAAV vector, or the supernatant conditioned with the transfected cell. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxyethyl starch and carboxymethylcellulose, or mixtures thereof. "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

In some embodiments, polymers as formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

Kits

In various embodiments, the present invention provides a kit for the various compositions of the invention.

The kit is an assemblage of materials or components, including at least one of the inventive vectors and compositions. Thus, in some embodiments the kit contains a composition including a drug delivery molecule complexed with a therapeutic agent, as described above.

The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat, reduce the severity of, inhibit or prevent schwannoma in a subject. Still in accordance with the present invention, "instructions for use" may include a tangible expression describing the preparation of virions and/or at least one method parameter, such as the relative amounts of a vector genome, dosage requirements and administration instructions, and the like, typically for an intended purpose. Optionally, the kit also contains other useful components, such as, measuring tools, diluents, buffers, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of a composition containing a volume of the AAV1-PO-ICE vector. The packaging material generally has an external label which indicates the contents and/or purpose of the kit and/or its components.

Various Non-Limiting Embodiments

Various embodiments of the present invention provide a compound selected from:

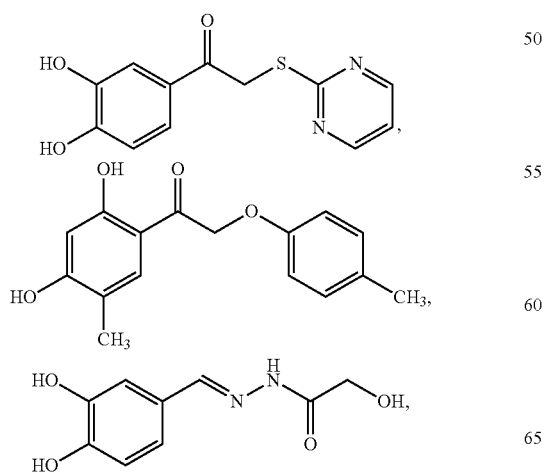

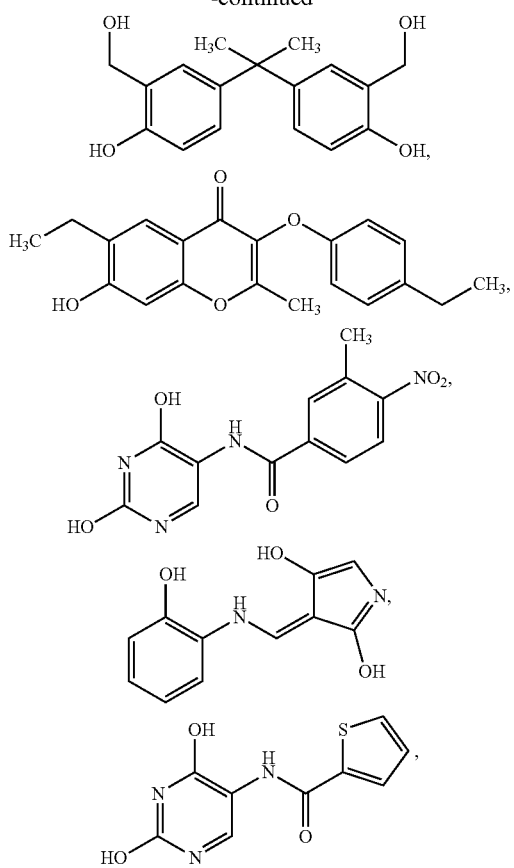

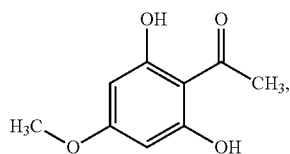

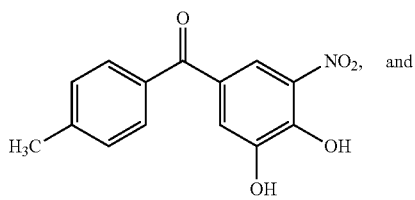

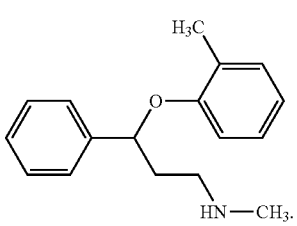

Various embodiments of the present invention provide a compound of a formula:

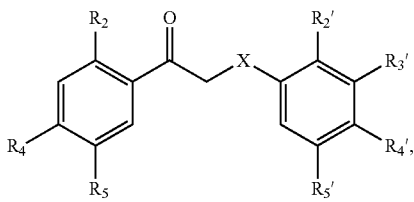

wherein,
$R_2$ is selected from H, OH, $CH_3$, and $OCH_3$;
$R_4$ is selected from H, OH, and $OCH_3$;
$R_5$ is selected from H, $CH_3$, and $C_2H_5$;
X is selected from H, O, and OC(=O);
$R_2'$ is selected from H and OH;
$R_3'$ is selected from H, $OCH_3$, and CH=CH—CH=CH;
$R_4'$ is selected from H, $CH_3$, $C_2H_5$, $CH(CH_3)_2$, $OCH_3$, Ph, F, I, and CH=CH—CH=CH; and
$R_5'$ is selected from H, $CH_3$, and $OCH_3$, wherein two or more of $R_2$, $R_4$, $R_5$ may be optionally connected, and two or more of $R_2'$, $R_3'$, $R_4'$ $R_5'$ may be optionally connected.

Various embodiments of the present invention provide a compound of a formula:

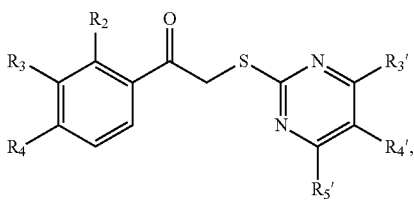

wherein,
$R_2$ is selected from H, OH, and $OCH_3$;
$R_3$ is selected from H, OH, $OCH_3$, and $COOCH_3$;
$R_4$ is selected from H, OH, and $CH_3$;
$R_3'$ is selected from H, $CH_3$, CH=CH—CH=CH, and S—C(—$CH_3$)=C(—$CH_3$);
$R_4'$ is selected from H and OH; and
$R_5'$ is selected from H, OH, and $CH_3$, wherein two or more of $R_2$, $R_3$, $R_4$ may be optionally connected, and two or more of $R_3'$, $R_4'$ $R_5'$ may be optionally connected.

Various embodiments of the present invention provide a compound selected from:

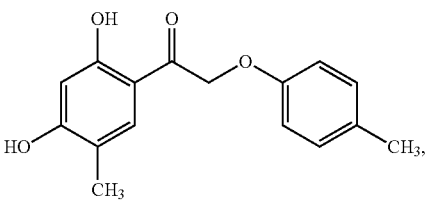

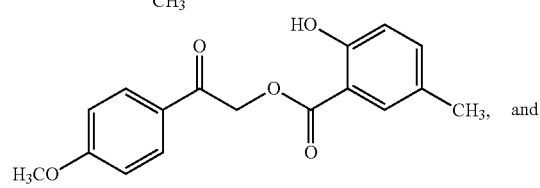

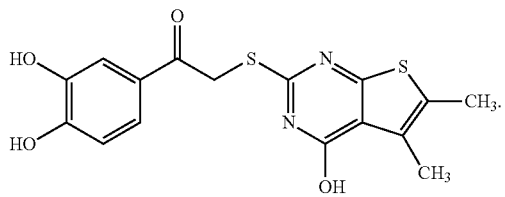

In some embodiments the compound is:

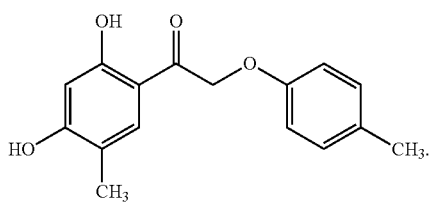 [SMILES: Cc1ccc(OCC(=O)c2cc(C)c(O)cc2O)cc1]

In some embodiments the compound is:

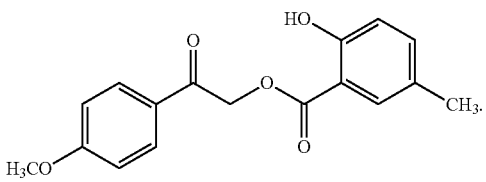

In some embodiments the compound is

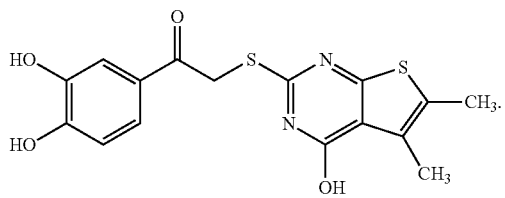 [SMILES: Cc1sc2nc(SCC(=O)c3ccc(O)c(O)c3)nc(O)c2c1C]

Various embodiments of the present invention provide a compound for inhibiting KLF10, wherein the compound is selected from:

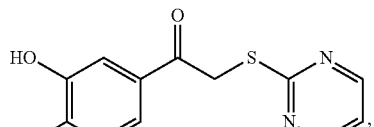

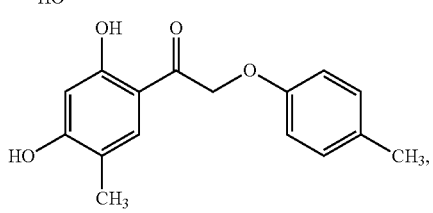

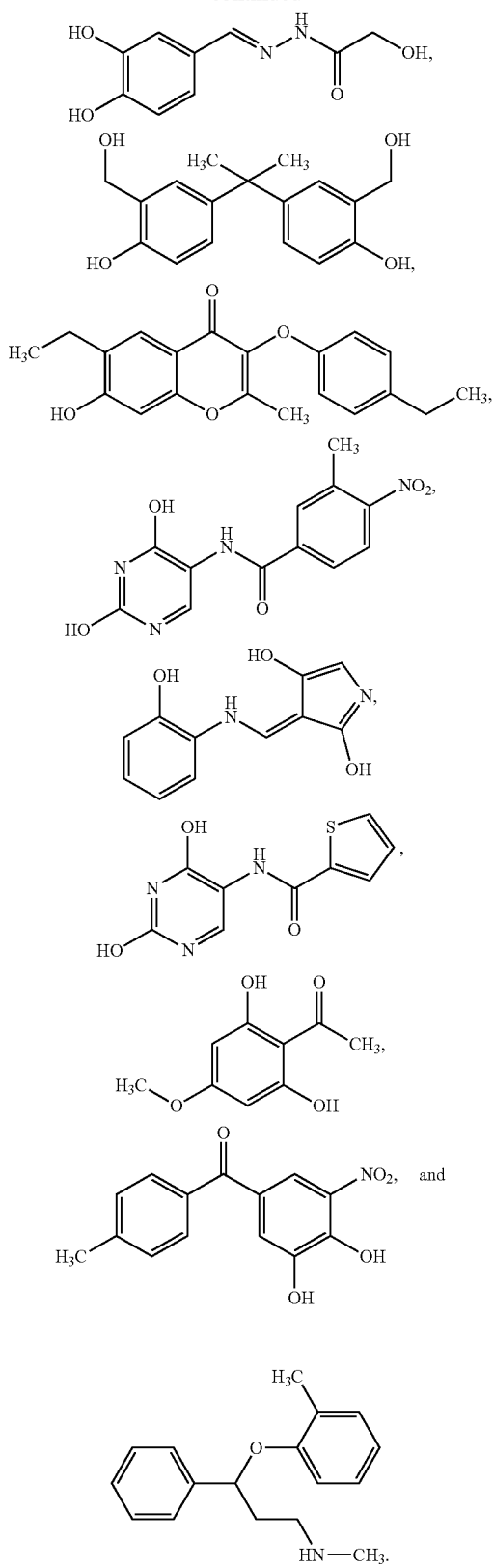

Various embodiments of the present invention provide a compound for inhibiting KLF10, wherein the compound has a formula:

wherein,
R$_2$ is selected from H, OH, CH$_3$, and OCH$_3$;
R$_4$ is selected from H, OH, and OCH$_3$;
R$_5$ is selected from H, CH$_3$, and C$_2$H$_5$;
X is selected from H, O, and OC(=O);
R$_2$' is selected from H and OH;
R$_3$' is selected from H, OCH$_3$, and CH=CH—CH=CH;
R$_4$' is selected from H, CH$_3$, C$_2$H$_5$, CH(CH$_3$)$_2$, OCH$_3$, Ph, F, I, and CH=CH—CH=CH; and
R$_5$' is selected from H, CH$_3$, and OCH$_3$, wherein two or more of R$_2$, R$_4$, R$_5$ may be optionally connected, and two or more of R$_2$', R$_3$', R$_4$' R$_5$' may be optionally connected.

Various embodiments of the present invention provide a compound for inhibiting KLF10, wherein the compound has a formula:

wherein,
R$_2$ is selected from H, OH, and OCH$_3$;
R$_3$ is selected from H, OH, OCH$_3$, and COOCH$_3$;
R$_4$ is selected from H, OH, and CH$_3$;
R$_3$' is selected from H, CH$_3$, CH=CH—CH=CH, and S—C(—CH$_3$)=C(—CH$_3$);
R$_4$' is selected from H and OH; and
R$_5$' is selected from H, OH, and CH$_3$, wherein two or more of R$_2$, R$_3$, R$_4$ may be optionally connected, and two or more of R$_3$', R$_4$' R$_5$' may be optionally connected.

Various embodiments of the present invention provide a compound for inhibiting KLF10, wherein the compound is selected from:

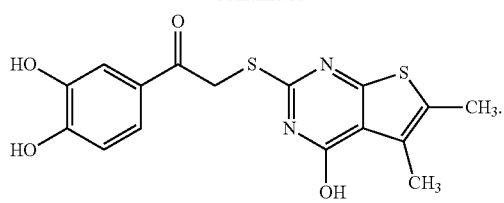

In some embodiments the compound is:

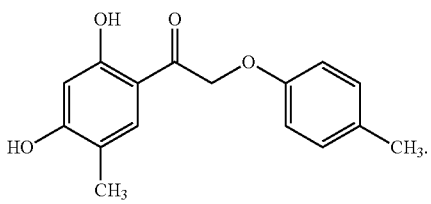 [SMILES: Cc1ccc(OCC(=O)c2cc(C)c(O)cc2O)cc1]

In some embodiments the compound is:

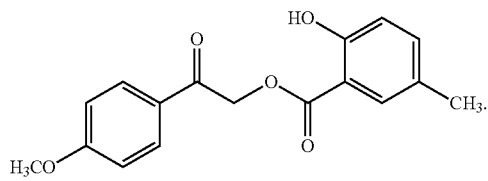 [SMILES: COc1ccc(C(=O)COC(=O)c2cc(C)ccc2O)cc1]

In some embodiments the compound is:

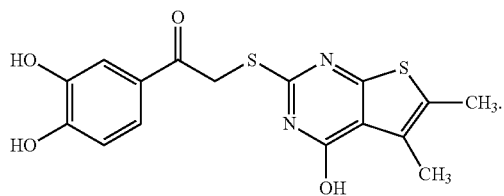

Various embodiments of the present invention provide a compound for inhibiting KLF10 reporter activity, wherein the compound is selected from:

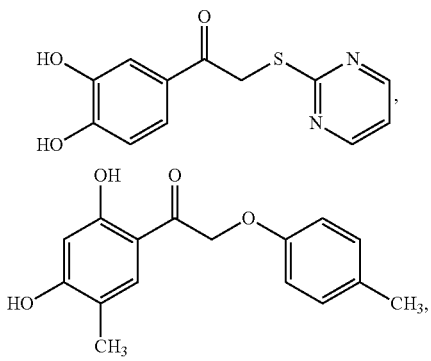

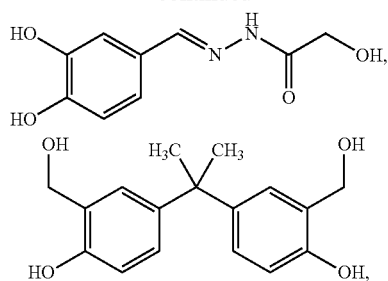

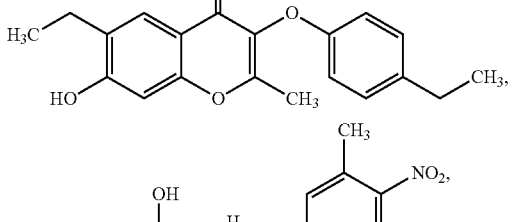

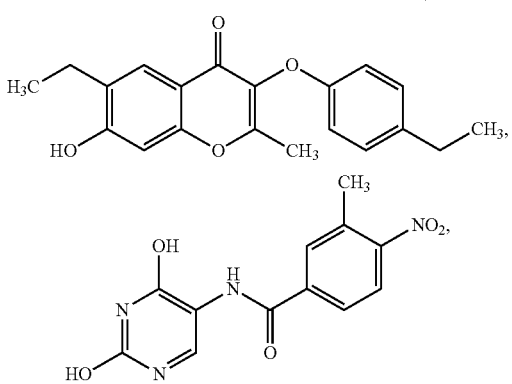

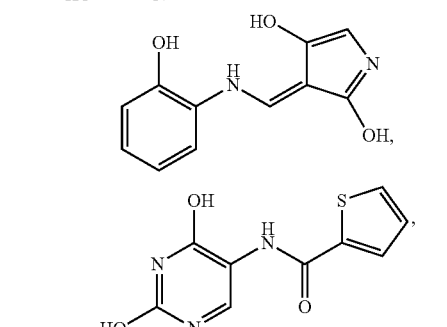

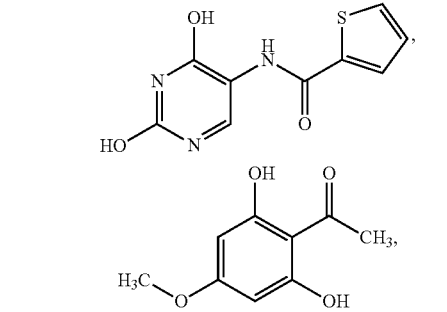

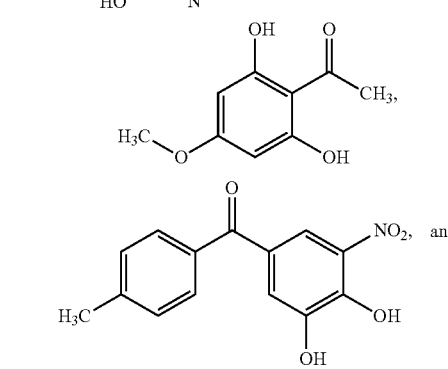

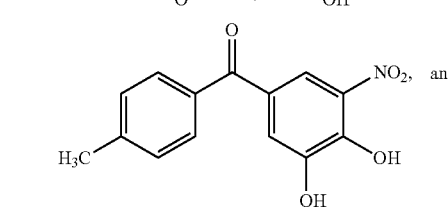

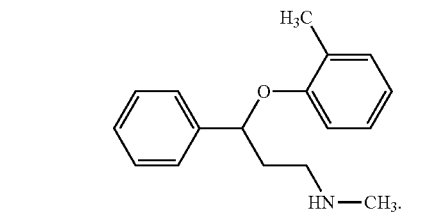

Various embodiments of the present invention provide a compound for inhibiting KLF10 reporter activity, wherein the compound has a formula:

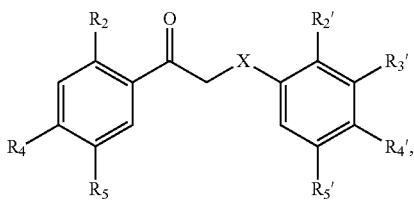

wherein,
R₂ is selected from H, OH, CH₃, and OCH₃;
R₄ is selected from H, OH, and OCH₃;
R₅ is selected from H, CH₃, and C₂H₅;
X is selected from H, O, and OC(=O);
R₂' is selected from H and OH;
R₃' is selected from H, OCH₃, and CH=CH—CH=CH;
R₄' is selected from H, CH₃, C₂H₅, CH(CH₃)₂, OCH₃, Ph, F, I, and CH=CH—CH=CH; and
R₅' is selected from H, CH₃, and OCH₃, wherein two or more of R₂, R₄, R₅ may be optionally connected, and two or more of R₂', R₃', R₄' R₅' may be optionally connected.

Various embodiments of the present invention provide a compound for inhibiting KLF10 reporter activity, wherein the compound has a formula:

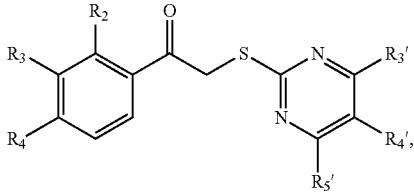

wherein,
R₂ is selected from H, OH, and OCH₃;
R₃ is selected from H, OH, OCH₃, and COOCH₃;
R₄ is selected from H, OH, and CH₃;
R₃' is selected from H, CH₃, CH=CH—CH=CH, and S—C(—CH₃)=C(—CH₃);
R₄' is selected from H and OH; and
R₅' is selected from H, OH, and CH₃, wherein two or more of R₂, R₃, R₄ may be optionally connected, and two or more of R₃', R₄' R₅' may be optionally connected.

Various embodiments of the present invention provide a compound for inhibiting KLF10 reporter activity, wherein the compound is selected from:

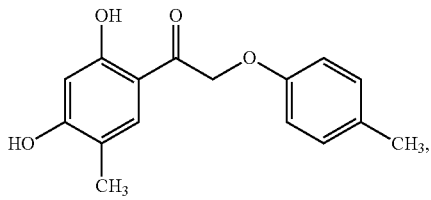

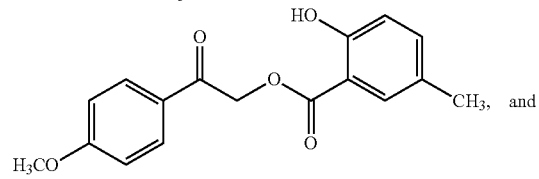

In some embodiments the compound is:

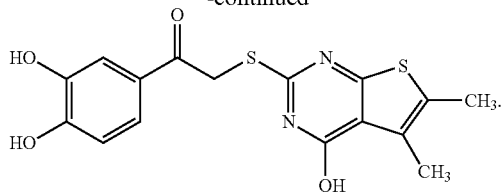

In some embodiments the compound is:

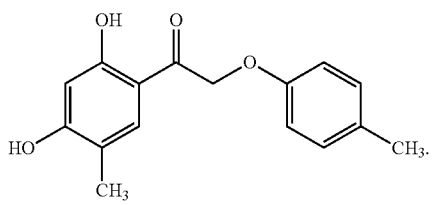

In some embodiments the compound is:

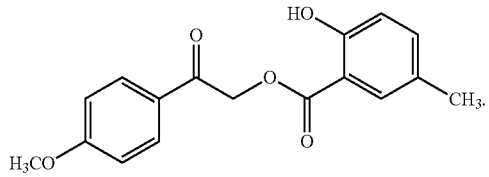

In some embodiments the compound is:

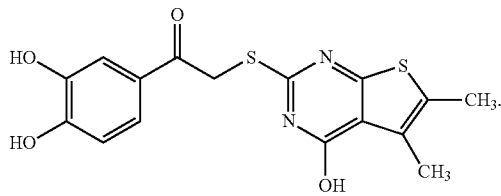 [SMILES: Cc1sc2nc(SCC(=O)c3ccc(O)c(O)c3)nc(O)c2c1C]

Various embodiments of the present invention provide a compound for inhibiting transcription of KLF10, wherein the compound is selected from the group consisting of:

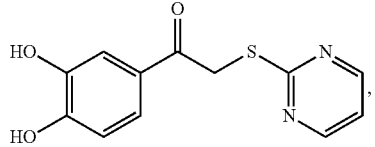

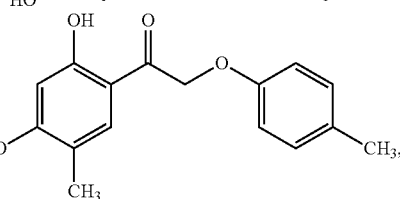

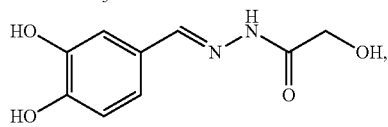

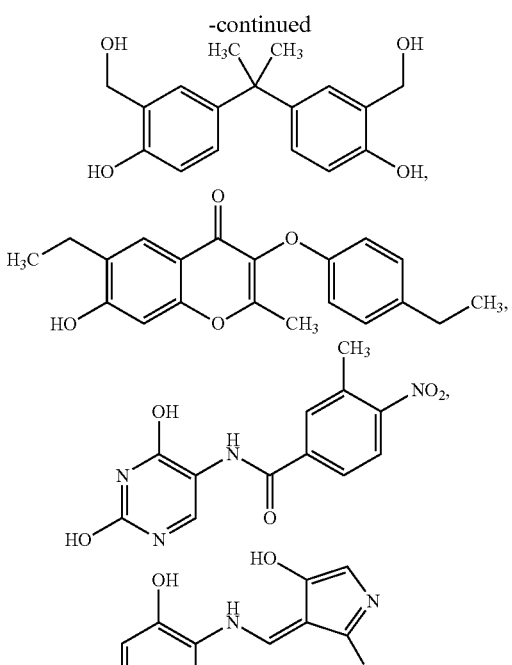

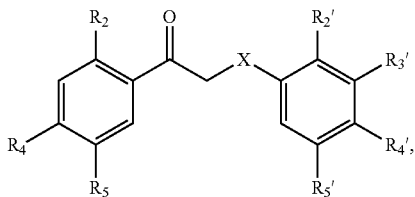

wherein,
$R_2$ is selected from H, OH, $CH_3$, and $OCH_3$;
$R_4$ is selected from H, OH, and $OCH_3$;
$R_5$ is selected from H, $CH_3$, and $C_2H_5$;
X is selected from H, O, and OC(=O);
$R_2'$ is selected from H and OH;
$R_3'$ is selected from H, $OCH_3$, and CH=CH—CH=CH;
$R_4'$ is selected from H, $CH_3$, $C_2H_5$, $CH(CH_3)_2$, $OCH_3$, Ph, F, I, and CH=CH—CH=CH; and
$R_5'$ is selected from H, $CH_3$, and $OCH_3$, wherein two or more of $R_2$, $R_4$, $R_5$ may be optionally connected, and two or more of $R_2'$, $R_3'$, $R_4'$ $R_5'$ may be optionally connected.

Various embodiments of the present invention provide a compound for inhibiting transcription of KLF10, wherein the compound has a formula:

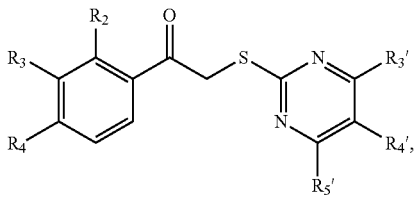

wherein,
$R_2$ is selected from H, OH, and $OCH_3$;
$R_3$ is selected from H, OH, $OCH_3$, and $COOCH_3$;
$R_4$ is selected from H, OH, and $CH_3$;
$R_3'$ is selected from H, $CH_3$, CH=CH—CH=CH, and S—C(—$CH_3$)=C(—$CH_3$);
$R_4'$ is selected from H and OH; and
$R_5'$ is selected from H, OH, and $CH_3$, wherein two or more of $R_2$, $R_3$, $R_4$ may be optionally connected, and two or more of $R_3'$, $R_4'$ $R_5'$ may be optionally connected.

Various embodiments of the present invention provide a compound for inhibiting transcription of KLF10, wherein the compound is selected from the group consisting of:

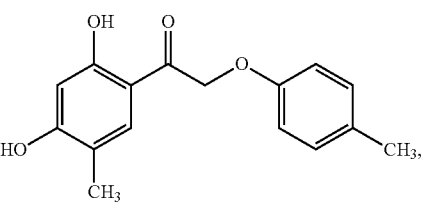 [SMILES: Cc1ccc(OCC(=O)c2cc(C)c(O)cc2O)cc1]

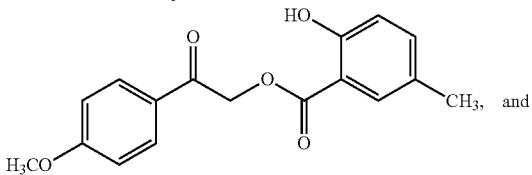

Various embodiments of the present invention provide a compound for inhibiting transcription of KLF10, wherein the compound has a formula:

-continued

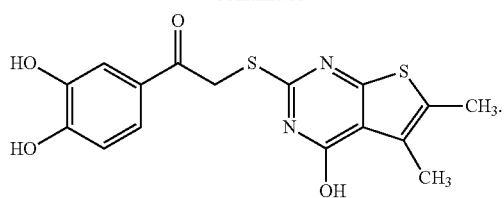 [SMILES: Cc1sc2nc(SCC(=O)c3ccc(O)c(O)c3)nc(O)c2c1C]

In some embodiments the compound is:

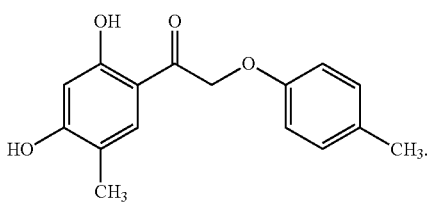 [SMILES: Cc1ccc(OCC(=O)c2cc(C)c(O)cc2O)cc1]

In some embodiments the compound is:

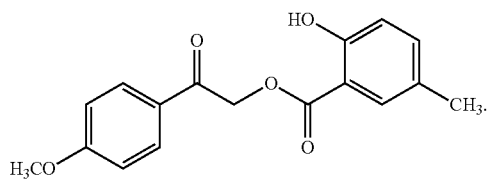 [SMILES: COc1ccc(C(=O)COC(=O)c2cc(C)ccc2O)cc1]

In some embodiments the compound is:

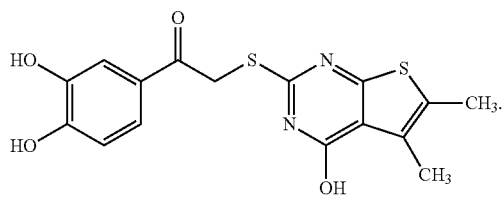 [SMILES: Cc1sc2nc(SCC(=O)c3ccc(O)c(O)c3)nc(O)c2c1C]

Various embodiments of the present invention provide a compound for inhibiting binding of KLF10 to DNA, wherein the compound is selected from the group consisting of:

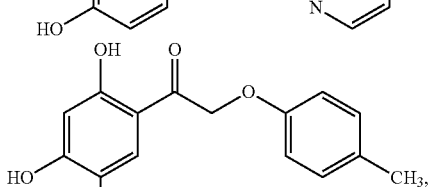

-continued

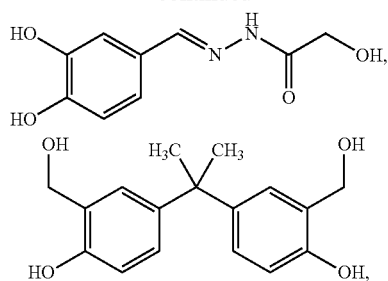

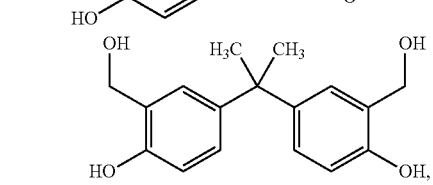

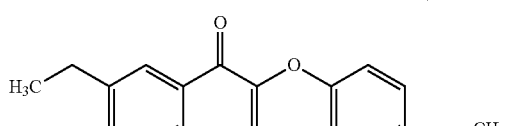

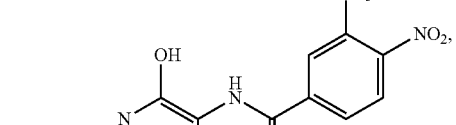

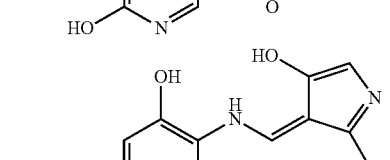

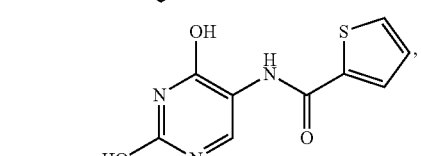

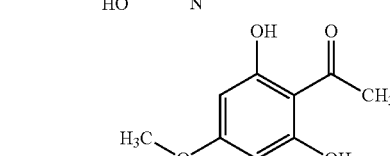

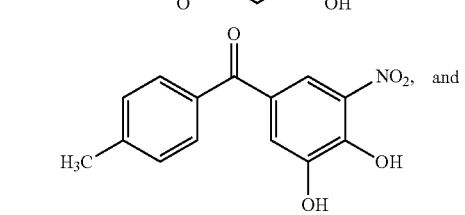

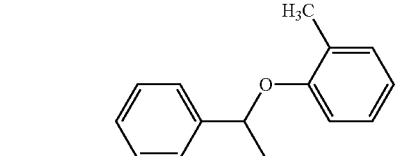

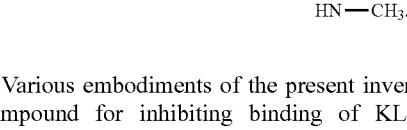

Various embodiments of the present invention provide a compound for inhibiting binding of KLF10 to DNA, wherein the compound has a formula:

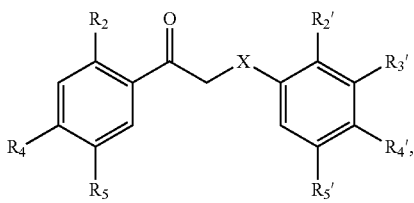

wherein,
R$_2$ is selected from H, OH, CH$_3$, and OCH$_3$;
R$_4$ is selected from H, OH, and OCH$_3$;
R$_5$ is selected from H, CH$_3$, and C$_2$H$_5$;
X is selected from H, O, and OC(=O);
R$_2$' is selected from H and OH;
R$_3$' is selected from H, OCH$_3$, and CH=CH—CH=CH;
R$_4$' is selected from H, CH$_3$, C$_2$H$_5$, CH(CH$_3$)$_2$, OCH$_3$, Ph, F, I, and CH=CH—CH=CH; and
R$_5$' is selected from H, CH$_3$, and OCH$_3$, wherein two or more of R$_2$, R$_4$, R$_5$ may be optionally connected, and two or more of R$_2$', R$_3$', R$_4$' R$_5$' may be optionally connected.

Various embodiments of the present invention provide a compound for inhibiting binding of KLF10 to DNA, wherein the compound has a formula:

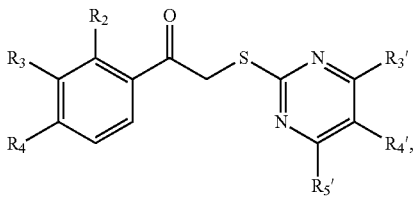

wherein,
R$_2$ is selected from H, OH, and OCH$_3$;
R$_3$ is selected from H, OH, OCH$_3$, and COOCH$_3$;
R$_4$ is selected from H, OH, and CH$_3$;
R$_3$' is selected from H, CH$_3$, CH=CH—CH=CH, and S—C(—CH$_3$)=C(—CH$_3$);
R$_4$' is selected from H and OH; and
R$_5$' is selected from H, OH, and CH$_3$, wherein two or more of R$_2$, R$_3$, R$_4$ may be optionally connected, and two or more of R$_3$', R$_4$' R$_5$' may be optionally connected.

Various embodiments of the present invention provide a compound for inhibiting binding of KLF10 to DNA, wherein the compound is selected from the group consisting of:

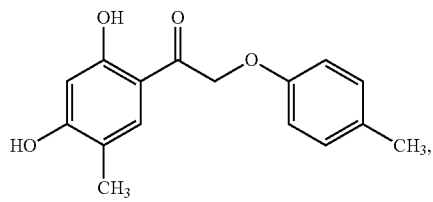

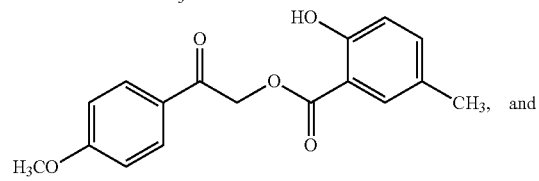

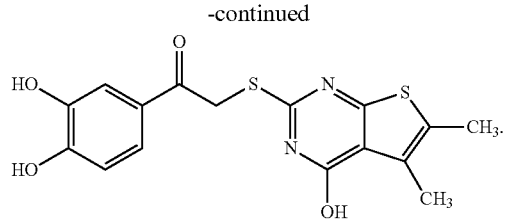

In some embodiments the compound is:

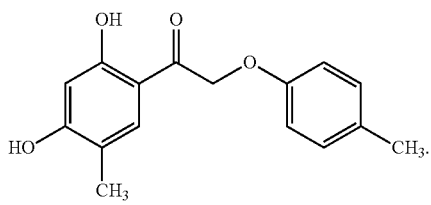

In some embodiments the compound is:

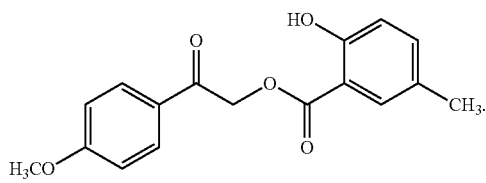 [SMILES: COc1ccc(C(=O)COC(=O)c2cc(C)ccc2O)cc1]

In some embodiments the compound is:

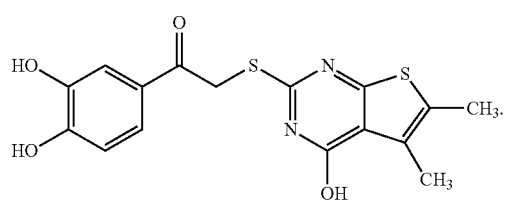

Various embodiments of the present invention provide a compound for inhibiting conversion of CD4+CD25− T cells to CD4+CD25+ T regulatory cells, wherein the compound is selected from the group consisting of:

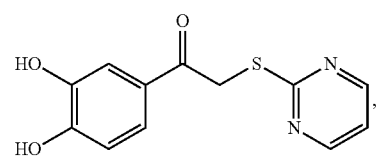

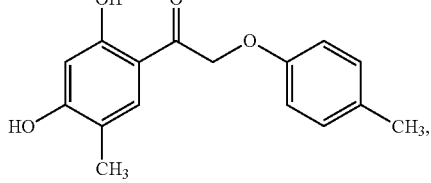

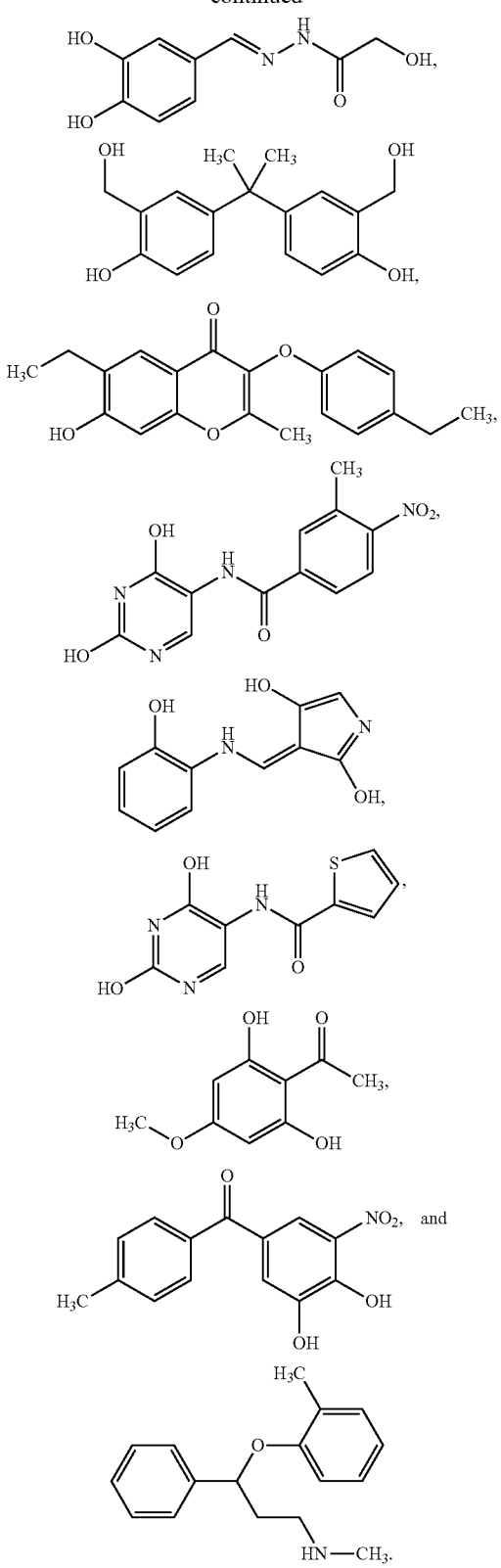

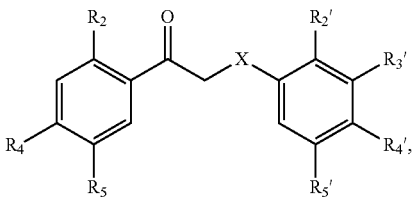

wherein,
R₂ is selected from H, OH, CH₃, and OCH₃;
R₄ is selected from H, OH, and OCH₃;
R₅ is selected from H, CH₃, and C₂H₅;
X is selected from H, O, and OC(=O);
R₂' is selected from H and OH;
R₃' is selected from H, OCH₃, and CH=CH—CH=CH;
R₄' is selected from H, CH₃, C₂H₅, CH(CH₃)₂, OCH₃, Ph, F, I, and CH=CH—CH=CH; and
R₅' is selected from H, CH₃, and OCH₃, wherein two or more of R₂, R₄, R₅ may be optionally connected, and two or more of R₂', R₃', R₄' R₅' may be optionally connected.

Various embodiments of the present invention provide a compound for inhibiting conversion of CD4+CD25− T cells to CD4+CD25+ T regulatory cells, wherein the compound has a formula:

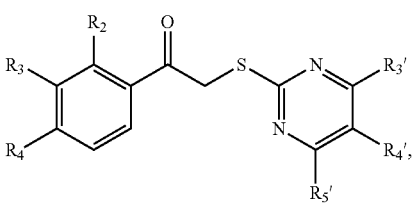

wherein,
R₂ is selected from H, OH, and OCH₃;
R₃ is selected from H, OH, OCH₃, and COOCH₃;
R₄ is selected from H, OH, and CH₃;
R₃' is selected from H, CH₃, CH=CH—CH=CH, and S—C(—CH₃)=C(—CH₃);
R₄' is selected from H and OH; and
R₅' is selected from H, OH, and CH₃, wherein two or more of R₂, R₃, R₄ may be optionally connected, and two or more of R₃', R₄' R₅' may be optionally connected.

Various embodiments of the present invention provide a compound for inhibiting conversion of CD4+CD25− T cells to CD4+CD25+ T regulatory cells, wherein the compound is selected from the group consisting of:

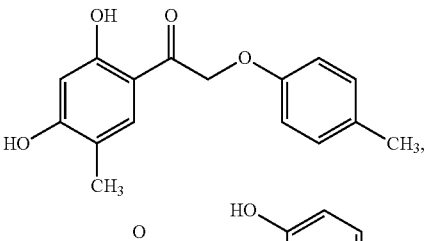

-continued

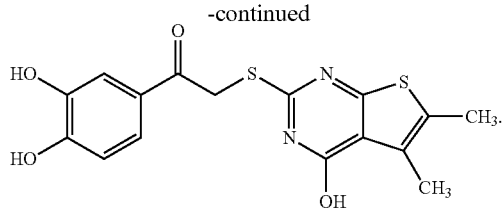

In some embodiments the compound is:

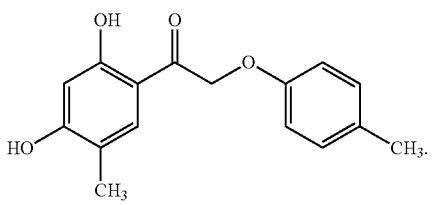

In some embodiments the compound is:

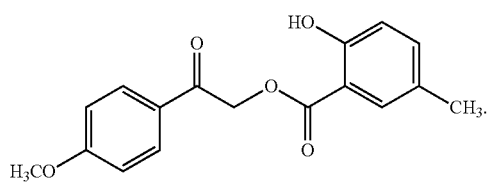

In some embodiments the compound is:

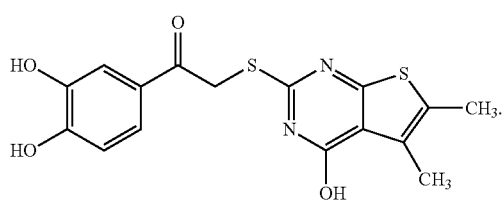 [SMILES: Cc1sc2nc(SCC(=O)c3ccc(O)c(O)c3)nc(O)c2c1C]

Various embodiments of the present invention provide a compound for inhibiting Foxp3 gene expression, wherein the compound is selected from the group consisting of:

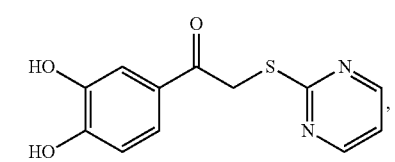

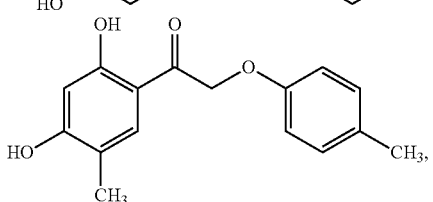

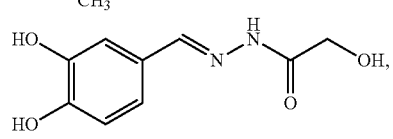

-continued

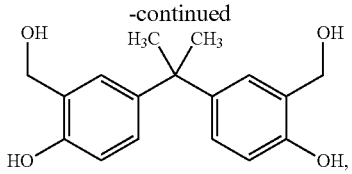

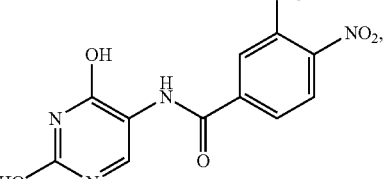

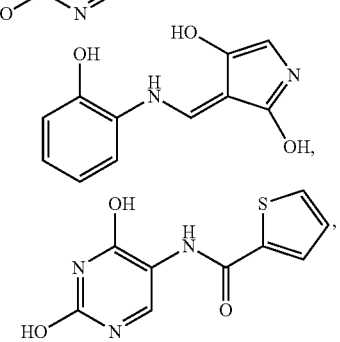

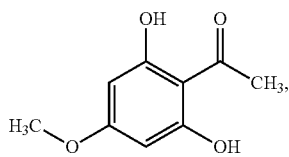

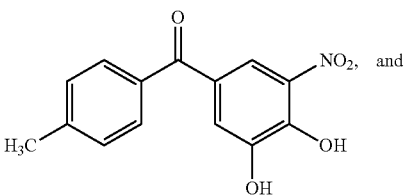

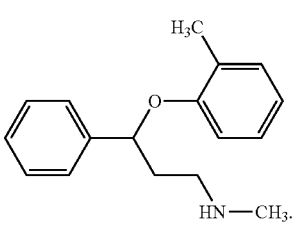

Various embodiments of the present invention provide a compound for inhibiting Foxp3 gene expression, wherein the compound has a formula:

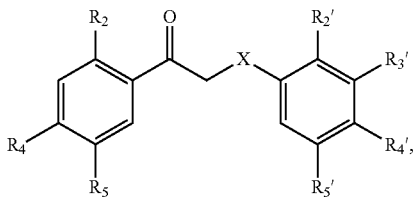

wherein,
R₂ is selected from H, OH, CH₃, and OCH₃;
R₄ is selected from H, OH, and OCH₃;
R₅ is selected from H, CH₃, and C₂H₅;
X is selected from H, O, and OC(=O);
R₂' is selected from H and OH;
R₃' is selected from H, OCH₃, and CH=CH—CH=CH;
R₄' is selected from H, CH₃, C₂H₅, CH(CH₃)₂, OCH₃, Ph, F, I, and CH=CH—CH=CH; and
R₅' is selected from H, CH₃, and OCH₃, wherein two or more of R₂, R₄, R₅ may be optionally connected, and two or more of R₂', R₃', R₄' R₅' may be optionally connected.

Various embodiments of the present invention provide a compound for inhibiting Foxp3 gene expression, wherein the compound has a formula:

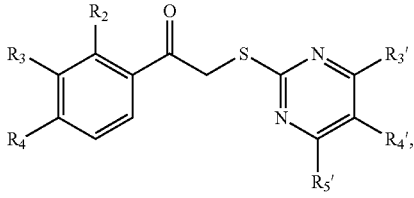

wherein,
R₂ is selected from H, OH, and OCH₃;
R₃ is selected from H, OH, OCH₃, and COOCH₃;
R₄ is selected from H, OH, and CH₃;
R₃' is selected from H, CH₃, CH=CH—CH=CH, and S—C(—CH₃)=C(—CH₃);
R₄' is selected from H and OH; and
R₅' is selected from H, OH, and CH₃, wherein two or more of R₂, R₃, R₄ may be optionally connected, and two or more of R₃', R₄' R₅' may be optionally connected.

Various embodiments of the present invention provide a compound for inhibiting Foxp3 gene expression, wherein the compound is selected from the group consisting of:

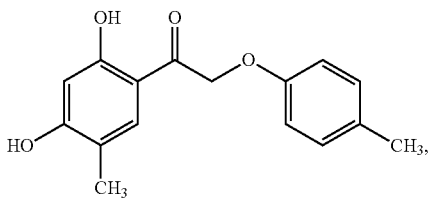

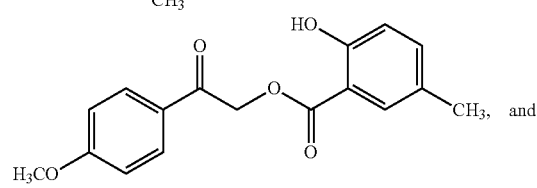

-continued

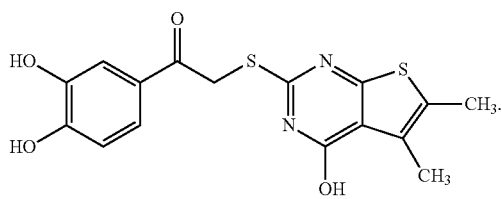 [SMILES: Cc1sc2nc(SCC(=O)c3ccc(O)c(O)c3)nc(O)c2c1C]

In some embodiments the compound is:

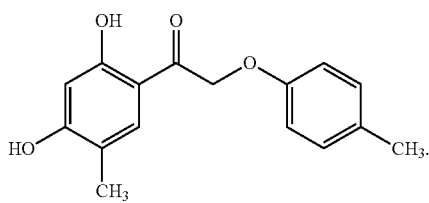 [SMILES: Cc1ccc(OCC(=O)c2cc(C)c(O)cc2O)cc1]

In some embodiments the compound is:

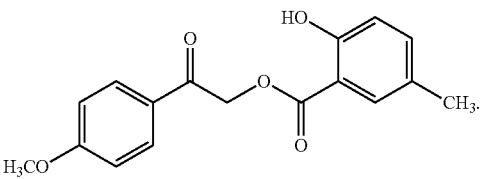 [SMILES: COc1ccc(C(=O)COC(=O)c2cc(C)ccc2O)cc1]

In some embodiments the compound is:

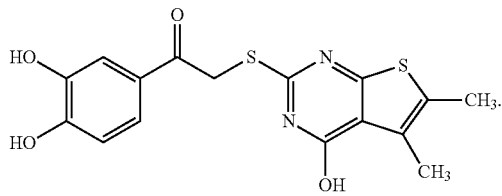 [SMILES: Cc1sc2nc(SCC(=O)c3ccc(O)c(O)c3)nc(O)c2c1C]

Various embodiments of the present invention provide a kit, comprising: one or more compounds selected from the group consisting of:

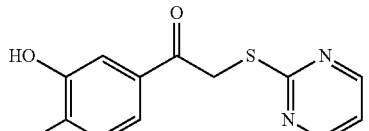

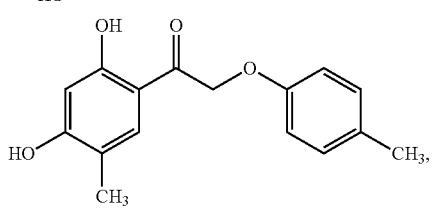

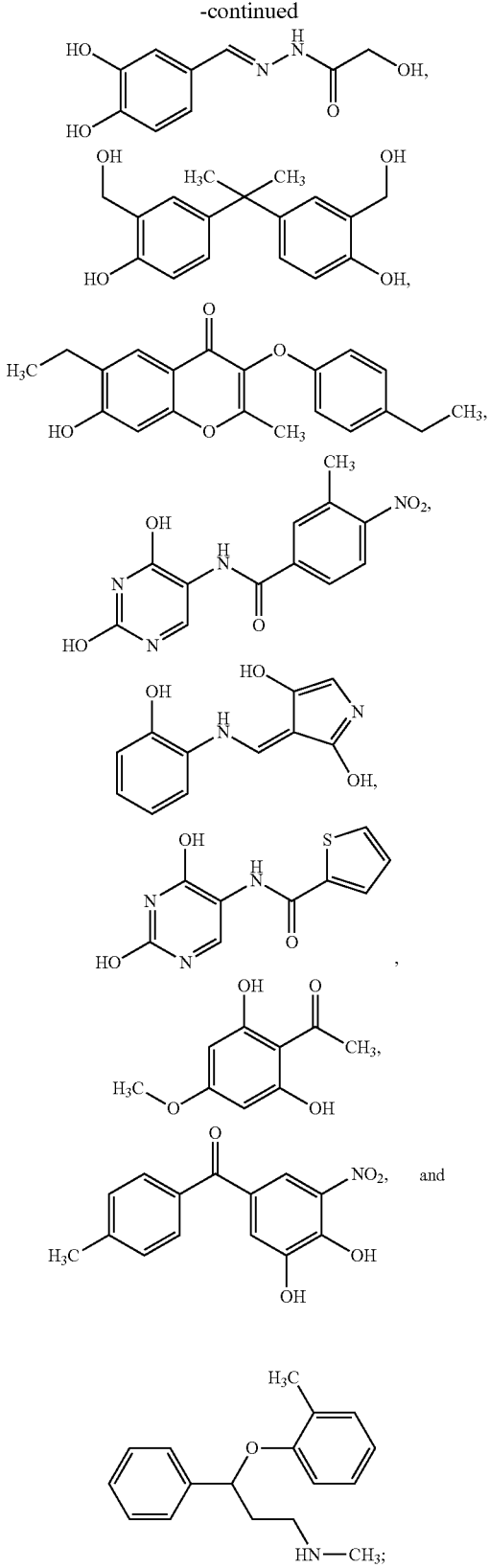

and instructions for administration to a subject.

Various embodiments of the present invention provide a kit, comprising: one or more compounds having a formula:

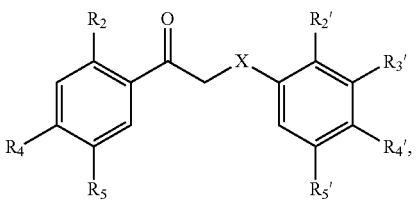

wherein,
R$_2$ is selected from H, OH, CH$_3$, and OCH$_3$;
R$_4$ is selected from H, OH, and OCH$_3$;
R$_5$ is selected from H, CH$_3$, and C$_2$H$_5$;
X is selected from H, O, and OC(=O);
R$_2$' is selected from H and OH;
R$_3$' is selected from H, OCH$_3$, and CH=CH—CH=CH;
R$_4$' is selected from H, CH$_3$, C$_2$H$_5$, CH(CH$_3$)$_2$, OCH$_3$, Ph, F, I, and CH=CH—CH=CH; and
R$_5$' is selected from H, CH$_3$, and OCH$_3$, wherein two or more of R$_2$, R$_4$, R$_5$ may be optionally connected, and two or more of R$_2$', R$_3$', R$_4$' R$_5$' may be optionally connected; and instructions for administration to a subject.

Various embodiments of the present invention provide a kit, comprising: one or more compounds having a formula:

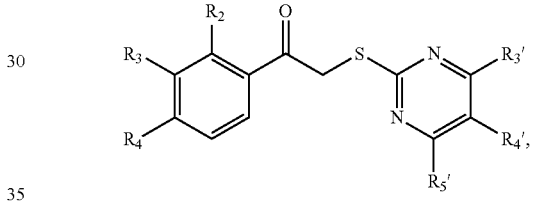

wherein,
R$_2$ is selected from H, OH, and OCH$_3$;
R$_3$ is selected from H, OH, OCH$_3$, and COOCH$_3$;
R$_4$ is selected from H, OH, and CH$_3$;
R$_3$' is selected from H, CH$_3$, CH=CH—CH=CH, and S—C(—CH$_3$)=C(—CH$_3$);
R$_4$' is selected from H and OH; and
R$_5$' is selected from H, OH, and CH$_3$, wherein two or more of R$_2$, R$_3$, R$_4$ may be optionally connected, and two or more of R$_3$', R$_4$' R$_5$' may be optionally connected; and instructions for administration to a subject.

Various embodiments of the present invention provide a kit, comprising: one or more compounds selected from the group consisting of:

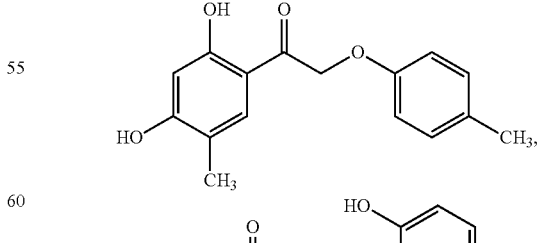

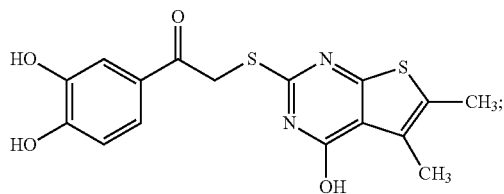

and instructions for administration to a subject. In some embodiments the compound is:

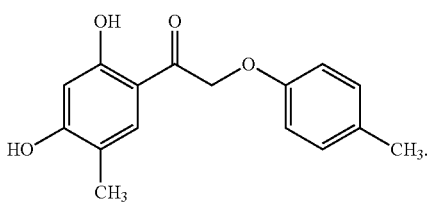 [SMILES: Cc1ccc(OCC(=O)c2cc(C)c(O)cc2O)cc1]

In some embodiments the compound is:

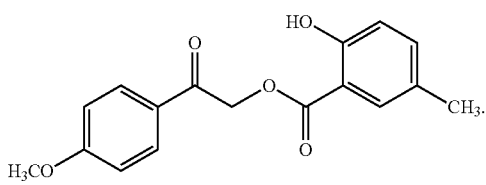 [SMILES: COc1ccc(C(=O)COC(=O)c2cc(C)ccc2O)cc1]

In some embodiments the compound is:

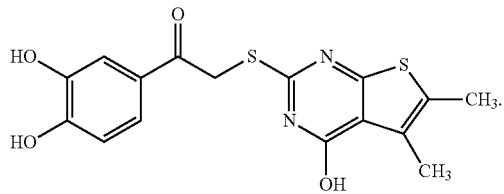 [SMILES: Cc1sc2nc(SCC(=O)c3ccc(O)c(O)c3)nc(O)c2c1C]

Various embodiments of the present invention provide a pharmaceutical composition, comprising: at least one compound selected from the group consisting of:

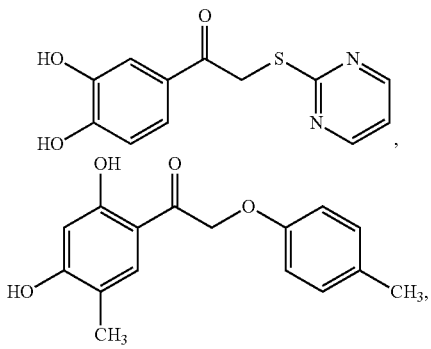

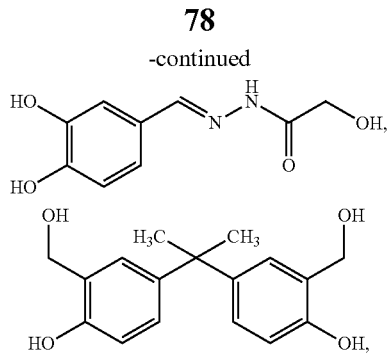

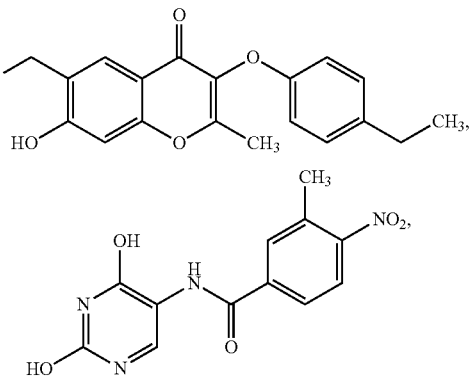

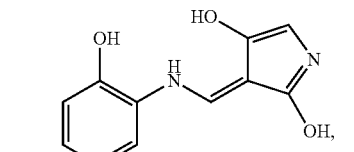

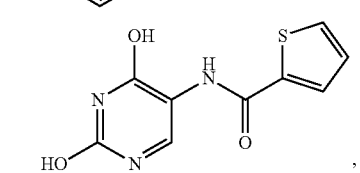

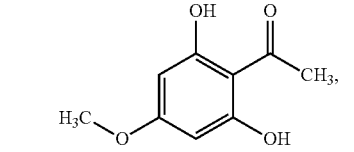

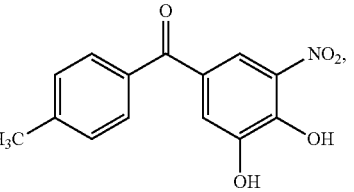

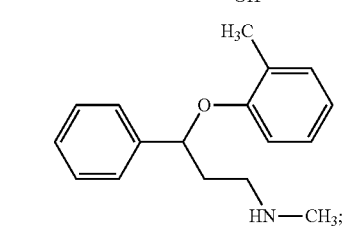

and a pharmaceutically acceptable carrier.

Various embodiments of the present invention provide a pharmaceutical composition, comprising: at least one compound having a formula:

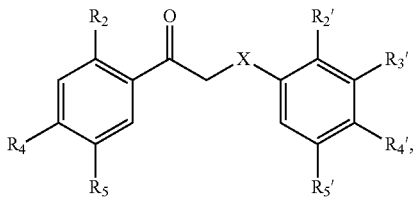

wherein,
R$_2$ is selected from H, OH, CH$_3$, and OCH$_3$;
R$_4$ is selected from H, OH, and OCH$_3$;
R$_5$ is selected from H, CH$_3$, and C$_2$H$_5$;
X is selected from H, O, and OC(=O);
R$_2$' is selected from H and OH;
R$_3$' is selected from H, OCH$_3$, and CH=CH—CH=CH;
R$_4$' is selected from H, CH$_3$, C$_2$H$_5$, CH(CH$_3$)$_2$, OCH$_3$, Ph, F, I, and CH=CH—CH=CH; and
R$_5$' is selected from H, CH$_3$, and OCH$_3$, wherein two or more of R$_2$, R$_4$, R$_5$ may be optionally connected, and two or more of R$_2$', R$_3$', R$_4$' R$_5$' may be optionally connected; and a pharmaceutically acceptable carrier.

Various embodiments of the present invention provide a pharmaceutical composition, comprising: at least one compound having a formula:

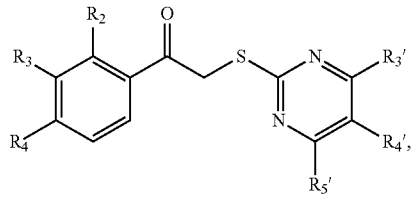

wherein,
R$_2$ is selected from H, OH, and OCH$_3$;
R$_3$ is selected from H, OH, OCH$_3$, and COOCH$_3$;
R$_4$ is selected from H, OH, and CH$_3$;
R$_3$' is selected from H, CH$_3$, CH=CH—CH=CH, and S—C(—CH$_3$)=C(—CH$_3$);
R$_4$' is selected from H and OH; and
R$_5$' is selected from H, OH, and CH$_3$, wherein two or more of R$_2$, R$_3$, R$_4$ may be optionally connected, and two or more of R$_3$', R$_4$' R$_5$' may be optionally connected; and a pharmaceutically acceptable carrier.

Various embodiments of the present invention provide a pharmaceutical composition, comprising: at least one compound selected from the group consisting of:

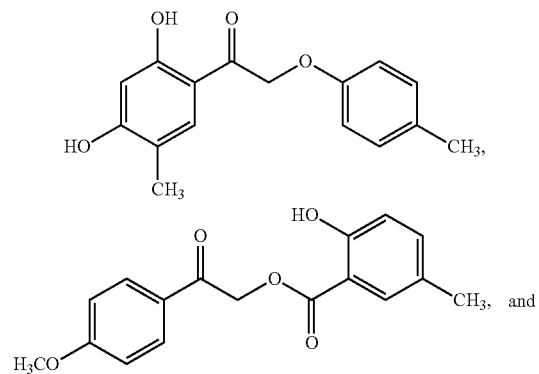

and a pharmaceutically acceptable carrier. In some embodiments the compound is:

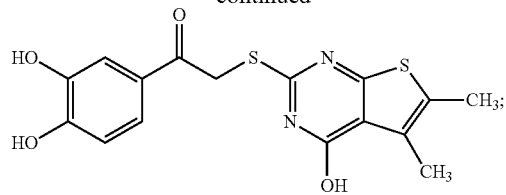

In some embodiments the compound is:

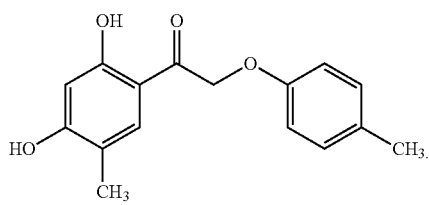

In some embodiments the compound is:

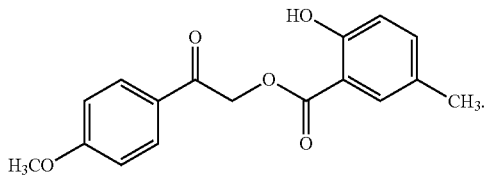 [SMILES: COc1ccc(C(=O)COC(=O)c2cc(C)ccc2O)cc1]

A method for identifying one or more compounds for inhibiting Krüppel-like Factor 10 (KLF10), comprising: a) selecting one or more compounds based on computer-aided drug design (CADD); b) analyzing if the one or more compounds inhibits Krüppel-like Factor 10 (KLF10) in an assay; and c) identifying those one or more compounds that inhibit Krüppel-like Factor 10 (KLF10). In some embodiments, the assay is an in vitro assay, in vivo assay, or ex vivo assay.

A method for identifying one or more compounds for inhibiting Krüppel-like Factor 10 (KLF10) transcription, comprising: a) selecting one or more compounds based on computer-aided drug design (CADD); b) analyzing if the one or more compounds inhibits Krüppel-like Factor 10 (KLF10) transcription in an assay; and c) identifying those one or more compounds that inhibit Krüppel-like Factor 10 (KLF10) transcription. In some embodiments, the assay is an in vitro assay, in vivo assay, or ex vivo assay.

Various embodiments of the present invention provide a method for inhibiting binding of KLF10 to DNA, comprising: a) providing a sample comprising KLF10 and DNA; b) contacting the sample with one or more compounds selected from:

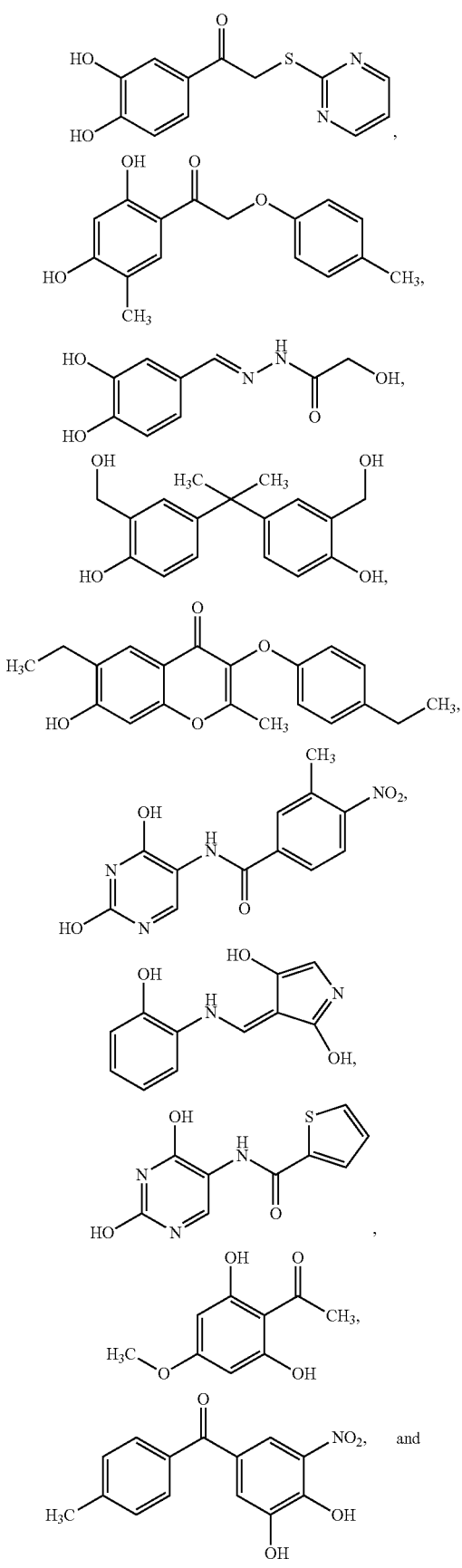

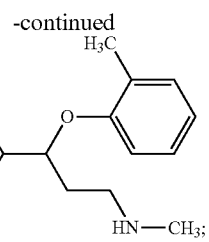

and c) performing an in vitro, in vivo, or ex vivo assay to identify the one or more compounds that inhibit binding of KLF10 to DNA.

Various embodiments of the present invention provide a method for inhibiting binding of KLF10 to DNA, comprising: a) providing a sample comprising KLF10 and DNA; b) contacting the sample with one or more compounds having a formula:

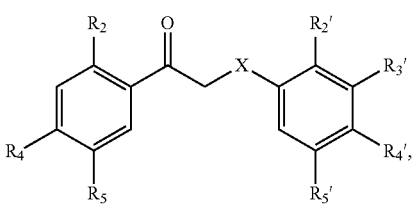

wherein,
$R_2$ is selected from H, OH, $CH_3$, and $OCH_3$;
$R_4$ is selected from H, OH, and $OCH_3$;
$R_5$ is selected from H, $CH_3$, and $C_2H_5$;
X is selected from H, O, and OC(=O);
$R_2'$ is selected from H and OH;
$R_3'$ is selected from H, $OCH_3$, and CH=CH—CH=CH;
$R_4'$ is selected from H, $CH_3$, $C_2H_5$, $CH(CH_3)_2$, $OCH_3$, Ph, F, I, and CH=CH—CH=CH; and
$R_5'$ is selected from H, $CH_3$, and $OCH_3$, wherein two or more of $R_2$, $R_4$, $R_5$ may be optionally connected, and two or more of $R_2'$, $R_3'$, $R_4'$ $R_5'$ may be optionally connected; and
c) performing an in vitro, in vivo, or ex vivo assay to identify the one or more compounds that inhibit binding of KLF10 to DNA.

Various embodiments of the present invention provide a method for inhibiting binding of KLF10 to DNA, comprising: a) providing a sample comprising KLF10 and DNA; b) contacting the sample with one or more compounds having a formula:

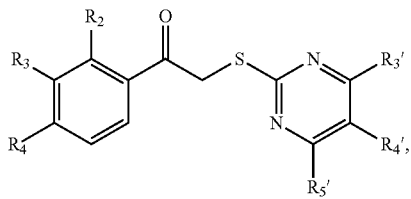

wherein,
$R_2$ is selected from H, OH, and $OCH_3$;
$R_3$ is selected from H, OH, $OCH_3$, and $COOCH_3$;
$R_4$ is selected from H, OH, and $CH_3$;
$R_3'$ is selected from H, $CH_3$, CH=CH—CH=CH, and S—C(—$CH_3$)=C(—$CH_3$);
$R_4'$ is selected from H and OH; and $R_5'$ is selected from H, OH, and $CH_3$, wherein two or more of $R_2$, $R_3$, $R_4$ may be optionally connected, and two or more of $R_3'$, $R_4'$ $R_5'$ may be optionally connected; and c) performing an in vitro, in vivo, or ex vivo assay to identify the one or more compounds that inhibit binding of KLF10 to DNA.

Various embodiments of the present invention provide a method for inhibiting binding of KLF10 to DNA, comprising: a) providing a sample comprising KLF10 and DNA; b) contacting the sample with one or more compounds selected from:

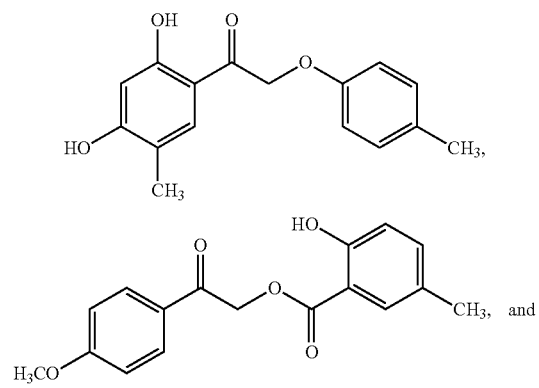

and c) performing an in vitro, in vivo, or ex vivo assay to identify the one or more compounds that inhibit binding of KLF10 to DNA. In some embodiments the compound is:

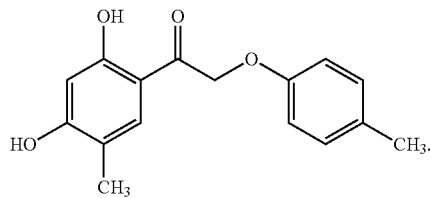 [SMILES: Cc1ccc(OCC(=O)c2cc(C)c(O)cc2O)cc1]

In some embodiments the compound is:

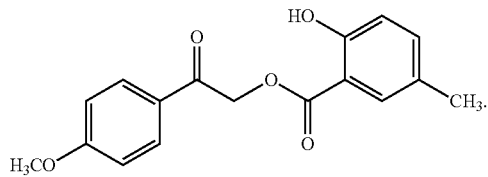 [SMILES: COc1ccc(C(=O)COC(=O)c2cc(C)ccc2O)cc1]

In some embodiments the compound is:

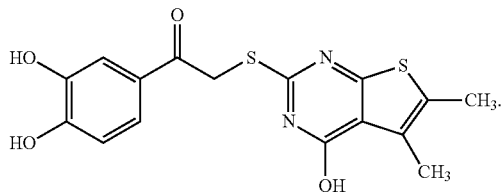 [SMILES: Cc1sc2nc(SCC(=O)c3ccc(O)c(O)c3)nc(O)c2c1C]

Various embodiments of the present invention provide a method for inhibiting binding of KLF10 to DNA, comprising: a) providing a KLF10 sample comprising KLF10; b) providing a DNA sample comprising DNA; c) providing one or more compounds selected from:

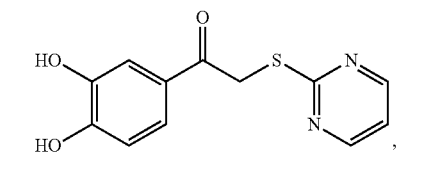

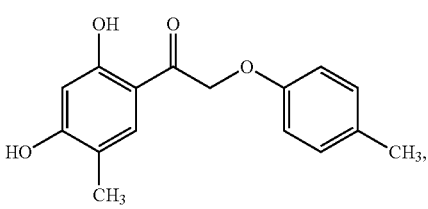

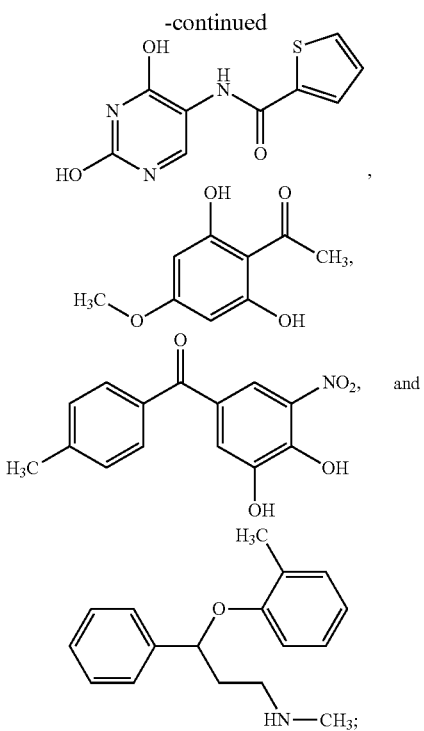

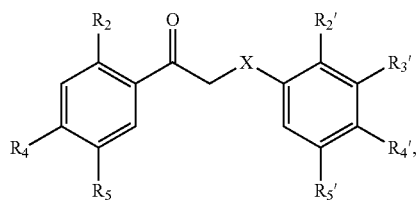

d) combining the KLF10 sample, the DNA sample, and the one or more compounds; and e) performing an in vitro, in vivo, or ex vivo assay to identify the one or more compounds that inhibit binding of KLF10 to DNA.

Various embodiments of the present invention provide a method for inhibiting binding of KLF10 to DNA, comprising: a) providing a KLF10 sample comprising KLF10; b) providing a DNA sample comprising DNA; c) providing one or more compounds having a formula:

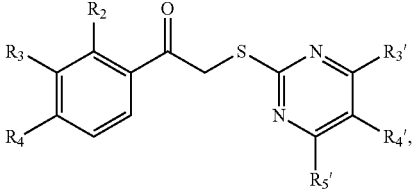

wherein,
R$_2$ is selected from H, OH, CH$_3$, and OCH$_3$;
R$_4$ is selected from H, OH, and OCH$_3$;
R$_5$ is selected from H, CH$_3$, and C$_2$H$_5$;
X is selected from H, O, and OC(=O);
R$_2$' is selected from H and OH;
R$_3$' is selected from H, OCH$_3$, and CH=CH—CH=CH;
R$_4$' is selected from H, CH$_3$, C$_2$H$_5$, CH(CH$_3$)$_2$, OCH$_3$, Ph, F, I, and CH=CH—CH=CH; and
R$_5$' is selected from H, CH$_3$, and OCH$_3$, wherein two or more of R$_2$, R$_4$, R$_5$ may be optionally connected, and two or more of R$_2$', R$_3$', R$_4$' R$_5$' may be optionally connected; d) combining the KLF10 sample, the DNA sample, and the one or more compounds; and e) performing an in vitro, in vivo, or ex vivo assay to identify the one or more compounds that inhibit binding of KLF10 to DNA.

Various embodiments of the present invention provide a method for inhibiting binding of KLF10 to DNA, comprising: a) providing a KLF10 sample comprising KLF10; b) providing a DNA sample comprising DNA; c) providing one or more compounds having a formula:

wherein,
R$_2$ is selected from H, OH, and OCH$_3$;
R$_3$ is selected from H, OH, OCH$_3$, and COOCH$_3$;
R$_4$ is selected from H, OH, and CH$_3$;
R$_3$' is selected from H, CH$_3$, CH=CH—CH=CH, and S—C(—CH$_3$)=C(—CH$_3$);
R$_4$' is selected from H and OH; and
R$_5$' is selected from H, OH, and CH$_3$, wherein two or more of R$_2$, R$_3$, R$_4$ may be optionally connected, and two or more of R$_3$', R$_4$' R$_5$' may be optionally connected; d) combining the KLF10 sample, the DNA sample, and the one or more compounds; and e) performing an in vitro, in vivo, or ex vivo assay to identify the one or more compounds that inhibit binding of KLF10 to DNA.

Various embodiments of the present invention provide a method for inhibiting binding of KLF10 to DNA, comprising: a) providing a KLF10 sample comprising KLF10; b) providing a DNA sample comprising DNA; c) providing one or more compounds selected from:

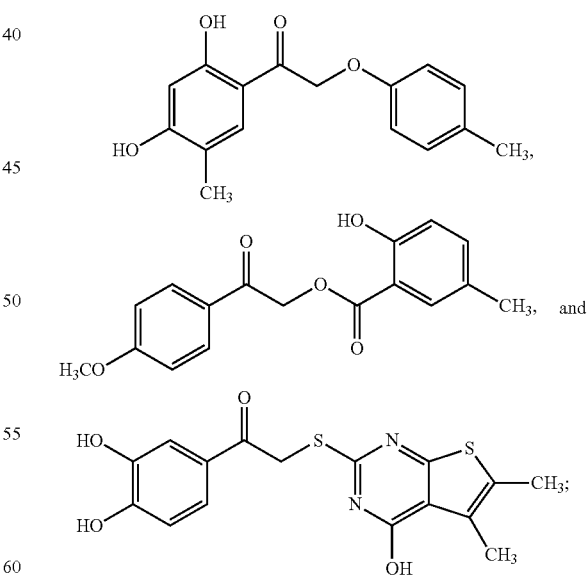

and d) combining the KLF10 sample, the DNA sample, and the one or more compounds; and e) performing an in vitro, in vivo, or ex vivo assay to identify the one or more compounds that inhibit binding of KLF10 to DNA. In some embodiments the compound is:

87

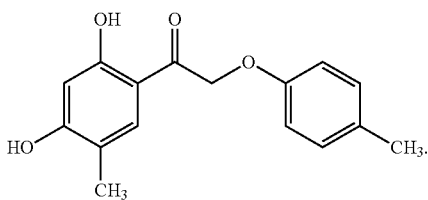 [SMILES: Cc1ccc(OCC(=O)c2cc(C)c(O)cc2O)cc1]

In some embodiments the compound is:

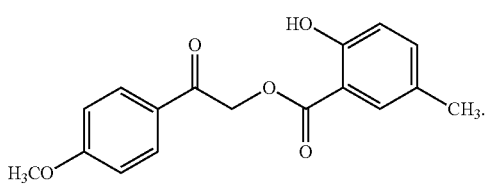 [SMILES: COc1ccc(C(=O)COC(=O)c2cc(C)ccc2O)cc1]

In some embodiments the compound is:

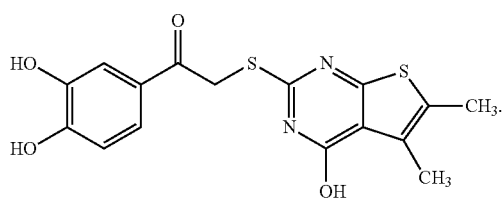 [SMILES: Cc1sc2nc(SCC(=O)c3ccc(O)c(O)c3)nc(O)c2c1C]

Various embodiments of the present invention provide a method for inhibiting conversion of CD4+CD25− T cells to CD4+CD25+ T regulatory cells, comprising: a) providing a sample comprising CD4+CD25− T cells; b) contacting the sample with one or more compounds selected from:

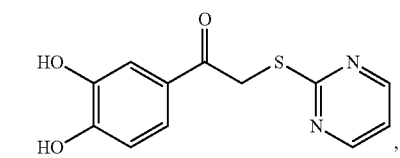

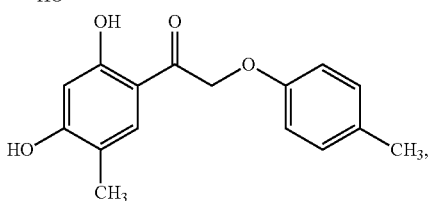

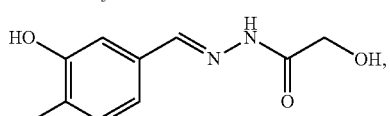

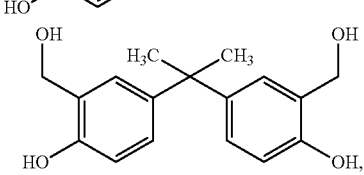

88

-continued

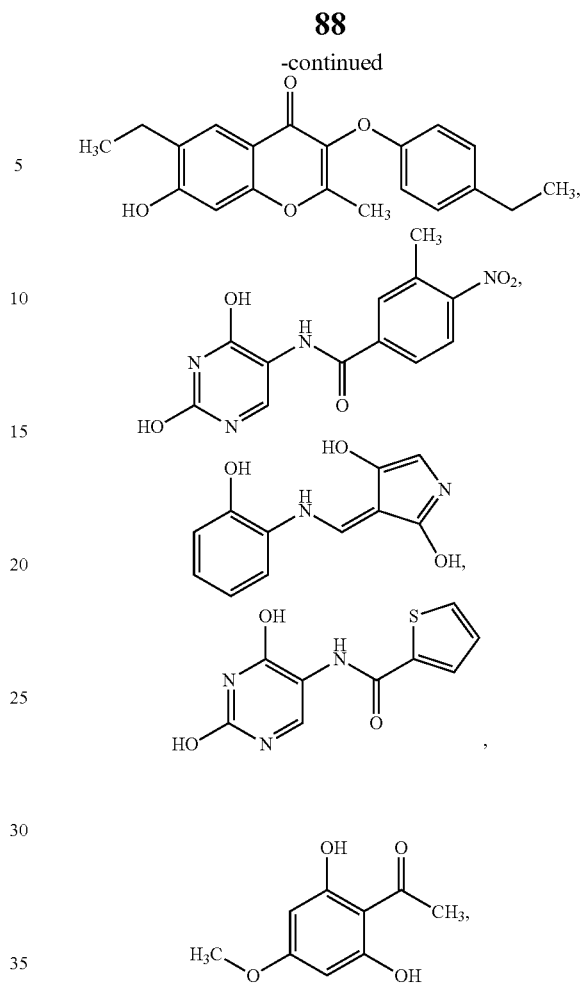

and c) performing an in vitro, in vivo, or ex vivo assay to identify the one or more compounds that inhibit conversion of CD4+CD25− T cells to CD4+CD25+ T regulatory cells.

Various embodiments of the present invention provide a method for inhibiting conversion of CD4+CD25− T cells to CD4+CD25+ T regulatory cells, comprising: a) providing a sample comprising CD4+CD25− T cells; b) contacting the sample with one or more compounds of formula:

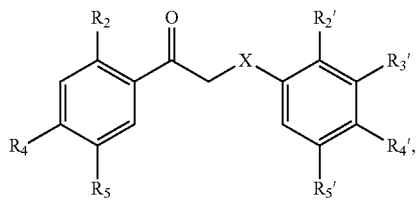

wherein,
R₂ is selected from H, OH, CH₃, and OCH₃;
R₄ is selected from H, OH, and OCH₃;
R₅ is selected from H, CH₃, and C₂H₅;
X is selected from H, O, and OC(=O);
R₂' is selected from H and OH;
R₃' is selected from H, OCH₃, and CH=CH—CH=CH;
R₄' is selected from H, CH₃, C₂H₅, CH(CH₃)₂, OCH₃, Ph, F, I, and CH=CH—CH=CH; and
R₅' is selected from H, CH₃, and OCH₃, wherein two or more of R₂, R₄, R₅ may be optionally connected, and two or more of R₂', R₃', R₄' R₅' may be optionally connected; and
c) performing an in vitro, in vivo, or ex vivo assay to identify the one or more compounds that inhibit conversion of CD4+CD25− T cells to CD4+CD25+ T regulatory cells.

Various embodiments of the present invention provide a method for inhibiting conversion of CD4+CD25− T cells to CD4+CD25+ T regulatory cells, comprising: a) providing a sample comprising CD4+CD25− T cells; b) contacting the sample with one or more compounds of formula:

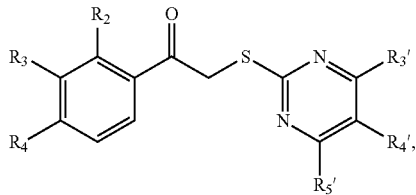

wherein,
R₂ is selected from H, OH, and OCH₃;
R₃ is selected from H, OH, OCH₃, and COOCH₃;
R₄ is selected from H, OH, and CH₃;
R₃' is selected from H, CH₃, CH=CH—CH=CH, and S—C(—CH₃)=C(—CH₃);
R₄' is selected from H and OH; and
R₅' is selected from H, OH, and CH₃, wherein two or more of R₂, R₃, R₄ may be optionally connected, and two or more of R₃', R₄' R₅' may be optionally connected; and c) performing an in vitro, in vivo, or ex vivo assay to identify the one or more compounds that inhibit conversion of CD4+CD25− T cells to CD4+CD25+ T regulatory cells.

Various embodiments of the present invention provide a method for inhibiting conversion of CD4+CD25− T cells to CD4+CD25+ T regulatory cells, comprising: a) providing a sample comprising CD4+CD25− T cells; b) contacting the sample with one or more compounds selected from:

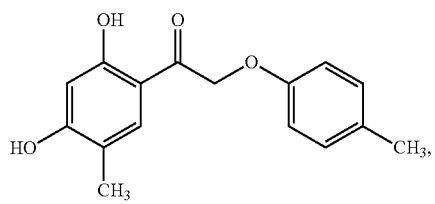

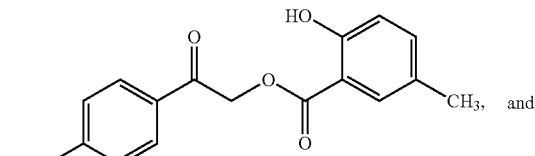

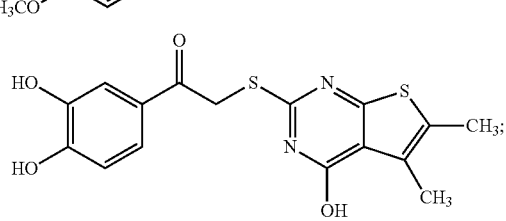

and c) performing an in vitro, in vivo, or ex vivo assay to identify the one or more compounds that inhibit conversion of CD4+CD25− T cells to CD4+CD25+ T regulatory cells.

Various embodiments of the present invention provide a method for inhibiting expression of Foxp3 gene, comprising: a) providing a sample comprising CD4+CD25− T cells; b) contacting the sample with one or more compounds selected from:

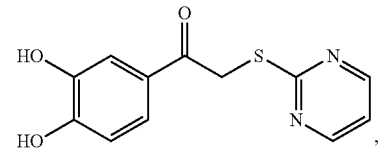

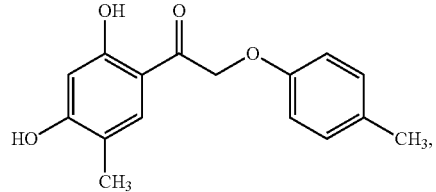

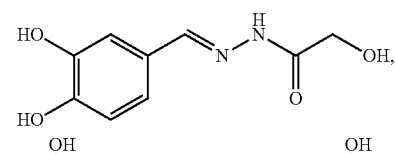

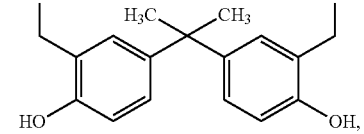

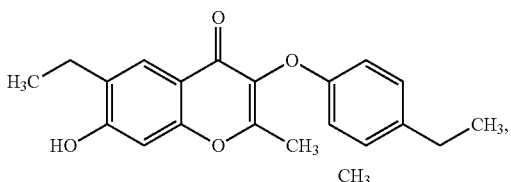

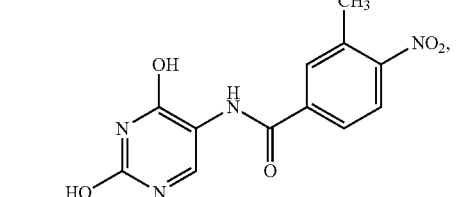

-continued

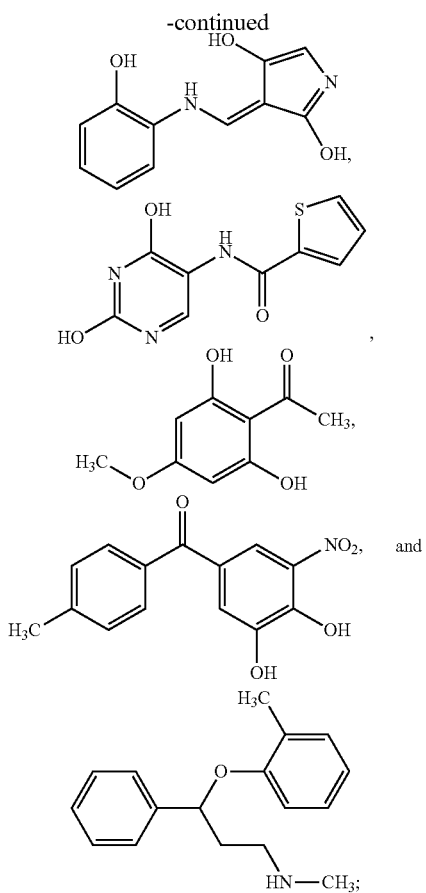

and c) performing an in vitro, in vivo, or ex vivo assay to identify the one or more compounds that inhibit expression of the Foxp3 gene.

Various embodiments of the present invention provide a method for inhibiting expression of Foxp3 gene, comprising: a) providing a sample comprising CD4+CD25− T cells; b) contacting the sample with one or more compounds of formula:

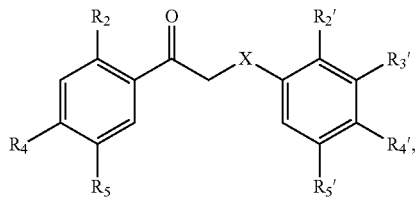

wherein,
R$_2$ is selected from H, OH, CH$_3$, and OCH$_3$;
R$_4$ is selected from H, OH, and OCH$_3$;
R$_5$ is selected from H, CH$_3$, and C$_2$H$_5$;
X is selected from H, O, and OC(=O);
R$_2$' is selected from H and OH;
R$_3$' is selected from H, OCH$_3$, and CH=CH—CH=CH;
R$_4$' is selected from H, CH$_3$, C$_2$H$_5$, CH(CH$_3$)$_2$, OCH$_3$, Ph, F, I, and CH=CH—CH=CH; and
R$_5$' is selected from H, CH$_3$, and OCH$_3$, wherein two or more of R$_2$, R$_4$, R$_5$ may be optionally connected, and two or more of R$_2$', R$_3$', R$_4$' R$_5$' may be optionally connected; and c) performing an in vitro, in vivo, or ex vivo assay to identify the one or more compounds that inhibit expression of the Foxp3 gene.

Various embodiments of the present invention provide a method for inhibiting expression of Foxp3 gene, comprising: a) providing a sample comprising CD4+CD25− T cells; b) contacting the sample with one or more compounds of formula:

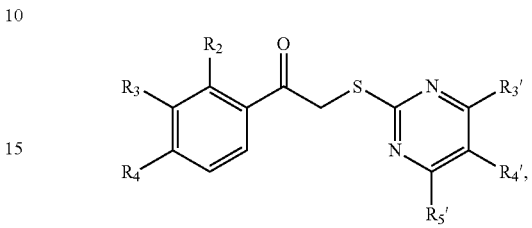

wherein,
R$_2$ is selected from H, OH, and OCH$_3$;
R$_3$ is selected from H, OH, OCH$_3$, and COOCH$_3$;
R$_4$ is selected from H, OH, and CH$_3$;
R$_3$' is selected from H, CH$_3$, CH=CH—CH=CH, and S—C(—CH$_3$)=C(—CH$_3$);
R$_4$' is selected from H and OH; and
R$_5$' is selected from H, OH, and CH$_3$, wherein two or more of R$_2$, R$_3$, R$_4$ may be optionally connected, and two or more of R$_3$', R$_4$' R$_5$' may be optionally connected; and c) performing an in vitro, in vivo, or ex vivo assay to identify the one or more compounds that inhibit expression of the Foxp3 gene.

Various embodiments of the present invention provide a method for inhibiting expression of Foxp3 gene, comprising: a) providing a sample comprising CD4+CD25− T cells; b) contacting the sample with one or more compounds selected from:

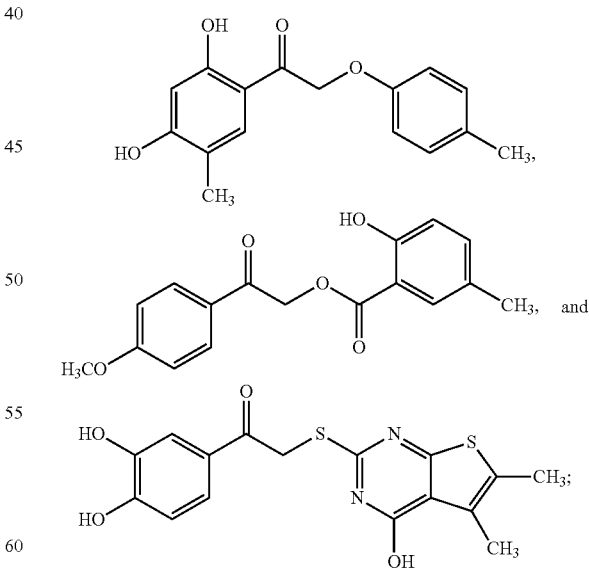

and c) performing an in vitro, in vivo, or ex vivo assay to identify the one or more compounds that inhibit expression of the Foxp3 gene.

Various embodiments of the present invention provide a method for inhibiting transcription of KLF10, comprising:

a) providing a sample comprising KLF10; b) contacting the sample with one or more compounds selected from:

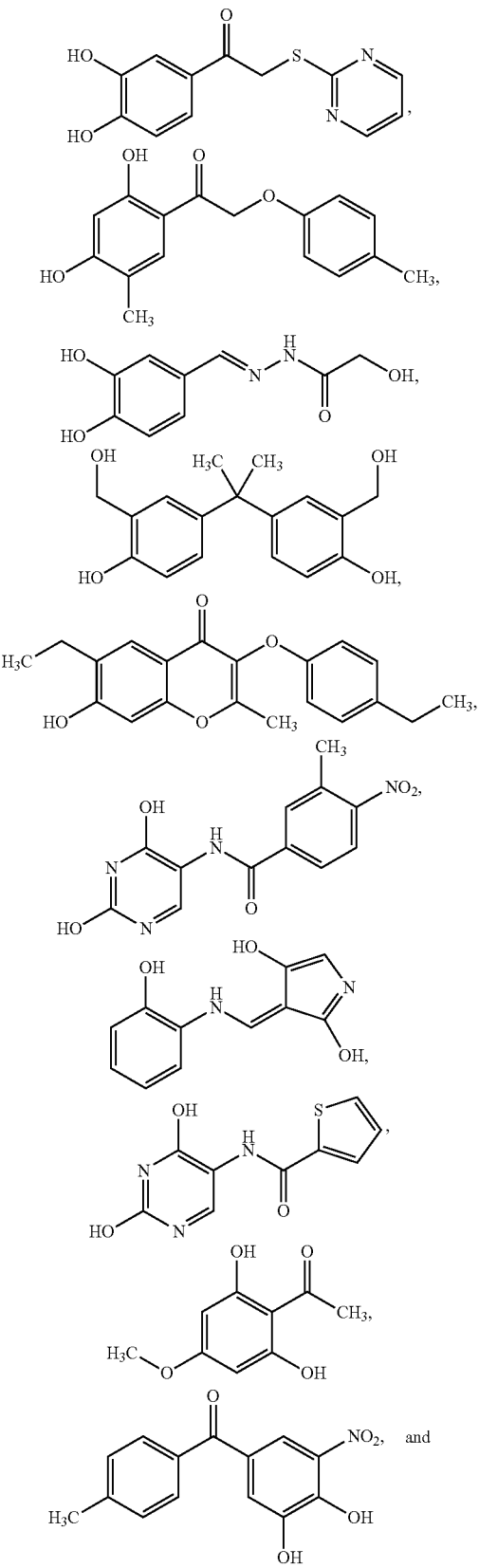

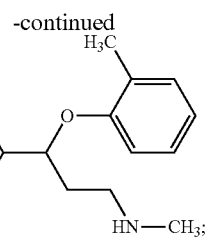

and c) performing an in vitro, in vivo, or ex vivo assay to identify the one or more compounds that inhibit transcription of KLF10.

Various embodiments of the present invention provide a method for inhibiting transcription of KLF10, comprising: a) providing a sample comprising KLF10; b) contacting the sample with one or more compounds of formula:

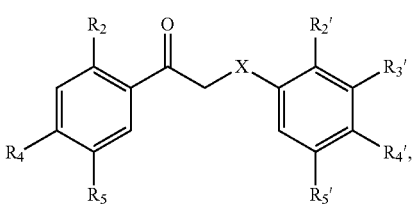

wherein,
$R_2$ is selected from H, OH, $CH_3$, and $OCH_3$;
$R_4$ is selected from H, OH, and $OCH_3$;
$R_5$ is selected from H, $CH_3$, and $C_2H_5$;
X is selected from H, O, and OC(=O);
$R_2'$ is selected from H and OH;
$R_3'$ is selected from H, $OCH_3$, and CH=CH—CH=CH;
$R_4'$ is selected from H, $CH_3$, $C_2H_5$, $CH(CH_3)_2$, $OCH_3$, Ph, F, I, and CH=CH—CH=CH; and
$R_5'$ is selected from H, $CH_3$, and $OCH_3$, wherein two or more of $R_2$, $R_4$, $R_5$ may be optionally connected, and two or more of $R_2'$, $R_3'$, $R_4'$ $R_5'$ may be optionally connected; and
c) performing an in vitro, in vivo, or ex vivo assay to identify the one or more compounds that inhibit transcription of KLF10.

Various embodiments of the present invention provide a method for inhibiting transcription of KLF10, comprising: a) providing a sample comprising KLF10; b) contacting the sample with one or more compounds of formula:

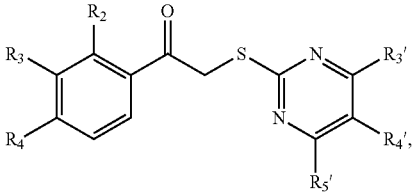

wherein,
$R_2$ is selected from H, OH, and $OCH_3$;
$R_3$ is selected from H, OH, $OCH_3$, and $COOCH_3$;
$R_4$ is selected from H, OH, and $CH_3$;
$R_3'$ is selected from H, $CH_3$, CH=CH—CH=CH, and S—C(—$CH_3$)=C(—$CH_3$);
$R_4'$ is selected from H and OH; and
$R_5'$ is selected from H, OH, and $CH_3$, wherein two or more of $R_2$, $R_3$, $R_4$ may be optionally connected, and two or more of $R_3'$, $R_4'$ $R_5'$ may be optionally connected; and c) performing an in vitro, in vivo, or ex vivo assay to identify the one or more compounds that inhibit transcription of KLF10.

Various embodiments of the present invention provide a method for inhibiting transcription of KLF10, comprising: a) providing a sample comprising KLF10; b) contacting the sample with one or more compounds selected from:

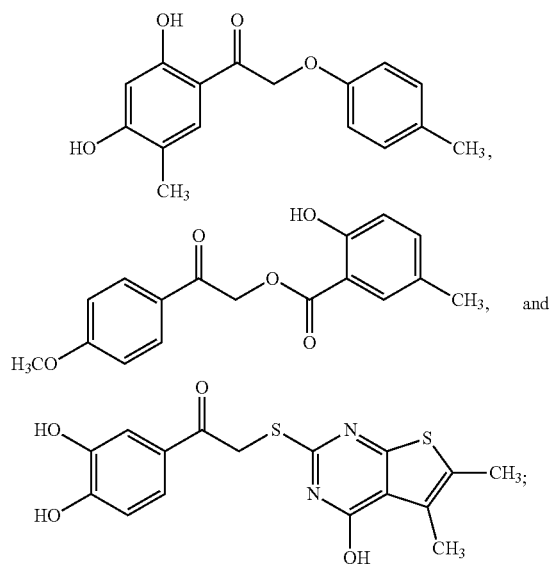

and c) performing an in vitro, in vivo, or ex vivo assay to identify the one or more compounds that inhibit transcription of KLF10.

Various embodiments of the present invention provide a method of modulating an immune response, comprising: administering to a subject an effective amount of an inhibitor of KLF10, wherein the inhibitor of KLF10 is a compound selected from:

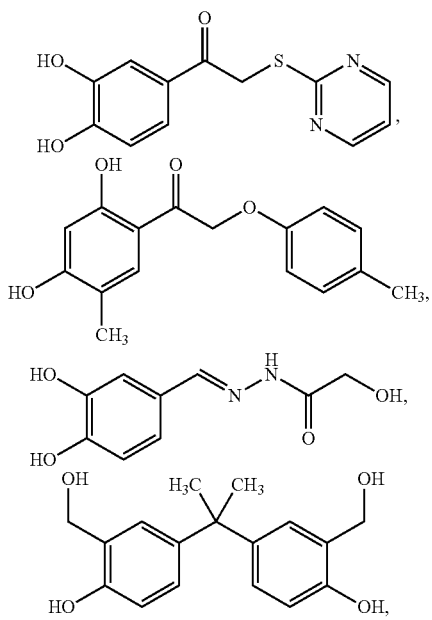

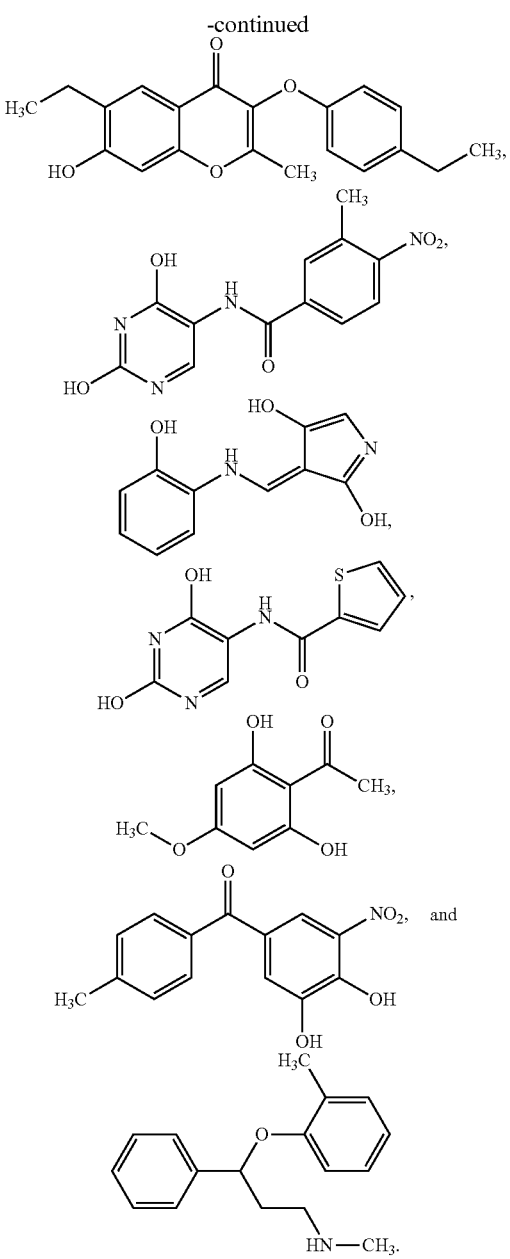

In some embodiments, inhibiting KLF10 decreases T regulatory (T reg) cells at a tumor site or a pathogen infected area of the subject. In some embodiments, the T reg cells are CD4+/CD25+ T reg cells. In some embodiments, the T reg cells are CD4+/CD25+/Fox3p+ T reg cells. In some embodiments, the infection is a chronic viral infection, a bacterial infection, a fungal infection, a mycoplasm infection, a parasitic infection, elicits disease mediated by a toxin during the acute phase of infection or where the infection is characterized by reduced T cell response. In some embodiments, the viral infection is an infection with a hepatitis virus, a human immunodeficiency virus, a human T-lymphotrophic virus, a herpes virus, an Epstein-Barr virus, filovirus, a human papilloma virus, an Epstein Barr virus, an influenza virus, a respiratory synticial virus, an encephalitis virus, a dengue fever virus, and a papilloma virus. In some embodiments, the parasitic infection is malaria or *Leishmania*. In some embodiments, the bacterial infection is caused by a bacterium selected from the group consisting of *Mycobacterium tuberculosis, Bacillus anthracis, Staphylococcus, Listeria*, and *Clamydia trachomatis*. In some embodiments, the method further comprises administering a disease antigen in combination with the immunomodulatory agent to enhance an immune response against the disease. In some embodiments, the method further comprises comprising administering with the inhibitor of KLF10 an additional active agent selected from the group consisting of immunomodulators, agents that deplete or inhibit the function of T regs, and costimulatory molecules. In some embodiments, the additional active agent is an agent that depletes or inhibits the function of CD4+CD25+ T regs. In some embodiments, the agent that depletes or inhibits the function of CD4+CD25+ Tregs is cyclophosphamide. In some embodiments, the tumor is selected from the group consisting of sarcoma, melanoma, lymphoma, neuroblastoma, and carcinoma.

Various embodiments of the present invention provide a method of modulating an immune response, comprising: administering to a subject an effective amount of an inhibitor of KLF10, wherein the inhibitor of KLF10 is a compound of formula:

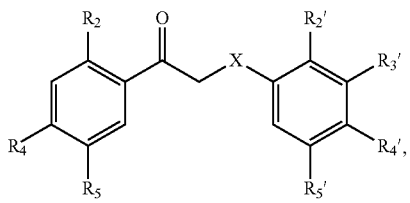

wherein,
$R_2$ is selected from H, OH, $CH_3$, and $OCH_3$;
$R_4$ is selected from H, OH, and $OCH_3$;
$R_5$ is selected from H, $CH_3$, and $C_2H_5$;
X is selected from H, O, and OC(=O);
$R_2'$ is selected from H and OH;
$R_3'$ is selected from H, $OCH_3$, and CH=CH—CH=CH;
$R_4'$ is selected from H, $CH_3$, $C_2H_5$, $CH(CH_3)_2$, $OCH_3$, Ph, F, I, and CH=CH—CH=CH; and
$R_5'$ is selected from H, $CH_3$, and $OCH_3$, wherein two or more of $R_2$, $R_4$, $R_5$ may be optionally connected, and two or more of $R_2'$, $R_3'$, $R_4'$ $R_5'$ may be optionally connected. In some embodiments, inhibiting KLF10 decreases T regulatory (T reg) cells at a tumor site or a pathogen infected area of the subject. In some embodiments, the T reg cells are CD4+/CD25+ T reg cells. In some embodiments, the T reg cells are CD4+/CD25+/Fox3p+ T reg cells. In some embodiments, the infection is a chronic viral infection, a bacterial infection, a fungal infection, a mycoplasm infection, a parasitic infection, elicits disease mediated by a toxin during the acute phase of infection or where the infection is characterized by reduced T cell response. In some embodiments, the viral infection is an infection with a hepatitis virus, a human immunodeficiency virus, a human T-lymphotrophic virus, a herpes virus, an Epstein-Barr virus, filovirus, a human papilloma virus, an Epstein Barr virus, an influenza virus, a respiratory synticial virus, an encephalitis virus, a dengue fever virus, and a papilloma virus. In some embodiments, the parasitic infection is malaria or *Leishmania*. In some embodiments, the bacterial infection is caused by a bacterium selected from the group consisting of *Mycobacterium tuberculosis, Bacillus anthracis, Staphylococcus, Listeria*, and *Clamydia trachomatis*. In some embodiments, the method further comprises administering a disease antigen in combination with the immunomodulatory agent to enhance an immune response against the disease. In some embodiments, the method further comprises comprising administering with the inhibitor of KLF10 an additional active agent selected from the group consisting of immunomodulators, agents that deplete or inhibit the function of T regs, and costimulatory molecules. In some embodiments, the additional active agent is an agent that depletes or inhibits the function of CD4+CD25+ T regs. In some embodiments, the agent that depletes or inhibits the function of CD4+CD25+ Tregs is cyclophosphamide. In some embodiments, the tumor is selected from the group consisting of sarcoma, melanoma, lymphoma, neuroblastoma, and carcinoma.

Various embodiments of the present invention provide a method of modulating an immune response, comprising: administering to a subject an effective amount of an inhibitor of KLF10, wherein the inhibitor of KLF10 is a compound of formula:

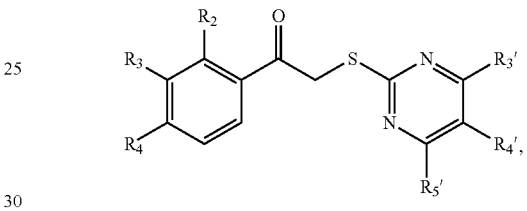

wherein,
$R_2$ is selected from H, OH, and $OCH_3$;
$R_3$ is selected from H, OH, $OCH_3$, and $COOCH_3$;
$R_4$ is selected from H, OH, and $CH_3$;
$R_3'$ is selected from H, $CH_3$, CH=CH—CH=CH, and S—C(—$CH_3$)=C(—$CH_3$);
$R_4'$ is selected from H and OH; and
$R_5'$ is selected from H, OH, and $CH_3$, wherein two or more of $R_2$, $R_3$, $R_4$ may be optionally connected, and two or more of $R_3'$, $R_4'$ $R_5'$ may be optionally connected. In some embodiments, inhibiting KLF10 decreases T regulatory (T reg) cells at a tumor site or a pathogen infected area of the subject. In some embodiments, the T reg cells are CD4+/CD25+ T reg cells. In some embodiments, the T reg cells are CD4+/CD25+/Fox3p+ T reg cells. In some embodiments, the infection is a chronic viral infection, a bacterial infection, a fungal infection, a mycoplasm infection, a parasitic infection, elicits disease mediated by a toxin during the acute phase of infection or where the infection is characterized by reduced T cell response. In some embodiments, the viral infection is an infection with a hepatitis virus, a human immunodeficiency virus, a human T-lymphotrophic virus, a herpes virus, an Epstein-Barr virus, filovirus, a human papilloma virus, an Epstein Barr virus, an influenza virus, a respiratory synticial virus, an encephalitis virus, a dengue fever virus, and a papilloma virus. In some embodiments, the parasitic infection is malaria or *Leishmania*. In some embodiments, the bacterial infection is caused by a bacterium selected from the group consisting of *Mycobacterium tuberculosis, Bacillus anthracis, Staphylococcus, Listeria*, and *Clamydia trachomatis*. In some embodiments, the method further comprises administering a disease antigen in combination with the immunomodulatory agent to enhance an immune response against the disease. In some embodiments, the method further comprises comprising administering with the inhibitor of KLF10 an additional active agent selected from the group consisting of immunomodulators, agents that deplete or inhibit the function of T regs, and costimulatory molecules. In some embodiments, the additional active agent is an agent that depletes or inhibits the function of CD4+CD25+ T regs. In some embodiments, the agent that depletes or inhibits the function of CD4+CD25+ Tregs is cyclophosphamide. In some embodiments, the tumor is selected from the group consisting of sarcoma, melanoma, lymphoma, neuroblastoma, and carcinoma.

Various embodiments of the present invention provide a method of modulating an immune response, comprising: administering to a subject an effective amount of an inhibitor of KLF10, wherein the inhibitor of KLF10 is a compound selected from:

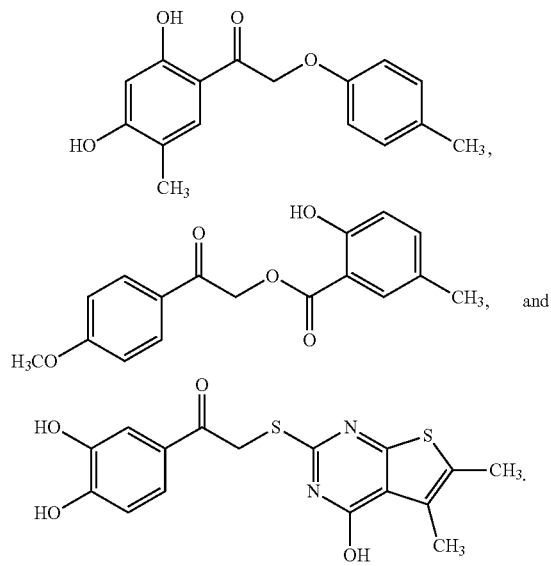

In some embodiments, inhibiting KLF10 decreases T regulatory (T reg) cells at a tumor site or a pathogen infected area of the subject. In some embodiments, the T reg cells are CD4+/CD25+ T reg cells. In some embodiments, the T reg cells are CD4+/CD25+/Fox3p+ T reg cells. In some embodiments, the infection is a chronic viral infection, a bacterial infection, a fungal infection, a mycoplasm infection, a parasitic infection, elicits disease mediated by a toxin during the acute phase of infection or where the infection is characterized by reduced T cell response. In some embodiments, the viral infection is an infection with a hepatitis virus, a human immunodeficiency virus, a human T-lymphotrophic virus, a herpes virus, an Epstein-Barr virus, filovirus, a human papilloma virus, an Epstein Barr virus, an influenza virus, a respiratory syncitial virus, an encephalitis virus, a dengue fever virus, and a papilloma virus. In some embodiments, the parasitic infection is malaria or *Leishmania*. In some embodiments, the bacterial infection is caused by a bacterium selected from the group consisting of *Mycobacterium tuberculosis, Bacillus anthracis, Staphylococcus, Listeria*, and *Clamydia trachomatis*. In some embodiments, the method further comprises administering a disease antigen in combination with the immunomodulatory agent to enhance an immune response against the disease. In some embodiments, the method further comprises comprising administering with the inhibitor of KLF10 an additional active agent selected from the group consisting of immunomodulators, agents that deplete or inhibit the function of T regs, and costimulatory molecules. In some embodiments, the additional active agent is an agent that depletes or inhibits the function of CD4+CD25+ T regs. In some embodiments, the agent that depletes or inhibits the function of CD4+CD25+ Tregs is cyclophosphamide. In some embodiments, the tumor is selected from the group consisting of sarcoma, melanoma, lymphoma, neuroblastoma, and carcinoma.

Various embodiments of the present invention provide a method of modulating an immune response, comprising: administering to a subject an effective amount of an inhibitor of KLF10 to decrease T regulatory (T reg) cells at a tumor site or a pathogen infected area of the subject, wherein the inhibitor of KLF10 is a compound selected from:

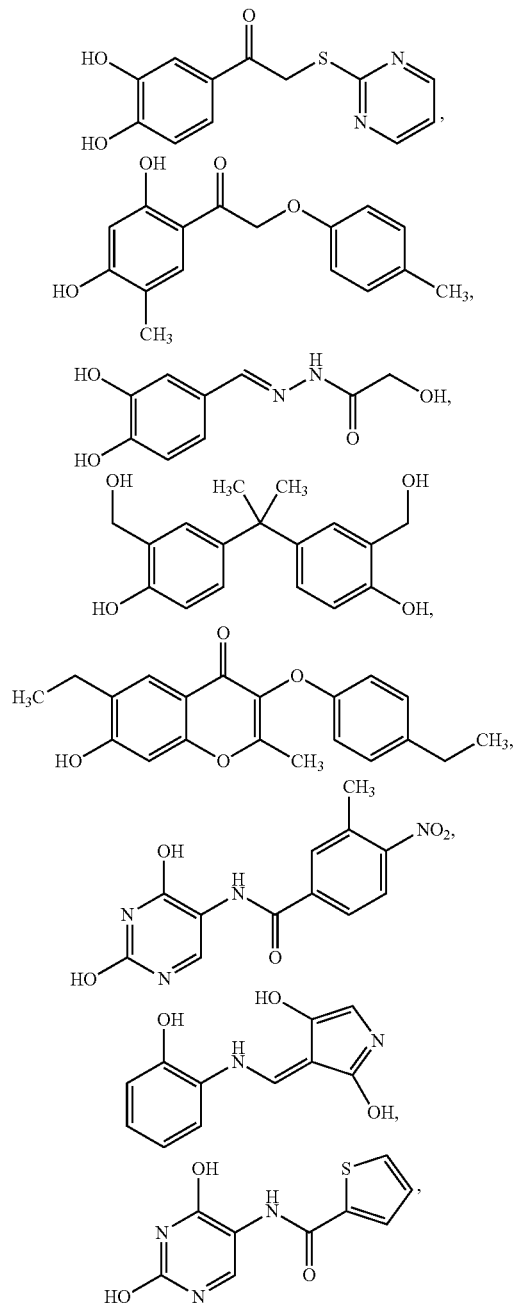

-continued

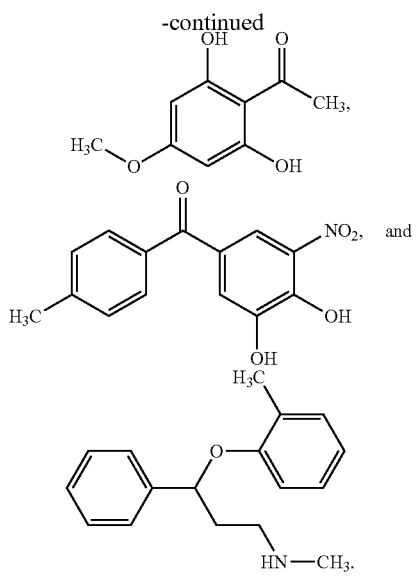

In some embodiments, the T reg cells are CD4+/CD25+ T reg cells. In some embodiments, the T reg cells are CD4+/CD25+/Fox3p+ T reg cells. In some embodiments, the infection is a chronic viral infection, a bacterial infection, a fungal infection, a mycoplasm infection, a parasitic infection, elicits disease mediated by a toxin during the acute phase of infection or where the infection is characterized by reduced T cell response. In some embodiments, the viral infection is an infection with a hepatitis virus, a human immunodeficiency virus, a human T-lymphotrophic virus, a herpes virus, an Epstein-Barr virus, filovirus, a human papilloma virus, an Epstein Barr virus, an influenza virus, a respiratory synticial virus, an encephalitis virus, a dengue fever virus, and a papilloma virus. In some embodiments, the parasitic infection is malaria or *Leishmania*. In some embodiments, the bacterial infection is caused by a bacterium selected from the group consisting of *Mycobacterium tuberculosis, Bacillus anthracis, Staphylococcus, Listeria*, and *Clamydia trachomatis*. In some embodiments, the method further comprises administering a disease antigen in combination with the immunomodulatory agent to enhance an immune response against the disease. In some embodiments, the method further comprises comprising administering with the inhibitor of KLF10 an additional active agent selected from the group consisting of immunomodulators, agents that deplete or inhibit the function of T regs, and costimulatory molecules. In some embodiments, the additional active agent is an agent that depletes or inhibits the function of CD4+CD25+ T regs. In some embodiments, the agent that depletes or inhibits the function of CD4+CD25+ Tregs is cyclophosphamide. In some embodiments, the tumor is selected from the group consisting of sarcoma, melanoma, lymphoma, neuroblastoma, and carcinoma.

Various embodiments of the present invention provide a method of modulating an immune response, comprising: administering to a subject an effective amount of an inhibitor of KLF10 to decrease T regulatory (T reg) cells at a tumor site or a pathogen infected area of the subject, wherein the inhibitor of KLF10 is a compound of formula:

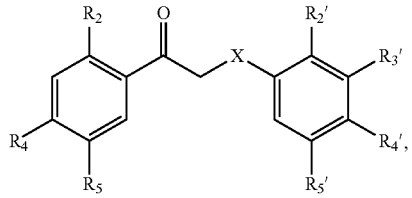

wherein, $R_2$ is selected from H, OH, $CH_3$, and $OCH_3$;

$R_4$ is selected from H, OH, and $OCH_3$;

$R_5$ is selected from H, $CH_3$, and $C_2H_5$;

X is selected from H, O, and OC(=O);

$R_2'$ is selected from H and OH;

$R_3'$ is selected from H, $OCH_3$, and CH=CH—CH=CH;

$R_4'$ is selected from H, $CH_3$, $C_2H_5$, $CH(CH_3)_2$, $OCH_3$, Ph, F, I, and CH=CH—CH=CH; and $R_5'$ is selected from H, $CH_3$, and $OCH_3$, wherein two or more of $R_2$, $R_4$, $R_5$ may be optionally connected, and two or more of $R_2'$, $R_3'$, $R_4'$ $R_5'$ may be optionally connected. In some embodiments, the T reg cells are CD4+/CD25+ T reg cells. In some embodiments, the T reg cells are CD4+/CD25+/Fox3p+ T reg cells. In some embodiments, the infection is a chronic viral infection, a bacterial infection, a fungal infection, a mycoplasm infection, a parasitic infection, elicits disease mediated by a toxin during the acute phase of infection or where the infection is characterized by reduced T cell response. In some embodiments, the viral infection is an infection with a hepatitis virus, a human immunodeficiency virus, a human T-lymphotrophic virus, a herpes virus, an Epstein-Barr virus, filovirus, a human papilloma virus, an Epstein Barr virus, an influenza virus, a respiratory synticial virus, an encephalitis virus, a dengue fever virus, and a papilloma virus. In some embodiments, the parasitic infection is malaria or *Leishmania*. In some embodiments, the bacterial infection is caused by a bacterium selected from the group consisting of *Mycobacterium tuberculosis, Bacillus anthracis, Staphylococcus, Listeria*, and *Clamydia trachomatis*. In some embodiments, the method further comprises administering a disease antigen in combination with the immunomodulatory agent to enhance an immune response against the disease. In some embodiments, the method further comprises comprising administering with the inhibitor of KLF10 an additional active agent selected from the group consisting of immunomodulators, agents that deplete or inhibit the function of T regs, and costimulatory molecules. In some embodiments, the additional active agent is an agent that depletes or inhibits the function of CD4+CD25+ T regs. In some embodiments, the agent that depletes or inhibits the function of CD4+CD25+ Tregs is cyclophosphamide. In some embodiments, the tumor is selected from the group consisting of sarcoma, melanoma, lymphoma, neuroblastoma, and carcinoma.

Various embodiments of the present invention provide a method of modulating an immune response, comprising: administering to a subject an effective amount of an inhibitor of KLF10 to decrease T regulatory (T reg) cells at a tumor site or a pathogen infected area of the subject, wherein the inhibitor of KLF10 is a compound of formula:

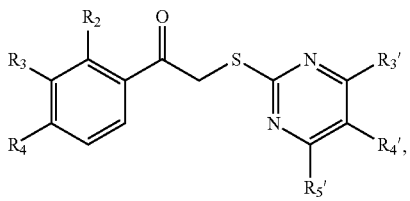

wherein,
R$_2$ is selected from H, OH, and OCH$_3$;
R$_3$ is selected from H, OH, OCH$_3$, and COOCH$_3$;
R$_4$ is selected from H, OH, and CH$_3$;
R$_3$' is selected from H, CH$_3$, CH=CH—CH=CH, and S—C(—CH$_3$)=C(—CH$_3$);
R$_4$' is selected from H and OH; and
R$_5$' is selected from H, OH, and CH$_3$, wherein two or more of R$_2$, R$_3$, R$_4$ may be optionally connected, and two or more of R$_3$', R$_4$' R$_5$' may be optionally connected. In some embodiments, the T reg cells are CD4+/CD25+ T reg cells. In some embodiments, the T reg cells are CD4+/CD25+/Fox3p+ T reg cells. In some embodiments, the infection is a chronic viral infection, a bacterial infection, a fungal infection, a mycoplasm infection, a parasitic infection, elicits disease mediated by a toxin during the acute phase of infection or where the infection is characterized by reduced T cell response. In some embodiments, the viral infection is an infection with a hepatitis virus, a human immunodeficiency virus, a human T-lymphotrophic virus, a herpes virus, an Epstein-Barr virus, filovirus, a human papilloma virus, an Epstein Barr virus, an influenza virus, a respiratory synticial virus, an encephalitis virus, a dengue fever virus, and a papilloma virus. In some embodiments, the parasitic infection is malaria or *Leishmania*. In some embodiments, the bacterial infection is caused by a bacterium selected from the group consisting of *Mycobacterium tuberculosis, Bacillus anthracis, Staphylococcus, Listeria*, and *Clamydia trachomatis*. In some embodiments, the method further comprises administering a disease antigen in combination with the immunomodulatory agent to enhance an immune response against the disease. In some embodiments, the method further comprises comprising administering with the inhibitor of KLF10 an additional active agent selected from the group consisting of immunomodulators, agents that deplete or inhibit the function of T regs, and costimulatory molecules. In some embodiments, the additional active agent is an agent that depletes or inhibits the function of CD4+CD25+ T regs. In some embodiments, the agent that depletes or inhibits the function of CD4+CD25+ Tregs is cyclophosphamide. In some embodiments, the tumor is selected from the group consisting of sarcoma, melanoma, lymphoma, neuroblastoma, and carcinoma.

Various embodiments of the present invention provide a method of modulating an immune response, comprising: administering to a subject an effective amount of an inhibitor of KLF10 to decrease T regulatory (T reg) cells at a tumor site or a pathogen infected area of the subject, wherein the inhibitor of KLF10 is a compound selected from:

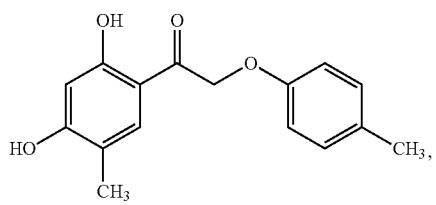

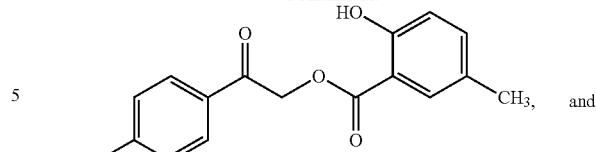

In some embodiments the compound is:

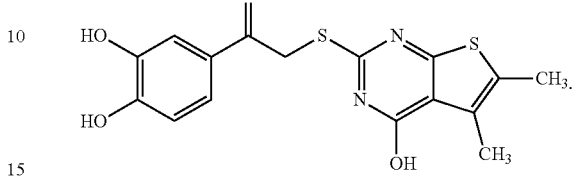

In some embodiments the compound is:

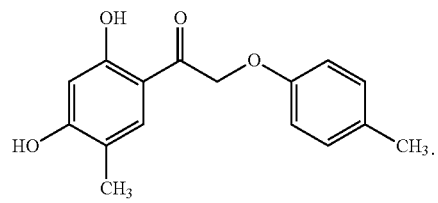

In some embodiments the compound is:

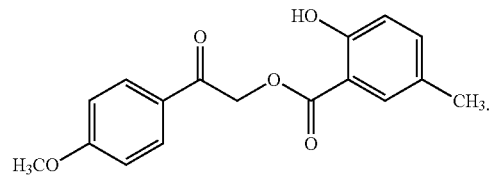 [SMILES: COc1ccc(C(=O)COC(=O)c2cc(C)ccc2O)cc1]

In some embodiments, the T reg cells are CD4+/CD25+ T reg cells. In some embodiments, the T reg cells are CD4+/CD25+/Fox3p+ T reg cells. In some embodiments, the infection is a chronic viral infection, a bacterial infection, a fungal infection, a mycoplasm infection, a parasitic infection, elicits disease mediated by a toxin during the acute phase of infection or where the infection is characterized by reduced T cell response. In some embodiments, the viral infection is an infection with a hepatitis virus, a human immunodeficiency virus, a human T-lymphotrophic virus, a herpes virus, an Epstein-Barr virus, filovirus, a human papilloma virus, an Epstein Barr virus, an influenza virus, a respiratory synticial virus, an encephalitis virus, a dengue fever virus, and a papilloma virus. In some embodiments, the parasitic infection is malaria or *Leishmania*. In some embodiments, the bacterial infection is caused by a bacterium selected from the group consisting of *Mycobacterium tuberculosis, Bacillus anthracis, Staphylococcus, Listeria,* and *Clamydia trachomatis*. In some embodiments, the method further comprises administering a disease antigen in combination with the immunomodulatory agent to enhance an immune response against the disease. In some embodiments, the method further comprises comprising administering with the inhibitor of KLF10 an additional active agent selected from the group consisting of immunomodulators, agents that deplete or inhibit the function of T regs, and costimulatory molecules. In some embodiments, the additional active agent is an agent that depletes or inhibits the function of CD4+CD25+ T regs. In some embodiments, the agent that depletes or inhibits the function of CD4+CD25+ Tregs is cyclophosphamide. In some embodiments, the tumor is selected from the group consisting of sarcoma, melanoma, lymphoma, neuroblastoma, and carcinoma Various embodiments of the present invention provide a composition, comprising: an effective amount of an inhibitor of KLF10 to decrease T regulatory (T reg) cells at a tumor site or a pathogen infected area of a subject, wherein the inhibitor of KLF10 is a compound selected from:

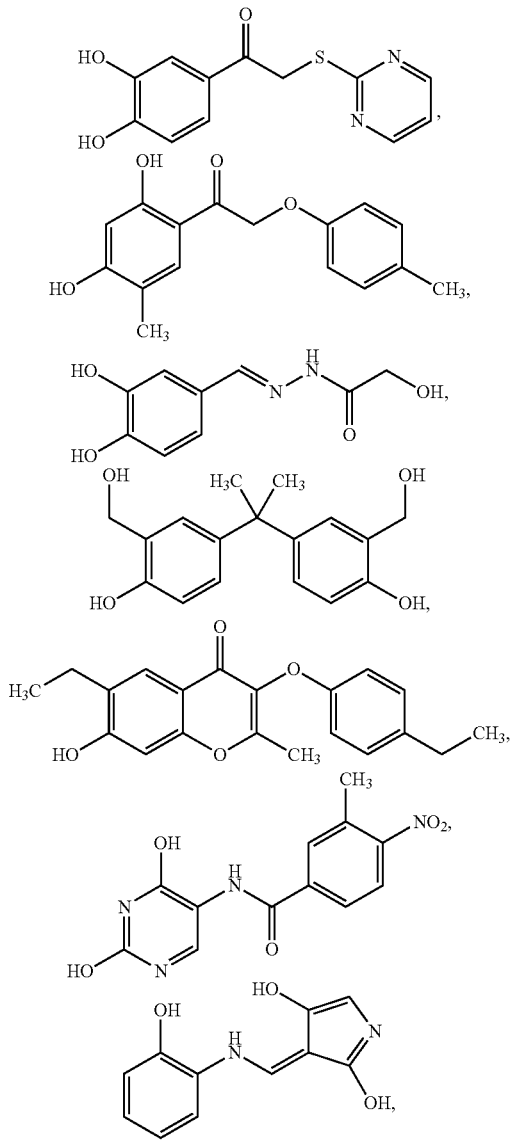

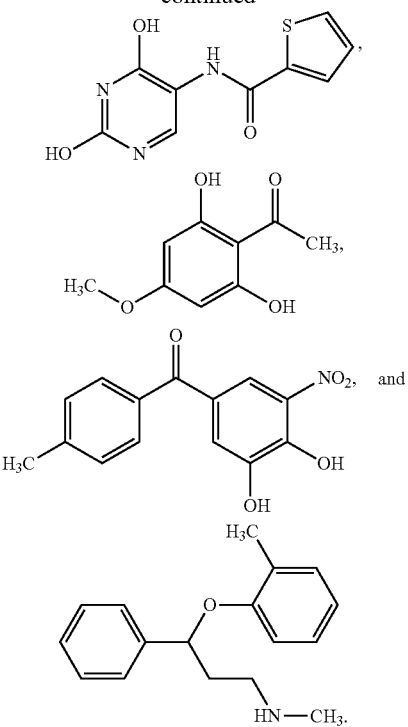

Various embodiments of the present invention provide a composition, comprising: an effective amount of an inhibitor of KLF10 to decrease T regulatory (T reg) cells at a tumor site or a pathogen infected area of a subject, wherein the inhibitor of KLF10 is a compound of formula:

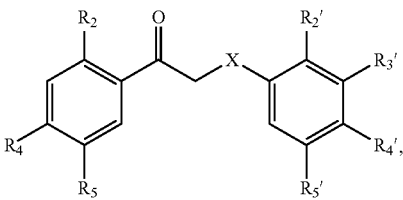

wherein, $R_2$ is selected from H, OH, $CH_3$, and $OCH_3$;

$R_4$ is selected from H, OH, and $OCH_3$;

$R_5$ is selected from H, $CH_3$, and $C_2H_5$;

X is selected from H, O, and OC(=O);

$R_2'$ is selected from H and OH;

$R_3'$ is selected from H, $OCH_3$, and CH=CH—CH=CH;

$R_4'$ is selected from H, $CH_3$, $C_2H_5$, $CH(CH_3)_2$, $OCH_3$, Ph, F, I, and CH=CH—CH=CH; and $R_5'$ is selected from H, $CH_3$, and $OCH_3$, wherein two or more of $R_2$, $R_4$, $R_5$ may be optionally connected, and two or more of $R_2'$, $R_3'$, $R_4'$ $R_5'$ may be optionally connected.

Various embodiments of the present invention provide a composition, comprising: an effective amount of an inhibitor of KLF10 to decrease T regulatory (T reg) cells at a tumor site or a pathogen infected area of a subject, wherein the inhibitor of KLF10 is a compound of formula:

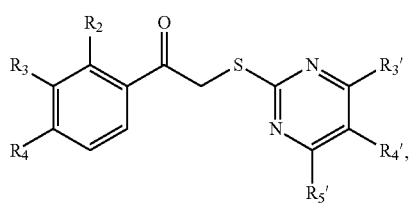

wherein,

R₂ is selected from H, OH, and OCH₃;

R₃ is selected from H, OH, OCH₃, and COOCH₃;

R₄ is selected from H, OH, and CH₃;

R₃' is selected from H, CH₃, CH=CH—CH=CH, and S—C(—CH₃)=C(—CH₃);

R₄' is selected from H and OH; and

R₅' is selected from H, OH, and CH₃, wherein two or more of R₂, R₃, R₄ may be optionally connected, and two or more of R₃', R₄' R₅' may be optionally connected.

Various embodiments of the present invention provide a composition, comprising: an effective amount of an inhibitor of KLF10 to decrease T regulatory (T reg) cells at a tumor site or a pathogen infected area of a subject, wherein the inhibitor of KLF10 is a compound selected from:

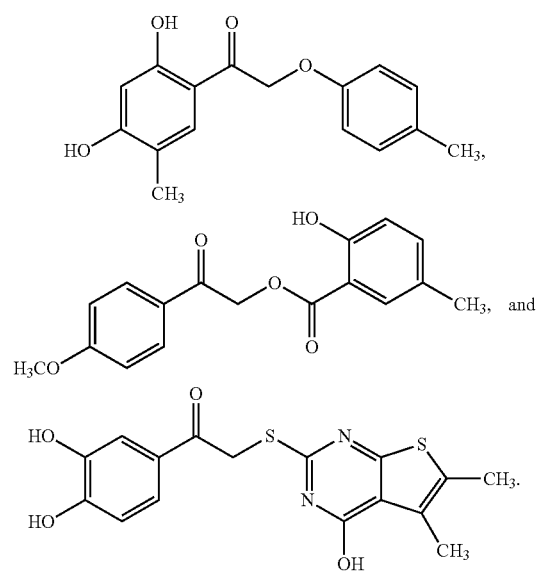

In some embodiments the compound is:

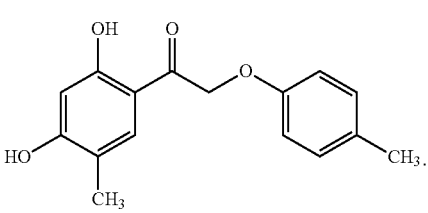

In some embodiments the compound is:

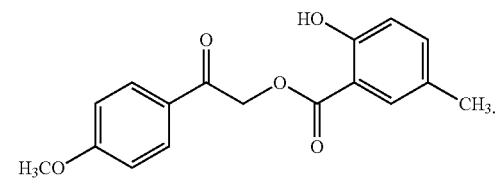 [SMILES: COc1ccc(C(=O)COC(=O)c2cc(C)ccc2O)cc1]

In some embodiments the compound is:

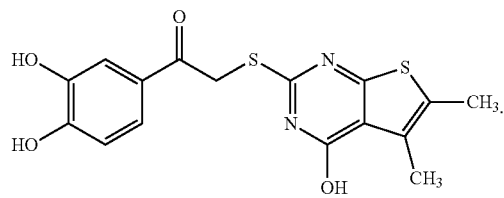 [SMILES: Cc1sc2nc(SCC(=O)c3ccc(O)c(O)c3)nc(O)c2c1C]

Various embodiments of the present invention provide a composition, comprising: an effective amount of an inhibitor of KLF10 to decrease T regulatory (T reg) cells at a tumor site or a pathogen infected area of a subject in combination with one or more disease antigens, wherein the inhibitor of KLF10 is a compound selected from:

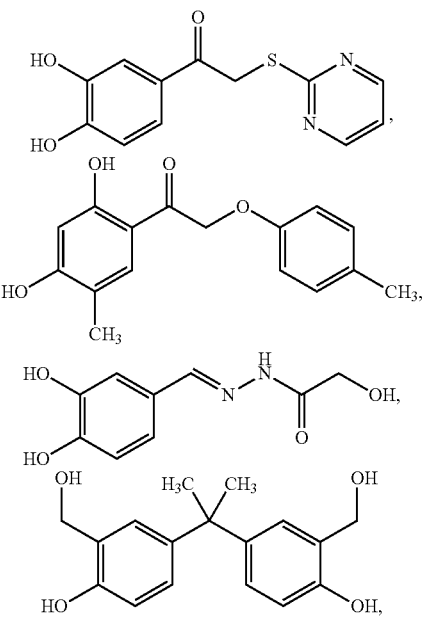

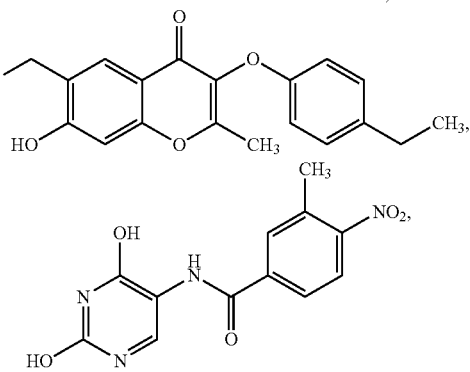

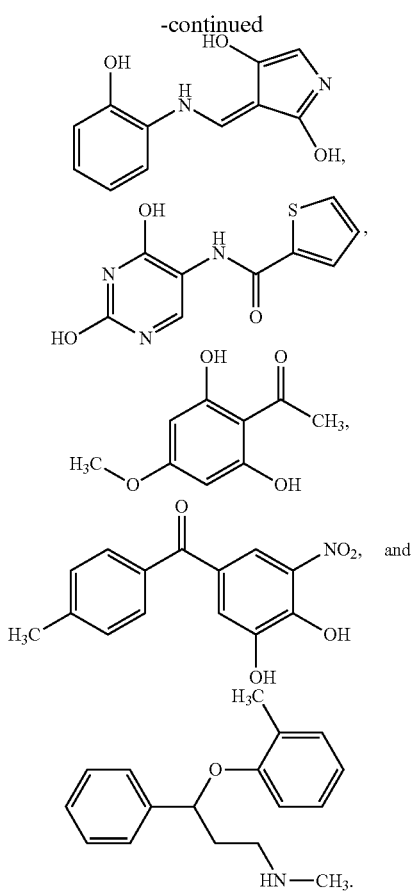

Various embodiments of the present invention provide a composition, comprising: an effective amount of an inhibitor of KLF10 to decrease T regulatory (T reg) cells at a tumor site or a pathogen infected area of a subject in combination with one or more disease antigens, wherein the inhibitor of KLF10 is a compound of formula:

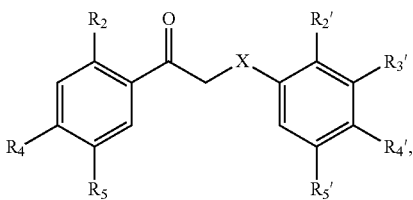

wherein,
R$_2$ is selected from H, OH, CH$_3$, and OCH$_3$;
R$_4$ is selected from H, OH, and OCH$_3$;
R$_5$ is selected from H, CH$_3$, and C$_2$H$_5$;
X is selected from H, O, and OC(=O);
R$_2$' is selected from H and OH;
R$_3$' is selected from H, OCH$_3$, and CH=CH—CH=CH;
R$_4$' is selected from H, CH$_3$, C$_2$H$_5$, CH(CH$_3$)$_2$, OCH$_3$, Ph, F, I, and CH=CH—CH=CH; and
R$_5$' is selected from H, CH$_3$, and OCH$_3$, wherein two or more of R$_2$, R$_4$, R$_5$ may be optionally connected, and two or more of R$_2$', R$_3$', R$_4$' R$_5$' may be optionally connected.

Various embodiments of the present invention provide a composition, comprising: an effective amount of an inhibitor of KLF10 to decrease T regulatory (T reg) cells at a tumor site or a pathogen infected area of a subject in combination with one or more disease antigens, wherein the inhibitor of KLF10 is a compound of formula:

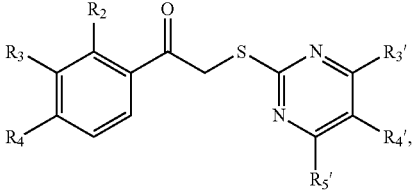

wherein,
R$_2$ is selected from H, OH, and OCH$_3$;
R$_3$ is selected from H, OH, OCH$_3$, and COOCH$_3$;
R$_4$ is selected from H, OH, and CH$_3$;
R$_3$' is selected from H, CH$_3$, CH=CH—CH=CH, and S—C(—CH$_3$)=C(—CH$_3$);
R$_4$' is selected from H and OH; and
R$_5$' is selected from H, OH, and CH$_3$, wherein two or more of R$_2$, R$_3$, R$_4$ may be optionally connected, and two or more of R$_3$', R$_4$' R$_5$' may be optionally connected.

Various embodiments of the present invention provide a composition, comprising: an effective amount of an inhibitor of KLF10 to decrease T regulatory (T reg) cells at a tumor site or a pathogen infected area of a subject in combination with one or more disease antigens, wherein the inhibitor of KLF10 is a compound selected from:

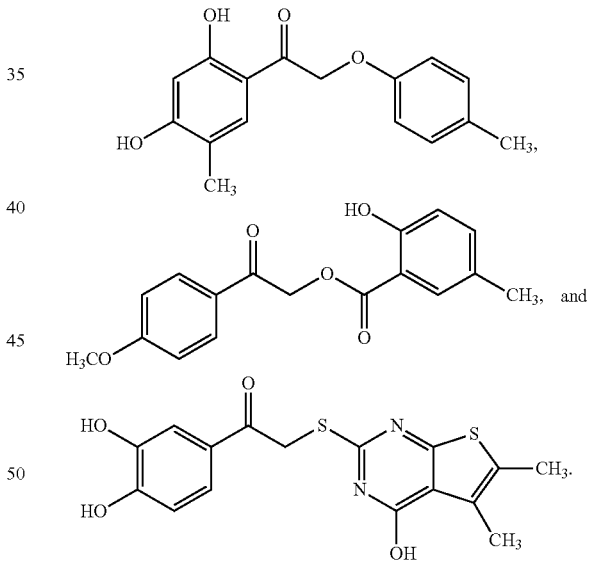

In some embodiments the compound is:

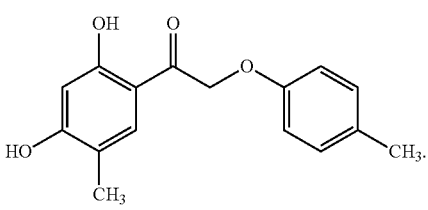 [SMILES: Cc1ccc(OCC(=O)c2cc(C)c(O)cc2O)cc1]

In some embodiments the compound is:

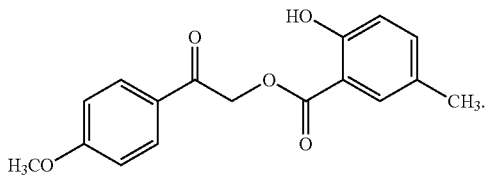 [SMILES: COc1ccc(C(=O)COC(=O)c2cc(C)ccc2O)cc1]

In some embodiments the compound is:

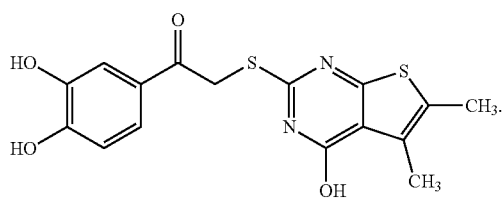 [SMILES: Cc1sc2nc(SCC(=O)c3ccc(O)c(O)c3)nc(O)c2c1C]

Various embodiments of the present invention provide a composition, comprising: an effective amount of an inhibitor of KLF10 to decrease T regulatory (T reg) cells at a tumor site or a pathogen infected area of a subject in combination with a vaccine, wherein the inhibitor of KLF10 is a compound selected from:

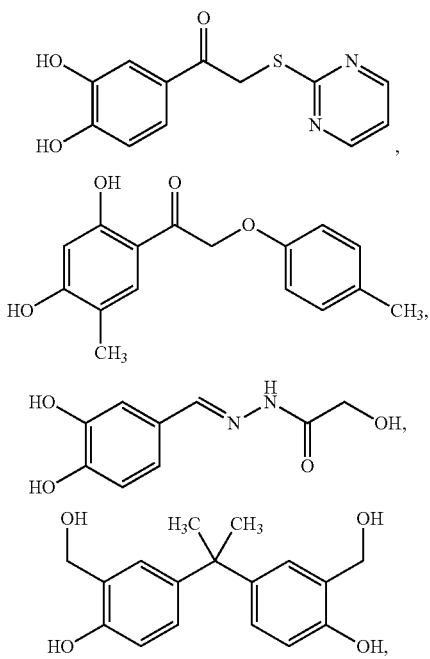

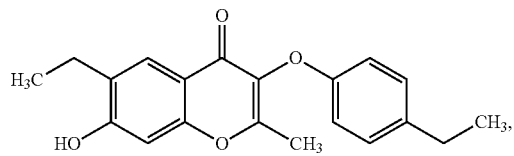

-continued

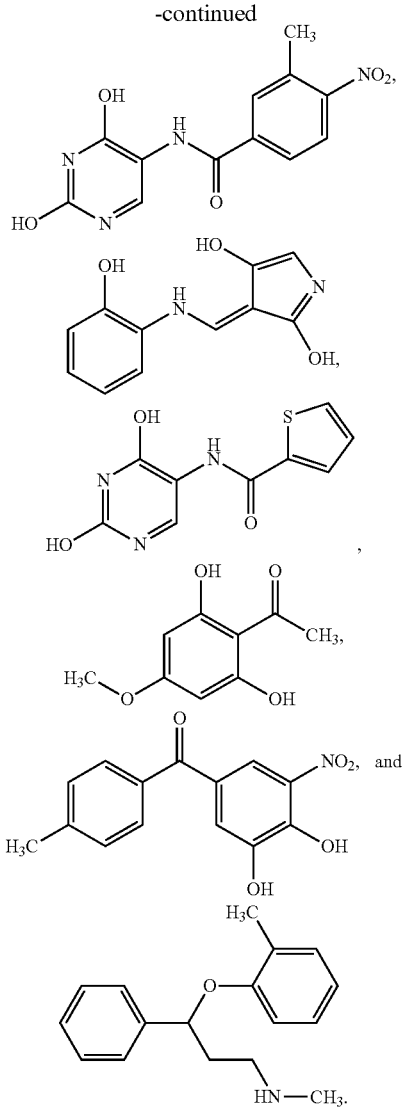

Various embodiments of the present invention provide a composition, comprising: an effective amount of an inhibitor of KLF10 to decrease T regulatory (T reg) cells at a tumor site or a pathogen infected area of a subject in combination with a vaccine, wherein the inhibitor of KLF10 is a compound of formula:

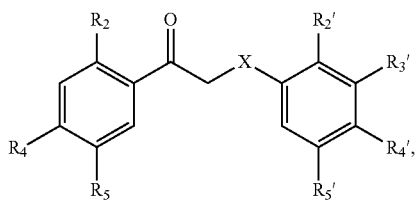

wherein,
$R_2$ is selected from H, OH, $CH_3$, and $OCH_3$;
$R_4$ is selected from H, OH, and $OCH_3$;
$R_5$ is selected from H, $CH_3$, and $C_2H_5$;
X is selected from H, O, and OC(=O);
$R_2'$ is selected from H and OH;
$R_3'$ is selected from H, $OCH_3$, and CH=CH—CH=CH;

$R_4'$ is selected from H, $CH_3$, $C_2H_5$, $CH(CH_3)_2$, $OCH_3$, Ph, F, I, and CH=CH—CH=CH; and $R_5'$ is selected from H, $CH_3$, and $OCH_3$, wherein two or more of $R_2$, $R_4$, $R_5$ may be optionally connected, and two or more of $R_2'$, $R_3'$, $R_4'$ $R_5'$ may be optionally connected.

Various embodiments of the present invention provide a composition, comprising: an effective amount of an inhibitor of KLF10 to decrease T regulatory (T reg) cells at a tumor site or a pathogen infected area of a subject in combination with a vaccine, wherein the inhibitor of KLF10 is a compound of formula:

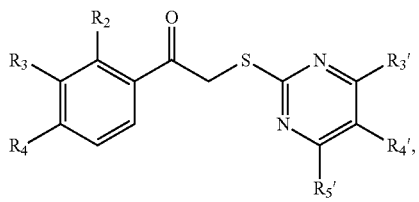

wherein, $R_2$ is selected from H, OH, and $OCH_3$;

$R_3$ is selected from H, OH, $OCH_3$, and $COOCH_3$;

$R_4$ is selected from H, OH, and $CH_3$;

$R_3'$ is selected from H, $CH_3$, CH=CH—CH=CH, and S—C(—$CH_3$)=C(—$CH_3$);

$R_4'$ is selected from H and OH; and $R_5'$ is selected from H, OH, and $CH_3$, wherein two or more of $R_2$, $R_3$, $R_4$ may be optionally connected, and two or more of $R_3'$, $R_4'$ $R_5'$ may be optionally connected.

Various embodiments of the present invention provide a composition, comprising: an effective amount of an inhibitor of KLF10 to decrease T regulatory (T reg) cells at a tumor site or a pathogen infected area of a subject in combination with a vaccine, wherein the inhibitor of KLF10 is a compound selected from:

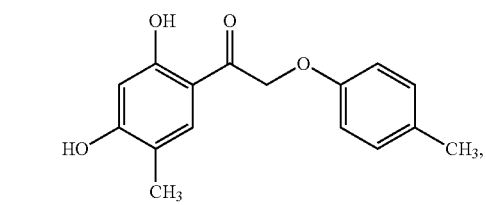

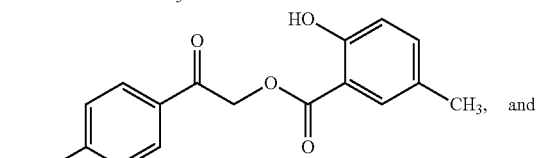

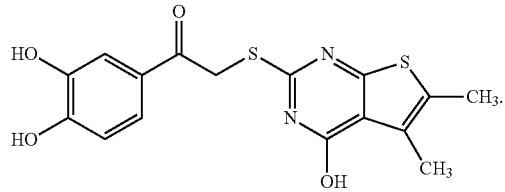

In some embodiments the compound is:

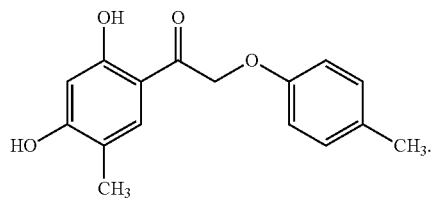

In some embodiments the compound is:

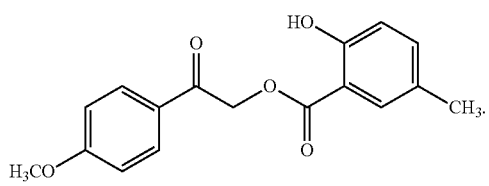

In some embodiments the compound is:

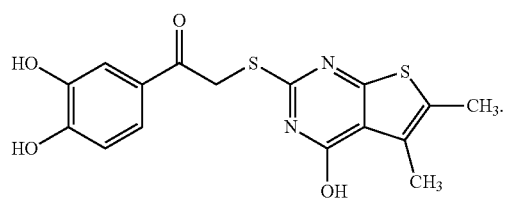 [SMILES: Cc1sc2nc(SCC(=O)c3ccc(O)c(O)c3)nc(O)c2c1C]

Various embodiments of the present invention provide a composition for treating cancer in a subject, comprising: a compound selected from:

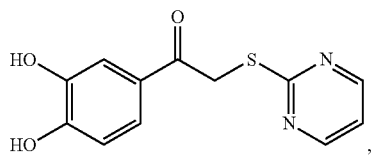

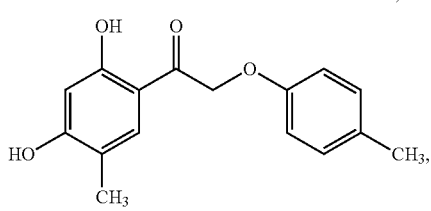

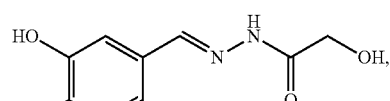

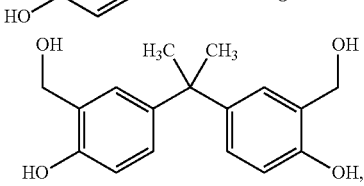

115
-continued

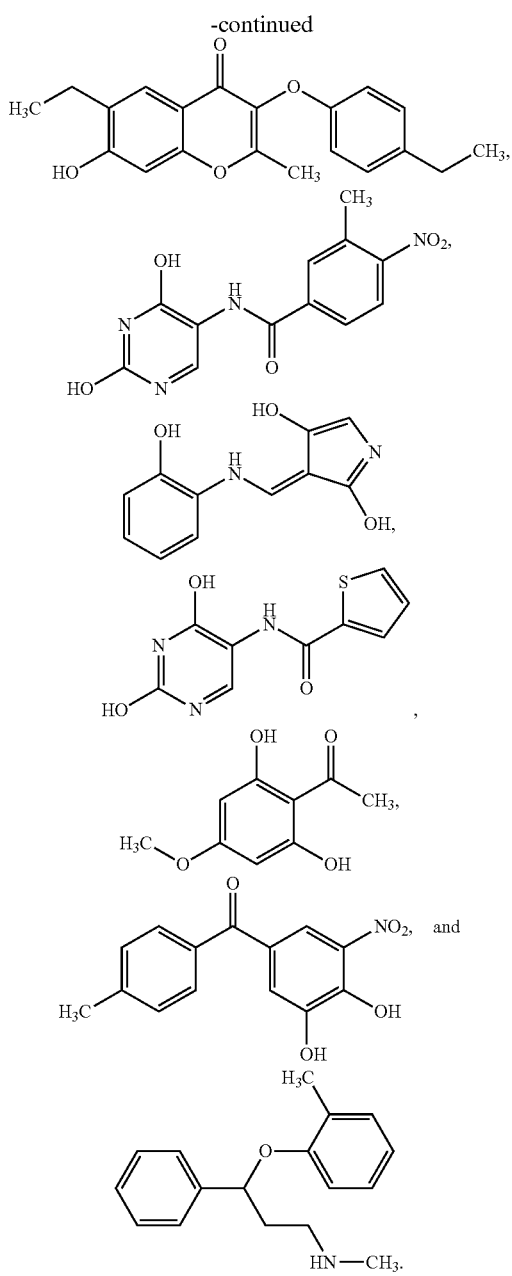

Various embodiments of the present invention provide a composition for treating cancer in a subject, comprising: a compound of formula:

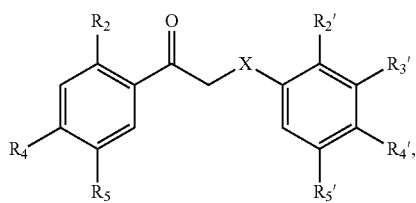

wherein,
R$_2$ is selected from H, OH, CH$_3$, and OCH$_3$;
R$_4$ is selected from H, OH, and OCH$_3$;
R$_5$ is selected from H, CH$_3$, and C$_2$H$_5$;

116

X is selected from H, O, and OC(=O);
R$_2$' is selected from H and OH;
R$_3$' is selected from H, OCH$_3$, and CH=CH—CH=CH;
R$_4$' is selected from H, CH$_3$, C$_2$H$_5$, CH(CH$_3$)$_2$, OCH$_3$, Ph, F, I, and CH=CH—CH=CH; and
R$_5$' is selected from H, CH$_3$, and OCH$_3$, wherein two or more of R$_2$, R$_4$, R$_5$ may be optionally connected, and two or more of R$_2$', R$_3$', R$_4$' R$_5$' may be optionally connected.

Various embodiments of the present invention provide a composition for treating cancer in a subject, comprising: a compound of formula:

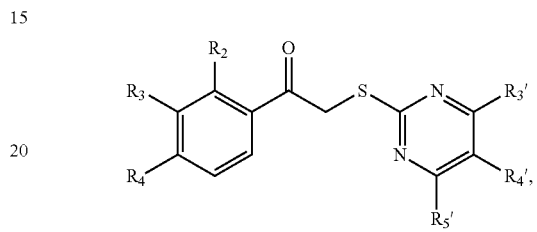

wherein,
R$_2$ is selected from H, OH, and OCH$_3$;
R$_3$ is selected from H, OH, OCH$_3$, and COOCH$_3$;
R$_4$ is selected from H, OH, and CH$_3$;
R$_3$' is selected from H, CH$_3$, CH=CH—CH=CH, and S—C(—CH$_3$)=C(—CH$_3$);
R$_4$' is selected from H and OH; and
R$_5$' is selected from H, OH, and CH$_3$, wherein two or more of R$_2$, R$_3$, R$_4$ may be optionally connected, and two or more of R$_3$', R$_4$' R$_5$' may be optionally connected.

Various embodiments of the present invention provide a composition for treating cancer in a subject, comprising: a compound selected from:

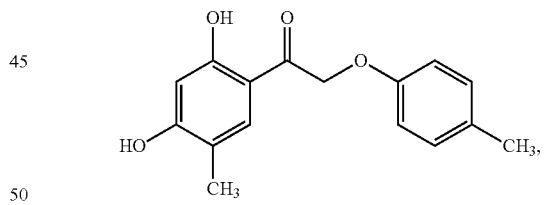

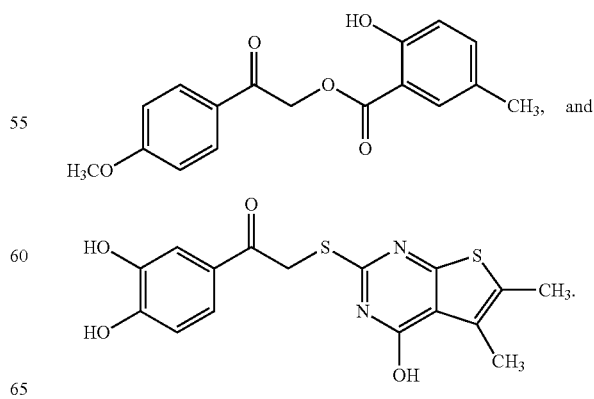

In some embodiments the compound is:

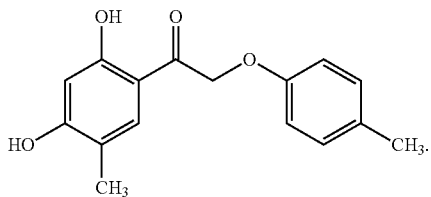

In some embodiments the compound is:

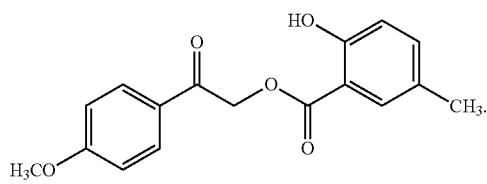 [SMILES: COc1ccc(C(=O)COC(=O)c2cc(C)ccc2O)cc1]

In some embodiments the compound is:

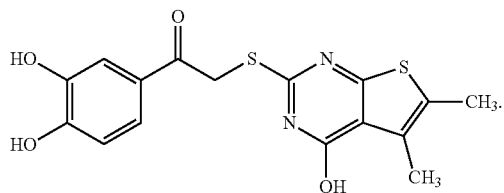 [SMILES: Cc1sc2nc(SCC(=O)c3ccc(O)c(O)c3)nc(O)c2c1C]

Various embodiments of the present invention provide method for treating cancer in a subject, comprising: administering the subject a composition comprising an inhibitor of KLF10, wherein the inhibitor of KLF10 is a compound selected from:

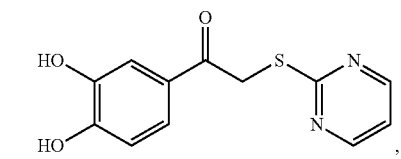

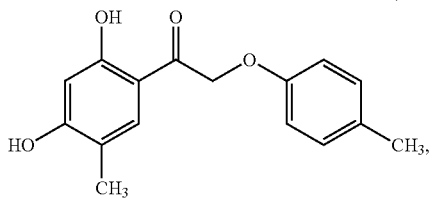

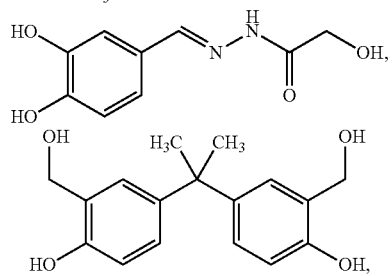

-continued

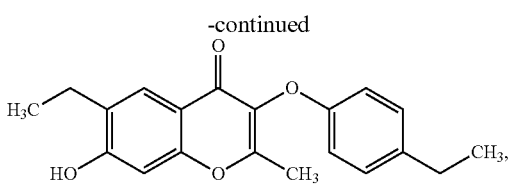

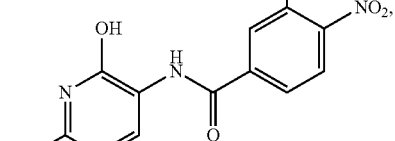

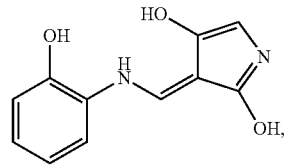

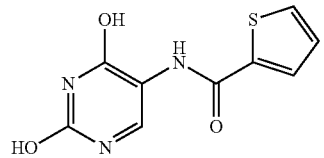

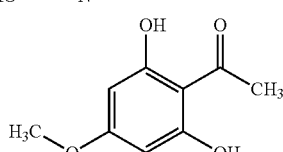

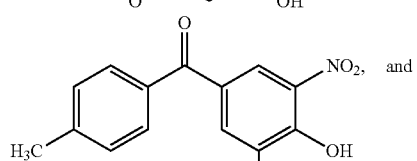

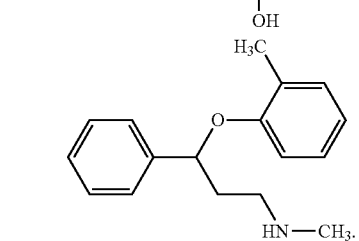

Various embodiments of the present invention provide method for treating cancer in a subject, comprising: administering the subject a composition comprising an inhibitor of KLF10, wherein the inhibitor of KLF10 is a compound of formula:

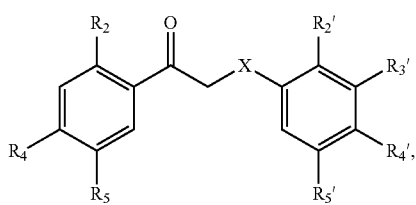

wherein,
$R_2$ is selected from H, OH, $CH_3$, and $OCH_3$;
$R_4$ is selected from H, OH, and $OCH_3$;
$R_5$ is selected from H, $CH_3$, and $C_2H_5$;
X is selected from H, O, and OC(=O);
$R_2'$ is selected from H and OH;
$R_3'$ is selected from H, $OCH_3$, and CH=CH—CH=CH;
$R_4'$ is selected from H, $CH_3$, $C_2H_5$, $CH(CH_3)_2$, $OCH_3$, Ph, F, I, and CH=CH—CH=CH; and
$R_5'$ is selected from H, $CH_3$, and $OCH_3$, wherein two or more of $R_2$, $R_4$, $R_5$ may be optionally connected, and two or more of $R_2'$, $R_3'$, $R_4'$ $R_5'$ may be optionally connected.

Various embodiments of the present invention provide method for treating cancer in a subject, comprising: administering the subject a composition comprising an inhibitor of KLF10, wherein the inhibitor of KLF10 is a compound of formula:

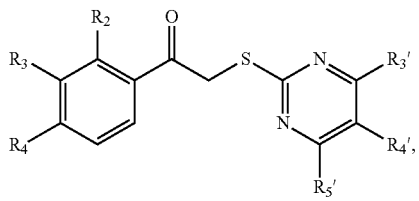

wherein,
$R_2$ is selected from H, OH, and $OCH_3$;
$R_3$ is selected from H, OH, $OCH_3$, and $COOCH_3$;
$R_4$ is selected from H, OH, and $CH_3$;
$R_3'$ is selected from H, $CH_3$, CH=CH—CH=CH, and S—C(—$CH_3$)=C(—$CH_3$);
$R_4'$ is selected from H and OH; and
$R_5'$ is selected from H, OH, and $CH_3$, wherein two or more of $R_2$, $R_3$, $R_4$ may be optionally connected, and two or more of $R_3'$, $R_4'$ $R_5'$ may be optionally connected Various embodiments of the present invention provide method for treating cancer in a subject, comprising: administering the subject a composition comprising an inhibitor of KLF10, wherein the inhibitor of KLF10 is a compound selected from:

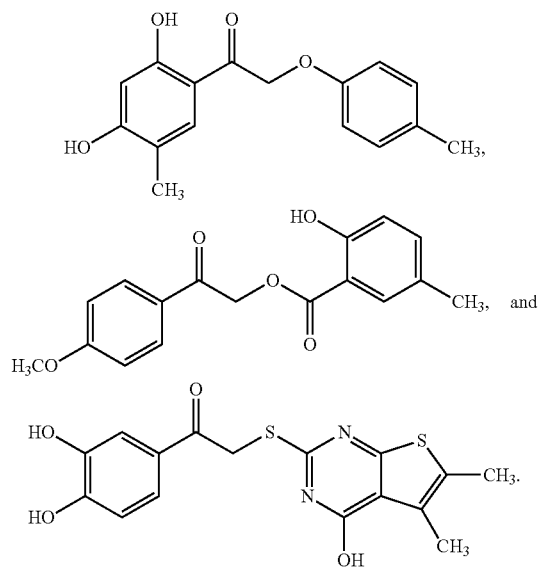

In some embodiments the compound is:

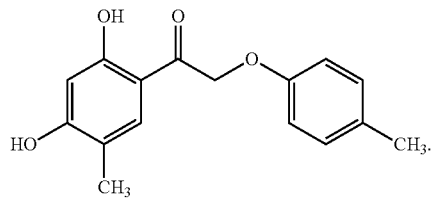

In some embodiments the compound is:

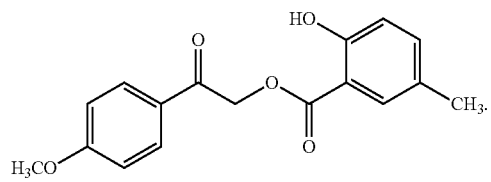 [SMILES: COc1ccc(C(=O)COC(=O)c2cc(C)ccc2O)cc1]

In some embodiments the compound is:

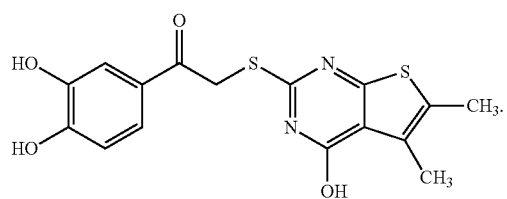 [SMILES: Cc1sc2nc(SCC(=O)c3ccc(O)c(O)c3)nc(O)c2c1C]

Some embodiments of the present invention can be defined as any of the following numbered paragraphs:

1. A compound selected from:

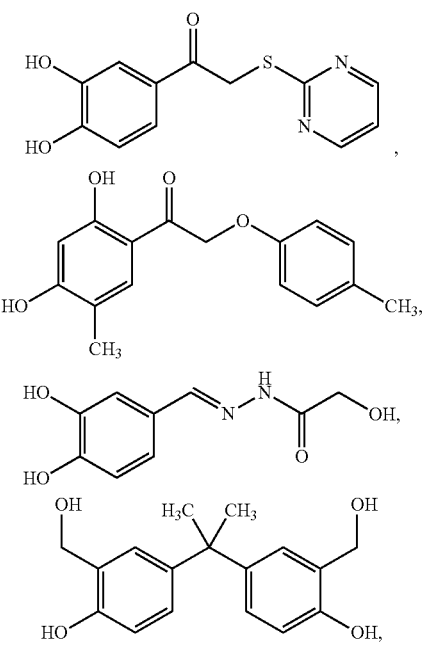

-continued

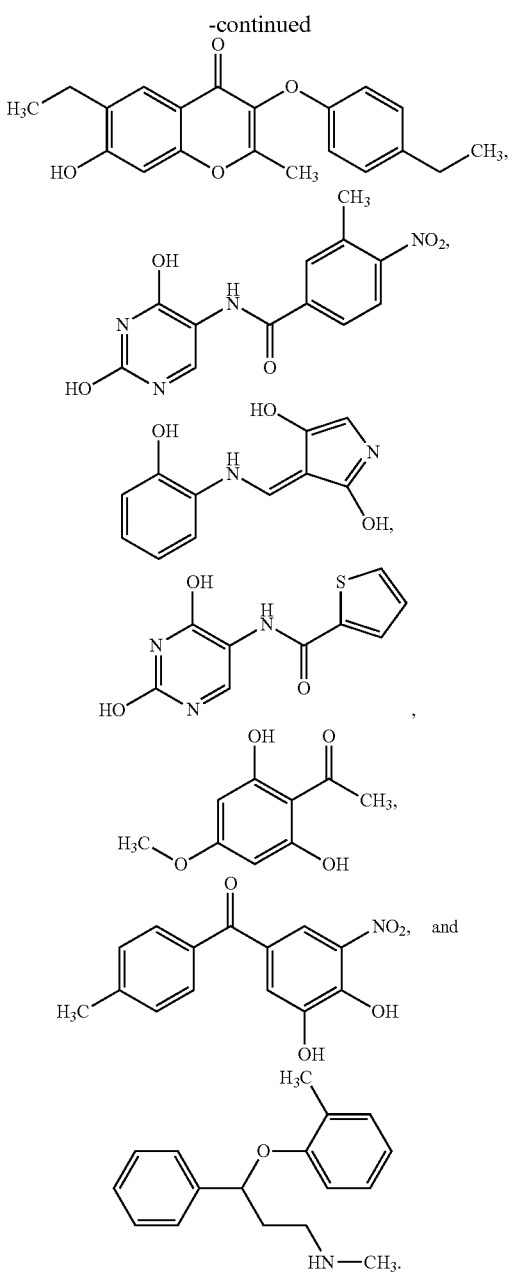

2. A compound of formula:

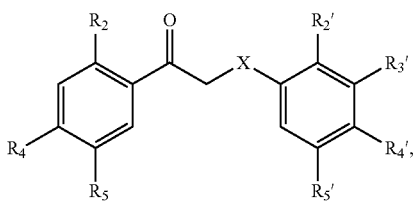

wherein,
R₂ is selected from H, OH, CH₃, and OCH₃;
R₄ is selected from H, OH, and OCH₃;
R₅ is selected from H, CH₃, and C₂H₅;
X is selected from H, O, and OC(=O);
R₂' is selected from H and OH;

R₃' is selected from H, OCH₃, and CH=CH—CH=CH;
R₄' is selected from H, CH₃, C₂H₅, CH(CH₃)₂, OCH₃, Ph, F, I, and CH=CH—CH=CH; and
R₅' is selected from H, CH₃, and OCH₃, wherein two or more of R₂, R₄, R₅ may be optionally connected, and two or more of R₂', R₃', R₄' R₅' may be optionally connected.

3. A compound of formula:

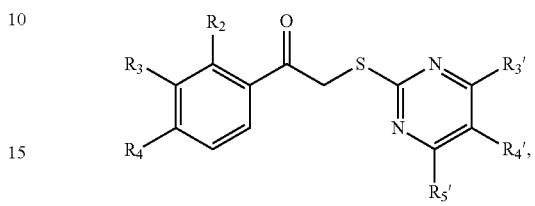

wherein,
R₂ is selected from H, OH, and OCH₃;
R₃ is selected from H, OH, OCH₃, and COOCH₃;
R₄ is selected from H, OH, and CH₃;
R₃' is selected from H, CH₃, CH=CH—CH=CH, and S—C(—CH₃)=C(—CH₃);
R₄' is selected from H and OH; and
R₅' is selected from H, OH, and CH₃, wherein two or more of R₂, R₃, R₄ may be optionally connected, and two or more of R₃', R₄' R₅' may be optionally connected.

4. The compound of paragraph 2 or paragraph 3, wherein the compound is selected from:

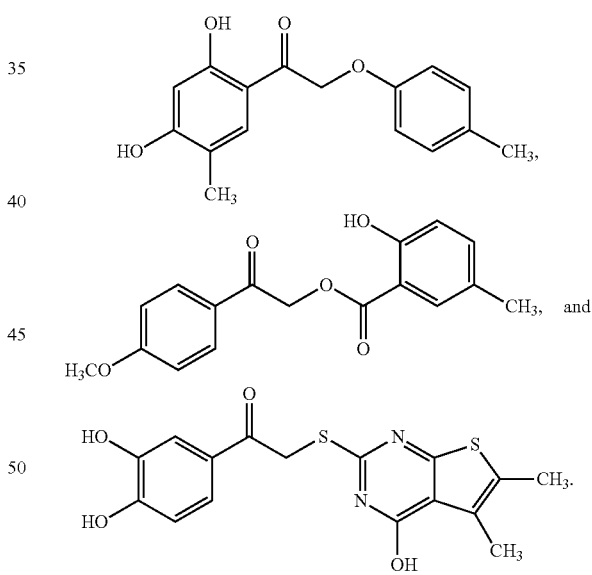

5. A method of modulating an immune response, comprising: administering to a subject an effective amount of an inhibitor of KLF10, wherein the inhibitor of KLF10 is a compound of any one of paragraphs 1 to 4.

6. The method of paragraph 5, wherein inhibiting KLF10 decreases T regulatory (T reg) cells at a tumor site or a pathogen infected area of the subject.

7. The method of paragraph 6, wherein the T reg cells are CD4+/CD25+ T reg cells or CD4+/CD25+/Fox3p+ T reg cells.

8. The method of paragraph 6, wherein the infection is a chronic viral infection, a bacterial infection, a fungal infection, a mycoplasm infection, a parasitic infection, elicits disease mediated by a toxin during the acute phase of infection or where the infection is characterized by reduced T cell response.

9. The method of paragraph 8, wherein the viral infection is an infection with a hepatitis virus, a human immunodeficiency virus, a human T-lymphotrophic virus, a herpes virus, an Epstein-Barr virus, filovirus, a human papilloma virus, an Epstein Barr virus, an influenza virus, a respiratory synticial virus, an encephalitis virus, a dengue fever virus, and a papilloma virus.

10. The method of paragraph 8, wherein the parasitic infection is malaria or *Leishmania*.

11. The method of paragraph 8, wherein the bacterial infection is caused by a bacterium selected from the group consisting of *Mycobacterium tuberculosis, Bacillus anthracis, Staphylococcus, Listeria*, and Clamydia *trachomatis*.

12. The method of paragraph 5, further comprising administering with the inhibitor of KLF10 an additional active agent selected from the group consisting of immunomodulators, agents that deplete or inhibit the function of T regs, and costimulatory molecules.

13. The method of paragraph 12, further comprising administering a disease antigen in combination with the immunomodulatory agent to enhance an immune response against the disease.

14. The method of paragraph 6, wherein the tumor is selected from the group consisting of sarcoma, melanoma, lymphoma, neuroblastoma, and carcinoma.

15. A composition, comprising: an effective amount of an inhibitor of KLF10 to decrease T regulatory (T reg) cells at a tumor site or a pathogen infected area of a subject, wherein the inhibitor of KLF10 is a compound of any one of paragraphs 1 to 4.

16. A composition, comprising: an effective amount of an inhibitor of KLF10 to decrease T regulatory (T reg) cells at a tumor site or a pathogen infected area of a subject in combination with one or more disease antigens, wherein the inhibitor of KLF10 is a compound of any one of paragraphs 1 to 4.

17. A composition, comprising: an effective amount of an inhibitor of KLF10 to decrease T regulatory (T reg) cells at a tumor site or a pathogen infected area of a subject in combination with a vaccine, wherein the inhibitor of KLF10 is a compound of any one of paragraphs 1 to 4.

18. A method for treating cancer in a subject, comprising: administering the subject a composition comprising an inhibitor of KLF10, wherein the inhibitor of KLF10 is a compound of any one of paragraphs 1 to 4.

19. A pharmaceutical composition, comprising: at least one compound of any one of paragraphs 1 to 4; and a pharmaceutically acceptable carrier.

20. A kit, comprising: at least one compound of any one of paragraphs 1 to 4; and instructions for administration to a subject.

Some embodiments of the present invention can be defined as any of the following numbered paragraphs:

1. A compound selected from:

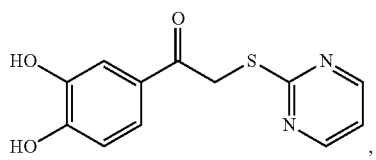

-continued

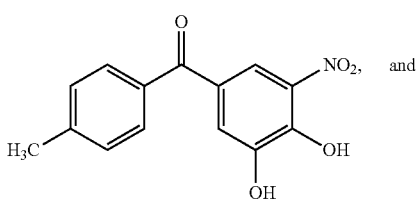

[Structure: 1-phenyl-1-(2-methylphenoxy)-3-(methylamino)propane shown at top of column 125]

2. A compound of formula:

[Structure: diaryl ketone with CH2-X linker, substituents R2, R4, R5 on left ring and R2', R3', R4', R5' on right ring]

wherein,
R$_2$ is selected from H, OH, CH$_3$, and OCH$_3$;
R$_4$ is selected from H, OH, and OCH$_3$;
R$_5$ is selected from H, CH$_3$, and C$_2$H$_5$;
X is selected from H, O, and OC(=O);
R$_2$' is selected from H and OH;
R$_3$' is selected from H, OCH$_3$, and CH=CH—CH=CH;
R$_4$' is selected from H, CH$_3$, C$_2$H$_5$, CH(CH$_3$)$_2$, OCH$_3$, Ph, F, I, and CH=CH—CH=CH; and
R$_5$' is selected from H, CH$_3$, and OCH$_3$, wherein two or more of R$_2$, R$_4$, R$_5$ may be optionally connected, and two or more of R$_2$', R$_3$', R$_4$' R$_5$' may be optionally connected.

3. A compound of formula:

[Structure: aryl ketone linked via CH2-S to a pyrimidine ring with substituents R2, R3, R4 on aryl ring and R3', R4', R5' on pyrimidine]

wherein,
R$_2$ is selected from H, OH, and OCH$_3$;
R$_3$ is selected from H, OH, OCH$_3$, and COOCH$_3$;
R$_4$ is selected from H, OH, and CH$_3$;
R$_3$' is selected from H, CH$_3$, CH=CH—CH=CH, and S—C(—CH$_3$)=C(—CH$_3$);
R$_4$' is selected from H and OH; and
R$_5$' is selected from H, OH, and CH$_3$, wherein two or more of R$_2$, R$_3$, R$_4$ may be optionally connected, and two or more of R$_3$', R$_4$' R$_5$' may be optionally connected.

4. The compound of paragraph 2, wherein the compound is selected from:

[Structure: 2,4-dihydroxy-5-methylphenyl ketone with CH2-O-phenyl-4-CH3], and

[Structure: 4-methoxyphenyl ketone with CH2-O-C(=O)-2-hydroxy-5-methylphenyl]

5. The compound of paragraph 3, wherein the compound is:

[Structure: 3,4-dihydroxyphenyl ketone with CH2-S-thienopyrimidine bearing CH3 groups and OH]

6. A method of modulating an immune response, comprising: administering to a subject an effective amount of an inhibitor of KLF10, wherein the inhibitor of KLF10 is a compound of paragraph 1.

7. A method of modulating an immune response, comprising: administering to a subject an effective amount of an inhibitor of KLF10, wherein the inhibitor of KLF10 is a compound of paragraph 2.

8. A method of modulating an immune response, comprising: administering to a subject an effective amount of an inhibitor of KLF10, wherein the inhibitor of KLF10 is a compound of paragraph 3.

9. A composition, comprising: an effective amount of an inhibitor of KLF10 to decrease T regulatory (T reg) cells at a tumor site or a pathogen infected area of a subject, wherein the inhibitor of KLF10 is a compound of paragraph 1.

10. A composition, comprising: an effective amount of an inhibitor of KLF10 to decrease T regulatory (T reg) cells at a tumor site or a pathogen infected area of a subject, wherein the inhibitor of KLF10 is a compound of paragraph 2.

11. A composition, comprising: an effective amount of an inhibitor of KLF10 to decrease T regulatory (T reg) cells at a tumor site or a pathogen infected area of a subject, wherein the inhibitor of KLF10 is a compound of paragraph 3.

12. A composition, comprising: an effective amount of an inhibitor of KLF10 to decrease T regulatory (T reg) cells at a tumor site or a pathogen infected area of a subject in combination with one or more disease antigens, wherein the inhibitor of KLF10 is a compound of paragraph 1.

13. A composition, comprising: an effective amount of an inhibitor of KLF10 to decrease T regulatory (T reg) cells at a tumor site or a pathogen infected area of a subject in combination with one or more disease antigens, wherein the inhibitor of KLF10 is a compound of paragraph 2.

14. A composition, comprising: an effective amount of an inhibitor of KLF10 to decrease T regulatory (T reg) cells at a tumor site or a pathogen infected area of a subject in combination with one or more disease antigens, wherein the inhibitor of KLF10 is a compound of paragraph 3.

15. A composition, comprising: an effective amount of an inhibitor of KLF10 to decrease T regulatory (T reg) cells at a tumor site or a pathogen infected area of a subject in combination with a vaccine, wherein the inhibitor of KLF10 is a compound of paragraph 1.

16. A composition, comprising: an effective amount of an inhibitor of KLF10 to decrease T regulatory (T reg) cells at a tumor site or a pathogen infected area of a subject in combination with a vaccine, wherein the inhibitor of KLF10 is a compound of paragraph 2.

17. A composition, comprising: an effective amount of an inhibitor of KLF10 to decrease T regulatory (T reg) cells at a tumor site or a pathogen infected area of a subject in combination with a vaccine, wherein the inhibitor of KLF10 is a compound of paragraph 3.

18. A method for treating cancer in a subject, comprising: administering the subject a composition comprising an inhibitor of KLF10, wherein the inhibitor of KLF10 is a compound of paragraph 1.

19. A method for treating cancer in a subject, comprising: administering the subject a composition comprising an inhibitor of KLF10, wherein the inhibitor of KLF10 is a compound of paragraph 2.

20. A method for treating cancer in a subject, comprising: administering the subject a composition comprising an inhibitor of KLF10, wherein the inhibitor of KLF10 is a compound of paragraph 3.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

To provide aspects of the present disclosure, embodiments may employ any number of programmable processing devices that execute software or stored instructions. Physical processors and/or machines employed by embodiments of the present disclosure for any processing or evaluation may include one or more networked (Internet, cloud, WAN, LAN, satellite, wired or wireless (RF, cellular, WiFi, Bluetooth, etc.)) or non-networked general purpose computer systems, microprocessors, filed programmable gate arrays (FPGAs), digital signal processors (DSPs), micro-controllers, smart devices (e.g., smart phones), computer tablets, handheld computers, and the like, programmed according to the teachings of the exemplary embodiments. In addition, the devices and subsystems of the exemplary embodiments can be implemented by the preparation of application-specific integrated circuits (ASICs) or by interconnecting an appropriate network of conventional component circuits. Thus, the exemplary embodiments are not limited to any specific combination of hardware circuitry and/or software.

Stored on any one or on a combination of computer readable media, the exemplary embodiments of the present disclosure may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, database management software, and the like. Computer code devices of the exemplary embodiments can include any suitable interpretable or executable code mechanism, including but not limited to scripts, interpretable programs, dynamic link libraries (DLLs), Java classes and applets, complete executable programs, and the like. Moreover, processing capabilities may be distributed across multiple processors for better performance, reliability, cost, or other benefits.

Common forms of computer-readable media may include, for example, a floppy disk, a flexible disk, a hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read. Such storage media can also be employed to store other types of data, e.g., data organized in a database, for access, processing, and communication by the processing devices.

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

Computational Methods.

All molecular modeling operations were carried out in the Maestro (version 9.0 Schrödinger Inc., USA), Sybyl (version 7.2; Certara Inc. USA) and Molecular Operating Environment (version 2009.10; Chemical Computing Group Inc., Canada) modeling packages running on Dell Precision 690 workstation with 8 CPUs, 10 GB memory and Red Hat Enterprise 5 Linux Operating System.

Homology Modeling of KLF10

A truncated model of three zinc-fingers of KLF10 (amino acids 361-459) was built using F-chain of X-ray crystal structure[2] (PDB code: 1MEY) of a designed zinc finger protein in complex with DNA. Sequences of KLF10 and template proteins exhibited 51% identity, leaving weaker coordinate information for two small loops: amino acids 431-436 and 449-451. The two loops were refined using Extended High (accuracy) loop sampling method in Prime (version 2.1).[35, 36] The coordinates for $Zn^{+2}$ ions were extracted from the template structure and verified for coordination distances with corresponding cystines and histidines. The (coordinate bonded) Cys-$Zn^{+2}$-His pattern was preserved from the X-ray structure positions during side chain refinements by applying distance constraints. This was followed by a protein structure analysis and refinement of disallowed backbone (θ, ψ, and Ω) and side chain dihedral angles, peptide planarity, bond length and angle deviations and steric clashes between side chains. Finally, DNA-bound KLF10 structure was built by extracting DNA coordinates from X-ray crystal structure and resolving steric clashes by rotamer search of side chains of interface residues having bumps with DNA nucleotides, followed by optimization of overall interaction energy of complex using OPLS-2005 (Optimized Potential for Liquid Simulations)[37] molecular mechanics energy minimizations (FIG. 1). The optimized structure (without DNA coordinates) was then subjected to binding pocket analysis using pocket identification algorithms employing different methods. For example, SiteMap[14, 15] which is a combination of geometry-based and energy-based methods[38] along with molecular surface calculations in Maestro was applied in addition to MolCad[16] (Sybyl/Tripos), which is a grid-based flood-filled solvation technique[39]. Another tool that was used in pocket identification, SiteFinder[17] is based on the calculation of appropriately exposed a spheres which are clustered to produce a collection of sites. Each site consists of several a spheres, at least one of which is hydrophobic. The sites are then ranked according to the number of hydrophobic contacts made with the receptor, i.e. the number of hydrophobic atoms within a contact distance of any of the retained a spheres to uniquely identify a "druggable" pocket at the interface.

These programs identified, with consensus, a relatively big pocket in the second ZF (aa 385-425) which spans from β-sheet to α-helix (near $Zn+^2$), subdivided with a small cleft into, correspondingly termed, α- and β-subpockets, which were subsequently used for high throughput docking (HTD) of chemical libraries (FIG. 1B).

Structure-Based Virtual Screening (SBVS).

Figure 17:
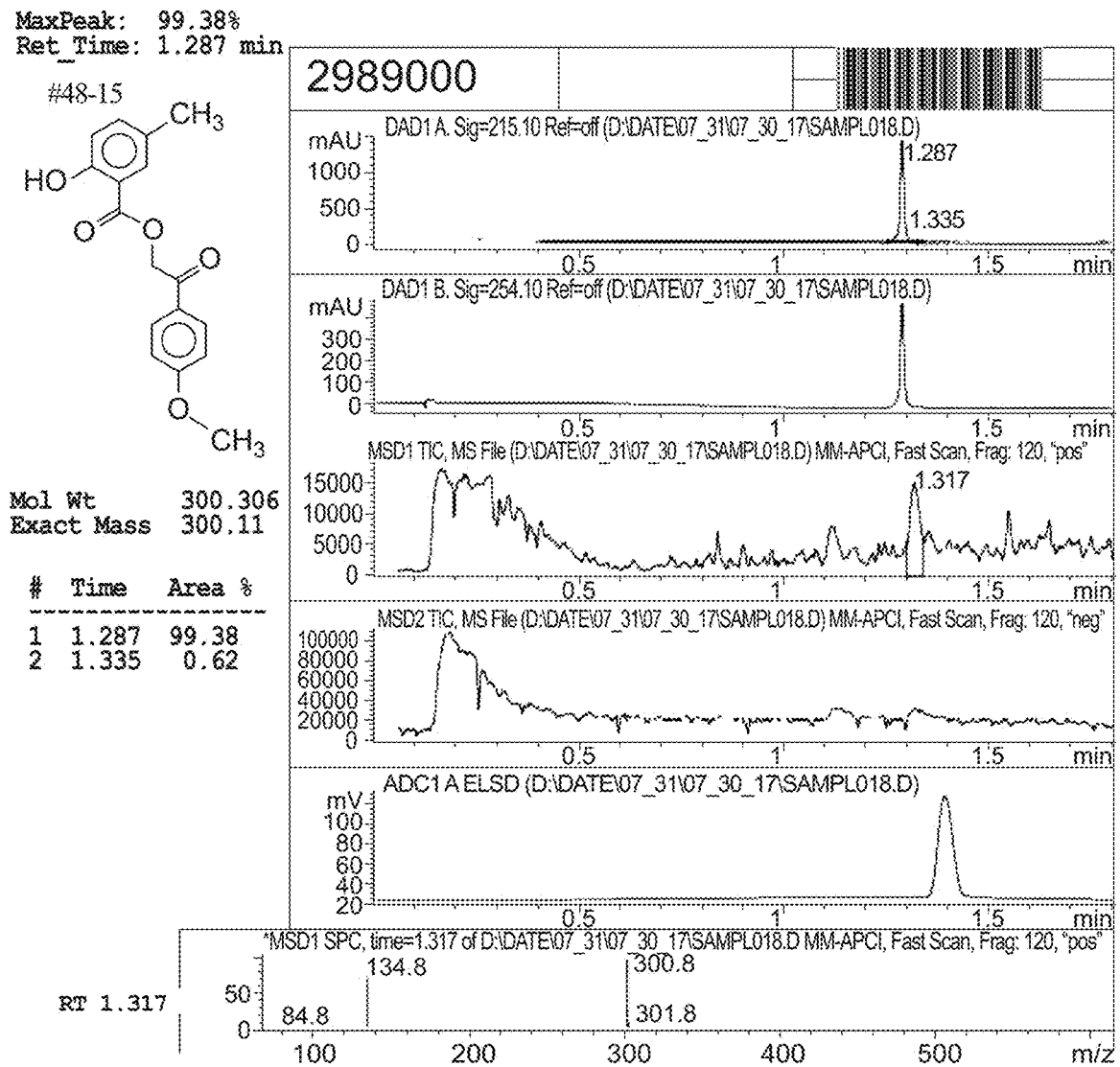
FIG. 17 depicts in accordance with various embodiments of the invention, analytical data supporting the purity of compound #48-15.
Figure 18:
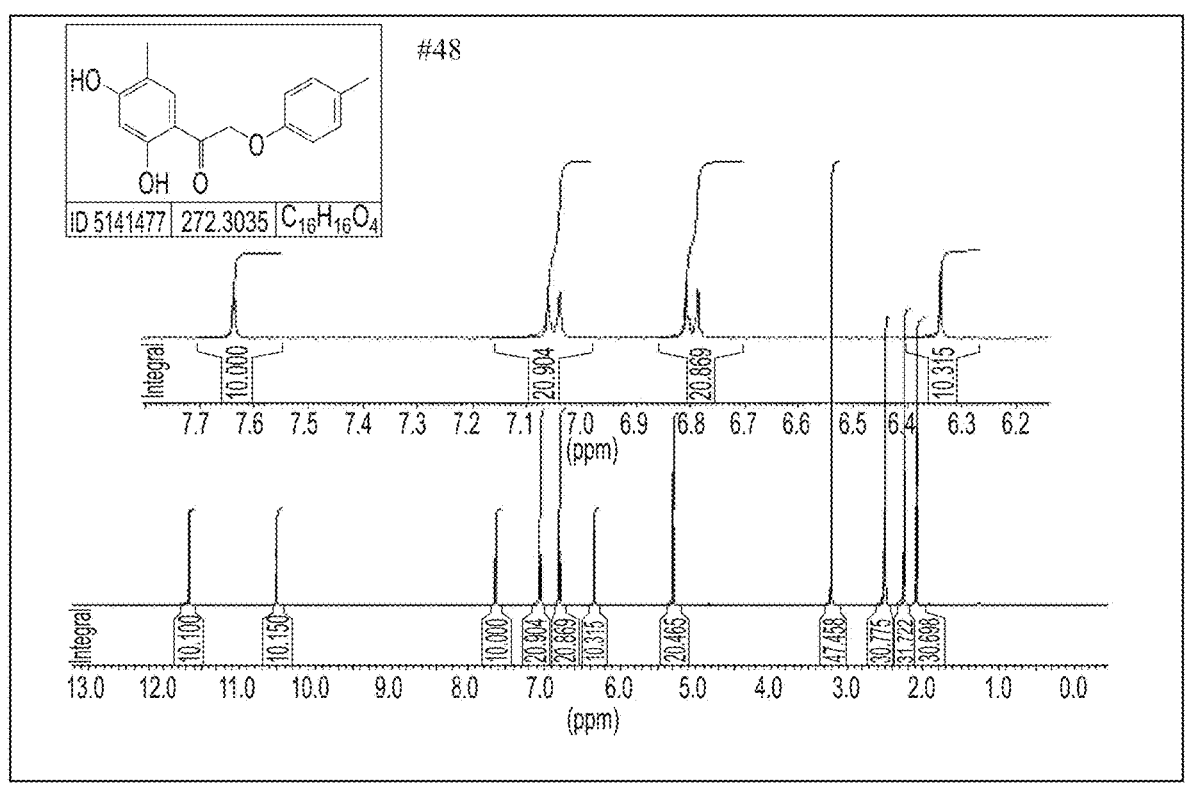
FIG. 18 depicts in accordance with various embodiments of the invention, analytical data supporting the purity of compound #48.
Figure 19:
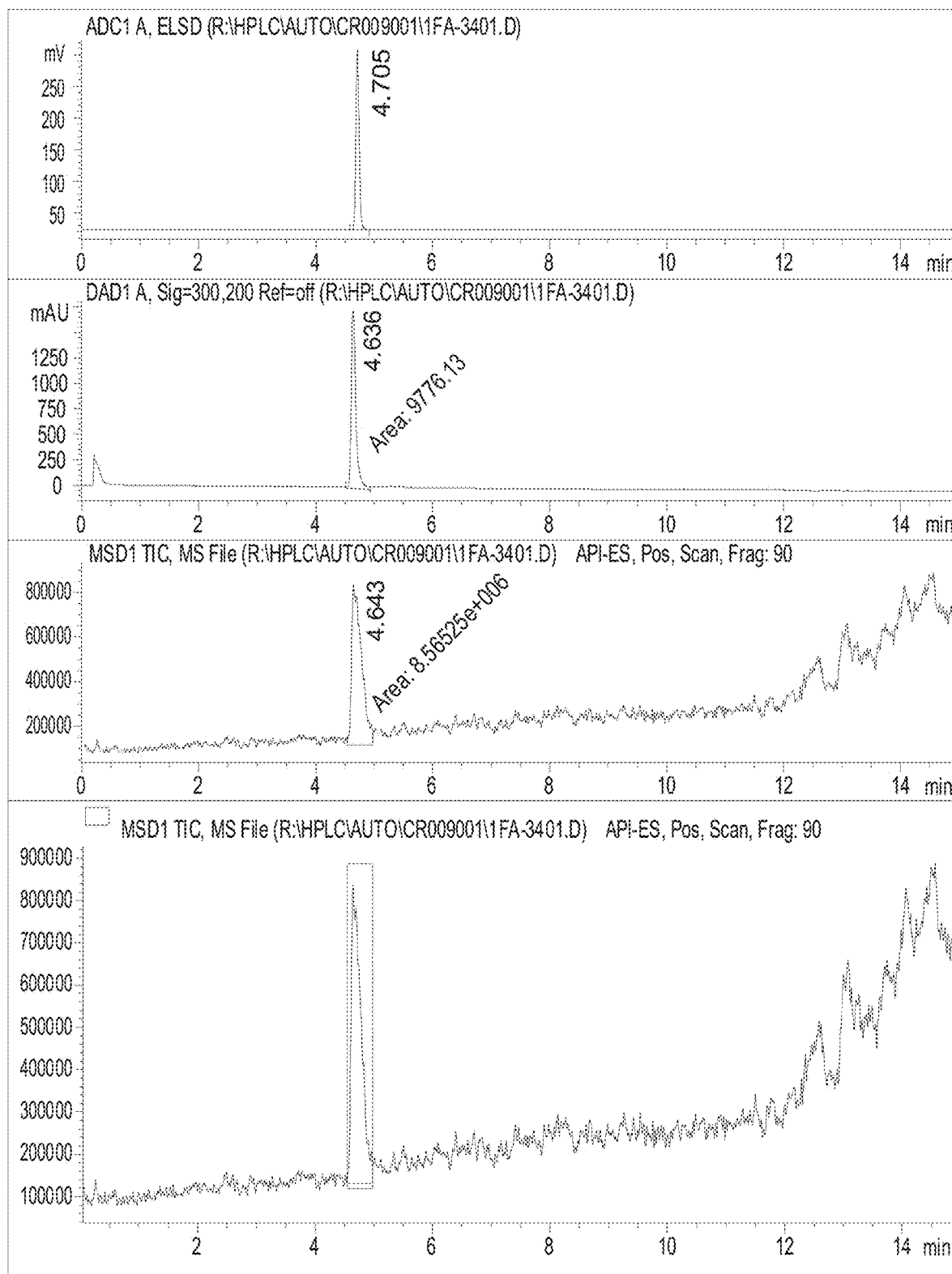
FIG. 19 depicts in accordance with various embodiments of the invention, analytical data supporting the purity of compound #15-09.
Figure 19:
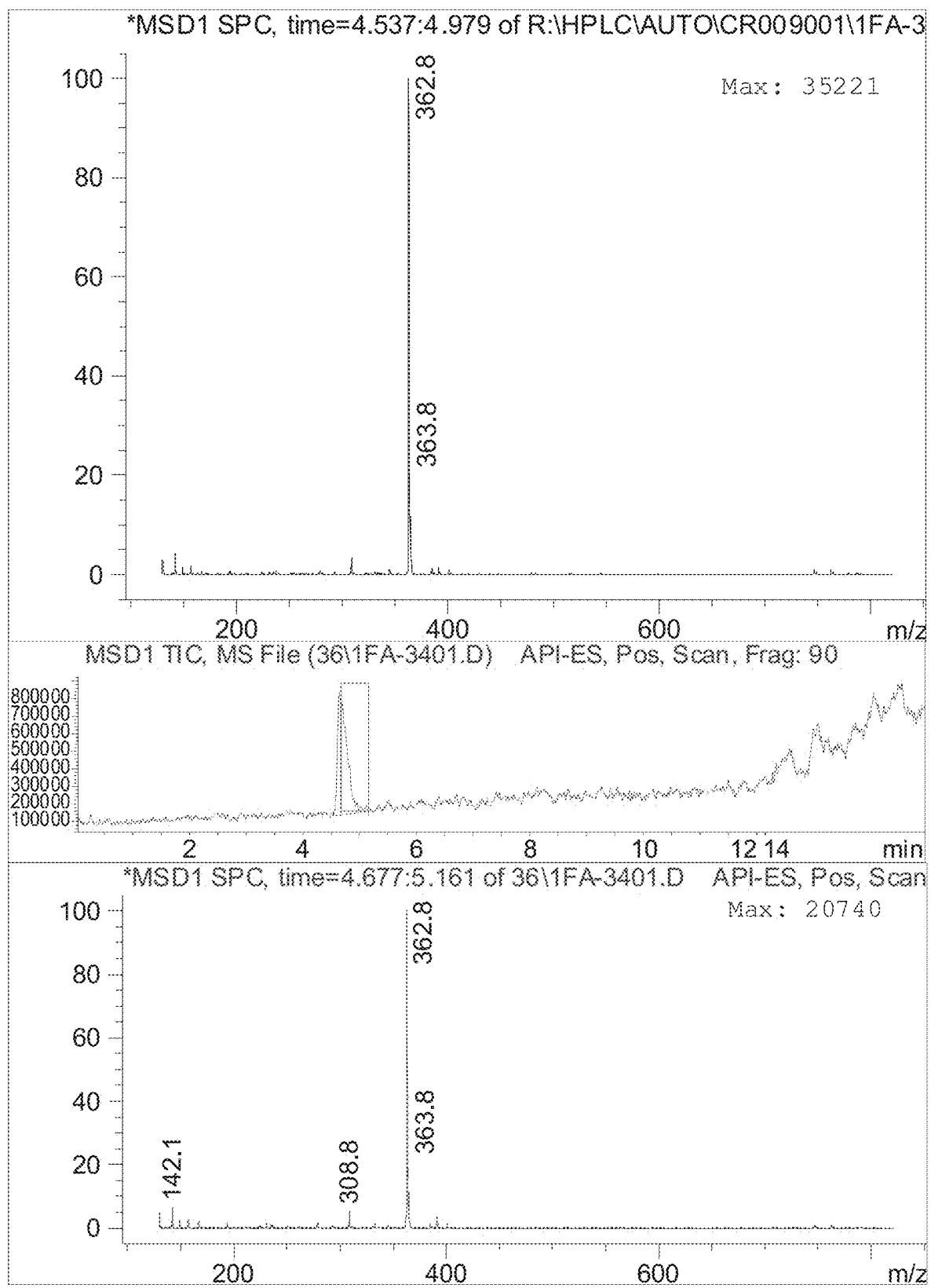

The chemical libraries used in the present screening included structures from Chembridge (http://www.chembridge.com; ~400,000 molecules), Asinex (http://www.asinex.com; ~200,000 molecules), National Cancer Institute (http://dtp.nci.nih.gov/docs/3d_database/dis3d.html; ~250,000 molecules), and ZINC[40] databases (downloaded as of June 2008 and accessed online later for similarity and substructure searches). The structures were prepared using Ligprep (version 2.2), which performed hydrogen addition and 3D structure optimization. Epik (through Ligprep) was used to identify possible ionization and tautomer states at physiological pH (7.0±2.0), along with generating ring conformers and stereoisomers using default settings. The ionization state penalties for each protomer state were also calculated and stored. Two separate receptor grids for docking calculations were prepared, one for each of α- and β-subpocket, by assigning individual residues forming the respective pocket, with hydrophobic and H-bond constraints. A high-throughput docking (HTD) was performed to filter out weak binders in α- and β-subpockets separately using Glide (version 5.0)[18, 19] in standard precision (SP) scoring mode. An analysis of hits that satisfied the hydrogen bond and hydrophobic constraints revealed that approximately 4 times more hits preferred α-pocket over β-pocket, and ~1800 hits were common to both pockets. A third receptor grid encompassing residues from both α- and β-subpockets was used for Glide (version 5.5) docking without constraints, and using more accurate extra precision (XP) scoring.[20] Post-docking analysis identified that 1400 hits occupied either α- and/or β-subpocket, leaving out remaining molecules docked off-site of the TF-DNA interface. This GlideXP-1400 set was then further docked using additional two independently developed dockers, Surflex[21] and FlexX[22] in Sybyl (version 7.2). The hits common in top 700 rank-order of each docking algorithm were compared to shortlist 150 molecules (SBVS-150 set) after ADMET evaluation using QikProp (version 3.1; Schrodinger) and Sarchitect (Strand Life Science). A subset of 40 compounds was evaluated in luciferase reporter assays. Compounds were acquired from different vendors and dissolved in DMSO. The 2D structures of active compounds are shown in Tables 1-3. The purity of compounds #48, #48-15, and #15-09 was verified to be ≥95% using HPLC equipped with (a) Column: Onyx C18 50×4.6 mm (flow rate=3.75 mL/min), (b) UV detector operating at dual wavelengths, and (c) evaporative light-scattering detector (FIG. 18, FIG. 17, FIG. 19). Additionally, small molecules were also screened for substructural features that appear in frequent hitters (promiscuous compounds) in several biochemical HTS. Such compounds are also known as Pan Assay Interference compounds (PAINS) and researchers have created systematic filters to remove such compounds from virtual screens[41]. We employed PAINS1, PAINS2, and PAINS3 filter definitions as implemented in Schrodinger's Canvas program that correspond to filter C, filter B, and filter A, respectively, of previous study[41]. None of our screened compounds (Tables 1-3) showed PAINS attributes as per the structure definitions of PAINS1 (filter C) and PAINS3 (filter A). However, compounds #57 (Table 1), #15-07 and #15-09 (Table 3) were marked as possible PAINS according to PAINS2 (filter B) substructure definitions. Since these compounds were passed in other two PAINS (1 and 3) filters, we assume that the promiscuous liability is relatively less, making worth investigating their effects in this novel (non-enzymatic) and relatively undruggable target space.

Chemical Structure Exploration of Lead Compound Scaffolds.

Potent and promising hits were subjected to chemical space exploration by performing sub-structure search of their scaffolds to find their close analogs (second-generation compounds) in databases. The structural information of inhibitors identified in SBVS screens was employed to identify a working pharmacophore query using Phase[42, 43] (version 3.1; Schrodinger, Inc). This query was used to bias the selection of second-generation compounds towards chemical features of known inhibitors to improve enrichment. The structural analogs were subsequently evaluated using Glide XP docking to rank-order a small subset for activity testing (Table 2 and Table 3).

Constructs, Cell Culture and Transfection, and Luciferase Reporter Assays.

CACC-TK-luc plasmid contains three tandem copies of CACCC sites upstream to a luciferase reporter in pGL3-basic as previously described.[12, 44] Empty vector pCMV-SPORT6 and human KLF10 expressing plasmid pCMV-SPORT6-KLF10 are from Open Biosystems (Huntsville, Ala.). HeLa cells from ATCC were cultured in DMEM medium with 10% Fetal Bovine Serum, 1% antibiotics. Cells were transfected by using Fugene® 6 transfection reagent from Roche. In brief, cells were plated (40 000/well) in triplicate in a 12-well plate. After growing to 70-80% confluency, cells were transfected with 500 ng of CACC-TK-luc reporter construct, 200 ng β-galactosidase expression plasmids, and 100 ng pcDNA3.1 empty vector or pcDNA3.1-KLF10. After 24 h incubation, cells were treated with 100 µM or indicated concentration of small molecule compounds for 24 h. Treated cells were collected in 200 µL of 1× Reporter Lysis Buffer (Promega). The activity of luciferase were measured and normalized to total protein read for the same lysate performed in triplicate replicates.

Real Time qPCR.

T cells were suspended in TRIzol® reagent (Invitrogen), and total RNA was isolated according to the manufacturer's instructions. Reverse transcriptions were performed by using the Reverse Transcription Kit and QuantiTect SYBR Green reverse transcription-PCR kit from Qiagen for quantitative real-time quantitative PCR analysis on a Mx3000P real-time PCR system (Stratagene) following the manufacturer's instructions. Primers were used to detect mouse FoxP3 as previously described.[12]

Gel Mobility Shift Assays.

KLF10 recombinant protein was obtained from Novus Biologicals. Oligonucleotides 5'-GCAGTGAAAAGGGGGTGTGTCAGGATGC (SEQ ID NO: 1) and 5'-GCATCCTGACACACCCCCTTTTCACTGC (SEQ ID NO: 2) were generated as previously described[45] and labeled with Biotin using Biotin 3' End DNA Labeling Kit (Pierce). End-labeled oligos (1 µmol/L) were annealed in a buffer system with 10 mM Tris, 50 mM NaCl, pH 8.0 by heating at 95° C. for 5 min, then slowly cooled to 65° C. for 30 min incubation, and cooled to room temperature. Lightshift chemiluminescent EMSA kit (20148) was from Thermo Scientific. Binding reactions contain 1× binding buffer, 2.5% glycerol, 5 mM $MgCl_2$, 50 ng/µL poly (dI.dC), 0.05% NP-40, and 5 fmol Biotin-labeled probes in the presence of different concentrations of compounds, and 100 ng purified recombinant KLF10. Compounds were incubated with KLF10 in a reaction system for 4 hrs at room temperature, and then Biotin-labeled probes were added for a 1 hr incubation. Binding reactions were electrophoresed for 80 min at 100 volts on 6% polyacrylamide gel in 0.5×TBE. The binding reactions were transferred to nylon membranes at 100 volts for 45 min, and transferred DNA was cross-linked to membrane using an HL-2000 Hybrilinker instrument. Biotin-labeled DNAs were detected by chemiluminescence.

T Regulatory Cell Differentiation Assay and Flow Cytometry.

Mouse spleens were meshed through a cell strainer into Phosphate Buffered Saline (PBS) with 2% Fetal Bovine Serum and 1% Penicillin/Streptomycin, and cells were collected by spinning at 1000 rpm for 10 min. CD4+CD25− T cells were purified by using CD4+CD25+ T cell isolation kit (Miltenyi Biotec) according to the manufacturer's instructions. Briefly, cells were incubated with Biotin-conjugated antibodies, followed by anti-biotin microbeads and PE-conjugated anti-CD25 antibody for 30 min on ice with gentle shaking. Mixtures were loaded into pre-washed LD columns in the Magnetic field, and CD4+ cells were collected and then incubated with anti-PE microbeads. Mixtures were loaded into pre-washed MS columns in the magnetic field to collect CD4+CD25− T cells (non-bound cell fraction). Cells were plated into 12-well plates pre-coated with 1 µg/mL anti-CD3e (eBioscience) overnight in RPMI1640 Medium with 10% FBS, 1% Penicillin/Streptomycin, 1% non-essential amino acids, and 2-mercaptoethanol, 1 µg/mL anti-CD28 (BD Biosciences), and 1 ng/mL TGF-β1 (Peprotech). Cells were cultured at 37° C. up to five days for the conversion of CD4+CD25− T cells to CD4+ CD25+ T regs. For flow cytometry, cells were stained with anti-mouse CD25 Alexa Fluo®488 (eBioscience) and analyzed by using multicolor FACS (ARIA; BD Biosciences) as previously described.[12]

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

REFERENCES

1. Venter, J. C.; Adams, M. D.; Myers, E. W.; Li, P. W.; Mural, R. J.; Sutton, G. G.; Smith, H. O.; Yandell, M.; Evans, C. A.; Holt, R. A.; Gocayne, J. D.; Amanatides, P.; Ballew, R. M.; Huson, D. H.; Wortman, J. R.; Zhang, Q.; Kodira, C. D.; Zheng, X. H.; Chen, L.; Skupski, M.; Subramanian, G.; Thomas, P. D.; Zhang, J.; Gabor Miklos, G. L.; Nelson, C.; Broder, S.; Clark, A. G.; Nadeau, J.; McKusick, V. A.; Zinder, N.; Levine, A. J.; Roberts, R. J.; Simon, M.; Slayman, C.; Hunkapiller, M.; Bolanos, R.; Delcher, A.; Dew, I.; Fasulo, D.; Flanigan, M.; Florea, L.; Halpem, A.; Hannenhalli, S.; Kravitz, S.; Levy, S.; Mobarry, C.; Reinert, K.; Remington, K.; Abu-Threideh, J.; Beasley, E.; Biddick, K.; Bonazzi, V.; Brandon, R.; Cargill, M.; Chandramouliswaran, I.; Charlab, R.; Chaturvedi, K.; Deng, Z.; Di Francesco, V.; Dunn, P.; Eilbeck, K.; Evangelista, C.; Gabrielian, A. E.; Gan, W.; Ge, W.; Gong, F.; Gu, Z.; Guan, P.; Heiman, T. J.; Higgins, M. E.; Ji, R. R.; Ke, Z.; Ketchum, K. A.; Lai, Z.; Lei, Y.; Li, Z.; Li, J.; Liang, Y.; Lin, X.; Lu, F.; Merkulov, G. V.; Milshina, N.; Moore, H. M.; Naik, A. K.; Narayan, V. A.; Neelam, B.; Nusskern, D.; Rusch, D. B.; Salzberg, S.; Shao, W.; Shue, B.; Sun, J.; Wang, Z.; Wang, A.; Wang, X.; Wang, J.; Wei, M.; Wides, R.; Xiao, C.; Yan, C.; Yao, A.; Ye, J.; Zhan, M.; Zhang, W.; Zhang, H.; Zhao, Q.; Zheng, L.; Zhong, F.; Zhong, W.; Zhu, S.; Zhao, S.; Gilbert, D.; Baumhueter, S.; Spier, G.; Carter, C.; Cravchik, A.; Woodage, T.; Ali, F.; An, H.; Awe, A.; Baldwin, D.; Baden, H.; Barnstead, M.; Barrow, I.; Beeson, K.; Busam, D.; Carver, A.; Center, A.; Cheng, M. L.; Curry, L.; Danaher, S.; Davenport, L.; Desilets, R.; Dietz, S.; Dodson, K.; Doup, L.; Ferriera, S.; Garg, N.; Glueksmann, A.; Hart, B.; Haynes, J.; Haynes, C.; Heiner, C.; Hladun, S.; Hostin, D.; Houck, J.; Howland, T.; Ibegwam, C.; Johnson, J.; Kalush, F.; Kline, L.; Koduru, S.; Love, A.; Mann, F.; May, D.; McCawley, S.; McIntosh, T.; McMullen, I.; Moy, M.; Moy, L.; Murphy, B.; Nelson, K.; Pfannkoch, C.; Pratts, E.; Puri, V.; Qureshi, H.; Reardon, M.; Rodriguez, R.; Rogers, Y. H.; Romblad, D.; Ruhfel, B.; Scott, R.; Sitter, C.; Smallwood, M.; Stewart, E.; Strong, R.; Suh, E.; Thomas, R.; Tint, N. N.; Tse, S.; Vech, C.; Wang, G.; Wetter, J.; Williams, S.; Williams, M.; Windsor, S.; Winn-Deen, E.; Wolfe, K.; Zaveri, J.; Zaveri, K.; Abril, J. F.; Guigo, R.; Campbell, M. J.; Sjolander, K. V.; Karlak, B.; Kejariwal, A.; Mi, H.; Lazareva, B.; Hatton, T.; Narechania, A.; Diemer, K.; Muruganujan, A.; Guo, N.; Sato, S.; Bafna, V.; Istrail, S.; Lippert, R.; Schwartz, R.; Walenz, B.; Yooseph, S.; Allen, D.; Basu, A.; Baxendale, J.; Blick, L.; Caminha, M.; Cames-Stine, J.; Caulk, P.; Chiang, Y. H.; Coyne, M.; Dahlke, C.; Mays, A.; Dombroski, M.; Donnelly, M.; Ely, D.; Esparham, S.; Fosler, C.; Gire, H.; Glanowski, S.; Glasser, K.; Glodek, A.; Gorokhov, M.; Graham, K.; Gropman, B.; Harris, M.; Heil, J.; Henderson, S.; Hoover, J.; Jennings, D.; Jordan, C.; Jordan, J.; Kasha, J.; Kagan, L.; Kraft, C.; Levitsky, A.; Lewis, M.; Liu, X.; Lopez, J.; Ma, D.; Majoros, W.; McDaniel, J.; Murphy, S.; Newman, M.; Nguyen, T.; Nguyen, N.; Nodell, M.; Pan, S.; Peck, J.; Peterson, M.; Rowe, W.; Sanders, R.; Scott, J.; Simpson, M.; Smith, T.; Sprague, A.; Stockwell, T.; Turner, R.; Venter, E.; Wang, M.; Wen, M.; Wu, D.; Wu, M.; Xia, A.; Zandieh, A.; Zhu, X. The sequence of the human genome. *Science* 2001, 291, 1304-1351.

2. Kim, C. A.; Berg, J. M. A 2.2 A resolution crystal structure of a designed zinc finger protein bound to DNA. *Nat Struct Biol* 1996, 3, 940-945.

3. Simpson, R. J.; Cram, E. D.; Czolij, R.; Matthews, J. M.; Crossley, M.; Mackay, J. P. CCHX zinc finger derivatives retain the ability to bind Zn(II) and mediate protein-DNA interactions. *J Biol Chem* 2003, 278, 28011-28018.

4. Pabo, C. O.; Peisach, E.; Grant, R. A. Design and selection of novel Cys2His2 zinc finger proteins. *Annu Rev Biochem* 2001, 70, 313-340.

5. van Vliet, J.; Turner, J.; Crossley, M. Human Krüppel-like factor 8: a CACCC-box binding protein that associates with CtBP and represses transcription. *Nucleic Acids Res* 2000, 28, 1955-1962.

6. Cao, Z.; Sun, X.; Icli, B.; Wara, A. K.; Feinberg, M. W. Role of Krüppel-like factors in leukocyte development, function, and disease. *Blood* 2010, 116, 4404-4414.

7. Gallimore, A.; Godkin, A. Regulatory T cells and tumour immunity—observations in mice and men. *Immunology* 2008, 123, 157-163.

8. Clarke, S. L.; Betts, G. J.; Plant, A.; Wright, K. L.; El-Shanawany, T. M.; Harrop, R.; Torkington, J.; Rees, B. I.; Williams, G. T.; Gallimore, A. M.; Godkin, A. J. CD4+CD25+FOXP3+ regulatory T cells suppress anti-tumor immune responses in patients with colorectal cancer. *PLoS One* 2006, 1, e129.

9. Rowe, J. H.; Ertelt, J. M.; Way, S. S. Foxp3(+) regulatory T cells, immune stimulation and host defence against infection. *Immunology* 2012, 136, 1-10.

10. Rowe, J. H.; Ertelt, J. M.; Aguilera, M. N.; Farrar, M. A.; Way, S. S. Foxp3(+) regulatory T cell expansion required for sustaining pregnancy compromises host defense against prenatal bacterial pathogens. *Cell Host Microbe* 2011, 10, 54-64.

11. Ertelt, J. M.; Rowe, J. H.; Mysz, M. A.; Singh, C.; Roychowdhury, M.; Aguilera, M. N.; Way, S. S. Foxp3+ regulatory T cells impede the priming of protective CD8+ T cells. *J Immunol* 2011, 187, 2569-2577.

12. Cao, Z.; Wara, A. K.; Icli, B.; Sun, X.; Packard, R. R.; Esen, F.; Stapleton, C. J.; Subramaniam, M.; Kretschmer, K.; Apostolou, I.; von Boehmer, H.; Hansson, G. K.; Spelsberg, T. C.; Libby, P.; Feinberg, M. W. Krüppel-like factor KLF10 targets transforming growth factor-beta1 to regulate CD4(+)CD25(-) T cells and T regulatory cells. *J Biol Chem* 2009, 284, 24914-24924.

13. Venuprasad, K.; Huang, H.; Harada, Y.; Elly, C.; Subramaniam, M.; Spelsberg, T.; Su, J.; Liu, Y. C. The E3 ubiquitin ligase Itch regulates expression of transcription factor Foxp3 and airway inflammation by enhancing the function of transcription factor TIEG1. *Nat Immunol* 2008, 9, 245-253.

14. Halgren, T. New method for fast and accurate binding-site identification and analysis. *Chem Biol Drug Des* 2007, 69, 146-148.

15. Halgren, T. A. Identifying and characterizing binding sites and assessing druggability. *J Chem Inf Model* 2009, 49, 377-389.

16. Brickmann, J. G., T.; Heiden, W.; Moeckel, G.; Reiling, S.; Vollhardt, H.; and Zachmann, C.-D. *Interactive Visualization of Molecular Scenarios with the MOLCAD/ SYBYL Package in Data Visualization in the Molecular Sciences: Tools for Insight and Innovation.* 1 ed.; Addison-Wesley Pub (Sd): 1994.

17. Soga, S.; Shirai, H.; Kobori, M.; Hirayama, N. Use of amino acid composition to predict ligand-binding sites. *J Chem Inf Model* 2007, 47, 400-406.

18. Friesner, R. A.; Banks, J. L.; Murphy, R. B.; Halgren, T. A.; Klicic, J. J.; Mainz, D. T.; Repasky, M. P.; Knoll, E. H.; Shelley, M.; Perry, J. K.; Shaw, D. E.; Francis, P.; Shenkin, P. S. Glide: a new approach for rapid, accurate docking and scoring. 1. Method and assessment of docking accuracy. *J Med Chem* 2004, 47, 1739-1749.

19. Halgren, T. A.; Murphy, R. B.; Friesner, R. A.; Beard, H. S.; Frye, L. L.; Pollard, W. T.; Banks, J. L. Glide: a new approach for rapid, accurate docking and scoring. 2. Enrichment factors in database screening. *J Med Chem* 2004, 47, 1750-1759.

20. Friesner, R. A.; Murphy, R. B.; Repasky, M. P.; Frye, L. L.; Greenwood, J. R.; Halgren, T. A.; Sanschagrin, P. C.; Mainz, D. T. Extra precision glide: docking and scoring incorporating a model of hydrophobic enclosure for protein-ligand complexes. *J Med Chem* 2006, 49, 6177-6196.

21. Jain, A. N. Surflex: fully automatic flexible molecular docking using a molecular similarity-based search engine. *J Med Chem* 2003, 46, 499-511.

22. Rarey, M.; Kramer, B.; Lengauer, T.; Klebe, G. A fast flexible docking method using an incremental construction algorithm. *J Mol Biol* 1996, 261, 470-489.

23. Sakaguchi, S. Naturally arising Foxp3-expressing CD25+CD4+ regulatory T cells in immunological tolerance to self and non-self. *Nat Immunol* 2005, 6, 345-352.

24. Bluestone, J. A.; Tang, Q. How do CD4+CD25+ regulatory T cells control autoimmunity? *Curr Opin Immunol* 2005, 17, 638-642.

25. Fontenot, J. D.; Gavin, M. A.; Rudensky, A. Y. Foxp3 programs the development and function of CD4+CD25+ regulatory T cells. *Nat Immunol* 2003, 4, 330-336.

26. Piccirillo, C. A.; Shevach, E. M. Naturally-occurring CD4+CD25+ immunoregulatory T cells: central players in the arena of peripheral tolerance. *Semin Immunol* 2004, 16, 81-88.

27. Ziegler, S. F. FOXP3: of mice and men. *Annu Rev Immunol* 2006, 24, 209-226.

28. Cao, Z.; Sun, X.; Icli, B.; Wara, A. K.; Feinberg, M. W. Role of Krüppel-like factors in leukocyte development, function, and disease. *Blood* 2010, 116, 4404-4414.

29. Majmudar, C. Y.; Mapp, A. K. Chemical approaches to transcriptional regulation. *Curr Opin Chem Biol* 2005, 9, 467-474.

30. Berg, T. Inhibition of transcription factors with small organic molecules. *Curr Opin Chem Biol* 2008, 12, 464-471.

31. Koehler, A. N. A complex task? Direct modulation of transcription factors with small molecules. *Curr Opin Chem Biol* 2010, 14, 331-340.

32. Lin, Q.; Barbas, C. F., 3rd; Schultz, P. G. Small-molecule switches for zinc finger transcription factors. *J Am Chem Soc* 2003, 125, 612-613.

33. Lauth, M.; Bergstrom, A.; Shimokawa, T.; Toftgard, R. Inhibition of GLI-mediated transcription and tumor cell growth by small-molecule antagonists. *Proc Natl Acad Sci USA* 2007, 104, 8455-8460.

34. Kroemer, R. T. Structure-based drug design: docking and scoring. *Curr Protein Pept Sci* 2007, 8, 312-328.

35. Jacobson, M. P.; Friesner, R. A.; Xiang, Z.; Honig, B. On the role of the crystal environment in determining protein side-chain conformations. *J Mol Biol* 2002, 320, 597-608.

36. Jacobson, M. P.; Pincus, D. L.; Rapp, C. S.; Day, T. J.; Honig, B.; Shaw, D. E.; Friesner, R. A. A hierarchical approach to all-atom protein loop prediction. *Proteins* 2004, 55, 351-367.

37. Kaminski, G. A.; Friesner, R. A.; Tirado-Rives, J.; Jorgensen, W. L. Evaluation and Reparametrization of the OPLS-AA Force Field for Proteins via Comparison with Accurate Quantum Chemical Calculations on Peptides†. *The Journal of Physical Chemistry B* 2001, 105, 6474-6487.

38. Kontoyianni, M.; Rosnick, C. B. Functional prediction of binding pockets. *J Chem Inf Model* 2012, 52, 824-833.

39. Ho, C. M.; Marshall, G. R. Cavity search: an algorithm for the isolation and display of cavity-like binding regions. *J Comput Aided Mol Des* 1990, 4, 337-354.

40. Irwin, J. J.; Sterling, T.; Mysinger, M. M.; Bolstad, E. S.; Coleman, R. G. ZINC: A Free Tool to Discover Chemistry for Biology. *J Chem Inf Model* 2012, 52, 1757-1768.

41. Baell, J. B.; Holloway, G. A. New substructure filters for removal of pan assay interference compounds (PAINS) from screening libraries and for their exclusion in bioassays. *J Med Chem* 2010, 53, 2719-2740.

42. Dixon, S. L.; Smondyrev, A. M.; Knoll, E. H.; Rao, S. N.; Shaw, D. E.; Friesner, R. A. PHASE: a new engine for pharmacophore perception, 3D QSAR model development, and 3D database screening: 1. Methodology and preliminary results. *J Comput Aided Mol Des* 2006, 20, 647-671.

43. Dixon, S. L.; Smondyrev, A. M.; Rao, S. N. PHASE: a novel approach to pharmacophore modeling and 3D database searching. *Chem Biol Drug Des* 2006, 67, 370-372.

44. Yet, S. F.; McA'Nulty, M. M.; Folta, S. C.; Yen, H. W.; Yoshizumi, M.; Hsieh, C. M.; Layne, M. D.; Chin, M. T.; Wang, H.; Perrella, M. A.; Jain, M. K.; Lee, M. E. Human EZF, a Kruppel-like zinc finger protein, is expressed in vascular endothelial cells and contains transcriptional activation and repression domains. *J Biol Chem* 1998, 273, 1026-1031.

45. Chrisman, H. R.; Tindall, D. J. Identification and characterization of a consensus DNA binding element for the zinc finger transcription factor TIEG/EGRalpha. *DNA Cell Biol* 2003, 22, 187-199.

What is claimed is:

1. A composition comprising: an effective amount of an inhibitor of KLF10 in combination with one or more disease antigens, wherein the inhibitor of KLF10 is a compound of formula:

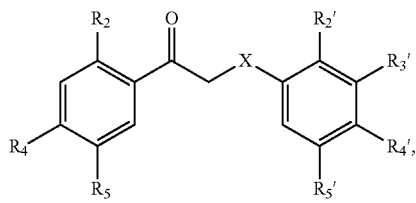

wherein:
(i)
$R_2$ is selected from H, OH, $CH_3$, and $OCH_3$;
$R_4$ is selected from H, OH, and $OCH_3$;
$R_5$ is selected from H, $CH_3$, and $C_2H_5$;
X is OC(=O);
$R_2'$ is selected from H and OH;
$R_3'$ is selected from H and $OCH_3$;
$R_4'$ is selected from H, $CH_3$, $C_2H_5$, $CH_2(CH_3)_2$, $OCH_3$, Ph, F, and I;
$R_5'$ is $CH_3$, or
wherein two of $R_2$, $R_4$, and $R_5$ may be optionally connected, and two of $R_2'$, $R_3'$, $R_4'$, or $R_5'$ may be optionally connected; or
(ii)
$R_2$ is selected from H, OH, $CH_3$, and $OCH_3$;
$R_4$ is selected from H, OH, and $OCH_3$;
$R_5$ is selected from H, $CH_3$, and $C_2H_5$;
X is OC(=O);
$R_2'$ is selected from H and OH;
$R_3'$ is H;
$R_4'$ is selected from H, $CH_3$, $C_2H_5$, $CH_2(CH_3)_2$, $OCH_3$, Ph, F, and I;

$R_5'$ is $OCH_3$, or
wherein two of $R_2$, $R_4$, and $R_5$ may be optionally connected, and two of $R_2'$, $R_3'$, $R_4'$, or $R_5'$ may be optionally connected.

2. The composition of claim 1, wherein the compound is

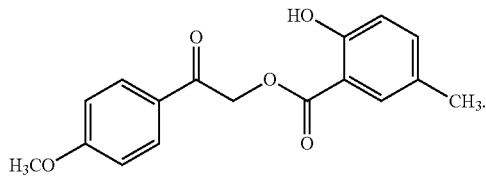

3. A composition comprising: an effective amount of an inhibitor of KLF10 in combination with a vaccine; wherein the inhibitor of KLF10 is a compound of formula:

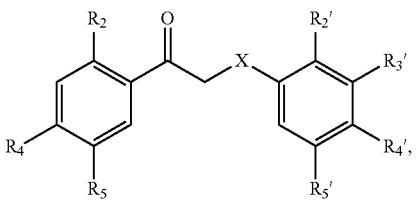

wherein:
(i)
$R_2$ is selected from H, OH, $CH_3$, and $OCH_3$;
$R_4$ is selected from H, OH, and $OCH_3$;
$R_5$ is selected from H, $CH_3$, and $C_2H_5$;
X is OC(=O);
$R_2'$ is selected from H and OH;
$R_3'$ is selected from H and $OCH_3$;
$R^{4'}$ is selected from H, $CH_3$, $C_2H_5$, $CH_2(CH_3)_2$, $OCH_3$, Ph, F, and I;

$R_5'$ is $CH_3$; or wherein two of $R_2$, $R_4$, and $R_5$ may be optionally connected, and two of $R_2'$, $R_3'$, $R_4'$, or $R_5'$ may be optionally connected; or (ii)

$R_2$ is selected from H, OH, $CH_3$, and $OCH_3$;

$R_4$ is selected from H, OH, and $OCH_3$;

$R_5$ is selected from H, $CH_3$, and $C_2H_5$;

X is OC(=O);

$R_2'$ is selected from H and OH;

$R_3'$ is H;

$R_4'$ is selected from H, $CH_3$, $C_2H_5$, $CH_2(CH_3)_2$, $OCH_3$, Ph, F, and I;

$R_5'$ is $OCH_3$, or wherein two of $R_2$, $R_4$, and $R_5$ may be optionally connected, and two of $R_2'$, $R_4'$, or $R_5'$ may be optionally connected.

4. The composition of claim 1, wherein the compound is

5. The composition of claim 1, wherein the compound is

6. The composition of claim 1, wherein
$R_3'$ and $R_4'$ can be taken together as CH=CH—CH=CH; and $R_5'$ is $CH_3$, or $OCH_3$; or
$R_4'$ and $R_5'$ can be taken together as CH=CH—CH=CH, and $R_3'$ is H or $OCH_3$.

7. The composition of claim 1, wherein the compound is

8. The composition of claim 3, wherein the compound is

9. The composition of claim 3, wherein the compound is

-continued

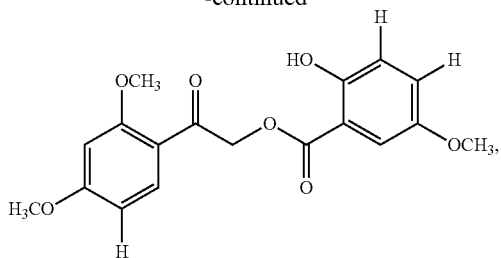

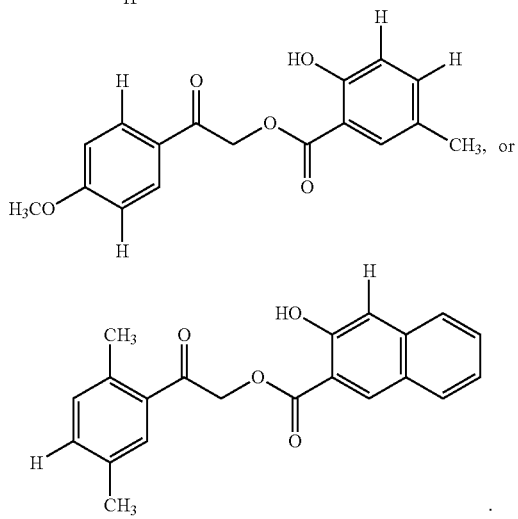

10. The composition of claim 3, wherein the compound is

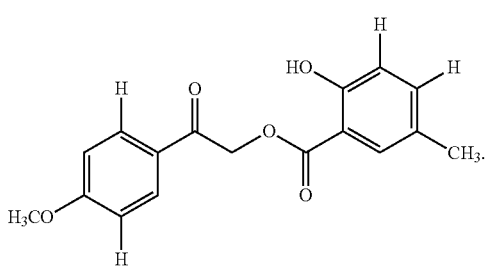 [SMILES: COc1ccc(C(=O)COC(=O)c2cc(C)ccc2O)cc1]

11. The composition of claim 3, wherein

R$_3$' and R$_4$' can be taken together as CH=CH—CH=CH, where R$_5$' is selected from CH$_3$, and OCH$_3$; or R$_4$' and R$_5$' can be taken together as CH=CH—CH=CH, where R$_3$' is selected from H and OCH$_3$.

12. The composition of claim 3, wherein the compound is

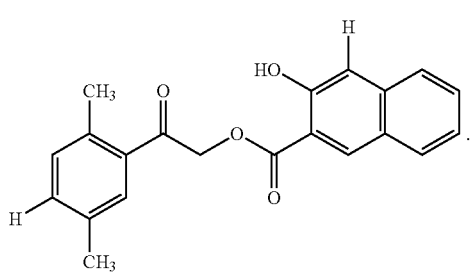 [SMILES: Cc1ccc(C)c(C(=O)COC(=O)c2cc3ccccc3cc2O)c1]

13. A method of modulating an immune response, comprising: administering to a subject an effective amount of a composition of claim 1.

14. A method of modulating an immune response, comprising: administering to a subject an effective amount of a composition of claim 3.

15. A method for treating cancer in a subject, comprising: administering to the subject having said cancer a composition of claim 1.

16. A method for treating cancer in a subject, comprising: administering to the subject having said cancer a composition of claim 3.

* * * * *